United States Patent
Rey et al.

(10) Patent No.: US 10,240,212 B2
(45) Date of Patent: *Mar. 26, 2019

(54) SYSTEMS AND METHODS FOR DETECTION OF CELLS USING ENGINEERED TRANSDUCTION PARTICLES

(71) Applicant: GeneWeave Biosciences, Inc., Los Gatos, CA (US)

(72) Inventors: Diego Ariel Rey, Palo Alto, CA (US); Shaunak Roy, Sunnyvale, CA (US); Leonardo Maestri Teixeira, Sergipe (BR); Ryan C. Griswold, Los Gatos, CA (US); Kenneth G. Olson, San Jose, CA (US); Bruce J. Richardson, Los Gatos, CA (US); Victor H. Yee, Castro Valley, CA (US); Werner Frei, Los Gatos, CA (US)

(73) Assignee: GeneWeave Biosciences, Inc., Los Gatos, CA (US)

( * ) Notice: Subject to any disclaimer, the term of this patent is extended or adjusted under 35 U.S.C. 154(b) by 61 days.

This patent is subject to a terminal disclaimer.

(21) Appl. No.: 15/388,750

(22) Filed: Dec. 22, 2016

(65) Prior Publication Data

US 2017/0152576 A1 Jun. 1, 2017

Related U.S. Application Data

(60) Division of application No. 14/480,269, filed on Sep. 8, 2014, now Pat. No. 9,546,391, which is a
(Continued)

(51) Int. Cl.
| | |
|---|---|
| *C12Q 1/06* | (2006.01) |
| *C12Q 1/10* | (2006.01) |
| *C12Q 1/66* | (2006.01) |
| *C12Q 1/68* | (2018.01) |
| *C12Q 1/6897* | (2018.01) |
| *C12Q 1/04* | (2006.01) |
| *B01L 3/00* | (2006.01) |
| *G01N 21/01* | (2006.01) |
| *G01N 21/76* | (2006.01) |
| *G01N 21/03* | (2006.01) |
| *G01N 21/13* | (2006.01) |
| *B01L 7/00* | (2006.01) |
| *C12Q 1/02* | (2006.01) |
| *G01J 1/00* | (2006.01) |

(Continued)

(52) U.S. Cl.
CPC ............ *C12Q 1/6897* (2013.01); *B01L 3/502* (2013.01); *B01L 3/50825* (2013.01); *B01L 3/52* (2013.01); *B01L 3/523* (2013.01); *B01L 3/54* (2013.01); *B01L 3/545* (2013.01); *B01L 7/00* (2013.01); *C12Q 1/02* (2013.01); *C12Q 1/04* (2013.01); *C12Q 1/06* (2013.01); *C12Q 1/10* (2013.01); *C12Q 1/14* (2013.01); *C12Q 1/66* (2013.01); *G01J 1/00* (2013.01); *G01N 21/01* (2013.01); *G01N 21/03* (2013.01); *G01N 21/13* (2013.01); *G01N 21/76* (2013.01); *G01N 21/763* (2013.01); *B01L 2200/028* (2013.01); *B01L 2200/16* (2013.01); *B01L 2300/021* (2013.01); *B01L 2300/042* (2013.01); *B01L 2300/047* (2013.01); *B01L 2300/049* (2013.01); *B01L 2300/0672* (2013.01); *B01L 2400/0478* (2013.01); *B01L 2400/06* (2013.01); *B01L 2400/0683* (2013.01); *G01N 2035/00346* (2013.01); *G01N 2035/0405* (2013.01); *G01N 2333/195* (2013.01)

(58) Field of Classification Search
None
See application file for complete search history.

(56) References Cited

U.S. PATENT DOCUMENTS

| | | |
|---|---|---|
| 3,122,420 A | 2/1964 | Rebar et al. |
| 3,826,574 A | 7/1974 | Brown, Jr. |

(Continued)

FOREIGN PATENT DOCUMENTS

| | | |
|---|---|---|
| CA | 1094477 | 1/1981 |
| DE | 1994/4423935 A1 | 1/1996 |

(Continued)

OTHER PUBLICATIONS

International Search Report and Written Opinion for International Application No. PCT/US2014/023422, dated Sep. 8, 2014.

(Continued)

*Primary Examiner* — Christopher M Babic
*Assistant Examiner* — Kimberly A. Aron

(57) ABSTRACT

Systems and methods for detecting and/or identifying target cells (e.g., bacteria) using engineered transduction particles are described herein. In some embodiments, a method includes mixing a quantity of transduction particles within a sample. The transduction particles are associated with a target cell. The transduction particles are non-replicative, and are engineered to include a nucleic acid molecule formulated to cause the target cell to produce a series of reporter molecules. The sample and the transduction particles are maintained to express the series of the reporter molecules when target cell is present in the sample. A signal associated with a quantity of the reporter molecules is received. In some embodiments, a magnitude of the signal is independent from a quantity of the transduction particle above a predetermined quantity.

19 Claims, 97 Drawing Sheets

Related U.S. Application Data continuation of application No. 14/048,974, filed on Oct. 8, 2013, now Pat. No. 8,829,473, which is a division of application No. 13/802,461, filed on Mar. 13, 2013, now Pat. No. 9,481,903.

(60) Provisional application No. 61/779,177, filed on Mar. 13, 2013.

(51) Int. Cl.
*C12Q 1/14* (2006.01)
*G01N 35/00* (2006.01)
*G01N 35/04* (2006.01)

(56) References Cited

U.S. PATENT DOCUMENTS

| | | | |
|---|---|---|---|
| 4,057,148 A | 11/1977 | Meyer et al. | |
| 4,730,933 A | 3/1988 | Lohr | |
| 4,861,709 A | 8/1989 | Ulitzur et al. | |
| 5,086,233 A | 2/1992 | Stafford et al. | |
| 5,128,104 A | 7/1992 | Murphy et al. | |
| 5,139,745 A | 8/1992 | Barr et al. | |
| 5,188,455 A | 2/1993 | Hammerstedt | |
| 5,221,623 A | 6/1993 | Legocki et al. | |
| 5,242,660 A | 9/1993 | Hsei | |
| 5,364,591 A | 11/1994 | Green et al. | |
| 5,447,687 A | 9/1995 | Lewis et al. | |
| 5,447,836 A | 9/1995 | Wolber et al. | |
| 5,494,646 A | 2/1996 | Seymour | |
| 5,498,525 A | 3/1996 | Rees et al. | |
| 5,582,969 A | 12/1996 | Pearson et al. | |
| 5,637,874 A | 6/1997 | Honzawa et al. | |
| 5,645,801 A | 7/1997 | Bouma et al. | |
| 5,656,424 A | 8/1997 | Jurgensen et al. | |
| 5,677,124 A | 10/1997 | DuBois et al. | |
| 5,730,938 A | 3/1998 | Carbonari et al. | |
| 5,814,022 A | 9/1998 | Antanavich et al. | |
| 5,824,468 A | 10/1998 | Scherer et al. | |
| 5,858,693 A | 1/1999 | Cottingham | |
| 5,912,119 A | 6/1999 | Radman et al. | |
| 5,917,592 A | 6/1999 | Skiffington | |
| 5,919,625 A | 7/1999 | DuBois et al. | |
| 5,939,262 A | 8/1999 | Pasloske et al. | |
| 5,965,415 A | 10/1999 | Radman et al. | |
| 5,989,499 A | 11/1999 | Catanzariti et al. | |
| 6,144,448 A | 11/2000 | Mitoma | |
| 6,189,580 B1 | 2/2001 | Thibault et al. | |
| 6,218,176 B1 | 4/2001 | Berthold et al. | |
| 6,271,034 B1 | 8/2001 | Bardarov et al. | |
| 6,300,061 B1 | 10/2001 | Jacobs, Jr. et al. | |
| 6,326,208 B1 | 12/2001 | Denney | |
| 6,451,258 B1 | 9/2002 | Malmqvist | |
| 6,544,729 B2 | 4/2003 | Sayler et al. | |
| 6,555,312 B1 | 4/2003 | Nakayama | |
| 6,737,266 B1 * | 5/2004 | Wicks | C12M 41/36 422/408 |
| 6,818,185 B1 | 11/2004 | Petersen et al. | |
| 7,001,719 B2 | 2/2006 | Wicks et al. | |
| 7,087,226 B2 | 8/2006 | Ramachandran et al. | |
| 7,125,727 B2 | 10/2006 | Massaro | |
| 7,160,511 B2 | 1/2007 | Takahashi et al. | |
| 7,166,425 B2 | 1/2007 | Madonna et al. | |
| 7,244,612 B2 | 7/2007 | Goodridge | |
| 7,284,900 B2 | 10/2007 | Mayer | |
| 7,364,843 B2 | 4/2008 | Peak | |
| 7,695,682 B2 | 4/2010 | Chojnacki et al. | |
| 7,854,104 B2 | 12/2010 | Cronin et al. | |
| 7,972,773 B2 | 7/2011 | Madonna et al. | |
| 8,021,343 B2 | 9/2011 | Nalesso et al. | |
| 8,057,756 B2 | 11/2011 | Londo et al. | |
| 8,092,990 B2 | 1/2012 | Voorhees | |
| 8,124,024 B2 | 2/2012 | Ching et al. | |
| 8,153,119 B2 | 4/2012 | Collins et al. | |
| 8,182,804 B1 | 5/2012 | Collins et al. | |
| 8,216,780 B2 | 7/2012 | Smith et al. | |
| 8,329,889 B2 | 12/2012 | Collins et al. | |
| 8,377,398 B2 | 2/2013 | McDevitt et al. | |
| 8,455,186 B2 | 6/2013 | Smith et al. | |
| 8,530,178 B2 | 9/2013 | Sobek et al. | |
| 8,619,257 B2 | 12/2013 | Plowman et al. | |
| 8,829,473 B1 | 9/2014 | Griswold et al. | |
| 9,133,497 B2 | 9/2015 | Frei et al. | |
| 2002/0001539 A1 | 1/2002 | DiCesare et al. | |
| 2003/0148536 A1 | 8/2003 | Liang et al. | |
| 2003/0162295 A1 | 8/2003 | Wilson | |
| 2004/0126783 A1 | 7/2004 | Bortolin et al. | |
| 2004/0214200 A1 | 10/2004 | Brown et al. | |
| 2005/0003346 A1 | 1/2005 | Voorhees et al. | |
| 2005/0048670 A1 | 3/2005 | Wu et al. | |
| 2005/0118719 A1 | 6/2005 | Schmidt et al. | |
| 2005/0155438 A1 | 7/2005 | Belgardt | |
| 2005/0180882 A1 | 8/2005 | Tung et al. | |
| 2005/0206895 A1 | 9/2005 | Salmelainen | |
| 2005/0227269 A1 | 10/2005 | Lloyd, Jr. et al. | |
| 2005/0273869 A1 | 12/2005 | Court et al. | |
| 2006/0099115 A1 | 5/2006 | Sandberg | |
| 2006/0205085 A1 | 9/2006 | Handique et al. | |
| 2006/0210968 A1 | 9/2006 | Goodridge | |
| 2006/0257991 A1 | 11/2006 | McDevitt et al. | |
| 2007/0003950 A1 | 1/2007 | Shen et al. | |
| 2007/0072174 A1 | 3/2007 | Sayler et al. | |
| 2007/0178450 A1 | 8/2007 | Wheeler et al. | |
| 2007/0263049 A1 | 11/2007 | Preckel et al. | |
| 2007/0292397 A1 | 12/2007 | McNulty et al. | |
| 2008/0003564 A1 | 1/2008 | Chen et al. | |
| 2008/0153096 A1 | 6/2008 | Witty et al. | |
| 2008/0193946 A1 | 8/2008 | McMillan | |
| 2008/0241819 A1 | 10/2008 | Smith | |
| 2008/0261294 A1 | 10/2008 | Noda et al. | |
| 2008/0272283 A1 | 11/2008 | Feldsine et al. | |
| 2008/0286757 A1 | 11/2008 | Gaisford et al. | |
| 2009/0155768 A1 | 6/2009 | Scholl et al. | |
| 2009/0155838 A1 | 6/2009 | Hale | |
| 2010/0028916 A1 | 2/2010 | Ambar et al. | |
| 2010/0055669 A1 | 3/2010 | Luque et al. | |
| 2010/0112549 A1 | 5/2010 | Rey et al. | |
| 2010/0133200 A1 | 6/2010 | Gin et al. | |
| 2010/0157303 A1 | 6/2010 | Ono | |
| 2010/0196877 A1 | 8/2010 | Smith et al. | |
| 2010/0225920 A1 | 9/2010 | Xia et al. | |
| 2011/0033847 A1 | 2/2011 | Walsh et al. | |
| 2011/0076672 A1 | 3/2011 | Schofield | |
| 2011/0097702 A1 | 4/2011 | Voorhees | |
| 2011/0117025 A1 | 5/2011 | Dacosta et al. | |
| 2011/0183314 A1 | 7/2011 | Smith | |
| 2011/0236960 A1 | 9/2011 | Bird et al. | |
| 2012/0003630 A1 | 1/2012 | Collins et al. | |
| 2012/0071342 A1 | 3/2012 | Lochhead et al. | |
| 2012/0134975 A1 | 5/2012 | Hyde et al. | |
| 2012/0143024 A1 | 6/2012 | Phillips et al. | |
| 2012/0225423 A1 | 9/2012 | Schwoebel et al. | |
| 2012/0252699 A1 | 10/2012 | Jaffrey et al. | |
| 2012/0288866 A1 | 11/2012 | Kozma et al. | |
| 2012/0288897 A1 | 11/2012 | Ching et al. | |
| 2012/0328576 A1 | 12/2012 | Jayasheela et al. | |
| 2013/0122549 A1 | 5/2013 | Lu et al. | |
| 2014/0134656 A1 | 5/2014 | Dortet et al. | |
| 2014/0272928 A1 | 9/2014 | Rey et al. | |
| 2015/0104787 A1 | 4/2015 | Rey et al. | |
| 2015/0132795 A1 | 5/2015 | Griswold et al. | |
| 2015/0218613 A1 | 8/2015 | de Forest et al. | |
| 2017/0233783 A1 | 8/2017 | de Forest et al. | |

FOREIGN PATENT DOCUMENTS

| | | |
|---|---|---|
| EP | 0274527 | 7/1987 |
| EP | 0168933 | 4/1993 |
| JP | 07083831 | 3/1995 |
| JP | 2001337039 | 12/2001 |
| JP | 2010107418 | 5/2010 |
| WO | WO 1987/006706 | 11/1987 |
| WO | WO 1994/025572 | 11/1994 |
| WO | WO 1995/007457 | 3/1995 |

(56) References Cited

FOREIGN PATENT DOCUMENTS

| WO | WO 2001/028683 | 4/2001 |
|---|---|---|
| WO | WO 2002/081679 | 10/2002 |
| WO | WO 2002/090995 | 11/2002 |
| WO | WO 2005/085855 | 9/2005 |
| WO | WO 2006/075996 | 7/2006 |
| WO | WO 2007/115378 | 10/2007 |
| WO | WO 2010/096584 | 8/2010 |
| WO | WO 2013/049121 | 4/2013 |
| WO | WO 2013/173524 | 11/2013 |
| WO | WO 2013/192396 | 12/2013 |
| WO | WO 2014/160418 | 10/2014 |
| WO | WO 2014/164768 | 10/2014 |

OTHER PUBLICATIONS

Office Action for U.S. Appl. No. 14/048,974, dated Jan. 28, 2014.
Office Action for U.S. Appl. No. 14/048,974, dated May 30, 2014.
Office Action for U.S. Appl. No. 14/611,902, dated Mar. 30, 2015, 12 pages.
Office Action for U.S. Appl. No. 14/480,269, dated Mar. 11, 2016.
European Search Report for European Application No. 14779477.0, dated Jun. 27, 2016.
Extended European Search Report for European Application No. 14779477.0, dated Aug. 17, 2016.
Search Report for Singapore Application No. 11201506977S, dated Jul. 28, 2016.
Dual-Glo Luciferase Assay System, Instructions for Use of Products E2920, E2940 and E2980, Technical Manual, Promega, 2011, 27 pages.
Hakamata, T. et al. (eds.), Chapter 14—Applications in Photomultiplier Tubes, Basics and Applications, Third Edition (Edition 3a), Hamamatsu Photonics K. K., 2007, 48 pages.
KeyPath MRSA/MSSA Blood Culture Test—BT, 510(k) Summary, MicroPhage, Inc., Apr. 29, 2011, 15 pages.
Lampinen, J. et al., Comparison of flash and glow ATP assays with thermo scientific varioskan flash luminometry: Application Note: AP-MIB-VARIO12-0108, Thermo Scientific, 2008, 6 pages.
Luciferase Measurements using the Clarity Luminescence Microplate Reader. Luminescence made easy. Application Note, BioTek Instruments, Inc., 2006, 5 pages.
NucliSENS EasyQ MRSA Assay, 510(k) Summary, bioMerieux, Inc., Sep. 20, 2010, 23 pages.
Ulitzur, S. et al., "Introduction of lux genes into bacteria: a new approach for specific determination of bacteria and their antibiotic susceptibility," In: Schlomerich J. et al. (eds.), Bioluminescence and Chemiluminescence New Perspectives, Chichester: John Wiley and Sons (1987), pp. 463-472.
Vandercam, B. et al., "Amplification-based DNA analysis in the diagnosis of prosthetic joint infection," Journal of Molecular Diagnostics, 10(6):537-543 (2008).
Watanabe, T. et al., "Studies on luciferase from photobacterium phosphoreum," Journal of Biochemistry, 72(3):647-653 (1972).
Office Action received for Japanese Patent Application No. 2016-501231.

\* cited by examiner

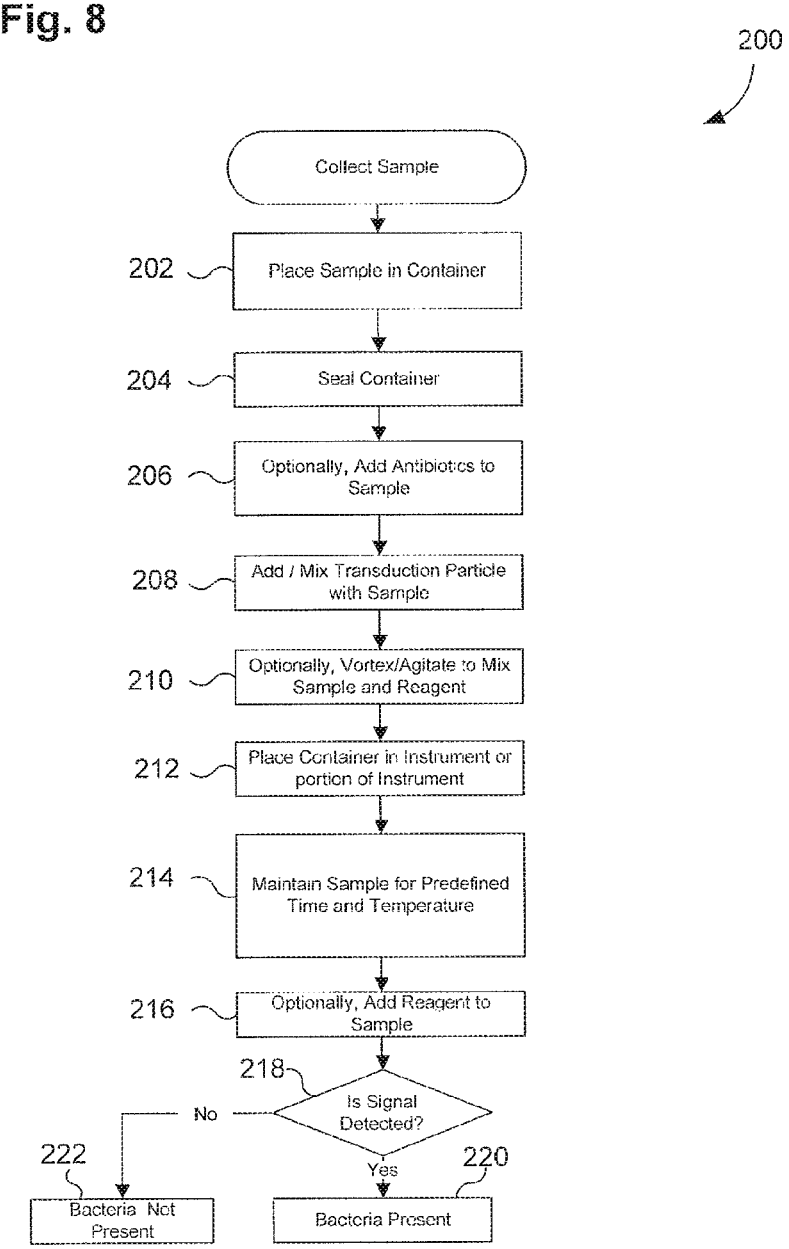

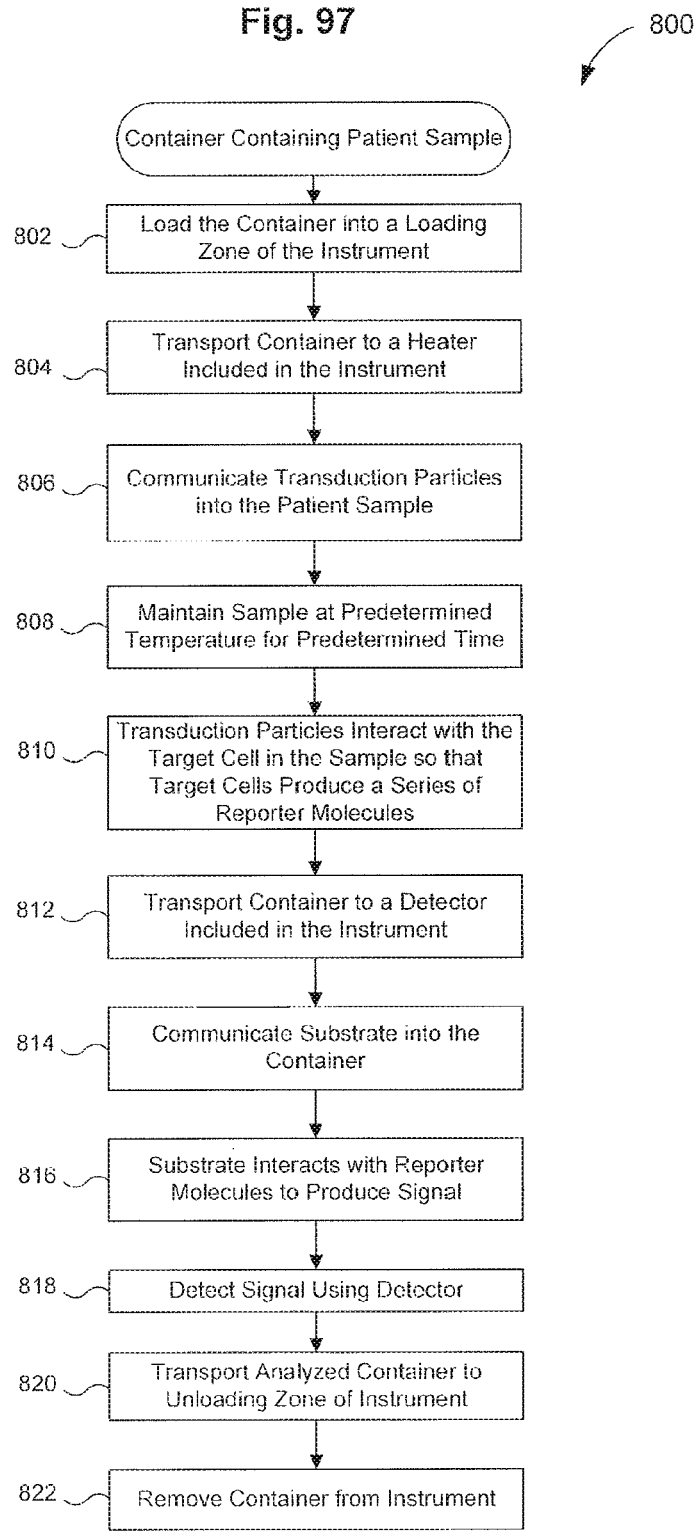

SYSTEMS AND METHODS FOR DETECTION OF CELLS USING ENGINEERED TRANSDUCTION PARTICLES

CROSS-REFERENCE TO RELATED APPLICATIONS

This application is a divisional of U.S. patent application Ser. No. 14/480,269, entitled "Systems and Methods for Detection of Cells Using Engineered Transduction Particles," filed Sep. 8, 2014, which is a continuation of U.S. patent application Ser. No. 14/048,974, now U.S. Pat. No. 8,829,473, entitled "Systems and Methods for Detection of Cells Using Engineered Transduction Particles," filed Oct. 8, 2013, which is a divisional of U.S. application Ser. No. 13/802,461, now U.S. Pat. No. 9,481,903, entitled "Systems and Methods for Detection of Cells Using Engineered Transduction Particles," filed Mar. 13, 2013, which claims priority to and the benefit of U.S. Provisional Application Ser. No. 61/779,177, entitled "Non-Replicative Transduction Particles and Transduction Particle-Based Reporter Systems," filed Mar. 13, 2013, all of which are incorporated herein by reference in their entirety.

BACKGROUND

The embodiments described herein relate to systems and methods for detection of cells using engineered transduction particles. More particularly, the embodiments described herein relate to methods for detecting bacteria using replication-deficient transduction particles as a reporter system. The embodiments described herein also relate to a container and instrument within which the detection of bacteria can be performed in an integrated, closed system with walkaway functionality.

Detection of bacteria, especially drug resistant strains, is a critical step in diagnosing and limiting spread of bacterial infections. For example, MRSA is a drug-resistant version of the common *Staphylococcus aureus* bacteria that is carried by a significant portion of the population in the U.S. Most infections of MRSA occur in hospitals, and can have a high mortality rate (MRSA infections kill approximately 19,000 people in the U.S. every year). Accordingly, there is a need for efficient, accurate and rapid identification of the bacterial strains (including their phenotype and/or genotype and other molecular targets) that cause infection, such as MRSA. Particularly important is the ability to identify the bacterial phenotype and/or genotype and other molecular targets from a variety of different samples (e.g., human samples, environmental samples, plant samples, veterinary samples, food samples or the like), so that the appropriate treatment and control regimen can be started in a timely fashion.

One known method for identifying bacteria includes bacterial culture. Culturing is highly sensitive, but often takes two to three days (or even longer) to yield a result, and is therefore not suitable for rapid diagnosis or for efficient screening purposes. Known culturing methods are often performed using systems that require highly trained personnel to perform the assay, and are therefore not suitable for use in a variety of different settings. Known culturing methods are also prone to contamination, which can result in false positives and/or misidentification of the bacteria. Moreover, known culturing methods employ specifically tailored culture protocols for identification of various bacterial species, thus testing a broad bacteria panel can rapidly elevate the cost.

Direct bacterial immunodetection, that is, detection using an antibody antigen reaction, is another method for bacterial detection. Known methods of immunodetection can produce results more quickly and at a lower cost than a culture, but are often limited by the availability of selective antibodies for the bacterial strain of interest and available antibodies are prone to cross-reactivity. Such known methods are also less sensitive than culturing, so there is often nevertheless a requirement of bacterial amplification that can lengthen the assay time.

Other known methods for detection of bacterial cells include isolation and analysis of nucleic acid such as DNA or RNA. Known methods for isolating nucleic acids from a sample often include several stringent sample preparation steps that require expensive and specialized equipment. In particular, such steps include 1) removing the proteins within a sample containing bacteria or cells by adding a protease; 2) breaking down the remaining bulk sample to expose the nucleic acids contained therein (also referred to as cell lysing); 3) precipitating the nucleic acid from the sample; 4) washing and/or otherwise preparing the nucleic acid for further analysis; 5) analyzing the nucleic acid to identify the species. After preparing the sample, known analysis methods can include polymerase chain reaction (PCR), gene sequencing, gene fingerprinting, fluorescence, immunoassay, electrochemical immunoassay, microarrays, any other suitable technique or a combination thereof. PCR has found widespread commercial usage but often requires multiple steps involving expensive reagents and instrumentation. Many known methods involving PCR are not suitable for bench top testing (e.g., they require relatively skilled personnel). Moreover, known PCR methods employ thermal cycling and/or elevated temperatures, which can increase the cost, time and/or complexity of the analysis. Finally, because PCR methods for detecting DNA sequences lyse the sample cells, such methods cannot distinguish between live and dead cells.

Some known systems and methods for cell identification include the use of bacteriophages to identify and/or detect certain bacteria. In some known methods, phages that are tagged with a reporter molecule can be used to target and infect a specific bacterial strain. After infection, the phages can undergo a lytic cycle (i.e., break the cell wall killing the target bacteria) and/or a lysogenic cycle (i.e., replication of the phage along with the bacteria without killing the bacteria), followed by detection of the amplified progeny phage. Such known methods relying on phage detection often include limiting or complex steps. For example, some known phage detection-based methods for identification rely on phage replication (during which the bacteria can be lysed), and typically require cell culturing for facilitating this process. Some known phage detection-based methods require removal or "unbinding" of specifically bound phages from the samples using carefully metered and/or pH controlled reagents. Moreover, some known phage detection-based methods rely on careful metering of the amount of phage added and/or include opening or closing of the reaction chamber to add/remove reagents, which can lead to contamination and/or premature mixing of reagents leading to erroneous results and making the assay complex in nature.

Other phage-based methods employ bacteriophages that are engineered to deliver into the target bacteria a nucleotide that can include a reporter gene, which cause the target bacteria to express a reporter molecule. Some known methods include phages that replicate during the assay, however, which can result in an undesirable lysing of the cells within which the reporter molecules are to be produced. Other known phage-based methods employ bacteriophages in which the replicative functions are suppressed during the assay conditions. Such known methods, however, are difficult to implement due to the tight range of conditions (e.g., temperature conditions) under which the replicative functions will remain suppressed. Such methods are not easily controlled, and thus can result in lytic activity. Still other methods suggest the use of temperate phages that undergo a lysogenic cycle instead of a lytic cycle. Such known methods, however, are also susceptible to sporadic lytic activity. Incorporation of native phage life cycles may also lead to limiting of the reporter phage host range due to superinfection immunity by target cells that may be lysogenized with a prophage. Thus, although known methods of this type have been performed in an academic setting, they are not applicable in a clinical setting.

In addition to the above-described drawbacks regarding the use of phage-based methods, known methods do not employ automation or instrumentation for enabling a "walk away" bacteriophage identification system. For example, many known systems do not accommodate closed system handling and/or measurement of a signal that is produced by certain reporter molecules, such as for example, a flash luminescence reaction. Thus, known systems and methods require skilled personnel and intimate handling of the samples, which can increase the possibility of false positives or negatives.

Thus, a need exists for improved apparatus and methods for rapid, cost effective and facile detection and identification of bacterial species in clinical samples.

SUMMARY

Systems and methods for detecting and/or identifying target cells (e.g., bacteria) using engineered viral vectors and/or transduction particles are described herein. In some embodiments, a method includes mixing a quantity of transduction particles within a sample. The transduction particles are associated with a target cell. The transduction particles are non-replicative, and are engineered to include a nucleic acid molecule formulated to cause the target cell to produce a series of reporter molecules. The sample and the transduction particles are maintained to express the series of the reporter molecules when target cell is present in the sample. A signal associated with a quantity of the reporter molecules is received. In some embodiments, a magnitude of the signal is independent from a quantity of the transduction particle above a predetermined quantity.

In some embodiments, a container includes a housing, a delivery member, and an actuator. The housing, which can be removably coupled to a reaction chamber, defines a reagent volume. The delivery member is coupled to the housing and defines a pathway between the reagent volume and the reaction chamber when the housing is coupled to the reaction chamber. A first end portion of the delivery member is disposed within the reagent volume and a second end portion of the delivery member is disposed outside of the reagent volume. The actuator has a plunger portion disposed within the reagent volume that can be moved within the reagent volume along a longitudinal axis of the housing to produce a flow or reagent from the reagent volume via the pathway. The delivery member is configured to direct the flow of the reagent exiting the second end portion of the delivery member in an exit direction non-parallel to the longitudinal axis of the housing.

In some embodiments, an instrument includes a retention assembly, an activation assembly and an actuator. The retention assembly includes a first gripper, a second gripper and a biasing member. The first gripper and the second gripper are configured to contact a first portion of a sample container to limit movement of the sample container. The sample container defines a reaction volume and a reagent volume. The activation member is movably coupled to the retention assembly, and is configured to engage a second portion of the sample container to convey a reagent from the reagent volume into the reaction volume. The actuator is configured to move the activation member relative to the retention assembly between a first position and a second position. In the first position, a surface of the activation member is in contact with a surface of the retention assembly to maintain the first gripper and the second gripper in an opened configuration. In the second position, the surface of the activation member is spaced apart from the surface of the retention assembly such that the biasing member urges the first gripper and the second gripper into a closed configuration. A plunger portion of the activation member is configured to move within the reagent volume when the activation member moves toward the second position.

BRIEF DESCRIPTION OF THE DRAWINGS

FIG. 8 illustrates a flow diagram of a method for the identification of a viable target cell, according to an embodiment.

FIG. 97 illustrates a flow diagram of a method for manipulating a container, according to an embodiment.

DETAILED DESCRIPTION

Figure 1:
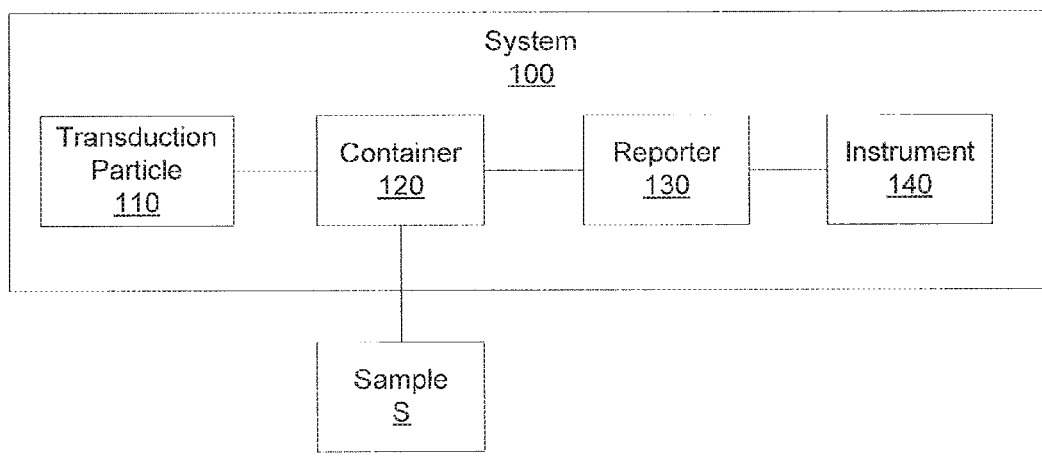
FIG. 1 is a block diagram of a system for bacteria identification, according to an embodiment.

Systems and methods for detecting and/or identifying target cells (e.g., bacteria) using engineered viral vectors and/or transduction particles are described herein. In some embodiments, a method includes mixing a quantity of transduction particles within a sample. The transduction particles are associated with a target cell. Similarly stated, the transduction particles are formulated to bind to and deliver a nucleic acid molecule into the target cell. The transduction particles are non-replicative, and are engineered to include a nucleic acid molecule formulated to cause the target cell to produce a series of reporter molecules. The sample and the transduction particles are maintained to express the series of the reporter molecules when target cell is present in the sample. A signal associated with a quantity of the reporter molecules is received. In some embodiments, a magnitude of the signal is independent from a quantity of the transduction particle above a predetermined quantity.

In some embodiments, a method for detecting a target cell includes mixing with a sample a series of transduction particles associated with the target cell. The transduction particles are engineered to include a nucleic acid molecule formulated to cause the target cell to produce a series of reporter molecules. The transduction particles are devoid of a wild-type DNA that is capable of exhibiting wild-type viral functions associated with a virus from which the series of transduction particles are derived. The sample and the series of transduction particles are maintained such that the series of reporter molecules is only expressed when the target cell is present in the sample. A signal associated with the quantity of reporter molecules is then received. In some embodiments, the magnitude of the signal is independent from the quantity of the series of transduction particles above a predetermined quantity. Similarly stated, in some embodiments, the strength of the signal is substantially independent from the quantity of the series of transduction particles.

In some embodiments, a method for detecting a target cell includes mixing within a sample a series of transduction particles associated with the target cell. The series of transduction particles are engineered to be incapable of lysogenic replication and to include a nucleic acid molecule formulated to cause the target cell to produce a series of reporter molecules. The sample and the series of transduction particles are maintained to express the series of reporter molecules when the sample includes the target cell. The method also includes receiving a signal associated with a quantity of the series of the reporter molecules.

In some embodiments, a container includes a housing, a first actuator and a second actuator. The housing is configured to be removably coupled to a reaction chamber (e.g., which can contain a sample including a target cell). The housing defines a first reagent volume and a second reagent volume, and includes a delivery portion that defines a first pathway between the first reagent volume and the reaction chamber and a second pathway between the second reagent volume and the reaction chamber. The first actuator has a plunger portion disposed within the first reagent volume, and an engagement portion configured to be manipulated to move the plunger portion within the first reagent volume. The second actuator has a plunger portion disposed within the second reagent volume, and an engagement portion of the second actuator is configured to be manipulated to move the plunger portion within the second reagent volume. The engagement portion of the second actuator at least partially surrounds the engagement portion of the first actuator.

In some embodiments, a container includes a housing, a delivery member, and an actuator. The housing, which can be removably coupled to a reaction chamber (e.g., that contains a target cell), defines a reagent volume. The delivery member is coupled to the housing and defines a pathway between the reagent volume and the reaction chamber when the housing is coupled to the reaction chamber. A first end portion of the delivery member is disposed within the reagent volume and a second end portion of the delivery member is disposed outside of the reagent volume. The actuator has a plunger portion disposed within the reagent volume that can be moved within the reagent volume along a longitudinal axis of the housing to produce a flow or reagent from the reagent volume via the pathway. The delivery member is configured to direct the flow of the reagent exiting the second end portion of the delivery member in an exit direction non-parallel to the longitudinal axis of the housing.

In some embodiments, a container includes a housing, a delivery member, and an actuator. The housing defines a reagent volume and is removably coupleable to a reaction chamber. The delivery member is coupled to the housing and defines a pathway between the reagent volume and the reaction chamber when the housing is coupled to the reaction chamber. A first end portion of the delivery member is disposed within the reagent volume and defines a first portion of the pathway. A second end portion of the delivery member is disposed outside the housing and defines a second portion of the pathway. A center line of the second portion of the pathway is angularly offset from a center line of the first portion of the pathway. The actuator has a plunger portion disposed within the reagent volume and is configured to be moved within the reagent chamber along a longitudinal axis of the housing to produce a flow of a reagent from the reagent volume via the pathway.

In some embodiments, a method for detecting a target cell includes placing a reaction chamber containing a sample and a series of reporter molecules in operable communication with a detector. A reagent is conveyed into the reaction chamber via a delivery member such that the reagent flows along a surface of the reaction chamber and into the sample. In this manner, aeration of the sample and the reagent and/or the production of bubbles within the sample is minimized. The reagent is formulated to react with the series of reporter molecules to enable and/or enhance the production of a signal associated with a quantity of the series of reporter molecules. The signal is received by a detector.

In some embodiments, an instrument includes a retention member, an activation member and an actuator. The retention member is configured to contact a first portion of a sample container, which defines a reaction volume and a reagent volume, to limit movement of the sample container. The activation member is coupled to the retention member, and is configured to engage a second portion of the sample container to convey a reagent from the reagent volume into the reaction volume. The actuator is configured to move the activation member relative to the retention member between a first position, a second position and a third position. In the first position, the retention member is configured to be spaced apart from the first portion of the sample container. In the second position, the activation member is configured to be spaced apart from the second portion of the sample container and the retention member is configured to contact the first portion of the sample container. In the third position, the activation member is configured to be engaged with the second portion of the sample container to convey the reagent such that the retention member is in contact with the first portion of the sample container.

In some embodiments, an instrument includes a retention assembly, an activation assembly and an actuator. The retention assembly includes a first gripper, a second gripper and a biasing member. The first gripper and the second gripper are configured to contact a first portion of a sample container to limit movement of the sample container. The sample container defines a reaction volume and a reagent volume. The activation member is movably coupled to the retention assembly, and is configured to engage a second portion of the sample container to convey a reagent from the reagent volume into the reaction volume. The actuator is configured to move the activation member relative to the retention assembly between a first position and a second position. In the first position, a surface of the activation member is in contact with a surface of the retention assembly to maintain the first gripper and the second gripper in an opened configuration. In the second position, the surface of the activation member is spaced apart from the surface of the retention assembly such that the biasing member urges the first gripper and the second gripper into a closed configuration. A plunger portion of the activation member is configured to move within the reagent volume when the activation member moves toward the second position.

In some embodiments, an instrument includes a housing and a shutter having a portion movably disposed within the housing between a first shutter position and a second shutter position. The housing defines a channel configured to receive a sample container, and further defines a detection volume configured to place the channel in communication with a detector. The housing including a first seal surface and a second seal surface. A first portion of the sample container and the first seal surface are configured to isolate the detection volume from a volume outside of the housing when a second portion (e.g., a distal end portion) of the sample container is disposed within the detection volume. A seal surface of the shutter and the second seal surface of the housing are configured to isolate the detection volume from the channel of the housing when shutter is in the first shutter position. The channel of the housing is in communication with the detection volume when the shutter is in the second shutter position.

In some embodiments, an instrument includes a housing and a shutter having a portion movably disposed within the housing between a first shutter position and a second shutter position. The housing defines a channel configured to receive a sample container, and also defines a detection volume configured to place the channel in communication with a detector. An actuation portion of the shutter is configured to engage a distal end portion of the sample container to move the shutter from the first shutter position to the second shutter position when the distal end portion of the container is moved towards the detection volume. A seal surface of the shutter and a seal surface of the housing are configured to isolate the detection volume from the channel of the housing when shutter is in the first shutter position. The channel of the housing is in communication with the detection volume when the shutter is in the second shutter position.

In some embodiments, an instrument includes a housing and a shutter disposed within the housing between a first shutter position and a second shutter position. The housing defines a channel configured to receive a sample container, and also defines a detection volume configured to place the channel in communication with a detector. The shutter defines a calibration port configured to receive a calibration light source, such as, for example, an LED. A seal surface of the shutter and a corresponding seal surface of the housing are configured to isolate the detection volume from the channel of the housing when shutter is in the first shutter position. The calibration port is in communication with the detection volume when shutter is in the first shutter position. The channel of the housing is in communication with the detection volume and the calibration port is isolated from the detection volume when the shutter is in the second shutter position.

In some embodiments, a method for receiving a signal includes receiving a first signal associated with a magnitude of light emission in a detection volume, at a first time. The detection volume is optically isolated from a channel by a movable shutter, which is in a first position. The method also includes applying a force to a sample container at least partially disposed within a channel such that a distal end portion of the sample container moves the shutter from the first position to a second position, and such that the distal end portion of the sample container is disposed within the detection volume. In this configuration, the channel is in optical communication with the detection volume. The method further includes receiving, a second signal associated with a magnitude of light emission in the detection volume at a second time, when the distal end portion of the sample container is in the detection volume.

As described herein, the terms "gene," "DNA" and "nucleotide" mean the whole or a portion of the genetic sequence of the target bacteria or the vector.

As described herein, the term "plasmid" means the engineered gene, sequence and/or molecule contained within the vector that includes regulatory elements, nucleic acid sequences homologous to target genes, and various reporter constructs for causing the expression of reporter molecules within a viable cell and/or when an intracellular molecule is present within a target cell.

Systems, devices and methods for detecting and identifying target cells (e.g., bacteria) can include a transduction particle that can identify and bind to the target cell and deliver into the target cell an engineered nucleotide. As shown in the block diagram of FIG. 1, in some embodiments, a system 100 includes a genetically engineered transduction particle 110, a container 120, a reporter 130, and a detection instrument 140. As described in detail herein, the system 100 is configured to manipulate, handle and/or actuate the container 120 and/or the detection instrument 140 such that the transduction particle 110 can, when mixed with a sample S that contains a particular target, produce the reporter 130. In this manner, the system 100 and methods associated therewith can be thought of as a "switchable" assay, meaning that no amount of the reporter 130 is present in the sample until the conditions (e.g., the presence of the target cell) are such that the reporter 130 is produced.

The transduction particle 110 can be any suitable particle capable of delivering via transduction non-viral DNA and/or RNA into a target cell. For example, in some embodiments, the transduction particle can be derived from a bacteriophage, or can be a non-biologically derived vector that is capable of introducing nucleic acid molecules into the target bacteria in the sample S. The transduction particle 110 is further engineered and/or configured to carry an engineered molecule, for example, recombinant DNA, RNA, nucleotide, plasmid, ribozyme, aptamer, and/or protein. In some embodiments, the transduction particle 110 does not contain any DNA from the viral vector (e.g., bacteriophage) from which it was derived. Similarly stated, in some embodiments, the transduction particle is a viral vector devoid of a wild-type DNA capable of exhibiting wild-type viral functions associated with the virus from which the viral vector is derived. In some embodiments, a transduction particle includes any of the transduction particles described herein.

In some embodiments, the transduction particle 110 is incapable of replicating via either the lytic or lysogenic cycle. By eliminating all forms of replication from the transduction particle, the target cells will be maintained (i.e., not destroyed, killed or lysed) during the production of the reporter molecules, thereby improving the accuracy and reliability of the methods used therewith. In this manner, the assays described herein reduce and/or eliminate the likelihood of a false negative, making the methods applicable in a clinical setting. In particular, because wild-type viral functions of viral particles can exhibit lysogenic replication and require the capability for lytic replication, attempts to suppress the replicative functions (e.g., the lytic cycle) may not provide sufficient certainty that the lytic cycle will not result in some population of assays. To demonstrate the advantages of the use a transduction particle in which the replication capability is eliminated, the lytic activity of two temperate S. aureus phages on ten MRSA clinical isolates was examined via plaque assay. As shown in Table 1, the phage phi11 exhibited lytic activity on each of the ten clinical MRSA isolates, and the phage phi80alpha exhibited lytic activity on six of the ten clinical MRSA isolates. As shown, assays relying on the natural lysogenic cycle of phages (e.g., the temperate phages as tested) can be expected to exhibit lytic activity sporadically. Accordingly, in some embodiments, the transduction particle 110, and other transduction particles described herein, is engineered to be non-replicative or replication deficient (i.e., incapable of replication).

TABLE 1

| MRSA Isolate | PFFGE Type | phi11 | phi80alpha |
|---|---|---|---|
| 1. | USA200 | x | |
| 2. | USA1000 | x | |
| 3. | USA800 | x | x |
| 4. | USA300 | x | x |
| 5. | USA300 | x | x |
| 6. | USA100 | x | |
| 7. | USA300 | x | x |
| 8. | USA100 | x | |
| 9. | USA300 | x | x |
| 10. | USA100 | x | x |

The transduction particle 110 is characterized by being associated with and/or specific to one or more target cells. Similarly stated, the transduction particle 110 is formulated to bind to and deliver a nucleic acid molecule into the target cell. For example, the transduction particle can be selected, engineered and/or produced to bind to any bacteria, e.g., Escherichia, Mycobacterium, Staphylococcus, Listeria, Clostridium, Enterococcus, Streptococcus, Helicobacter, Rickettsia, Haemophilus, Xenorhabdus, Acinetobacter, Bordetella, Pseudomonas, Aeromonas, Actinobacillus, Pasteurella, Vibrio, Legionella, Bacillus, Calothrix, Methanococcus, Stenotrophomonas, Chlamydia, Neisseria, Salmonella, Shigella, Campylobacter and Yersinia.

In some embodiments, the non-replicative transduction particle 110, as well as any of the non-replicative transduction particles described herein, can be developed by packaging nucleic acid into the structural components of a virus and/or bacteriophage where the packaged nucleic acid is devoid from exhibiting native viral and/or bacteriophage functions that allow for the virus and/or bacteriophage to replicate whether the replication is via a lytic or lysogenic pathway.

In one embodiment, a plasmid packaging system can be developed in which the small terminase gene containing the pac-site of a pac-type prophage is deleted and then complemented via a plasmid. When the lytic cycle of the lysogenized prophage is induced, the bacteriophage packaging system packages plasmid DNA into progeny bacteriophage structural components rather than packaging native bacteriophage DNA. The packaging system thus produces non-replicative transduction particles carrying plasmid DNA.

In another embodiment, genomic island (GI)-packaging systems can be exploited such that exogenous nucleic acid sequences are packaged by the bacteriophage. This can be accomplished by incorporating such exogenous nucleic acids sequences into the GI. Natural GI-packaging systems result in both non-replicative GI-containing transduction particles as well as native replicative phage, thus in order to eliminate the native phage from this process, the small terminase gene of the prophage is deleted. The small terminase gene sequence contains the pac-site sequence of the native phage and thus this deletion has the effect of preventing the packaging of native phage DNA. If at the same time a GI to be packaged includes its own pac-site and a small terminase gene that expresses a suitable small terminase protein, then only GI DNA will be amenable for packaging in this system. By incorporating exogenous DNA into this system, non-replicative transduction particles that incorporate GI DNA and exogenous DNA can be produced.

The transduction particle 110 can be further produced and/or engineered to contain genes and/or a nucleic acid molecule for expressing a reporter 130 that can be detected (e.g., via the instrument 140). The reporter 130 can be any one of a bacterial luciferase, a eukaryotic luciferase, a fluorescent protein (e.g., GFP, etc.), an enzyme suitable for colorimetric detection (e.g., horseradish peroxidase) a protein suitable for immunodetection (e.g., protein A, etc.), a peptide or peptide tag suitable for immunodetection (e.g., 3X FLAG, etc.) and/or a nucleic acid that functions as an aptamer or that exhibits enzymatic activity. More particularly, the transduction particle 110 does not produce the reporter 130 autonomously and/or does not include the reporter 130. Instead, transduction particle 110 is configured to communicate an engineered nucleic acid molecule contained therein into the target cell, e.g., bacteria, such that the engineered nucleic acid molecule uses the natural transcription and translation functions of the bacteria DNA to produce the reporter 130. Thus, the reporter 130 can be thought of as a "switchable" reporter, meaning that no amount of the reporter 130 is present in the sample until the conditions (e.g., the presence of the target cell) are such that the reporter 130 is produced. In this manner, the methods described herein include no washing of non-bound reporter 130, no signal subtraction to account for initial quantities of reporter or the like. Thus, the system 100 and the methods associated therewith allows for the development of a homogeneous assay. Further, no temperature cycling is required, and heating at a low temperature, for example 37 degrees Celsius, for a short time can be sufficient.

The reporter system formulated to cause the expression of the reporter 130 and any of the reporter systems disclosed herein can be developed for reporting on the presence of viable bacteria and/or target cells by incorporating into the non-replicative transduction particle 110 (or any of the other transduction particles disclosed herein) a reporter molecule under the control of a promoter. When this transduction particle 110 introduces the reporter system into a cell within the host range of the transduction particle 110, the promoter is able to drive the expression of the reporter molecule.

In one embodiment, a MSSA/MRSA reporter assay can be developed and/or performed using any suitable system and method as described herein (such as, for example the system 1000). In such embodiments, a non-replicative transduction particle (e.g., the transduction particle 110, the transduction particle 160 or the like) is developed from a S. aureus-specific bacteriophage and the bacterial luciferase genes luxAB under the control of a constitutive promoter are incorporated. When this transduction particle introduces the reporter system into S. aureus, the constitutive promoter can express luxAB suitable for reporting on the presence of a viable S. aureus. If in addition, the antibiotic cefoxitin, or a similar anti-biotic, is also added prior to or simultaneously with mixing the transduction particles with S. aureus cells, if the cells do not contain and express the mecA gene, no luxAB will be expressed in the assay, thus indicating that the cells are MSSA (i.e., sensitive to inhibition by cefoxitin). If, however, the cells do contain and express the mecA gene, luxAB will be expressed in the assay, thus indicating that the cells are MRSA (i.e., resistant to inhibition by cefoxitin).

Although described as being developed for reporting on the presence of viable bacteria, in other embodiments the reporter 130 and any of the applicable reporter systems (e.g., the reporter 630) can be developed for reporting on the presence of target genes within target bacteria. In this system a promoter-less reporter gene is placed downstream of a nucleic acid sequence that is homologous to a target gene sequence and this reporter construct is incorporated into a non-replicative transduction particle. When the transduction particle introduces the reporter construct into a target cell, the reporter gene will not be expressed unless the target cell contains the target gene and a homologous recombination event integrates the reporter gene within the target gene loci in the target cell such that the reporter gene becomes operatively linked to the target gene promoter within target cell.

In one such embodiment, a MRSA reporter system can be developed by incorporating into a S. aureus-specific non-replicative transduction particle (e.g., the transduction particle 110, the transduction particle 160 or the like) a reporter construct consisting of a nucleic acid sequence that is homologous to the mecA gene upstream of promoter-less bacterial luciferase genes, luxAB. When the transduction particle introduces the reporter construct into a target S. aureus cell, the reporter gene will not be expressed unless the target cell contains the target mecA gene and a homologous recombination event integrates the luxAB genes within the mecA gene loci in the target cell such that the reporter gene becomes operatively linked to the mecA gene promoter within target cell.

In some embodiments, transduction particle 110, the nucleic acid molecule contained within the transduction particle 110 and/or the reporter systems associated therewith can include any of the portions of the recombinant bacteriophages shown and described in U.S. Patent Publication No. 2010/0112549, entitled "Microorganism Detection Method and Apparatus," filed as an International Patent Application on Apr. 18, 2008, which is incorporated herein by reference in its entirety.

The sample S can be any sample that possibly contains the target bacteria, for example, human nasal swab, blood, urine, veterinary samples, food samples, and/or environmental samples. In some embodiments, the sample S can be a raw sample as obtained from the source that does not need any preparation, e.g., any separation or washing steps are not needed. Thus, the system 100 and the methods associated therewith are homogeneous. In some embodiments, the sample S can include a low load of target cell (e.g., nasal swab for MRSA detection). When used with such samples, the system 100 and the methods associated therewith can include a heating and/or incubation period to promote cell replication, which results in higher production of the reporter molecules 130, for example, to generate a signal that is greater than a minimum signal threshold.

In other embodiments, the sample S can have a higher load of target cell (e.g., positive bacterial blood culture). In such cases, cell replication is not needed to produce a positive signal sufficient to identify the target cell. In some such embodiments, the sample can be maintained at a specific condition e.g., maintained at a temperature of greater than or equal to approximately room temperature, 25 degrees Celsius, or 37 degrees Celsius for a predefined time period e.g., less than approximately 4 hours. In such embodiments, the temperature and time period at which the sample S is maintained are such that the quantity of reporter molecules 130 produced is sufficient to generate a measurable signal, independent of cell replication. In such embodiments, the sample can be maintained at the predefined temperature for a longer time period, e.g., 6 hours, 8 hours, up to 18 hours, or even longer.

In some embodiments, the container 120 that can contain a first reagent, for example, a bacterial nutrient or growth media (e.g., minimal essential media) and/or suitable buffer (e.g. Amies, PBS, TRIS, HEPES, etc) for maintaining the target cell in a viable state, promoting bacterial cell growth or the like. In some embodiments, an antibiotic, for example, cefoxitin can also be included in the first reagent, for example, when a viable cell assay is intended. A sample S containing the target cell can be added to the sample container 120 followed by addition of the transduction particle 110 to the sample container 120 according to any of the methods and using any of the instruments described herein. If the target cells are present, the transduction particle 110 transfers the nucleic acid sequence contained therein into the target cell such that the nucleotide contained in the transduction particle 110 is integrated with the genes of the target cell, e.g., host bacteria. In some embodiments, the container 120 is configured to fluidically isolate the sample S from a region outside the container 120. In such embodiments, the transduction particle 110 is maintained in fluidic isolation from the sample S before the transduction particle 110 is mixed therein. In some embodiments, the maintaining can include maintaining the sample S for a time period such that the quantity of the plurality of the reporter molecules 130 sufficient to produce the signal is produced independent from target cell replication. As described herein, mixing includes disposing the transduction particle 110 into the sample S while maintaining isolation between the region and the container 120.

In some embodiments, the container 120 can be configured to include any additional reagent that is formulated to react with the reporter molecules 130 to produce, catalyze and/or enhance the production of the signal. For example, the reporter molecule 130 can be luciferase and the container 120 can be configured to contain an aldehyde reagent formulated to trigger, initiate and/or catalyze a luminescence reaction that can be detected by the production of the signal. In some embodiments, the reagent can include a 6-carbon aldehyde (hexanal), a 13-carbon aldehyde (tridecanal) and/or a 14-carbon aldehyde (tetradecanal), inclusive of all the varying carbon chain length aldehydes therebetween. In some embodiments, the container 120 can be configured to maintain the additional reagent in fluidic isolation from sample S before being disposed into the sample S. In this manner the timing of the delivery of the additional reagent into the sample S can be controlled. In some embodiments, the system 100 can include a mechanism for adding the additional reagent at any suitable time and/or in any suitable manner to induce the detectable signal. For example, as described in more detail herein, in some embodiments, the system 100 and/or the container 120 can include a mechanism for conveying an additional reagent into the sample S at a predetermined velocity (or flow rate) to promote the desired level of mixing.

The instrument 140 can be any appropriate instrument to detect the reporter molecule 130 and/or a reaction catalyzed by the reporter molecule 130. For example, the instrument 140 can include optical (e.g. photomultiplier tubes, fluorometers, spectrometers, colorimetric detection on a lateral flow assay, imaging based detection, CCDs, luminescence detectors for detecting bioluminescence, colorimetric or fluorometric microarrays) and/or electrical detection means (e.g. electrochemical amperometric, potentiometric, conductometric, impedrometric, and/or any other electrochemical sensors).

In some embodiments, the system 100 and/or the methods associated therewith can be configured to be a rapid test that does not require any amplification of the target cells. Using the system 100 and the methods described herein, a relatively small time, for example, 1 hour, 2 hour, 3 hour or 4 hour, up to 18 hours can be needed for the target cell containing the nucleic acid sequence from the transduction particle 110 to produce a sufficient quantity of reporter molecules 130 that can be detected. In some embodiments, the system 100 can be configured to be a closed system after collection of sample S and/or addition of transduction particle 110. Said another way, in some embodiments, the container is maintained in fluidic isolation from the external environment after the addition of the sample S. This can, for example, reduce chances of contamination. As described above, because the system 100 can accommodate raw sample, the system 100 and the methods associated therewith do not require any washing or fluid transfer steps away from the sample S. The system 100 can therefore be easy to operate, be rapid, inexpensive, and be easily automated. In some embodiments, the system 100 can be a platform system that can be configured to operate in various regimes, for example, viable cell reporting, gene reporting, measuring bacterial resistance and/or susceptibility to antibiotics, and/or bacterial toxin detection, etc. Additional examples of components and methods associated with and/or complementary to the system 100 are described further.

Figure 2:
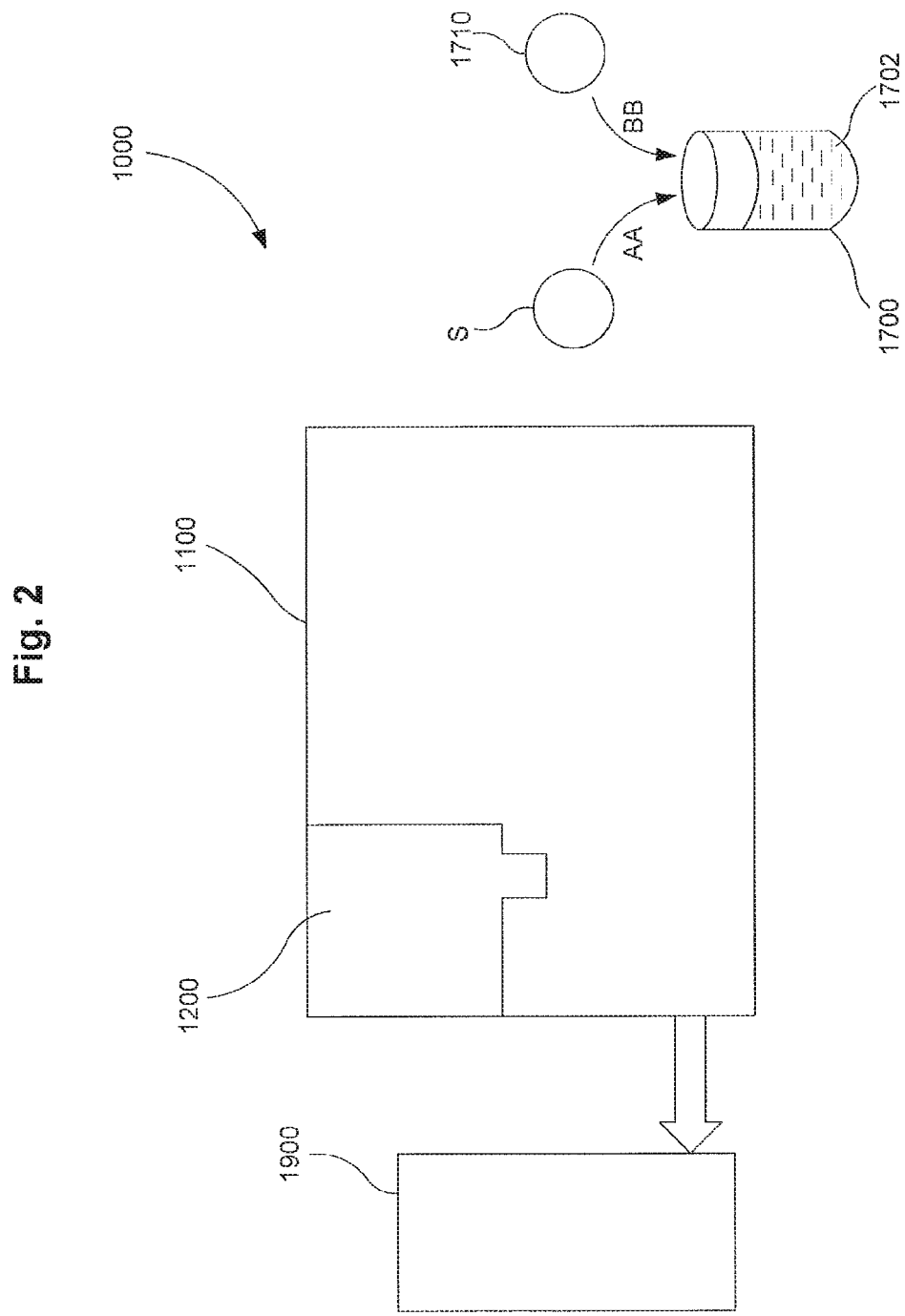
FIGS. 2 and 3 are schematic illustrations of a cartridge according to an embodiment, in a first configuration and a second configuration.
Figure 3:
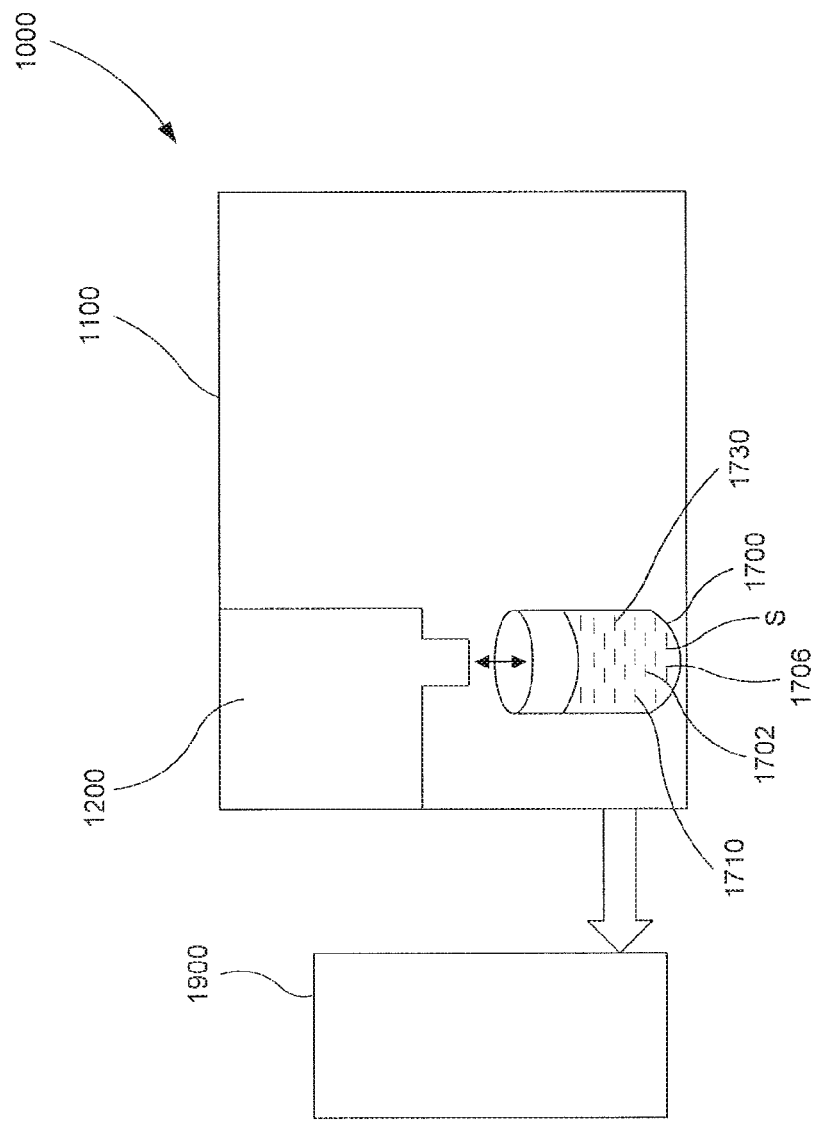

FIGS. 2 and 3 are schematic illustrations of a system 1000 according to an embodiment. The system 1000 is configured to be communicatively coupled to any suitable laboratory information system (LIS) 1900, and includes an instrument 1100 that is configured to manipulate and/or receive a container 1700. The system 1000 can be used to identify target cells in a clinical environment according to any suitable method, such as any of the methods described herein.

The container 1700 can be any suitable container that can be manipulated and/or actuated by the instrument 1100 or any other instruments described herein. The container 1700 defines an internal volume within which a sample S can be disposed as shown by arrow AA. In some embodiments, the container 1700 can include a solution 1702 disposed in the internal volume of the container 1700 for interacting with the sample S. The solution 1702 can be predisposed in the internal volume defined by the container 1700 or added after the sample S is conveyed into the container 1700. The solution 1702 can include, for example, a bacterial nutrient and/or growth media (e.g., undefined medium, defined medium, differential medium, minimal media, selective media, etc.) to enable bacteria to grow and multiply, a buffer to maintain pH (e.g., Amies, PBS, HEPES, TRIS, TAPSO, Bicine, MES, MOPS, Tricine, PIPES, SSC, succinic acid, etc.) and/or a surfactant (e.g., Tween 20, Tween 80, TritonX, X-114, CHAPS, DOC, NP-40 CTAB, SDS, etc.). In some embodiments, the solution 1702 can also include antibiotics (e.g. cefoxitin, oxacillin, cefotetan, amoxycillin, penicillin, erythromycin, azythromycin, cephalosporins, carbapenems, aminoglycosides, sulfonamides, quinolones, oxazolidinones, etc.). The inclusion of antibiotics can kill or otherwise prevent the expression and/or generation of a signal from reporter molecule from all drug-susceptible bacteria, e.g., in a bacteria cell viability and/or susceptibility assay of the types shown and described herein.

In some embodiments, the solution 1702 can be tailored to enhance growth, shorten lag phase, sustain, and/or attack a particular target cell, e.g., bacterium. In some embodiments, specific versions of the solution 1702 can be employed for specific target cells and/or samples. For example, a first preparation of the solution 1702 can be tailored for nasal swab samples containing MRSA, a second preparation of the solution 1702 can be tailored for urine samples containing *E. coli*, a third preparation of the solution 1702 can be tailored for stool samples containing *C. difficile*, and the like The container 1700 can be configured to receive a first reagent 1710 containing a transduction particle and/or an engineered viral vector as shown by the arrow BB (FIG. 2). In some embodiments, the container 1700 can further receive any other reagents in connection with the implementation of any of the methods described herein. In some embodiments, the transduction particle 1710, and/or any other reagents can be predisposed in the container 1700, such that, for the example the vector 1710 or any other reagents do not need to be separately added to the container 1700 after the sample S is placed therein. For example, in some embodiments, the transduction particle 1710 can be disposed in a cap or separate portion (not shown) of the container 1700 such that the respective solutions (e.g., the solution 1702, the sample S and the transduction particle 1710) can remain isolated from each other during shipping, initial handling or the like. The container 1700 can be further configured to convey the respective solutions into the interior volume of the container 1700 at a suitable time. For example, in some embodiments, the cap can have frangible portions that can be broken by the instrument 1100 and/or the user at a desired time. For example, the frangible portions can be broken using plungers, crushing manually, or any other suitable mechanism. In some embodiments, the container 1700 can be multi-portion container such that, for example, the container 1700 can have frangible portions, each portion containing a separated fluid. The container 1700 can be configured such that while fluids can be predisposed in the container 1700 and urged to mix at specific times, the container 1700 does not contain any fluid transfer paths, fluid transfer mechanisms (e.g., electrophoretic transfer, electrokinetic transfer, pumps, etc.), valves and/or any complex fluid transport schemes.

The container 1700 can be any suitable container for containing the sample S in a manner that permits the monitoring, identification and/or detection of a target cell, e.g., bacteria, within the sample S. In some embodiments, at least a portion of the container 1700 can be substantially transparent, for example, to allow viewing, and/or optical monitoring of the contents contained therein. The container 1700 can be any suitable size or shape, for example, cylindrical square, rectangular, elliptical, conical, etc. The container 1700 can be constructed from any suitable material, for example, glass, plastic, acrylic, etc. In some embodiments, the container 1700 can be a commercially available container, for example a centrifuge tube, an Eppendorf® tube, a glass vial, flat bottomed vial/tube, round bottomed vial/tube or any other suitable container. In some embodiments, the container 1700 can also include additional components, for example, swabs for collecting patients' samples, cap to protect container 1700 from atmosphere and/or containing assay reagents, labels for identification, bar codes, RFID tags, etc.

Sample S and any other samples described herein can be any suitable sample S that can potentially contain the target cell, e.g., bacteria. For example, the sample S can be a human sample (e.g., a nasal swab, mucosal swab, saliva sample, blood sample, urine sample, fecal sample, tissue biopsy, bone marrow and/or cerebrospinal fluid), veterinary sample, food sample, plant sample, and/or environmental sample. In some embodiments, the sample S can be a raw and substantially unprocessed sample. In such embodiments, the system 1000 (including the container 1700 and/or the instrument 1100) is configured such that no modifications to the sample are required to run the methods associated described in connection with the system 1000. In other embodiments, however, the sample S can undergo minor processing, for example, filtration, sedimentation or any other process required to produce a suitable sample. Such processing can be performed by any suitable mechanism of the instrument 1100.

The transduction particle and/or engineered viral vector 1710 and any of the transduction particles and/or vectors disclosed herein, can be any suitable transduction particle that can specifically identify and bind to a target cell, and perform the functions described herein. In some embodiments, the transduction particle 1710 can be derived from a bacteriophage. Examples of suitable transduction particles 1710 can include vectors biologically derived from, for example, T2, T4, T7, T12, R17, M13, MS2, G4, p1, enterobacteria phage P4, Phi X 174, N4, pseudomonas phage, lambda phage, and/or any other vector. In some embodiments, the transduction particle 1710 includes modified DNA from the phage from which the vector 1710 is derived. In some embodiments, the biologically derived transduction particle 1710 does not include any DNA associated with the phage from which it was derived. Said another way, the transduction particle 1710, e.g., a vector, is devoid of a wild-type DNA capable of exhibiting wild-type viral functions associated with a virus from which the transduction particle 1710 is derived. In some embodiments, the lack of any phage DNA removes the capability of the transduction particle 1710 to reproduce, replicate or propagate. Said another way, after infecting the bacteria, neither the lytic cycle nor the lysogenic cycle of the transduction particle 1710 and/or the target bacteria can cause the transduction particle 1710 to multiply or amplify. Similarly stated, in some embodiments, the transduction particle and/or engineered viral vector 1710 is non-replicative, i.e., cannot undergo lytic or lysogenic replication.

In some embodiments, the transduction particle and/or engineered viral vector 1710 can be formulated, selected and/or engineered to include and/or carry an engineered molecule, for example, recombinant DNA, RNA, nucleic acid sequence, nucleotide, plasmid, ribozyme, aptamer and/or protein. In some embodiments, the transduction particle 1710 can be configured to specifically identify and detect the presence of a viable target bacteria e.g., *Escherichia, Mycobacterium, Staphylococcus, Listeria, Clostridium, Enterococcus, Streptococcus, Helicobacter, Rickettsia, Haemophilus, Xenorhabdus, Acinetobacter, Bordetella, Pseudomonas, Aeromonas, Actinobacillus, Pasteurella, Vibrio, Legionella, Bacillus, Calothrix, Methanococcus, Stenotrophomonas, Chlamydia, Neisseria, Salmonella, Shigella, Campylobacter* and *Yersinia*. In some embodiments, the transduction particle 1710 can be configured to specifically identify a bacteria genotype including specific gene targets and other molecular targets indicative of the genotype and/or phenotype of the bacteria, e.g., methicillin resistant *Staphylococcus aureus* (MRSA), *E. coli, Salmonella, C. difficile*, vancomycin-resistant Enterococci (VRE), or any other bacteria. In one such embodiment, the plasmid can include a nucleic acid molecule that is homologous for a specific gene sequence associated with the DNA of the target bacteria. For example, the transduction particle 1710 can be engineered and/or configured to include a plasmid that incorporates nucleic acid sequences homologous to the mecA gene found in MRSA, e.g., in an assay for the detection of MRSA (as described above).

The transduction particle 1710 can be further configured to contain genes and/or a nucleic acid molecule for expressing a detectable reporter molecule 1730. The reporter molecule 1730 can be any one of a bacterial luciferase, eukaryotic luciferase, fluorescent protein, enzyme suitable for colorimetric detection, protein suitable for immunodetection, peptide suitable for immunodetection or a nucleic acid that functions as an aptamer or that exhibits enzymatic activity. In some embodiments, a reagent (or substrate, not shown in FIGS. 2 and 3) can be added to the solution 1702 to urge the reporter molecule 1730 to produce a detectable signal. For example, in some embodiments, tridecanal can be added to allow the luciferase to catalyze a luminescence reaction that can be detected. In some embodiments, two or more transduction particles 1710 specific towards two separate target cells can be used together in the same reagent, for example, to detect multiple bacteria simultaneously.

The instrument 1100 includes the detector 1200, and is configured to receive, manipulate and/or handle the container 1700 to convey, mix and/or add the sample S, the solution 1702 and/or the transduction particles 1710, and detect and/or identify a constituent within the sample S. In particular, the instrument 1100 can include any suitable systems/mechanisms (not shown in FIGS. 2 and 3) for handling/manipulating the container 1700. For example, the instrument 1100 can include receptacles, racks, vices, jaws, grippers or any other suitable mechanism for removably receiving the container 1700. In some embodiments, the instrument 1100 can include mechanisms for manipulating and/or changing the configuration of the container 1700. For example, the instrument 1100 can include plungers, conveyor belts, stepper motors (e.g. to move and position the container 1700 in X/Y/Z plane), rollers, shakers, clamps, X/Y movable tables, encoders, any other instrumentation for positioning or manipulating the container 1700 or a combination thereof. For example, the container 1700 can be disposed in a receptacle included in the instrument 1100 that can transport the container 1700 via a conveyor belt to a location in the instrument 1100 (see e.g., FIG. 3) where the detector 1200 can interface with the container 1700 and detect the signal produced by the reporter molecule 1730 that indicates the presence of target cell (e.g., bacteria). In some embodiments, the instrument 1100 can include a gripper and an actuator mechanism, configured such that the gripper prevents and/or limits movement of the container 1700 when signal is being detected by the detector 1200. In this manner, the instrument 1100 can minimize signal noise by holding and maintaining the container 1700 at a predetermined distance from the detector 1200. Moreover, such a mechanism can ensure that the position of the container 1700 is maintained when the actuator actuates the container 1700, for example, to convey fluid from one portion of the container 1700 to another.

In some embodiments, the container 1700 and/or the instrument 1100 can also include light seal mechanisms, for example, shutters, to light seal the container 1700. In this manner, the instrument can limit and/or prevent ambient light from interfering with the signal produced by the reporter 1730. Such systems can also limit and/or prevent any undesired motion of the container 1700 during signal detection. In some embodiments, the container 1700 and instrument 1100 are configured such that the entire process including loading of the container 1700, handling/manipulation of the container 1700 by the instrument 1100, and signal detection by the detector 1200 occurs in a closed process. Said another way, detection of bacteria in the container 1700 by the instrument 1100 can be performed without opening the container 1700, does not require fluid handlers or any reagents in the instrument, and does not require any sample manipulation.

Although only one container 1700 is shown in FIG. 2 and FIG. 3, in other embodiments the instrument 1100 can be configured to receive a series of containers 1700. For example, the instrument 1100 can include a container rack or magazine, within which a user can removably dispose multiple containers 1700 that can contain multiple samples S for analysis. In some embodiments, the containers 1700 can be loaded on the instrument 1100 in a batch process. In other embodiments, the containers 1700 can be delivered to the instrument 1100 in a "flow through" process. For example, the containers 1700 can be disposed on a conveyor belt that can deliver a plurality of containers 1700 sequentially to the reader of the instrument 1100. In some embodiments, the instrument 1100 can be automated and be configured for "walk away" analysis. For example, the user can load a plurality of containers 1700 for analysis, on the instrument 1100 and walk away. The instrument 1100 can automatically perform container 1700 manipulation and detection on all the containers 1700.

The detector 1200 can be any suitable detector than can detect the signal produced by the reporter molecule 1730. For example, the detector 1200 can be an optical detector such as, for example, a fluorescence detector (e.g. to detect a fluorescent reporter molecule such as GFP, etc.), a luminescence detector (e.g. to detect bioluminescence produced by a reporter molecule such as luciferase), color detector (e.g. to detect a colored precipitate produced by a reporter enzyme such as HRP), a spectrometer, and/or an image capture device. In some embodiments, the detector 1200 can further include a light source associated with the mechanism for detection. Although described as being primarily based on optical detection, in some embodiments, the detector 1200 can be an electrochemical detector. For example, the detector 1200 can include an amperometric detector, potentiometric detector, conductometric, and/or impedometric detector, configured to detect a current, voltage, or conductance, resistance/impedance change produced by the reporter molecules 1730. In some embodiments employing electrochemical detection, the detector 1200 can be configured to come in physical contact with the sample solution 1706 (FIG. 3) that contains the sample S, solution 1702, transduction particle 1710, reporter molecule 1730, and/or any other substrate that can be necessary for inducing a signal from the reporter molecule.

In some embodiments, the detector 1200 can use other detection methods, e.g., surface acoustic wave, surface plasmon resonance, Raman spectroscopy, magnetic sensors, and/or any other suitable detection method known in the art. In some embodiments, the detector 1200 can only provide a qualitative answer, for example, a YES/NO answer on the presence of target cell. In other embodiments, however, the detector 1200 can quantify the target cell, for example, determine the cfu/ml of target bacteria in the sample S according to any of the methods described herein. In some embodiments, the detector 1200 can include an end read system, e.g., to allow flexible placement of a label on the container 1700. In some embodiments, the end read system includes direct contact of a transparent end of the container 1700 with the detector, e.g., to minimize optical instruments and/or background signal interference. In some embodiments, the detector 1200 is devoid of an incident light source. Said another way, no external light is needed for signal detection from the reporter molecules 1730 produced by the target cell disposed in the container 1700.

In some embodiments, the systems 100, 1000, or any other systems described herein can be used to identify and/or detect a target cell, such as a bacteria. In particular, in some embodiments, the system 1000 can be used in conjunction with a replication-deficient transduction particle to identify and/or detect a target cell. By employing a replication-deficient transduction particle, the likelihood of a false negative (e.g., caused by cell destruction from the lytic cycle) is minimized and/or eliminated, thereby producing a result that is suitable in a clinical setting. Such methods can be used, for example, as a screening tool in hospitals. In particular, FIG. 4 is a flow chart of a method 150 according to an embodiment.

Figure 4:
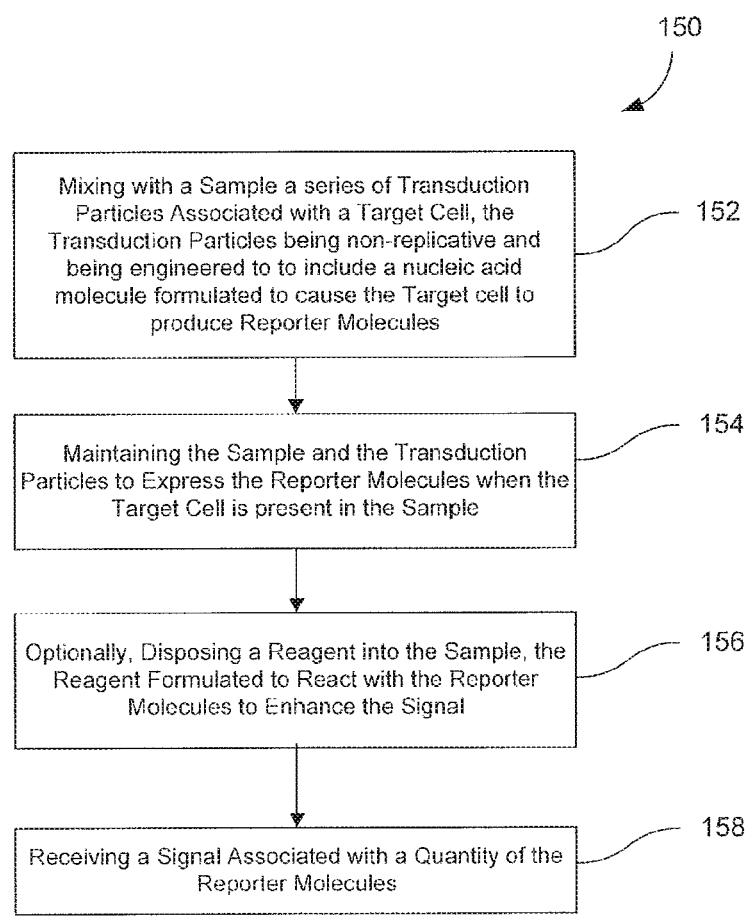
FIG. 4 illustrates a flow diagram of a method for detecting a target cell in a sample, according to an embodiment.

As shown in FIG. 4, the method 150 includes mixing with a sample a substance including transduction particles associated with a target cell, 152. Similarly stated, the transduction particles are formulated to bind to and deliver a nucleic acid molecule into the target cell. The transduction particles are engineered to include a nucleic acid molecule formulated to cause the target cell to produce a series of reporter molecules. The series of transduction particles are non-replicative. Similarly stated, the transduction particles can be formulated and/or engineered to be incapable of lysogenic or lytic replication. In this manner, the target cells will be maintained (i.e., not destroyed, killed or lysed) during the production of the reporter molecules. Thus, the method 150 reduces and/or eliminates the likelihood of a false negative, which can result when the target cells are lysed thereby preventing and/or reducing the production of the reporter molecules.

The transduction particles can be any suitable transduction particles of the types shown and described herein. For example, in some embodiments, the transduction particles can be an engineered viral vector devoid of a wild-type DNA capable of exhibiting wild-type viral functions associated with a virus from which the viral vector is derived. In some embodiments, the transduction particles can be engineered to be derived from a bacteriophage. For example, in some embodiments, the transduction particles can be developed by packaging nucleic acid into the structural components of a virus and/or bacteriophage where the packaged nucleic acid is devoid from exhibiting native viral and/or bacteriophage functions that allow for the virus and/or bacteriophage to replicate whether the replication is via a lytic or lysogenic pathway.

In one embodiment, a plasmid packaging system can be developed in which the small terminase gene containing the pac-site of a pac-type prophage is deleted and then complemented via a plasmid. When the lytic cycle of the lysogenized prophage is induced, the bacteriophage packaging system packages plasmid DNA into progeny bacteriophage structural components rather than packaging native bacteriophage DNA. The packaging system thus produces non-replicative transduction particles carrying plasmid DNA.

In another embodiment, genomic island (GI)-packaging systems can be exploited such that exogenous nucleic acid sequences are packaged by the bacteriophage. This can be accomplished by incorporating such exogenous nucleic acids sequences into the GI. Natural GI-packaging systems result in both non-replicative GI-containing transduction particles as well as native replicative phage, thus in order to eliminate the native phage from this process, the small terminase gene of the prophage is deleted. The small terminase gene sequence contains the pac-site sequence of the native phage and thus this deletion has the effect of preventing the packaging of native phage DNA. If at the same time a GI to be packaged includes its own pac-site and a small terminase gene that expresses a suitable small terminase protein, then only GI DNA will be amenable for packaging in this system. By incorporating exogenous DNA into this system, non-replicative transduction particles that incorporate GI DNA and exogenous DNA can be produced.

In some embodiments, the transduction particles can be selected, engineered and/or formulated to specifically bind to, and transfer the nucleic acid molecule contained therein into the viable cells. For example, the transduction particles can be selected, engineered and/or produced to bind to and deliver a nucleic acid molecule into any bacteria, e.g., *Escherichia, i'vlycobacterium, Staphylococcus, Li steria, Clostridium, Enterococcus, Streptococcus, Helicobacter, Rickettsia, Haemophilus, Xenorhabdus, Acinetobacter, Bordetella, Pseudomonas, Aeromonas, Actinobacillus, Pasteurella, Vibrio, Legionella, Bacillus*, Calothrix, Methanococcus, StenotrophOITIOnaS, Chlamydia, *Neisseria, Salmonella, Shigella, Campylobacter* and *Yersinia*.

The sample and the series of transduction particles are maintained such that the series of the reporter molecules is produced when the sample includes the target cell, 154. Similarly stated, the sample and the series of transduction particles are maintained to express the plurality of reporter molecules when the target cell is present in the sample. In this manner, production of the reporter molecules, and the detection thereof, indicates that the target cell is present in the sample. More particularly, the transduction particles do not produce the reporter molecules autonomously and/or do not include the reporter molecule. Instead, transduction particles are engineered, configured and/or formulated to communicate the nucleic acid molecule contained therein (i.e., an engineered plasmid) into the target cell. Upon being delivered into the target cell, reporter molecules are produced using the natural transcription and translation functions of the target cell and via the expression of a reporter gene that is operatively linked to a promoter that is included in the nucleic acid molecule. Thus, the method 150 employs a "switchable" reporter, meaning that no amount of the reporter molecules is present in the sample until the conditions (e.g., the presence of the target cell) are such that the reporter molecules are produced. Notably, because the method 150 employs a "switchable" reporter molecule, no washing and/or removal of the transduction particles and/or other constituents within the sample is necessary. The reporter molecule can be any one of a bacterial luciferase, eukaryotic luciferase, fluorescent protein, enzyme suitable for colorimetric detection, protein suitable for immunodetection, peptide suitable for immunodetection or a nucleic acid that functions as an aptamer or that exhibits enzymatic activity.

In some embodiments, the method 150 can be used as a viable cell reporter assay. When the method 150 is used as a viable cell reporter assay, in some embodiments, antibiotics (e.g., cefoxitin) can be added to and/or mixed with the sample to kill and/or eliminate all drug-susceptible target cells (e.g., in a bacteria) thereby allowing the method 150 to be used to identify particular target cell drug resistant phenotype (e.g., methicillin resistant *Staphylococcus aureus* (MRSA), Salmonellavancomycin-resistant Enterococci (VRE)) within the sample.

For example, in some embodiments, a MSSA/MRSA reporter assay can be developed in accordance with the method 150. In such embodiments, a non-replicative transduction particle (e.g., the transduction particle 110, the transduction particle 160 or the like) is developed from a *S. aureus*-specific bacteriophage and the bacterial luciferase genes luxAB under the control of a constitutive promoter are incorporated. When this transduction particle is mixed with the sample (operation 152) thus introducing the reporter system into *S. aureus*, the constitutive promoter can express luxAB suitable for reporting on the presence of a viable *S. aureus*, as discussed below with reference to operations 154 and 158. If in addition, the antibiotic cefoxitin is also added prior to or simultaneously with mixing the transduction particles with *S. aureus* cells, if the cells do not contain and express the mecA gene, no luxAB will be expressed in the assay, thus indicating that the cells are MSSA. If, however, the cells do contain and express the mecA gene, luxAB will be expressed in the assay, thus indicating that the cells are MRSA.

In other embodiments, the nucleic acid molecule can be formulated to cause the target cell to produce the series of reporter molecules only when the target cell includes a particular target gene (e.g., a drug resistant gene, a drug-susceptibility gene, a toxin, or a species specific gene). For example, in some embodiments, the method 150 can be performed in conjunction with a transduction particle and/or reporter system in which a promoter-less reporter gene is placed downstream of a nucleic acid sequence that is homologous to a target gene sequence and this reporter construct is incorporated into a non-replicative transduction particle. When the transduction particle introduces the reporter construct into a target cell, the reporter gene will not be expressed unless the target cell contains the target gene and a homologous recombination event integrates the reporter gene within the target gene loci in the target cell such that the reporter gene becomes operatively linked to the target gene promoter within target cell allowing for the expression of the reporter genes driven by the target gene promoter.

In one such embodiment, a MRSA reporter system can be developed by incorporating into a *S. aureus*-specific non-replicative transduction particle (e.g., the transduction particle 110, the transduction particle 160 or the like) a reporter construct consisting of a nucleic acid sequence that is homologous to the mecA gene upstream of promoter-less bacterial luciferase genes, luxAB. When the transduction particle introduces the reporter construct into a target *S. aureus* cell, the reporter gene will not be expressed unless the target cell contains the target mecA gene and a homologous recombination event integrates the luxAB genes within the mecA gene loci in the target cell such that the reporter gene becomes operatively linked to the mecA gene promoter within target cell allowing for the expression of luxAB driven by the mecA gene promoter.

The sample with the transduction particles mixed therein can be maintained at any suitable temperature and for any suitable time to promote production of the reporter molecules and/or growth of the target cells within the sample. For example, in some embodiments the sample and the transduction particles are maintained at a temperature of greater than or equal to room temperature, 25 degrees Celsius, or 37 degrees Celsius, and for a predefined time period of less than 2 hours, 2 hours, 3 hours, 4 hours, 6, hours, up to 18 hours or even more, inclusive of any ranges therebetween. In this manner, the maintaining of the sample at the predefined temperature for the predefined time period is sufficient to generate a quantity of the series of reporter molecules sufficient to produce a measurable signal. In some embodiments, the maintaining need only be sufficient to promote the production of the reporter molecules in the target cells initially present in the sample. Said another way, in some embodiments, the conditions under which the sample is maintained (e.g., the temperature and/or duration) prior to the detection operation need not be sufficient to promote repeatable target cell replication.

In some embodiments, the method optionally includes disposing a second substance into the sample, 156. The second substance can be formulated to react with the series of reporter molecules to catalyze, enhance the production of and/or produce a measureable signal, such as, for example, a luminescence signal, a fluorescence signal, a color-based signal, a chemical signal or electrochemical signal. For example, in some embodiments, the nucleic acid molecule can include luxA/luxB sequences such that the reporter molecule produced can be luciferase. In such embodiments, the second substance (or reagent) can be an aldehyde reagent (e.g., tridecanal). The tridecanal urges the luciferase to produce luminescence that can be measured. In some embodiments, the reagent can include a 6-carbon aldehyde (hexanal), a 13-carbon aldehyde (tridecanal) and/or a 14-carbon aldehyde (tetradecanal), inclusive of all the varying carbon chain length aldehydes therebetween. In some embodiments, the reagent formulation can also include a maintaining medium and/or buffer, e.g., TSB broth, citrate buffer, etc., a surfactant, e.g., Tween 20, and be adjusted to a predetermined pH, e.g., pH 3.

The identification of the target cell is performed by receiving a signal associated with a quantity of the series of the reporter molecules, 158. The signal can be measured using any suitable detector as described herein, (e.g., the detector 1200 of the instrument 1100 described above, the detector 11200 of the instrument 11000 described below, or the like). In some embodiments, the magnitude of the signal is independent from a quantity of transduction particles mixed with the sample. More particularly, because the transduction particles are not "tagged" with the reporter molecule (i.e., they do not include the reporter molecule), the strength of the signal is dependent not upon the initial quantity of the transduction reporters, but rather upon the production of the reporter molecules by the target cell. Thus, the signal is independent from the quantity of transduction particle (when the quantity is above some de minimus amount or lower threshold).

Any of the steps of the method 150 can be performed using any of the containers and/or instruments described herein. For example, the method 150 can be performed using the containers 1700, 2700, 3700, 4700, etc. and the instrument 1100, 11000 or the like. For example, in some embodiments, the sample can be disposed within a portion of a container that is fluidically isolated from a region outside the container. For example, the sample can be disposed or maintained in a reaction chamber (e.g., the reaction chamber 3732 or 4732 of the container assemblies 3700 and 4700, respectively) that is sealed and/or closed via a reagent module (e.g., the reagent module 3740 or 4740). In some embodiments, the transduction particles can also be maintained in fluidic isolation from the sample before the mixing, e.g., in an internal volume of the container assembly (e.g., such as the reagent module 3740 or 4740). In some embodiments, the mixing includes disposing the transduction particles into the sample while maintaining fluidic isolation between the container and an outside region. In this manner, the method can be performed in a closed system and/or a homogeneous assay. In some embodiments, the reagent can also be maintained in fluidic isolation from the sample before disposing, e.g., stored in an internal volume of the container. In some embodiments, the reagent can also be disposed into the sample while maintaining fluidic isolation between the container and the outside region.

Figure 5:
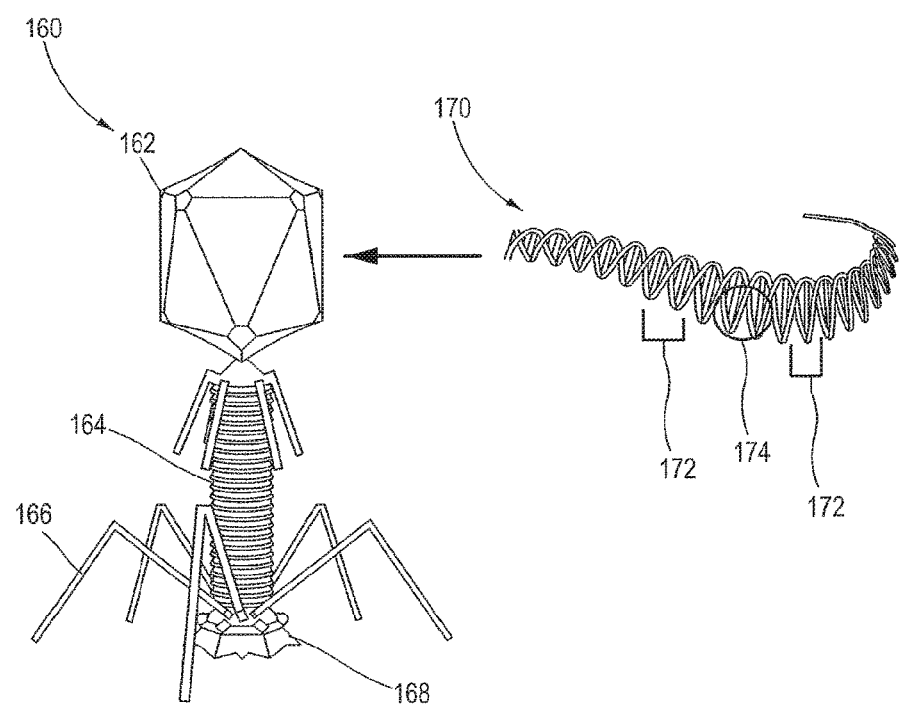
FIG. 5 is a schematic illustration of a transduction particle and an engineered nucleic acid molecule contained therein, according to an embodiment.

In some embodiments, the system 1000 and/or the method 150 (or any other systems and methods described herein) can be used to identify and/or detect a drug resistant strain of bacteria. In some embodiments, a method according to an embodiment can use bacterial viability as the method of identification, using viral vectors and/or transduction particles associated with a particular target bacteria. More particularly, in some embodiments, the transduction particles can be a biologically derived viral vector engineered, selected and/or formulated to perform a detection function. For example, as shown in FIG. 5, in some embodiments, a transduction particle 160 can be derived from a bacteriophage in accordance with any of the methods and descriptions herein. Similarly stated, the transduction particle 160 can include the structural proteins and/or envelope from a bacteriophage. In particular, the transduction particle 160 can be engineered to include a capsid 162 of a phage engineered to retain the capability to bind to the target bacteria (e.g., via the sheath 164, tail fibers 166 and/or base plate 168. In this manner, the transduction particle 160 can selectively identify, bind to and deliver a nucleic acid molecule 170 into a desired target bacteria.

As shown in FIG. 5, the transduction particle 160 contains a nucleic acid molecule 170 formulated to cause the target cell to produce a plurality of reporter molecules. In some embodiments, the transduction particle 160 and/or the nucleic acid molecule 170 are substantially devoid of the native DNA of the phage from which the transduction particle 160 is derived. Similarly stated, the DNA of the phage from which the transduction particle 160 is replaced by the engineered plasmid or nucleic acid molecule 170.

Said another way, the transduction particle 160 is substantially devoid of a wild-type DNA capable of exhibiting wild-type viral functions, such as replication functions, associated with a phage from which the transduction particle 160 is derived. Thus, in such embodiments, the transduction particle 160 is "replication-deficient" or incapable of reproducing or replicating by any means (e.g., by lysogenic and/or lytic replication).

As shown in FIG. 5, the engineered nucleic acid molecule 170 in the transduction particle 160 contains a reporter sequence 174 that provides instructions for the target bacteria to express a reporter molecule. For example, the reporter sequence 174 can include promoter less sequences luxA/luxB for expressing luciferase, which cannot be expressed by the transduction particle 160 autonomously. Rather after the luxA/luxB sequences are inserted into the target bacteria by the transduction particle 160 and are operatively coupled with the target bacteria DNA, the natural transcription machinery of the target bacteria is used to express the reporter molecule, i.e., luciferase. In other embodiments, the reporter sequence 174 can also include a promoter included with the luxA/luxB sequences. In such embodiments, after the promoter coupled luxA/luxB sequences are inserted into the target bacteria by the transduction particle 160, the promoter coupled luxA/luxB sequences can express luciferase without coupling with the target bacteria DNA.

As described herein, in some embodiments, the transduction particle 160 can be engineered for reporting on the presence of viable bacteria. In such embodiments, the transduction particle 160 is engineered to identify and/or recognize a target bacteria, attach thereto and communicate the engineered nucleic acid 170 into the target bacteria. Upon being conveyed into the target bacteria, the engineered nucleic acid 170 can produce reporter molecules due to the incorporation of a promoter operatively linked to the reporter genes (e.g., the reporter sequence luxA/luxB as described before herein) within the engineered nucleic acid. The engineered nucleic acid 170 then causes the target bacteria to produce the reporter molecules using the natural transcription and translation systems of the target bacteria. In such viable cell reporter embodiments, further specificity can be achieved by eliminating all other phenotypes. For example, in some embodiments, MRSA can be identified in a cell viability assay by killing or otherwise suppressing signal generation from all non-drug resistant phenotypes within the sample by using antibiotics.

Figure 6A:
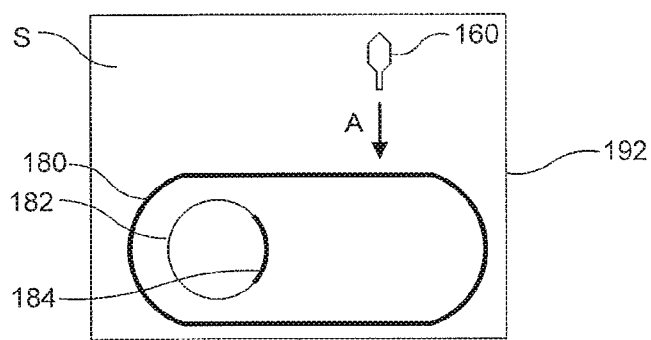
FIGS. 6A, 6B, and 6C show schematic illustrations of a method for identification of a target cell, according to an embodiment.
Figure 6B:
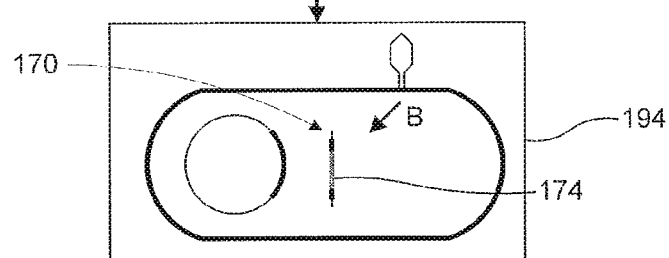
Figure 6C:
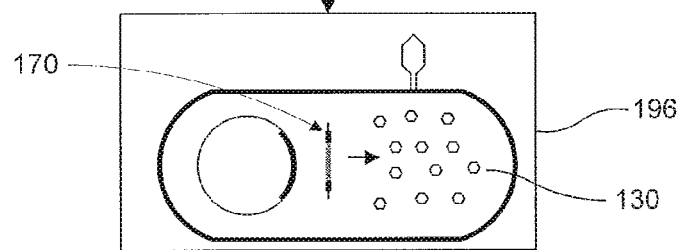

As shown schematically in FIGS. 6A, 6B, and 6C, the transduction particle 160 can be used to detect target bacteria 180 in any sample S. In the first operation (indicated by the schematic illustration 192), the transduction particle 160 is brought into contact and/or mixed with the sample S containing the target bacteria 180. The transduction particle 160 can be mixed with and/or introduced into the sample S using any suitable methods or mechanisms as described herein. The transduction particle 160 is selected, formulated and/or engineered to specifically identify and bind to the cell wall of the target bacteria 180, as shown by arrow A. At operation 194, the transduction particle 160 communicates the engineered nucleic acid 170 contained therein, into the target bacteria 180 cytoplasm, as shown by arrow B. In some embodiments, when viable cell reporting is performed, the engineered nucleic acid 170 can include the reporter sequence 174 (e.g., luxA/luxB) coupled to a promoter and configured to cause the production of reporter molecules in the target cell 180, as shown in operation 196.

The presence of reporter molecules 130 indicates that the target bacteria 180 are present in the sample S. Accordingly, the reporter molecules 130 are "switchable" (i.e., only present under certain conditions). Moreover, because in some embodiments the transduction particle 160 is non-replicative (i.e., incapable of lytic or lysogenic replication), the target bacteria 180 remain alive or otherwise un-inhibited during the assay. Therefore, the systems and methods described herein can be used to detect live bacteria. Furthermore, while not shown in FIG. 6A, 6B, or 6C, an antibiotic (e.g., cefoxitin) can be added to the sample S, for example, before adding the transduction particle 160. The antibiotic can eliminate or otherwise inhibit all non-antibiotic resistant bacteria (e.g., MSSA) such that only the antibiotic resistant strains (e.g., MRSA) remain viable in the sample S. In this way, only the antibiotic resistant bacteria, for example, target bacteria 180 are able to produce a detectable signal.

Figure 7A:
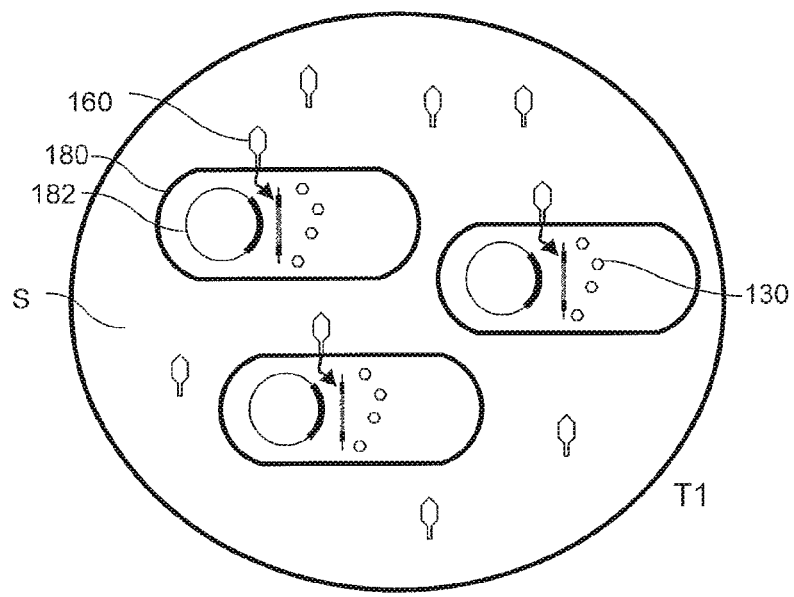
FIGS. 7A and 7B show a schematic illustration of transduction particles interacting with target cells at a first time (FIG. 7A) and a second time (FIG. 7B), according to an embodiment.
Figure 7B:
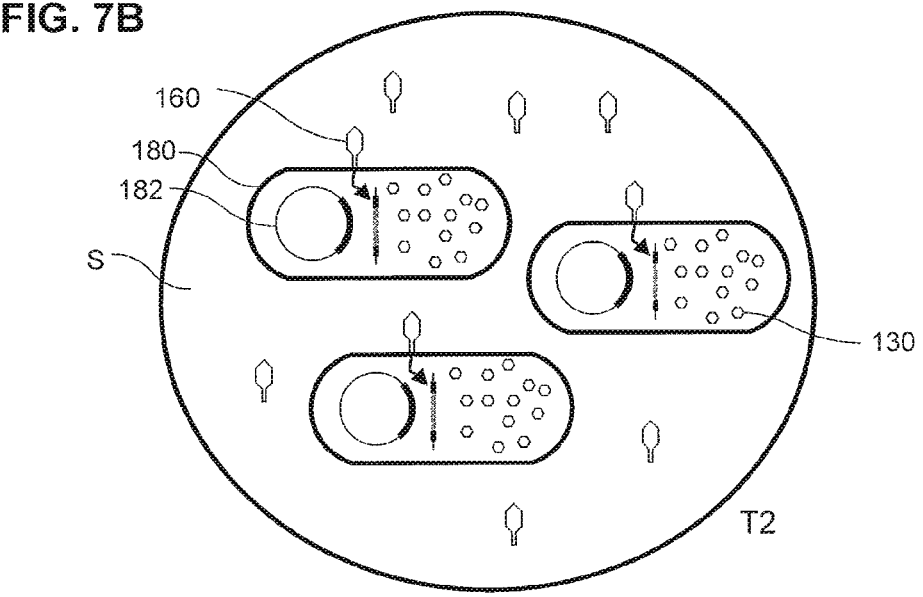

In some embodiments, the signal produced by the reporter molecules 130 is independent of the quantity of the transduction particles 160 mixed with the sample (when the quantity is above some de minimus value or predetermined quantity). This is illustrated by FIGS. 7A and 7B. FIG. 7A shows a schematic of the sample S containing the target bacteria 180, and that has been mixed with a series of transduction particles 160. A portion of the transduction particles 160 are bound to the target bacteria cells 180 in the sample S, such that the engineered nucleic acid 170 is conveyed into the target bacteria cells 180, as described above. The engineered nucleic acid 170 can then mediate the production of reporter molecules (e.g., either via the viable cell reporter methods or the gene reporter methods). After a first time period T1, a first quantity of reporter molecules 130 is produced by the target bacteria 180. As shown in FIG. 7B, after a second time period T2 greater than the first time period, the number of reporter molecules 130 increases to a second quantity, greater than the first quantity. Because the reporter molecules 130 are not tagged by and/or contained within the transduction particles 160, the amount of reporter molecules is substantially independent of the amount of transduction particles 160 initially mixed with the sample S. Moreover, as shown in FIG. 7B, the transduction particles 160 are non-replicative, and there is no increase in the quantity of transduction particles 160 between the first time period T1 and the second time period T2. Because the transduction particles 160 are incapable of lytic replication, there is no decrease in the quantity of target bacteria.

FIG. 8 is a flow chart of a method 200 of identifying viable bacteria in biological samples, according to an embodiment. The method 200 can be performed using any of the containers described herein (e.g., container 1700, 2700, 3700, 4700 or the like), and any of the instruments (e.g., instrument 1100, 11000) and/or any components shown and described herein. The method 200 can also be performed using any of the transduction particles and/or viral vectors described herein, such as, for example, the transduction particle 160. More particularly, the operations of the method 200 described below can be performed in a container, without exposing the samples, and/or reagents to outside conditions. For purposes of the description, the method 200 is described as being performed with the container 1700 and instrument 1100, shown and described above with reference to FIGS. 2-3.

The method 200 includes communicating a collected sample that can contain target bacteria, for example, a patient nasal swab, to a container, 202. In some embodiments, this operation can be optional. For example, in some embodiments, the container can be received by a user with the sample predisposed therein. The container can be any suitable container, such as, for example, the container 1700 or any other container described herein. The container can have a solution disposed in an interior region of the container. The solution can include, for example, a bacterial nutrient media, buffers, surfactants or any other component to facilitate growth of the target bacteria, production of reporter molecules within the target bacteria, detection of bacteria or the like. In some embodiments, the solution can be added after the sample is conveyed into the container. In some embodiments, the solution can be predisposed in the container, isolated from the sample, e.g., in a separate compartment in the container or the cap of the container such that it can be communicated to the sample on demand and/or in a closed-system environment.

The container is then sealed, 204, for example, with a cap, reagent module or the like. In some embodiments, the seal can be formed by a reagent module (see e.g., the reagent modules 3740 and 4740 described below), that can include compartments, frangible portions, reagents, actuators, and/or nozzles. In some embodiments, an antibiotic or a series of antibiotics is optionally added to the sample disposed in the container, 206. The antibiotics can be selected and/or formulated to kill other non-targeted bacterial strains, for example, non-drug resistant strains, so that only the drug resistant strain survives. In this manner, the reporter molecules produced are necessarily produced by the remaining, targeted bacterial strains. In some embodiments, the antibiotic/series of antibiotics can be predisposed in the container (for example, in the solution). In other embodiments, the antibiotic/series of antibiotics can be disposed in a separate compartment (e.g., in the body or cap of the container assembly), and can be communicated into the sample solution on demand or at a predetermined time.

A first reagent or substance containing the transduction particles, is communicated into and/or mixed with the sample, 208. The transduction particles can be any of the transduction particles described herein, such as, for example the transduction particle 160. In particular, the transduction particles include a nucleic acid molecule that contains a reporter sequence that provides instructions for the target bacteria to express a reporter molecule. In some embodiments, the transduction particles need not be added to the solution, but rather are predisposed in the solution. In such embodiments, the transduction particles are mixed with the sample to enable identification of the target bacterium by the transduction particles. In some embodiments, for example, the transduction particles are disposed in a separate compartment of the cap of the container, and are released and/or mixed with the sample on demand or at a predetermined time.

In some embodiments, the container solution can optionally be agitated, 210 to efficiently mix the transduction particles and the solution to facilitate interaction. Methods of mixing can include vortexing, manual shaking, stirring or the like, automated agitation (e.g., via a shaker table), or any other suitable agitation method. The container is then placed in the instrument or a portion of an instrument, 212, and maintained for a predefined time and/or at a predetermined temperature, 214. Such conditions can include, for example maintaining the sample for less than 2 hours, approximately 2 hours, 4 hours, 6 hours, 8 hours, up to18 hours, or even more, at temperature, e.g., less than or equal to approximately 37 degrees Celsius. The conditions under which the sample is maintained are defined to allow the transduction particle to bind to the target bacteria and communicate engineered nucleic acid to the target bacteria, and to promote the expression of the reporter molecules (e.g., luciferase). In the viable cell reporter embodiment, the engineered nucleic acid can be introduced to all of the target bacteria irrespective of, for example, the presence of a gene imparting drug resistance in the bacteria. Further specificity can be achieved, for example, by eliminating all other phenotypes imparted by particular genotypes, e.g., by adding anti-biotic to the sample as described above with reference to operation 206, and thereby eliminating or otherwise preventing the generation of a signal from cells lacking a drug resistance gene and/or expressed drug resistant genotype.

In some embodiments, a reagent is then communicated into the sample to enhance, catalyze and/or promote the production of a signal from the reporter molecules, 216. For example, the reagent can be a substrate formulated to catalyze the production of a light signal by the reporter molecules. Such substrates can include an active ingredient, for example, tridecanal that can interact with the reporter molecule to produce a detectable signal, for example, luminescence. In some embodiments, the substrate can include a 6-carbon aldehyde (hexanal), a 13-carbon aldehyde (tridecanal) and/or a 14-carbon aldehyde (tetradecanal), inclusive of all the varying carbon chain length aldehydes therebetween. In some embodiments, the reagent can be formulated to include Tween 20 or other surfactants, tridecanal or other aldehydes, and adjusted to a particular pH. In some embodiments, the substrate can be stored in the container, for example, in an isolated compartment in the container cap, and can be delivered to the sample on demand or at predetermined time.

The signal is detected, 218, using any suitable the detector. The detector can be, for example, the detector 1200 disposed in the instrument 1100 or the detector (PMT) 11200 shown and described below. If a measurable signal is detected, then the target bacteria are present in the sample, 220. If no signal is detected, then the sample is free of target bacteria, 222.

Although, the method 200 shown and described above can be used for detection of viable bacteria and identification (e.g., by optionally including antibiotics to eliminate non-targeted strains), in other embodiments, methods can include transduction particles and/or engineered viral vectors that can selectively identify and/or recognize a bacteria by genotype. Said another way, the transduction particles can conditionally produce reporter molecules only after recognizing and/or identifying a gene sequence within the target bacteria, as described below.

The transduction particle can be engineered to encapsulate and deliver an engineered nucleic acid molecule, such as the nucleic acid molecule 170, into the target bacteria. In some embodiments, the nucleic acid molecule is engineered and/or formulated to include a nucleic acid sequence that is homologous to a target gene, a reporter gene, and any other suitable regulatory genes. The recognition gene can be, for example, homologous to a portion of the target bacteria gene and configured to probe for and recognize the portion of the bacterial gene, and operably couple itself to the bacterial gene and result in the integration of the reporter gene within the target gene locus, e.g., using homologous recombination. In some embodiments, the reporter gene can be a promoter-less gene and thus is only expressed if it becomes operatively linked to a target gene promoter after insertion of the reporter gene into a target gene locus.

Figure 9:
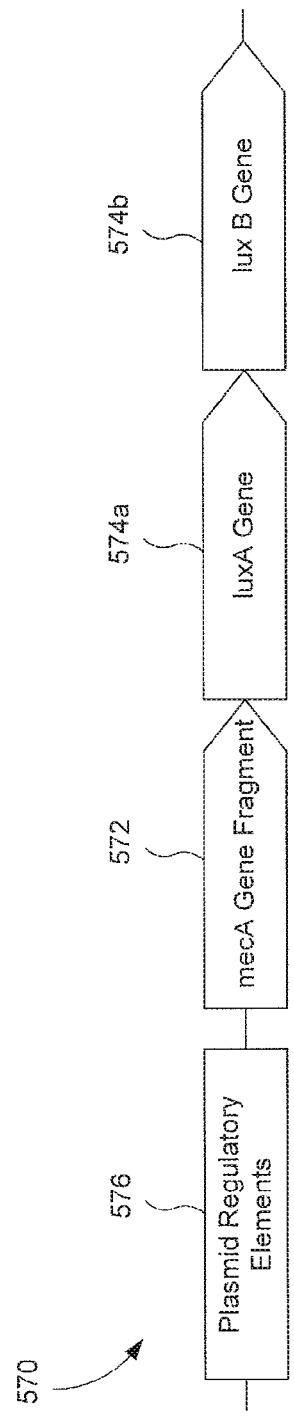
FIG. 9 is a schematic illustration of a formulation of an engineered nucleic acid, according to an embodiment.

In some embodiments, an engineered nucleic acid molecule can be formulated and/or configured to conditionally recombine in the presence of a target gene present in and/or specific to particular drug-resistant bacteria genotype. For example, FIG. 9 is a schematic illustration of formulation of an engineered nucleic acid molecule 570 and/or plasmid specific for MRSA, according to an embodiment. The engineered nucleic acid sequence 500 includes plasmid regulatory elements 576 (e.g. an origin of replication, etc.), a mecA gene fragment 572, a luxA gene 574a, a luxB gene 574b, and a selectable marker (e.g. tetracycline resistance gene, etc.) (not shown). The plasmid regulatory elements 576 can be any plasmid regulatory element as known in the arts. The mecA gene fragment 572 is homologous to a segment of the mecA gene. Once inside the bacteria, the mecA gene fragment 572 can probe for and/or identify the mecA sequence on the MRSA gene, and mediate the integration of the reporter genes into the mecA gene locus via homologous recombination in a manner that operatively links the mecA gene promoter to the luxAB genes. In some embodiments, the engineered nucleic acid 500 can include any other recognition sequence, e.g., tcdB, vanA, etc., specific for any gene sequence on any other bacteria, for example, E. coli, Salmonella, C. difficile, VRE, etc. The luxA 574a and luxB 574b genes, together serve as the reporter gene that can be controlled by the natural bacteria transcription and translation cycle to express the reporter molecule luciferase. In some embodiments, any other reporter gene can be used, for example, a gene for expressing an enzyme (e.g., glucose oxidase, horseradish peroxidase) or a fluorescent protein (e.g., green fluorescent protein, etc.).

Figure 10:
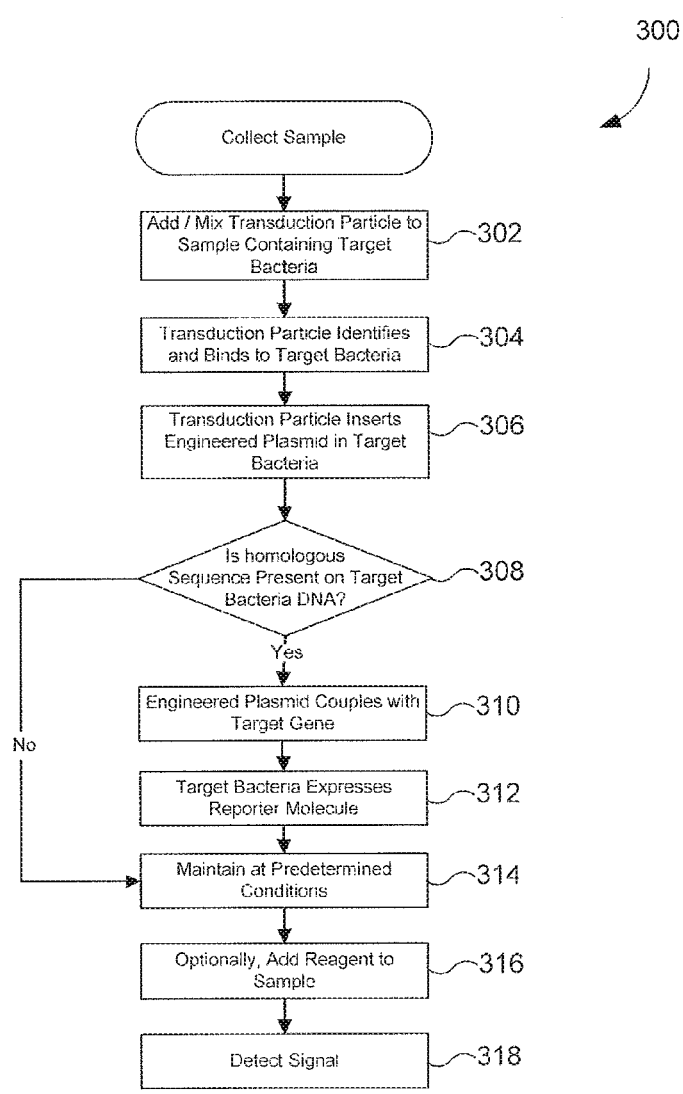
FIG. 10 illustrates a flow diagram of a method for genotypic identification of a target cell, according to an embodiment.

FIG. 10 is a flow chart of a method 300 for genotypic identification of bacteria using a transduction particle and/or engineered viral vector, e.g., transduction particle 160 that contains an engineered nucleic acid molecule (e.g., the nucleic acid molecule 570). The method 300 can be performed using any of the containers described herein, for example, container 1700, 2700, 3700, 4700 and the like, and any instruments and components thereof described as herein, such as, for example instruments 1100 and 11000.

The method 300 includes adding a transduction particle to a sample, e.g. a patient nasal swab that can contain target bacteria genotype, 302. The sample can be disposed in a container, such as, for example, container 1700, and can further include solutions such as, for example, bacterial nutrient media, buffers, and/or surfactants. In some embodiments, the transduction particle can be included in the solution and disposed in the container prior to adding the sample. The transduction particles and the solution are maintained under conditions such that the transduction particles identify and bind to the target bacteria present in the sample, 304. The transduction particle then inserts the engineered plasmid or engineered nucleic acid molecule into the target bacteria, 306.

The recognition gene portion of the engineered nucleic acid molecule, for example, a mecA gene fragment, as described herein, then probes the bacteria DNA for a homologous sequence, 308. If the homologous sequence is present, the engineered nucleic acid molecule inserts into and operatively couples the reporter gene sequences with an endogenous promoter of the target gene 310. In this manner, the target bacteria express reporter molecules, for example luciferase, through its natural transcription/translation process, 312.

The sample is then maintained for a predefined time and/or at a predetermined temperature, 314. Such conditions can include, for example maintaining the sample for less than 2 hours, approximately 2 hours, 4 hours, 6 hours, 8 hours, up to 18 hours, or even more, at temperature, e.g., less than or equal to approximately 37 degrees Celsius. The conditions under which the sample is maintained are defined to allow the transduction particle to bind to the target bacteria and communicate engineered nucleic acid to the target bacteria, and to promote the expression of the reporter molecules (e.g., luciferase).

In some embodiments, a reagent is then communicated into the sample to enhance, catalyze and/or promote the production of a signal from the reporter molecules, 316. For example, the reagent can be a substrate formulated to trigger the production of a light signal by the reporter molecules. Such substrates can be any suitable substrates of the types shown and described herein. The signal is detected, 318, with any suitable instrument. If the sample contained any other bacteria genotype, the gene sequence homologous to the recognition gene would not be present in the bacteria DNA. Accordingly, there would be no homologous recombination of transduction particle DNA with bacteria DNA and the reporter molecule would not be produced. Therefore, adding substrate to the sample solution 316 would not produce any detectable signal indicating that the sample does not contain the target bacteria genotype.

Figure 11A:
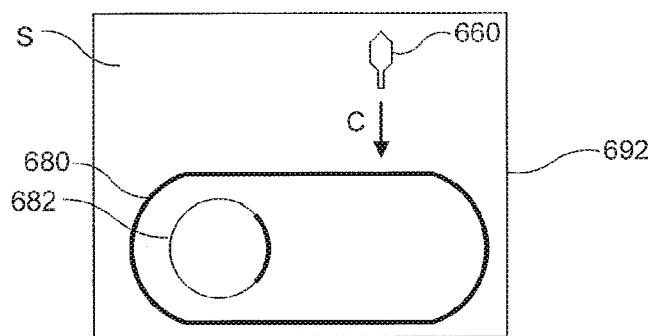
FIGS. 11A, 11B, 11C, and 11D show schematic illustrations of genotypic method for identification of a target cell, according to an embodiment.
Figure 11B:
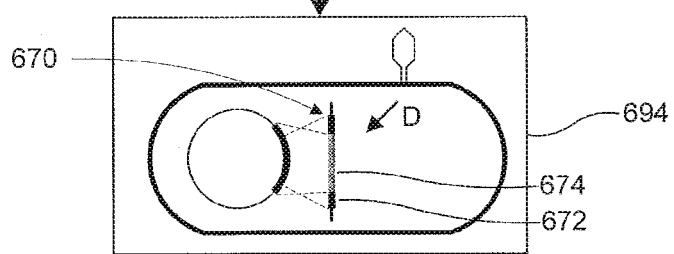
Figure 11C:
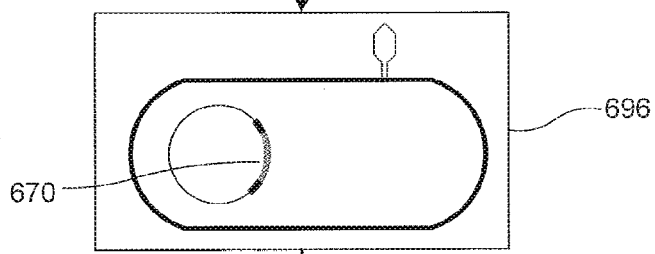
Figure 11D:
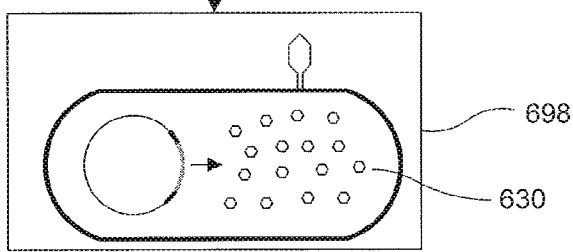

FIGS. 11A, 11B, 11C, and 11D show a schematic illustration of portions of the method 300 for genotypic identification and detection of a target bacteria. As shown in FIG. 11A, a transduction particle 660 added to and/or mixed with a sample S to detect a particular genotype of a target bacteria 680 that may be present in the sample S. In the first operation (indicated by the schematic illustration 692), the transduction particle 660 is brought into contact with the sample S containing the target bacteria 680. The transduction particle 660 can specifically identify and bind to the target bacteria 680 cell wall as shown by arrow C. The transduction particle 660 then communicates an engineered nucleic acid or plasmid 670 contained therein, into the target bacteria 680 cytoplasm, as shown by arrow D (see operation 694).

The engineered nucleic acid 670 can be any of the engineered nucleic acid molecules described herein, such as, for example, the nucleic acid molecule 570. In particular, the engineered nucleic acid molecule 670 includes a recognition sequence 672, engineered and/or formulated to recognize a target gene 684 in the DNA 682 of the target bacteria 680. The engineered nucleic acid also includes a reporter gene sequence 674 (e.g., the reporter sequence luxA/luxB). If the target bacteria 680 contains the target gene 684, the engineered nucleic acid 670 will recognize the target gene 684 and inserts the reporter gene sequence 674 into the target gene loci in a manner that operatively links the reporter gene sequences 674 with a target gene 682 promoter (see operation 696). For example, the engineered nucleic acid 670 can include a recognition sequence 672 specific for the mecA sequence on MRSA DNA. In the final operation (see schematic 698), the transcription and translation machinery of the target bacteria 680 read the genes encoding the reporter sequence 674 and produce the reporter molecules 630. If the target gene 684 is not present, recombination does not take place and the reporter molecules 630 are not expressed. Therefore, presence of the reporter molecules 630 indicates that the target gene is present in the viable bacteria 680 in the sample S. Since the transduction particle 660 is non-replicative and is incapable of lytic or lysogenic replication, the target bacteria 680 remain alive during the assay. Therefore, the systems and methods described herein can be used to detect genes within live bacteria.

Figure 12:
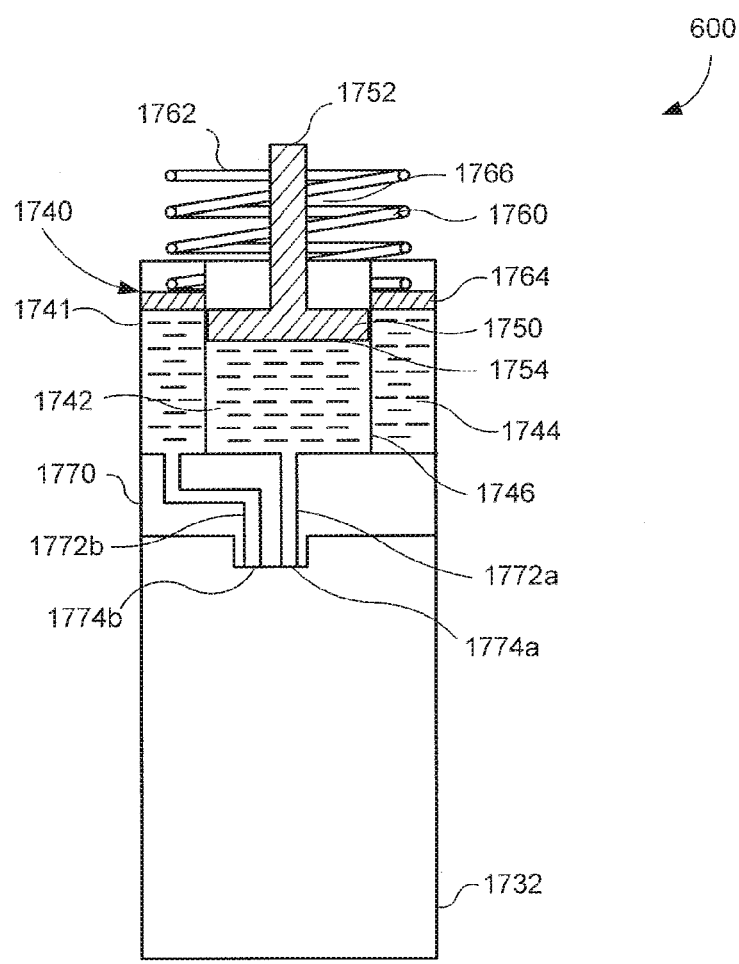
FIGS. 12-14 are schematic cross sectional views of a sample container according to an embodiment, in a first configuration, a second configuration and a third configuration, respectively.
Figure 13:
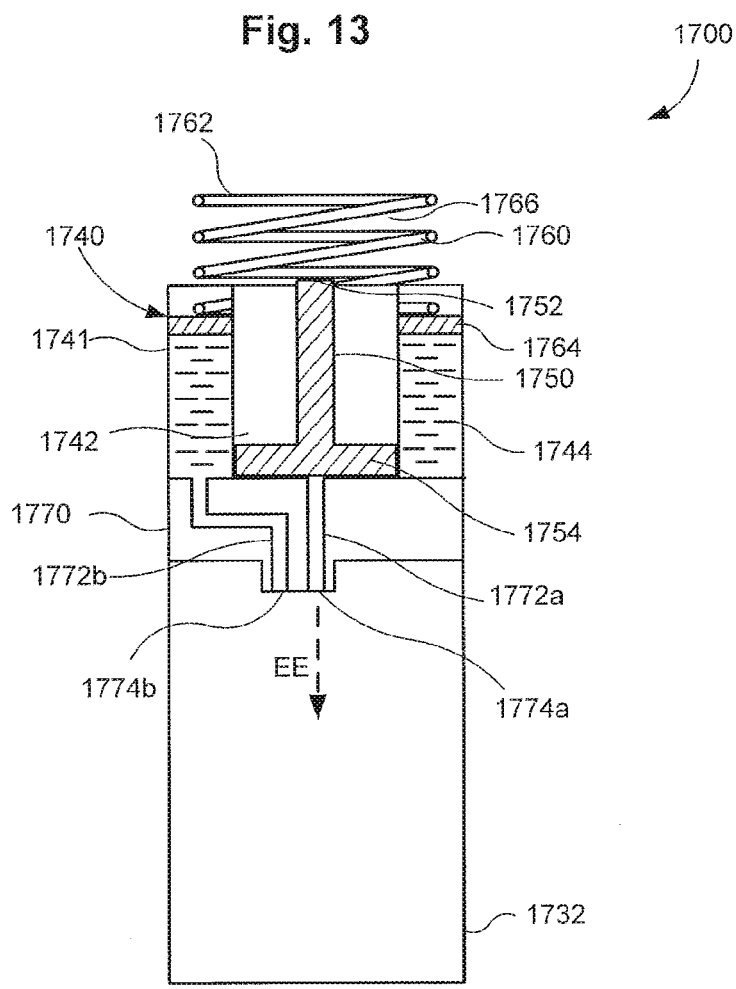
Figure 14:
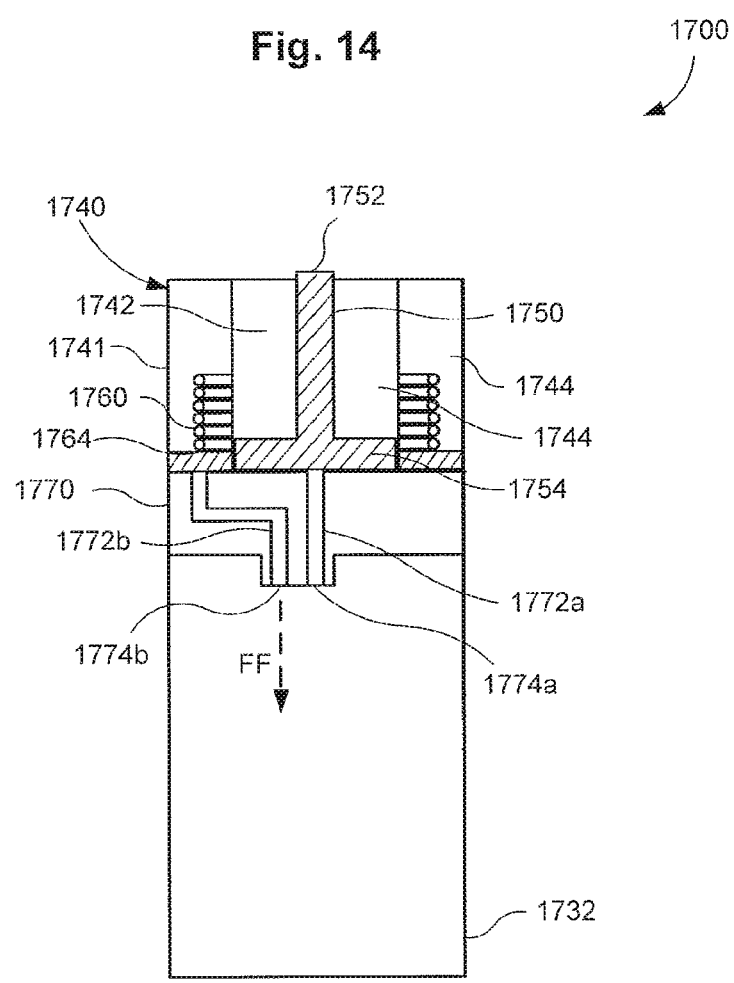

In some embodiments, a system 1000 and/or any of the methods disclosed herein can include and/or be performed with a container configured to facilitate communication of a solution (e.g., nutrient media, buffers, surfactants), transduction particles, biologic vectors such as engineered viral vector, abiologic vectors consisting of polymers, liposomes or virus-like particles, and/or reagent (e.g., substrate, antibiotics, etc.) into the sample. For example, FIGS. 12-14 show a container assembly 1700 according to an embodiment, in a first configuration, a second configuration and a third configuration, respectively. One or more container assemblies 1700 can be disposed within any suitable instrument of the type disclosed herein (see e.g., instrument 11000 described below) configured to manipulate, actuate and/or interact with the container assembly 1700 to perform the methods associated with the identification of the target cell described herein. The container assembly 1700 allows for efficient and accurate diagnostic testing of samples by limiting the amount of sample handling during assay. Moreover, modular arrangement of the container components (e.g., the reaction chamber 1732 and the reagent module 1740) allows any number of different reagent modules 1740, each containing different reagents and/or formulations to be interchangeably used to detect a different type of target cell. This arrangement also allows the transduction particles and the reagents to be stored separately and communicated to the sample on demand, as described below. Separate storage can be useful, for example, if the reagents included within the reagent module 1740 have different storage requirements (e.g., expiration dates, lyophilization requirements, storage temperature limits, etc.) than the reagents, solution and/or sample included within the reaction chamber 1732.

As shown, the container assembly includes a reaction chamber 1732 and a reagent module 1740. The reaction chamber 1732 can be coupled to the reagent module 1740 to form an integrated assembly. The reaction chamber 1732 can be formed from any suitable material, such as, for example, light weight, rigid and inert materials (e.g., plastics). At least a portion of the reaction chamber 1732 can be at least partially transparent to allow viewing and/or detection of the internal volume of the reaction chamber 1732 (for example, to view luminescence in the reaction chamber 1732). In some embodiments, the reaction chamber 1732 can be shaped as a cylinder with a rounded bottom, or flat base. In other embodiments, the reaction chamber 1732 can have any other suitable shape, e.g., square, rectangular, oval, polygonal, etc. In some embodiments, the reaction chamber 1732 can have a diameter of 12 mm and a height of 75 mm. In some embodiments, the diameter of the reaction chamber 1732 can be sized to optimally match the cross-section of a detector (e.g., detector 1200, or 11212 included in the instrument 11000, or any other detector). In some embodiments, the container assembly 1700 can be provided with one or more solutions and/or reagents of the types shown and described herein (e.g., bacterial nutrient solution, buffers, surfactants, transduction particles, and/or antibiotics), predisposed within the reaction chamber 1732.

The reagent module 1740 of the container 1700 includes a housing 1741, a first actuator 1750 and a second actuator 1760. The housing 1741 is configured to be removably coupled to the reaction chamber 1732 by any suitable mechanism. For example, in some embodiments, the housing 1741 can be coupled to the reaction chamber 1732 by a threaded coupling, an interference fit, snap-fit, or the like. In some embodiments, the housing 1741 and the reaction chamber 1732 define a substantially fluid tight seal.

The housing 1741 defines a first reagent volume 1742 and a second reagent volume 1744. The first reagent volume 1742 and the second reagent volume 1744 can be separated by a sidewall 1746. In some embodiments, the first reagent volume 1742 contains biologic or abiologic vectors, transduction particles and/or a viral vector (e.g., transduction particle 110, 160 or any of the other transduction particles described herein), that includes an engineered nucleic acid molecule (e.g., engineered nucleic acid 170) formulated to cause the target cell (e.g., bacteria) to produce a series of reporter molecules (e.g., luciferase). In some embodiments the transduction particle is formulated to be non-replicative (i.e., incapable of replication), as described herein. In some embodiments, the second reagent volume 1744 can contain a reagent formulated to interact with the reporter molecule to catalyze, enhance the production of and/or produce a measurable signal, such as, for example an optical signal. In some embodiments, the reagent is a luciferase substrate of the types shown and described herein, such as, for example, a composition including tridecanal. Although the transduction particles and the reagent are shown as being disposed directly within the first reagent volume 1742 and the second reagent volume 1744, respectively, in other embodiments, the transduction particles and/or reagents can be disposed inside reagent containers (not shown) shaped and sized to be disposed substantially inside the first reagent volume 1742 and/or the second reagent volume 1744.

In some embodiments, the housing 1741 and/or any reagent containers therein (not shown) can include frangible portions configured to rupture when actuated or compressed (e.g., by the first actuator 1750 and/or the second actuator 1760). In this manner, the reagents and constituents can be stored in isolation and released upon actuation. In some embodiments, the housing 1741, first actuator 1750, second actuator 1760 and/or such reagent containers can include features to facilitate repeatable delivery, e.g., curved edges, flat bottom, bellowed walls, or any other suitable feature. In some embodiments, for example, the housing 1741 can include a puncturer or a series of puncturers (not shown) disposed within the first reagent volume 1742, configured to puncture a portion of a reagent container when the plunger portion 1754 of the first actuator 1750 is moved within the first reagent volume 1742. In some embodiments, a puncturer can also be disposed within the second reagent volume 1744.

The first reagent volume 1742 and the second reagent volume 1744 can have any suitable shape, orientation and/or size. In some embodiments, as shown in FIGS. 12-14, the first reagent volume 1742 and the second reagent volume 1744 can be concentric. In other embodiments, the first reagent volume 1742 and the second reagent volume 1744 can be located parallel to each other. Although shown as having a substantially constant cross-sectional area, in some embodiments, a cross-sectional dimension, e.g., diameter or area, of the housing 1741 and/or the first reagent volume 1742 and the second reagent volume 1744 can be varied to increase/decrease a volume of the reagent contained therein. In this manner, the housing 1741 can be configured to provide the desired quantity and/or a flow rate of reagent to be delivered into the reaction chamber 1732.

The housing 1741 includes a delivery portion 1770 that, when the housing 1741 is coupled to the reaction chamber 1732, defines a first fluidic pathway 1772*a* between the first reagent volume 1742 and the reaction chamber 1732, and a second fluidic pathway 1772*b* between the second reagent volume 1744 and the reaction chamber 1732. As shown, the first fluidic pathway 1772*a* and the second fluidic pathway 1772*b* are separate from each other. The first fluidic pathway 1772*a* and the second fluidic pathway 1772*b* include a first outlet 1774*a* and a second outlet 1774*b*, respectively, that each open into the reaction chamber 1732. The first fluidic pathway 1772*a* and the second fluidic pathway 1772*b* provide a pathway for the transduction particles and reagents disposed in the first reagent volume 1742 and/or the second reagent volume 1744, respectively, to be communicated into the reaction chamber 1732.

The delivery portion 1770 can be configured to provide any suitable pathway and/or mechanism for delivering the transduction particles and reagents disposed in the first reagent volume 1742 and/or the second reagent volume 1744 into the reaction chamber 1732. For example, in some embodiments, the delivery portion 1770 can include a single fluidic pathway for communicating fluids from the first reagent volume 1742 and the second reagent volume 1744 into the reaction chamber 1732. In some embodiments, the delivery portion 1770 can be configured to deliver reagents from the first reagent volume 1742 and/or the second reagent volume 1744 into the reaction chamber 1732 in a manner that promotes mixing and/or that minimizes aeration, overspray and/or undesirable turbulence. In some embodiments, the first fluidic pathway 1772a and/or the second fluidic pathway 1772b can have a varying cross-sectional (or flow) areas (e.g., the pathways can resemble nozzles) to produce a controlled flow rate of the substances flowing therethrough. In some embodiments, the flow rate of the transduction particles and/or reagents, can be 1 ml/sec, 2 ml/sec, 3 ml/sec, 4 ml/sec, 5 ml/sec, or any suitable flow rate to sufficiently mix the substance and/or to minimize aeration.

The reagent module 1740 includes the first actuator 1750 at least partially disposed in the housing 1741. The first actuator 1750 includes an engagement portion 1752 and a plunger portion 1754, which is disposed within the first reagent volume 1742. The engagement portion 1752 of the first actuator 1750 is configured to be manipulated (for example, by any instrument shown and described herein, such as the instrument 11000) to move the plunger portion 1754 within the first reagent volume 1742. In some embodiments, the plunger portion 1754 of the first actuator 1750 and a portion of the housing 1741 define and/or include a seal to fluidically isolate the first reagent volume 1742 from a volume outside of the housing 1741. In some embodiments, the seal can be, for example, a gasket, an o-ring, a rubber seal, or any suitable seal. As shown, the engagement portion 1752 and the plunger portion 1754 of the first actuator 1750 can have different cross-sectional dimensions (e.g., diameter). In other embodiments, however, the engagement portion 1752 and the plunger portion 1754 of the first actuator 1750 can have the same cross-sectional dimension (e.g., diameter). In some embodiments, the engagement portion 1752 can be offset from (e.g., non-coaxial with) the plunger portion 1754.

The reagent module 1740 includes the second actuator 1760 at least partially disposed in the housing 1741. The second actuator 1760 includes an engagement portion 1762 and a plunger portion 1764, which is movably disposed within the second reagent volume 1744. The engagement portion 1762 of the second actuator 1760 is configured to be manipulated (for example, by any instrument shown and described herein, such as the instrument 11000) to move the plunger portion 1764 of the second actuator 1760 within the second reagent volume 1744. In some embodiments, the plunger portion 1764 of the second actuator 1760 and a portion of the housing 1741 define and/or include a seal to fluidically isolate the second reagent volume 1742 from a volume outside of the housing 1741. In some embodiments, the seal can be, for example, a gasket, an o-ring, a rubber seal, or any suitable seal, and can be substantially similar to the seal of the first actuator 1750. As shown, the engagement portion 1762 and the plunger portion 1764 of the second actuator 1760 can have different cross-sectional dimensions (e.g., diameter). In other embodiments, however, the engagement portion 1762 and the plunger portion 1764 of the second actuator 1760 can have the same cross-sectional dimension (e.g., diameter). In some embodiments, the engagement portion 1762 can be offset from (e.g., non-coaxial with) the plunger portion 1764.

As shown, the engagement portion 1762 of the second actuator 1760 at least partially surrounds the engagement portion 1752 of the first actuator 1750. Similarly stated, at least a portion of the first actuator 1750 and a portion of the second actuator 1760 are disposed concentrically in the housing 1741. In this manner, the reagent module 1740 can be coupled to the reaction chamber 1732 and/or disposed in an instrument in any angular orientation about the longitudinal axis of the container assembly 1700. This arrangement allows a single actuator assembly to manipulate both the first actuator 1750 and the second actuator 1760.

More particularly, the second actuator 1760 defines a channel 1766 within which the engagement portion 1752 of the first actuator 1750 can move when the first actuator 1750 is manipulated to move the plunger portion 1754. In some embodiments the engagement portion 1762 of the second actuator 1760 can define an opening within which the engagement portion 1752 of the first actuator 1750 can be substantially disposed. Although a longitudinal axis of the plunger portion 1754 of the first actuator 1750 is shown as being concentric to a longitudinal axis of the plunger portion 1764 of the second actuator 1760, in other embodiments, the longitudinal axis of the plunger portion 1754 can be offset from and/or nonconcentric with the longitudinal axis of the plunger portion 1764. In some embodiments, for example, the first actuator 1750 and the second actuator 1760 can be disposed adjacent but not concentric to each other. In some embodiments, the first actuator 1750 and the second actuator 1760 can be disposed parallel to each other. In some embodiments the engagement portions 1752 and/or the engagement portion 1762 can be recessed in the housing 1741, e.g., to prevent accidental actuation.

The first actuator 1750 and the second actuator 1760 can be moved in any suitable manner to perform the functions described herein. For example, in some embodiments, the plunger portion 1754 of the first actuator 1750 can be moved independently of the movement of the plunger portion 1764 of the second actuator 1760. In some embodiments, the first actuator 1750 and second actuator 1760 can have the same stroke length. In other embodiments, the first actuator 1750 and second actuator 1760 can have different stroke lengths. In this manner, different volumes (and/or different flow rates) of transduction particles or reagents can be conveyed into the reaction chamber 1732.

In use, the container assembly 1700 is configured to be manipulated to perform the methods and/or assays described herein while maintaining fluidic isolation of the reaction chamber 1732. Similarly stated, the reaction chamber 1732 and the reagent module 1740 of the container assembly 1700 can collectively define a closed system within which target cell identification can be performed (i.e., without decoupling the reagent module 1740 from the reaction chamber 1732). In particular, the container assembly 1700 can be delivered to the user in a first configuration (FIG. 12), in which the first actuator 1750 and the second actuator 1760 are each their respective first positions. Although the reagent module 1740 is shown as being coupled to the reaction chamber 1732 in FIG. 12, the reagent module 1740 can initially be decoupled from the reaction chamber 1732 to allow a sample containing the target cell (e.g., bacteria) to be disposed in the internal volume defined by the reaction chamber 1732. The reagent module 1740 can be coupled to the reaction chamber 1732 to define a fluid-tight seal.

To move the container assembly 1700 and/or the reagent module 1740 to the second configuration (FIG. 13), the engagement portion 1752 of the first actuator is manipulated to move within the channel 1766. In this manner, the plunger portion 1754 of the first actuator 1750 moves within the first reagent volume 1742 to convey and/or expel the reagent (e.g., transduction particles) from the first reagent volume 1742 through the first fluidic pathway 1742a and first outlet 1744a, and into the reaction chamber 1732 as shown by arrow EE. In some embodiments, the reagent includes transduction particles that interact with the target cell contained in the sample such that the target cells produce a series of reporter molecules according to any of the methods described herein. Manipulation and/or maintaining of the container assembly 1700 (and the sample contained therein) can be performed by the instruments 1100 and/or 11000 as described herein and/or any other instruments or components described herein.

To move the container assembly 1700 and/or the reagent module 1740 to the third configuration (FIG. 14), the engagement portion of 1762 of the second actuator 1760 is manipulated to move at least partially about the first actuator 1750. The movement of the engagement portion 1762 moves the plunger portion 1764 of the second actuator 1760 from the first position to a second position within the second reagent volume 1744. The displacement of the plunger portion 1764 conveys and/or expels the reagent (e.g., a substrate such as tridecanal) from within the second reagent volume 1744 through the second fluidic pathway 1772b and second outlet 1774b into the reaction chamber 1732, as shown by arrow FF. In some embodiments, the reagent is a substrate that can interact with the reporter molecules produced to urge, catalyze and/or enhance the reporter molecules to produce a signal, e.g., via a luminescence reaction.

Figure 15:
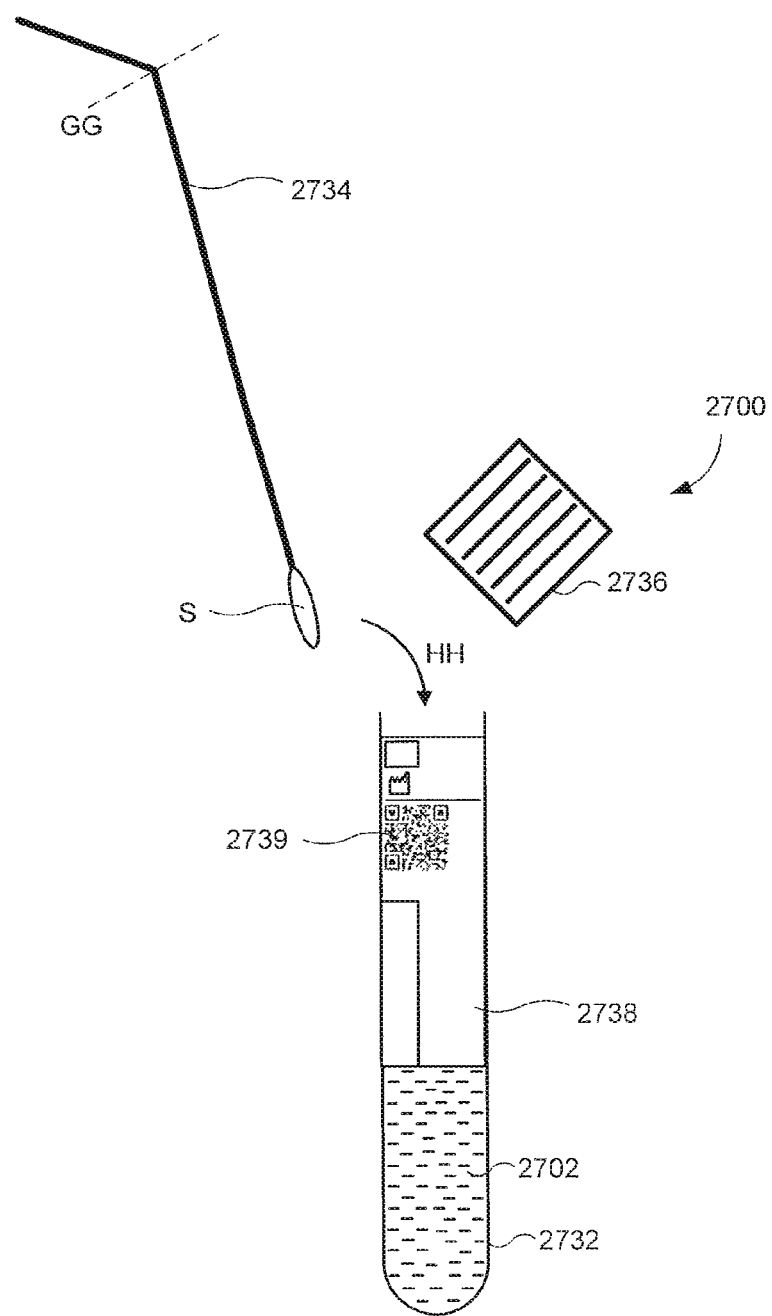
FIGS. 15-17 are side views of a container assembly according to an embodiment, in a first configuration, a second configuration and a third configuration, respectively.
Figure 16:
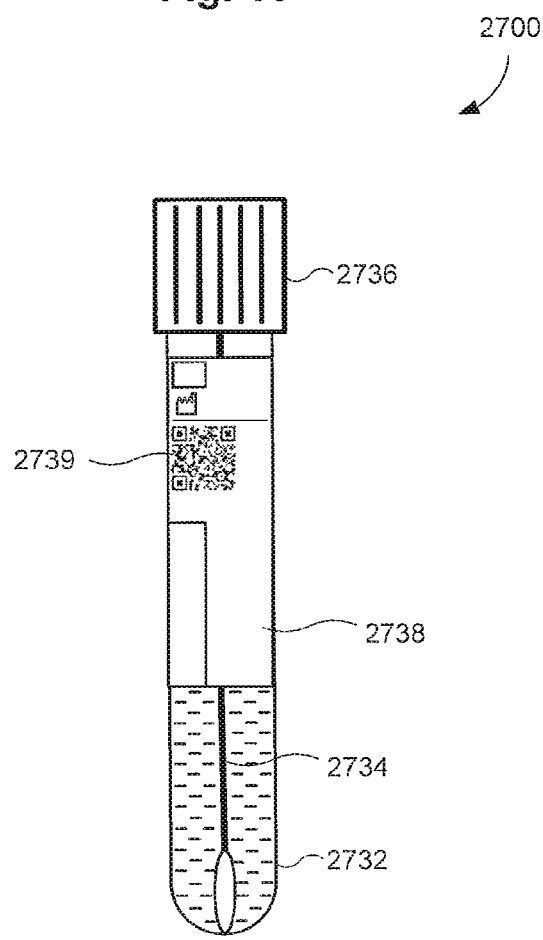
Figure 17:
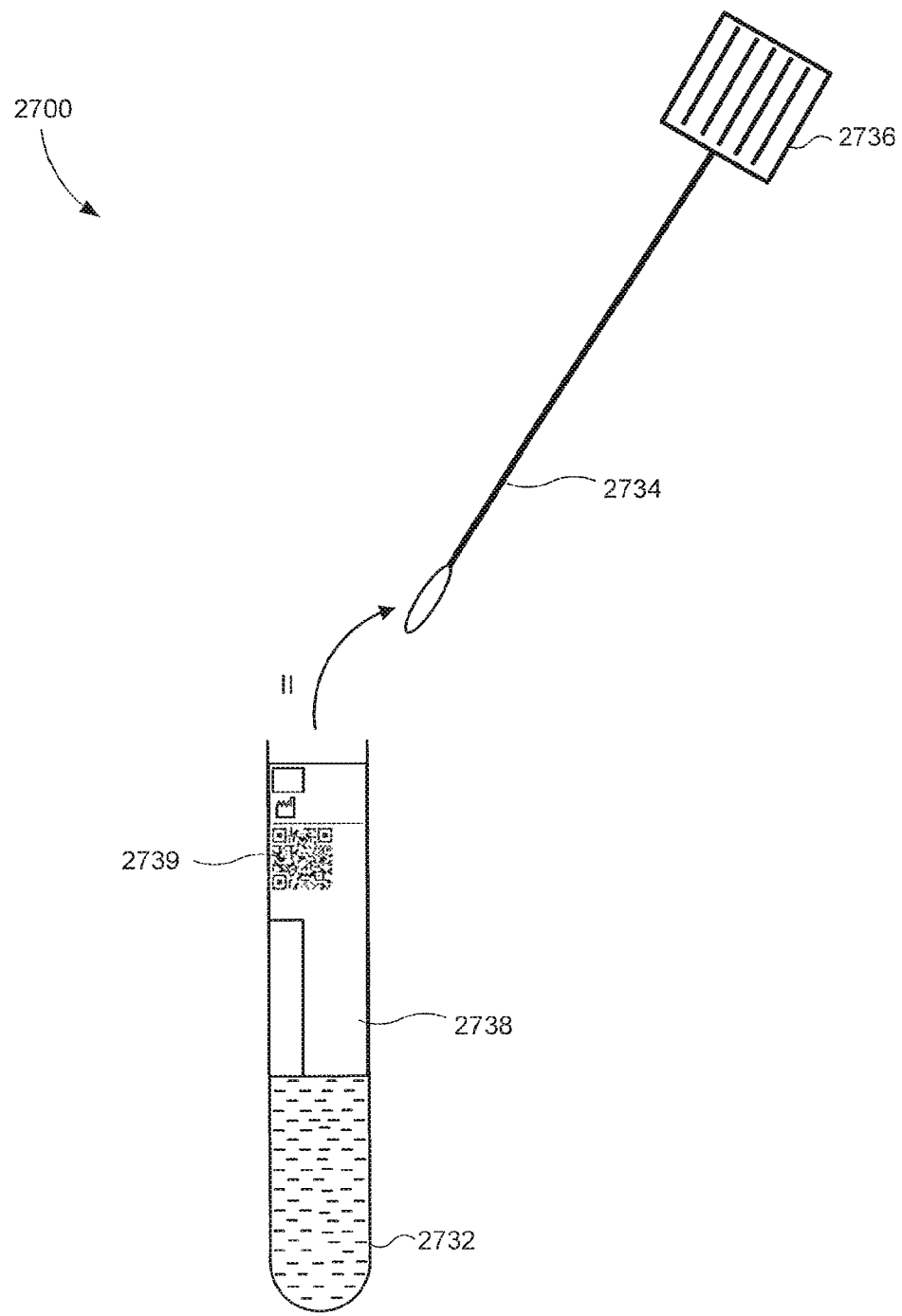

In some embodiments, a container assembly can include a mechanism for collecting a sample and/or disposing a sample into the container assembly. For example, in some embodiments, a sample can be collected using a swab, which is then disposed into the reaction chamber of the container. FIGS. 15-17 show a container assembly 2700 in a first configuration, a second configuration, and a third configuration, respectively. The container assembly 2700 includes a reaction chamber 2732 and a temporary cap 2739. The reaction chamber 2732 of the container assembly 2700 can be coupleable to any reagent module, such as, for example, the reagent module 1740 as described above, or any other reagent module described herein.

The sample S containing the target cell can be collected in a swab 2734, which can be a nasal swab, saliva swab, environmental swab, or the like. In some embodiments, after collecting the sample S, the nasal swab 2734 is broken at a predefined position and/or length of the swab 2734 as shown by the line GG (FIG. 15). The reaction chamber 2732 can contain a solution 2702, e.g., nutrient media, buffers, surfactants, and/or any other reagents formulated to maintain the target cells, promote the production of reporter molecules or the like. The swab 2734 is inserted into the reaction chamber 2732, as shown by arrow HH, until it is immersed in the solution 2702.

The temporary cap 2736 can then be coupled to the reaction chamber 2732 to place the container assembly 2700 in the second configuration (FIG. 16). In some embodiments, the temporary cap 2736 can define a substantially fluid-tight seal when coupled to the reaction chamber 2732.

In this manner, the container assembly 2700 can be agitated, e.g., vortexed or shaken, to allow a significant portion of the sample S containing the target cells to communicate into the solution 2702 from the swab 2734. In some embodiments, the swab 2734 and the sample collection protocol can be defined such that as much as 50%, 60%, and up to 70%, and any quantity therebetween or even higher, of the collected target cells are transferred into the solution 2702.

In some embodiments, the swab 2734 can be removed for testing. Removal of the swab, in certain situations, can limit interference with sample measurements. Accordingly, in some embodiments, the temporary cap 2736 can include a gripping mechanism, e.g., notches, grooves, sleeve, or any other feature for gripping the swab 2734. In such embodiments, when the temporary cap 2736 is removed from the reaction chamber 2732 as shown in the third configuration by arrow II (FIG. 17), the swab 2734 is also removed with it. In some embodiments, the reaction chamber 2732 can include one or more labels 2738 disposed on an exterior surface of the reaction chamber 2732. The labels 2738 can include information associated with the container assembly 2700, e.g., target cell, serial number, lot number, expiration date, and/or warning information. In some embodiments, the container 2700 can also include a tracking mechanism 2739, e.g., bar codes on labels and/or RFID tags.

FIGS. 18-25 show a container assembly 3700 according to an embodiment that includes a reaction chamber 3732 and a reagent module 3740 that is coupleable to the reaction chamber. The container assembly 3700 can be used with and manipulated by any of the instruments described herein, e.g., instrument 11000, and/or any of the components described herein. The container assembly 3700 can also be used to perform any of the methods described herein, e.g., such as the methods 150, 200 and 300 described above.

The reaction chamber 3732 is configured to contain a sample and/or other reagents, and can be formed from a light weight, rigid and inert material. At least a portion of the reaction chamber 3732 (e.g., the distal end portion) can be at least partially transparent to allow viewing, optical access and/or detection of the internal volume of the reaction chamber 3732. Although shown as being shaped as a cylinder with a rounded bottom, in other embodiments, the reaction chamber 3732 can have any other suitable shape, e.g., square, rectangular, oval, polygonal, etc. In some embodiments, the reaction chamber 3732 can have a diameter of 12 mm and a height of 75 mm. In some embodiments, the container assembly 3700 can be provided with one or more solutions/reagents (e.g., bacterial nutrient solution, buffers, surfactants, transduction particle, and/or antibiotics), predisposed within the reaction chamber 3732.

Figure 18:
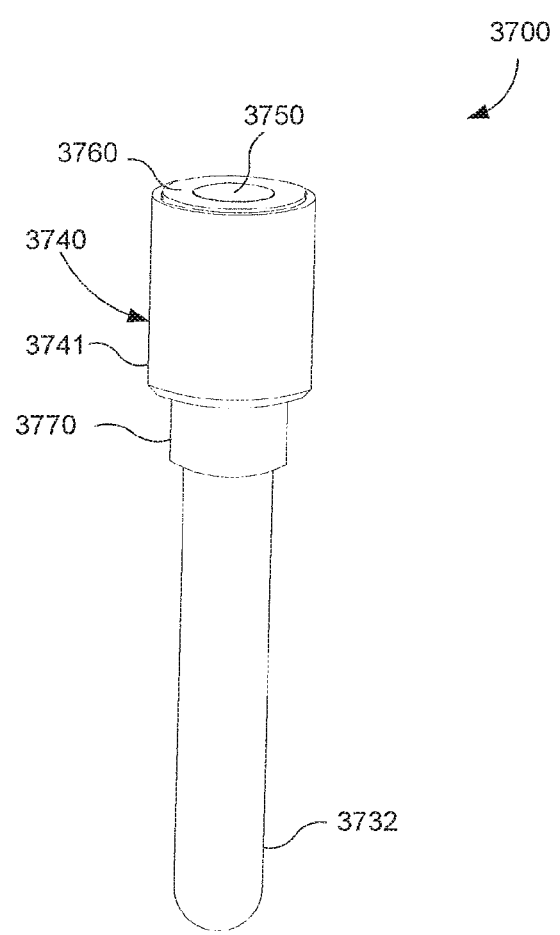
FIG. 18 is a perspective view of a container assembly according to an embodiment.

The reagent module 3740 includes a housing 3741, a first actuator 3750, a second actuator 3760, a delivery portion 3770, a first reagent container 3780a and a second reagent container 3780b. As shown in FIG. 18, the housing 3741 is configured to be removably coupled to the reaction chamber 3732 by any suitable mechanism. For example, in some embodiments, the housing 3741 can be coupled to the reaction chamber 3732 by a threaded coupling, an interference fit or the like. In some embodiments, the housing 3741 and the reaction chamber 3732 define a substantially fluid tight seal.

Figure 20:
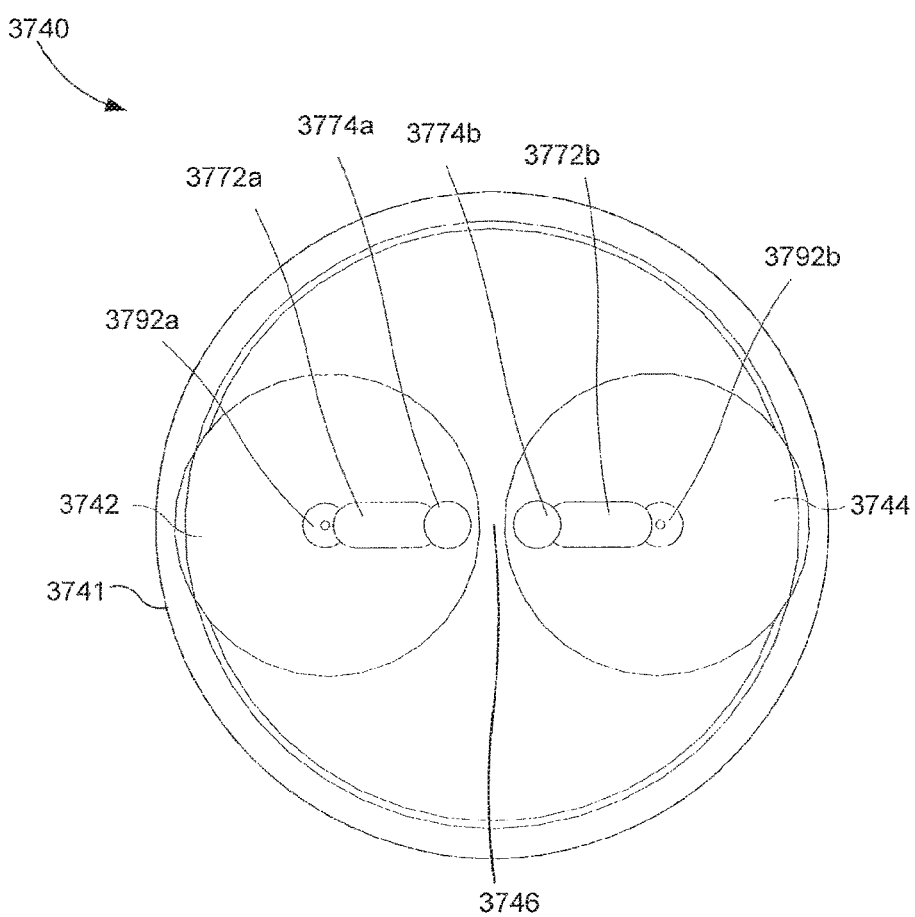
FIG. 20 shows a top view of a housing included in the container assembly of FIG. 19.

FIG. 20 shows a top view of the housing 3741. The housing 3740 defines a first reagent volume 3742 and a second reagent volume 3744 that can be separated by a sidewall 3746. The housing 3741 can be formed from a lightweight and rigid material, such as, for example, injection molded plastic. In some embodiments, the housing 3741 can have a diameter of approximately 24 mm. In some embodiment, the diameter of the housing 3741 can be varied to increase or decrease the capacity of the first reagent volume 3742 and the second reagent volume 3744. In some embodiments, the diameter of the first reagent volume 3742 and/or the second reagent volume 3744 can be varied (i.e., not equal to each other).

Figure 21:
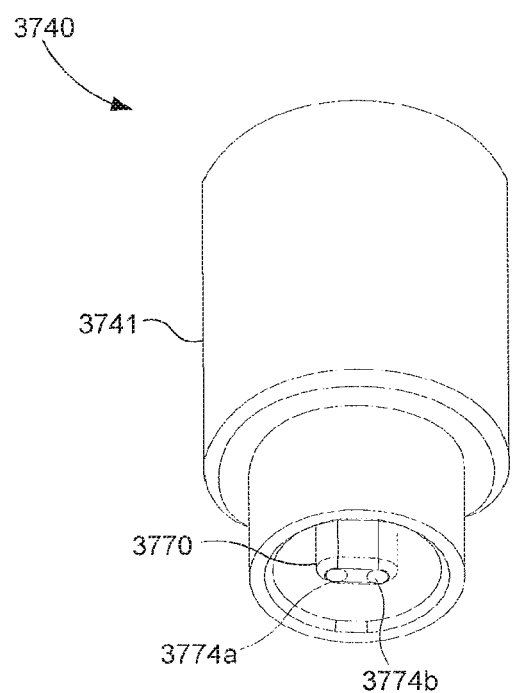
FIG. 21 shows a perspective bottom view of the housing included in the container assembly of FIG. 19.

As shown in the top view of the housing 3741 in FIG. 20 and inclined bottom view of the housing 3741 shown in FIG. 21, the housing 3741 includes a delivery portion 3770 that, when the housing 3741 is coupled to the reaction chamber 3732, defines a first fluidic pathway 3772a between the first reagent volume 3742 and the reaction chamber 3732, and a second fluidic pathway 3772b between the second reagent volume 3744, and the reaction chamber 3732. The first fluidic pathway 3772a and the second fluidic pathway 3772b include a first outlet 3774a and a second outlet 3774b, respectively, that open into the reaction chamber 3732, when the reaction chamber 3732 is coupled to the housing 3741. The first fluidic pathway 3772a (and the outlet 3774a) and the second fluidic pathway 3772b (and the outlet 3774b) provide a pathway for reagents disposed in the first reagent volume 3742 and the second reagent volume 3744 to be communicated into the reaction chamber 3732. Although the first fluidic pathway 3772a and the second fluidic pathway 3772b are shown as being separate from each other, in other embodiments, the first fluidic pathway 3772a and the second fluidic pathway 3772b can include a common boundary and/or be in fluid communication with each other.

The delivery portion 3770 is configured to provide any suitable pathway and/or mechanism for delivering the transduction particles and reagents disposed in the first reagent volume 3742 and/or the second reagent volume 3744 into the reaction chamber 3732. For example, in some embodiments, the first fluidic pathway 3772a and the second fluidic pathway 3772b can be configured to deliver reagents from the first reaction volume 3742 and the second reaction volume 3744, respectively, to the reaction chamber 3732 in a manner that promotes mixing and/or minimizes aeration, overspray and/or undesirable turbulence. The first fluidic pathway 3772a and the second fluidic pathway 3772b can accommodate any suitable flow rate, e.g., 1 ml/sec, 2 ml/sec, 3 ml/sec, 4 ml/sec, 5 ml/sec. In some embodiments, at least a portion of the delivery portion 3770, can be disposed within the reaction chamber 3732 when the housing 3741 is coupled to the reaction chamber 3732.

Figure 19:
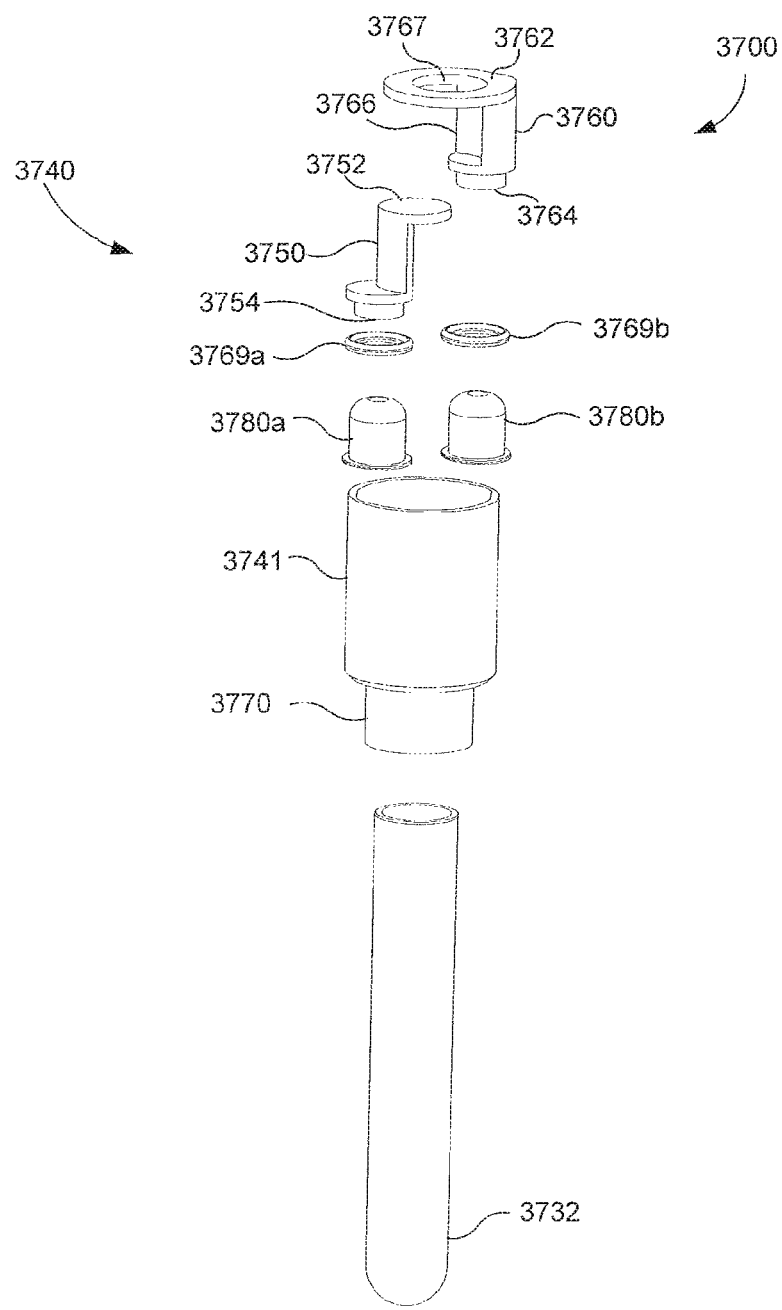
FIG. 19 shows an exploded view of the container assembly of FIG. 18.
Figure 23:
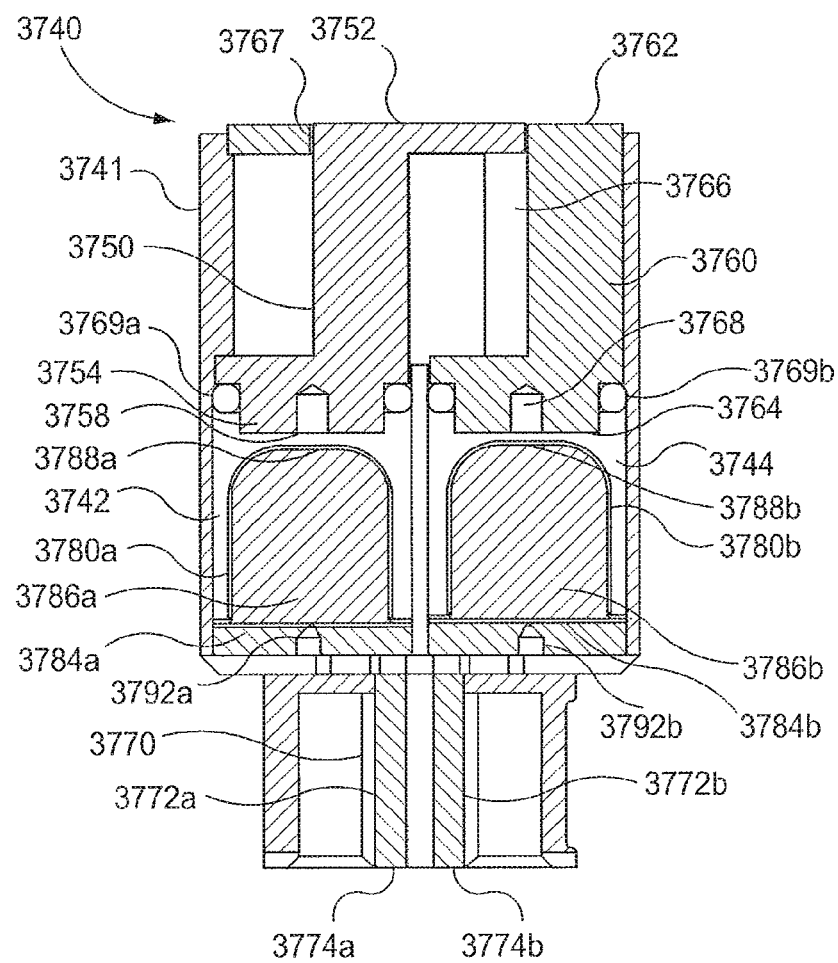
FIGS. 23-25 are side cross-sectional views of a portion of the container of FIG. 19 in a first configuration, a second configuration and a third configuration, respectively.

As shown in FIG. 19 and the side cross-section of the container shown in FIG. 23 the reagent module 3740 includes the first actuator 3750 disposed in the housing 3741. The first actuator 3740 includes an engagement portion 3752 and a plunger portion 3754, which is movably disposed within the first reagent volume 3742. When actuated, the engagement portion 3752 of the first actuator 3750 moves the plunger portion 3754 within the first reagent volume 3742. As shown, the plunger portion 3754 of the first actuator 3750 includes a seal 3769a to fluidically isolate the first reagent volume 3742 from a volume outside of the housing 3741. In some embodiments, the seal 3769a can be, for example, a gasket, an o-ring, a rubber seal, or any suitable seal.

The reagent module 3740 includes the second actuator 3760. The second actuator 3760 includes an engagement portion 3762 and a plunger portion 3764 that is movably disposed within the second reagent volume 3744. When actuated, the engagement portion 3762 of the second actuator 3760 moves the plunger portion 3764 of the second actuator 3760 within the second reagent volume 3744. The plunger portion 3764 of the second actuator 3760 includes a seal 3769b to fluidically isolate and/or prevent leakage of any reagent contained in the second reagent volume 3744.

The first actuator 3750 and the second actuator 3760 can be disposed in a nested configuration in the housing 3741. Said another way, the first actuator 3750 and the second actuator 3760 can be disposed concentrically, such that the first actuator 3750 is nested within the second actuator 3760. In this manner, the reagent module 3740 can be coupled to the reaction chamber 3732 and/or disposed in an instrument in any angular orientation about the longitudinal axis of the container assembly 3700. More particularly, the second actuator 3760 defines a channel 3766 within which the engagement portion 3752 of the first actuator 3750 can move when the first actuator 3750 is manipulated to move the plunger portion 3754. Further, the engagement portion 3762 of the second actuator 3760 defines an opening 3767 within which the engagement portion 3752 of the first actuator 3750 is substantially disposed (when the reagent module 3740 is in the first configuration or the third configuration). A longitudinal axis of the plunger portion 3754 of the first actuator 3750 is offset from (i.e., non-coaxial with) a longitudinal axis of the plunger portion 3764 of the second actuator 3760. The plunger portion 3754 of the first actuator 3750 can be moved independently of the movement of the plunger portion 3764 of the second actuator 3760. Furthermore, the first actuator 3750 and the second actuator 3760 can be recessed inside the housing, for example, to prevent accidently actuation of the first actuator 3750 and the second actuator 3760.

Figure 22:
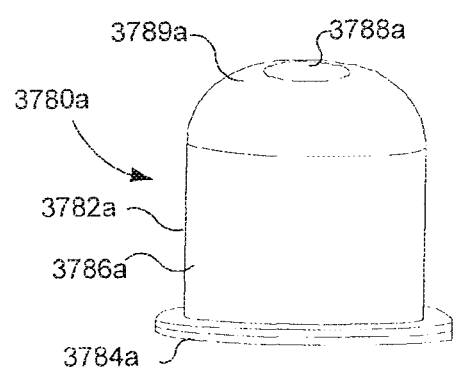
FIG. 22 shows a perspective view of a reagent container included in the container assembly of FIG. 19, according to an embodiment.

The first reagent volume 3742 can include the first reagent container 3780a and the second reagent volume 3744 can contain the second reagent container 3780b. As shown in FIG. 22 (which only shows the first reagent container 3780a for clarity), the first reagent container 3780a (and the second reagent container 3780b) includes a sidewall 3782a and a frangible member 3784a, that together define an internal volume 3786a. In some embodiments, the sidewall 3782a can also be frangible. The internal volume 3786a can be completely or partially filled with a reagent. For example, in some embodiments, the first reagent container 3780a can contain transduction particles (e.g., transduction particles 110, 160 or any other transduction particles described herein) that includes an engineered nucleic acid (e.g., engineered nucleic acid 170) formulated to cause the target cell (e.g., bacteria) to produce a plurality of reporter molecules. The second reagent container 3780b can contain a second reagent formulated react with the reporter molecules to enhance the production of a signal. For example, in some embodiments, the reagent is a substrate, such as tridecanal, that can interact with the reporter molecule (e.g., luciferase), to produce a measurable signal, e.g., via a luminescence reaction.

The reagent containers can be shaped and sized to be disposed substantially inside the first reagent volume 3742 and the second reagent volume 3744. The housing 3741 include a first puncturer 3792a and a second puncturer 3792b disposed within the first reagent volume 3742 and the second reagent volume 3744, respectively. The puncturers are configured to rupture the respective frangible portions of the first reagent containers 3780a and the second reagent container 3780b when the plunger portion 3754 and the plunger portion 3764 are displaced within the first reagent volume 3742 and the second reagent volume 3744, respectively. In some embodiments, the reagent containers can include curved edges (see e.g., the curved edge 3789a) and a bottom portion (see e.g., the bottom portion 3788a) that can be substantially flat. The flat bottom portion and the curved edges can allow for spreading of the compressive force applied by the first actuator 3750 and the second actuator 3760 on the first reagent container 3780*a* and the second reagent container 3780*b*, respectively, to ensure repeatable delivery.

The reagent containers can be constructed from materials that are substantially impermeable to and/or substantially chemically inert from the substance contained therein, e.g., transduction particle, substrate, antibiotics, buffers, surfactants, or any other reagent that can be required for the detection assay. In this manner, the reagents can be stored in the reagent containers for extended periods of time. For example, the side wall 3782*a* of the reagent container 3780*a* can be formed from a flexible and inert material, e.g., blister plastic, aluminum foil, aluminum laminate or any other suitable material. Moreover, in some embodiments, the frangible member 3784*a* can be constructed from a material having certain temperature characteristics such that the desired properties and integrity of the frangible member 3784*a* are maintained over a certain temperature. For example, in some embodiments, it can be desirable to store the reagent container 3780*a* containing reagent or substrate in a refrigerated condition. In some embodiments, the frangible member 3784*a* can be constructed from a polymer film, such as any form of polypropylene. In some embodiments, the frangible member 3784*a* can be constructed from bi-axially oriented polypropylene (BOP). In some embodiments, the frangible member 3784*a* can be constructed from aluminum.

Figure 24:
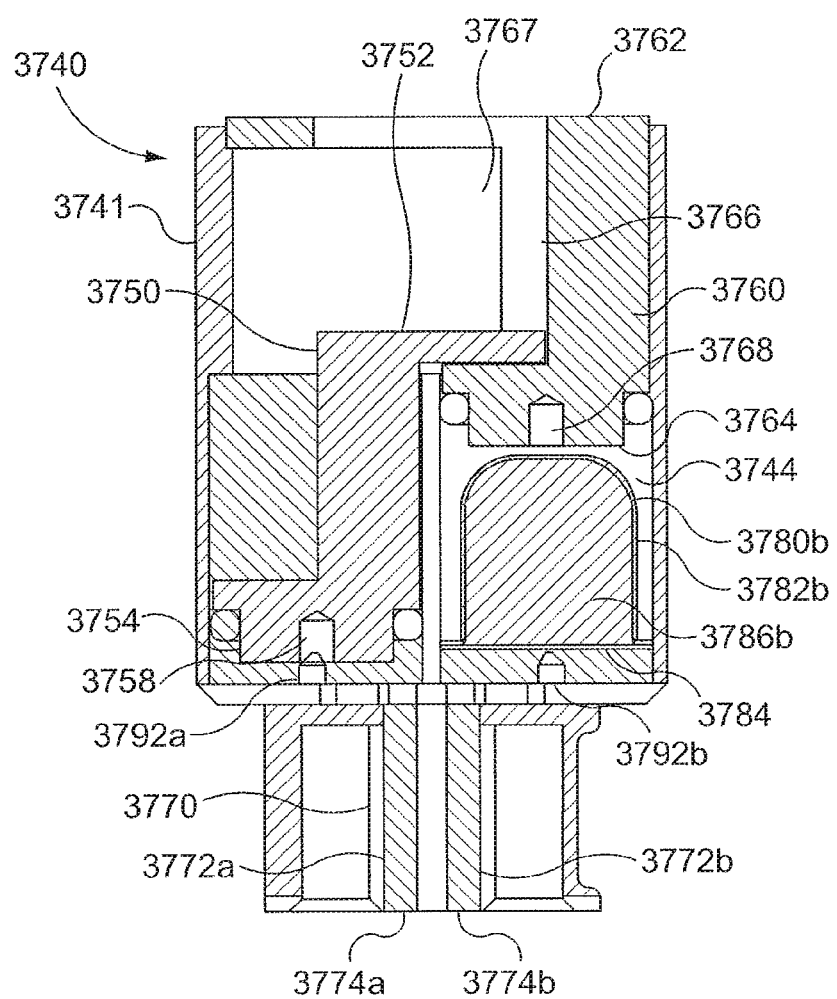
Figure 25:
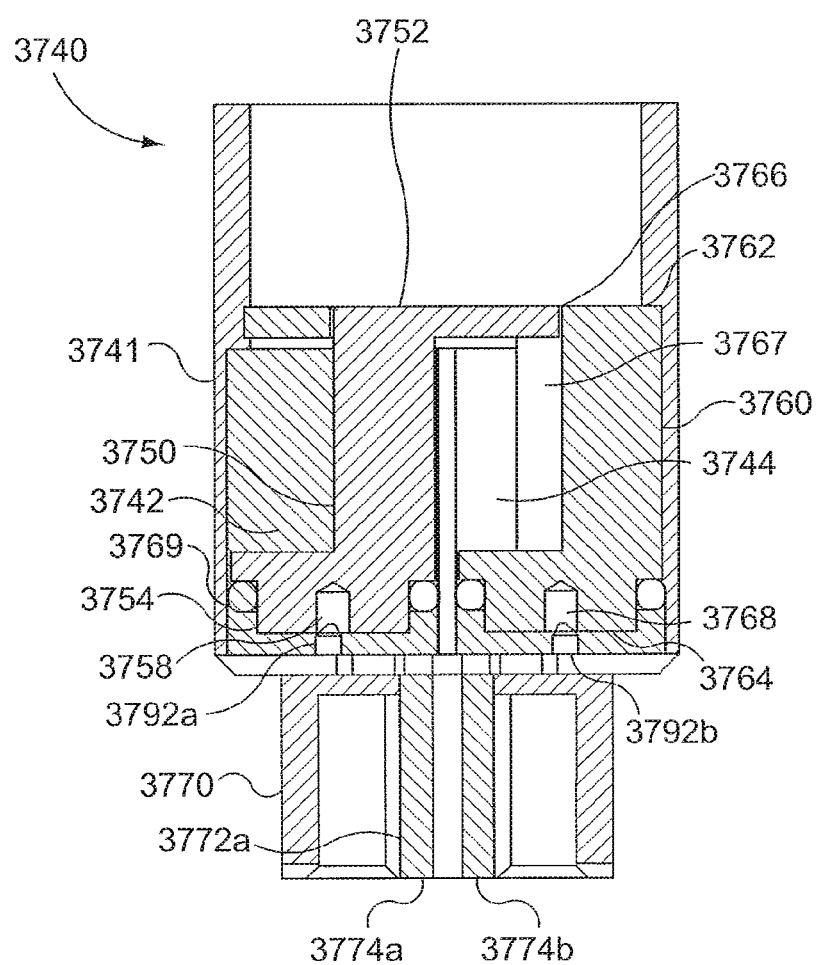

The reaction chamber 3732 and the reagent module 3740 of the container assembly 3700 can collectively define a closed system within which target cell identification can be performed (i.e., without decoupling the reagent module 3740 from the reaction chamber 3732). The container assembly 3700 and/or the reagent module 3740 can be moved between multiple different configurations to transfer reagents and/or substances from the first reagent chamber 3742 and the second reagent chamber 3744. In particular, FIGS. 23-25 show the reagent module 3740 in a first configuration, a second configuration and a third configuration, respectively. The reaction chamber 3732 is not shown for clarity.

The container assembly 3700 can be delivered to the user in the first configuration (FIG. 23), wherein the first actuator 3750 is in a first position and the second actuator 3760 is in a first position. The first reagent volume 3742 includes the reagent container 3780*a* containing the reagent (e.g., transduction particles), and the second reagent volume 3744 contains the second reagent container 3780*b* that includes a reagent (e.g., tridecanal, formulated to react with the reporter molecules).

To move the container assembly 3700 to the second configuration (FIG. 24), the engagement portion 3752 of the first actuator 3750 is manipulated to displace the plunger portion 3754 of the first actuator 3750 within the first reagent volume 3742 from the first position to a second position. Similarly stated, the engagement portion 3752 moves distally within the channel 3766 and/or the opening 3767 of the second actuator 3760. In this manner, the plunger portion 3754 of the first actuator 3750 applies a force on the bottom portion 3788*a* of the first reagent container 3780*a*. This pushes the frangible portion 3784*a* of the first reagent container 3780*a* against the puncturer 3769*a*, until the frangible portion 3784*a* ruptures, releasing the reagent contained therein e.g., transduction particle, into the first reagent volume 3742. Further displacement of the plunger portion 3754 of the first actuator 3750 towards the second position decreases the internal volume 3786*a* of the reagent container 3780*a* and the first reagent volume 3742. This communicates the reagent e.g., transduction particle from the first reagent volume 3742 through the first fluidic pathway 3772*a* and the first outlet 3774*a* of the delivery portion 3770, and into the reaction chamber 3732. As shown, the first actuator 3750 include a recess 3758 configured to receive a portion of the puncturer 3792*a* to prevent the puncturer from damaging the first actuator 3750 and/or from limiting the travel of the first actuator 3750 towards the second position. In some embodiments, the reagent, e.g., transduction particle can interact with the target cell contained in the sample and urge the target cell to produce the reporter molecule as described herein.

To move the container assembly 3700 to the third configuration (FIG. 25), the engagement portion of 3762 of the second actuator 3760 is manipulated to displace the plunger portion 3764 of the second actuator 3760 from the first position to a second position within the second reagent volume 3744. Similar to the second configuration, the displacement of the second actuator 3760 causes a puncturer 3792*b* to rupture the frangible portion 3784*b* of the second reagent container 3780*b* and communicate the substrate contained therein (e.g., tridecanal) through the second fluidic pathway 3772*b* and second outlet 3774*b* into the reaction chamber 3732. The substrate can interact with the reporter molecules and urge, enhance and/or catalyze the reporter molecule to produce a signal, e.g., via a luminescence reaction. As shown, the second actuator 3760 include a recess 3768 configured to receive a portion of the puncturer 3792*b* to prevent the puncturer from damaging the second actuator 3760 and/or from limiting the travel of the second actuator 3760 towards the second position. In some embodiments, the reagent, e.g., transduction particles, can interact with the target cell contained in the sample and urge the target cell to produce the reporter molecule as described herein.

Although the exit portions of the first fluidic pathway 3772*a* and the second fluidic pathway 3772*b* are shown as being substantially linear, and having a substantially constant flow area, in other embodiments, a delivery portion can define any suitable flow pathways through which the reagents, substances, transduction particles and the like can be delivered. For example, in some embodiments, a delivery portion can be configured to deliver one or more reagents into a reaction chamber in a manner that promotes mixing, that minimizes aeration, overspray and/or undesirable turbulence.

For example, in some embodiments, a reagent module can be configured to deliver a substance containing transduction particles of the types shown and described herein into a reaction chamber in a manner that efficiently mixes the transduction particles with the sample. For example, in those embodiments in which a swab (such as the swab 2734) is retained within the reaction chamber, a reagent module can include a delivery nozzle or other mechanism for delivering transduction particles that enhances removal of portions of the sample from the swab. In this manner, the mechanism of delivery can enhance the performance of the assay by improving the mixture of the sample and the transduction particles. Such mechanisms can include, for example, high pressure jet nozzles, angled nozzles, multiple flow paths from a single reagent chamber into a reaction chamber, or the like.

In other embodiments, a reagent module can be configured to deliver a reagent formulated to enhance, catalyze or trigger the production of a light signal (e.g., a substrate of the types shown and described herein) into a reaction chamber in a manner that enhances the measurement of the light signal. For example, in some embodiments, a method of detecting the reporter molecules includes detecting the intensity (or strength) of a luminescence reaction triggered by the addition of a substrate into the sample in which reporter molecules have been expressed. More particularly, in some embodiments, the expressed reporter molecules and the substrate are collectively formulated to produce a flash reaction in response to the addition of the substrate to the sample. Flash reactions are luminescence reactions in which a distinct peak intensity occurs very quickly after the addition of the substrate (e.g., substantially instantaneously, within several seconds and/or less than one minute). Although flash reactions can produce very sensitive results (which are beneficial for detection of small quantities, etc.), the accurate measurement of such transient reactions can be challenging. In contrast, glow reactions are longer lasting luminescence reactions characterized by a stable signal that can be maintained for up to an hour or more. Although less sensitive than flash reactions, glow reactions can allow time for additional sample operations (e.g., mixing, transporting, or the like) to be completed before the signal is detected.

In some embodiments, a reagent module can be configured to deliver a substrate into a reaction chamber in a manner that enhances the measurement of the light signal. More particularly, in some embodiments, a reagent module can be configured to deliver a substrate in a manner that allows the substrate to sufficiently mix with the sample, while also minimizing aeration of the sample, the production of bubbles, excessive splashing, or the like, all of which can be detrimental to the optical detection to be completed within seconds after delivering the substrate. For example, in some embodiments, a reagent module can define a fluidic pathway that is angled with respect to a longitudinal axis of the reaction chamber, such that the reagent and/or substrate is delivered to a sidewall of the reaction chamber and then into the sample solution. In other embodiments, a reagent module can define a fluidic pathway that is substantially parallel with respect to a longitudinal axis of the reaction chamber, but that includes an exit opening positioned such that the reagent and/or substrate is delivered to a sidewall of the reaction chamber. In yet other embodiments, a reagent module can define a fluidic pathway that has a curved, arced and/or helical shape. In yet other embodiments, a reagent module can define a fluidic pathway that includes grooves, ribs, slots, or any other flow-adjusting features, to maximize mixing and/or minimize aeration.

Figure 26:
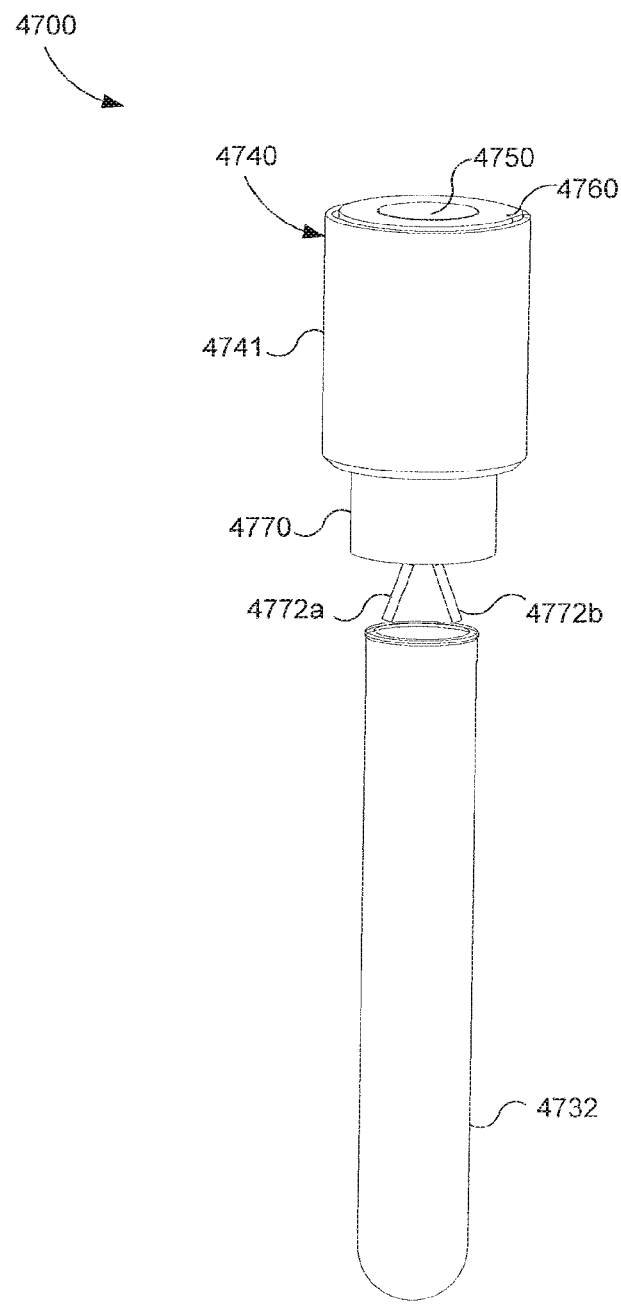
FIG. 26 shows a perspective view of a container assembly, according to an embodiment.
Figure 27:
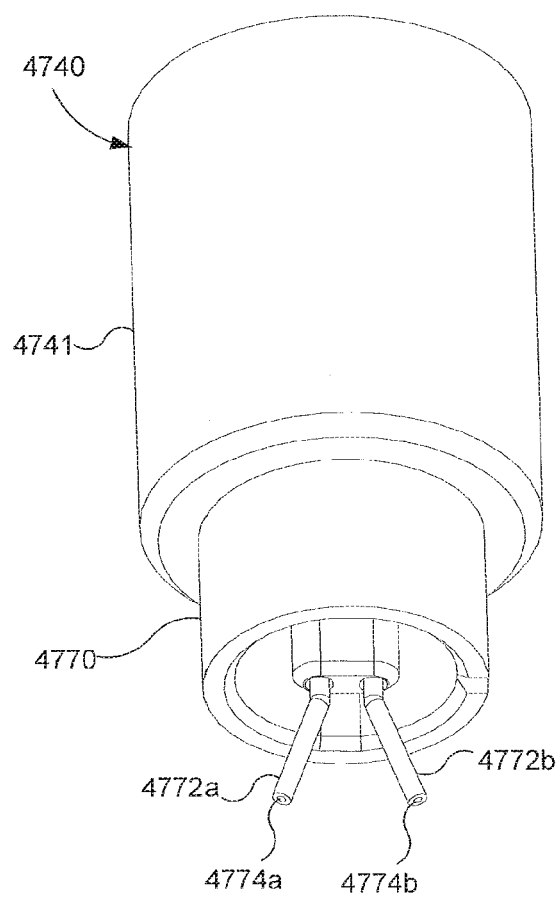
FIG. 27 shows a perspective bottom view of a housing included in the container assembly of FIG. 26.
Figure 28:
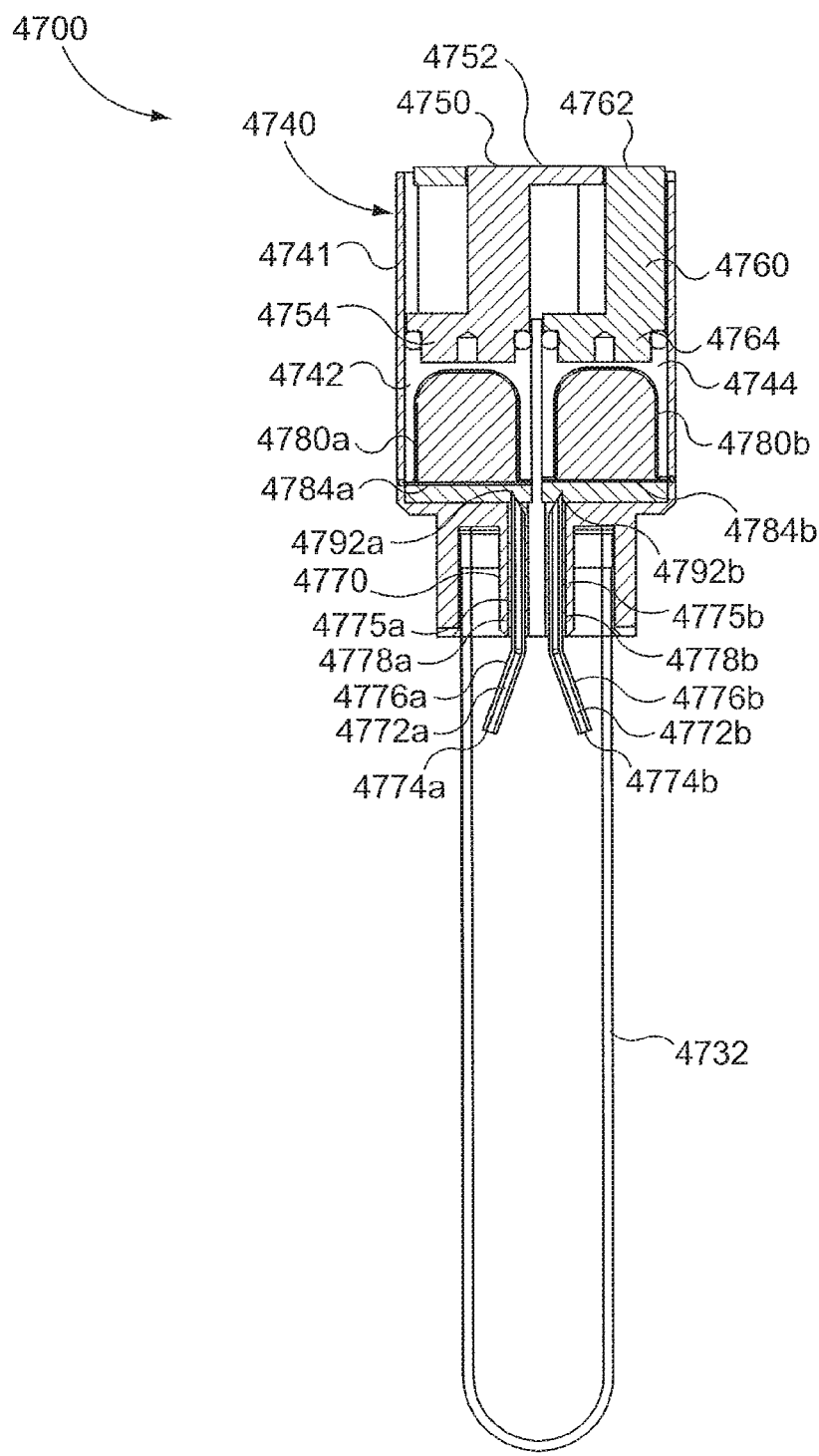
FIG. 28 shows a side cross-sectional view of the container assembly of FIG. 26.

As another example, FIGS. 26-28 show a container assembly 4700 that include a reaction chamber 4732 and a reagent module 4740. The container assembly 4700 can be used and/or manipulated by any instrument described herein, e.g., instrument 1100, 11000, and/or any components described herein. The container assembly 4700 can also be used to perform any methods described herein, e.g., methods 200 and/or 300.

The reagent module 4740 includes a housing 4741, a first actuator 4750, a second actuator 4760, a first delivery member 4772a and a second delivery member 4772b. As shown in the side cross-section view of FIG. 28, the housing 4741 defines a first reagent volume 4742 and a second reagent volume 4744. The housing 4741 can also include a delivery portion 4770. The first reagent volume 4742 can include a first reagent container 4780a that contains a first reagent (e.g., transduction particle). The second reagent volume 4744 can include a second reagent container 4780b that contains a second reagent (e.g., substrate). The housing 4741 of the container assembly 4700 can be substantially similar to the housing 3741 of the container assembly 3700 described before, and is therefore not described further in detail herein. The first reagent containers 4780a and the second reagent container 4780b are also substantially similar to the first reagent container 3780a and the second reagent container 3780b, respectively, of container assembly 3700 and are therefore not described in detail herein.

The first actuator 4750 includes an engagement portion 4752 and a plunger portion 4754. The second actuator 4760 includes an engagement portion 4762 and a plunger portion 4764. The first actuator 4750 and the second actuator 4760 are substantially similar to the first actuator 3750 and second actuator 3760, respectively, of container assembly 3700 as described before in structure and function, and are therefore not described in further herein.

As shown in the bottom view of the reagent module 4740 in FIG. 27 and the side cross-section of the container assembly 4700 in FIG. 28, the delivery portion 4770 of the housing 4741 includes a first delivery member 4772a that provides a conduit for fluid communication of a reagent, e.g., transduction particle, from the first reagent volume 4742 to the reaction chamber 4732 through a first outlet 4774a. The delivery portion 4770 of the housing 4741 includes a second delivery member 4772b that provides a conduit for fluid communication of a reagent, e.g., substrate, from the second reagent volume 4742 to the reaction chamber 4732 through a second outlet 4774a.

As shown in FIG. 28, the first delivery member 4772a includes a first portion 4775a and a second portion 4776a. The first portion 4775a is at least partially disposed inside the first reagent volume 4742. The second portion 4776a is at least partially disposed inside the reaction chamber 4732. The first portion 4775a defines a longitudinal axis that is substantially parallel to a longitudinal axis defined by the reagent module 4740 and/or the reaction chamber 4732. The second portion 4776a is angularly offset from a centerline of the first portion 4775a such that the outlet 4774a points towards a sidewall of the reaction chamber 4732. Similarly stated, the second portion 4776a is nonparallel to a longitudinal axis defined by the reagent module 4740 and/or the reaction chamber 4732. In some embodiments, the angle can be between the longitudinal axis and the second portion 4776a can be about 15-45 degrees, inclusive of all angles therebetween. In such embodiments, the reagent and/or transduction particles conveyed from the first reagent volume 4742 into the reaction chamber 4732 does not impinge directly upon a surface of the sample, but instead is propelled onto or along the sidewall of the reaction chamber, such that it can flow at a controlled speed into the sample solution.

As shown in FIG. 28, the second delivery member 4772b includes a first portion 4775b and a second portion 4776b. The first portion 4775b is at least partially disposed inside the second reagent volume 4744. The second portion 4776b is at least partially disposed inside the reaction chamber 4732. The first portion 4775b defines a longitudinal axis that is substantially parallel to a longitudinal axis defined by the reagent module 4740 and/or the reaction chamber 4732. The second portion 4776b is angularly offset from a centerline of the first portion 4775b, such that the outlet 4774b points towards a sidewall of the reaction chamber 4732. Similarly stated, the second portion 4776b is nonparallel to a longitudinal axis defined by the reagent module 4740 and/or the reaction chamber 4732. In some embodiments, the angle can be between the longitudinal axis and the second portion 4776b can be about 15-45 degrees, inclusive of all angles therebetween. In such embodiments, the reagent and/or substrate conveyed from the second reagent volume 4744 into the reaction chamber 4732 does not impinge directly upon a surface of the sample, but instead is propelled onto or along the sidewall of the reaction chamber, wherein it can flow at a controlled speed into the sample solution.

The first portion 4775a, 4775b of each of the delivery members 4772a, 4772b includes a puncturer 4792a, 4792b (respectively) at an end portion thereof. In this manner, the puncturer 4792a protrudes into the first reagent volume 4742, and the puncturer 4792b protrudes into the second reagent volume 4744. In particular, the end of the fluidic pathways delivery members can be tapered or chamfered to produce a sharp edge that serves as the puncturers. The puncturer 4792a and the puncturer 4792b can be used to puncture the frangible portion 4784a and the frangible portion 4784b, respectively, of the reagent containers to release the reagents, transduction particles or other substances contained therein. Although the delivery member 4772a and the deliver member 4772b are shown as being constructed separately from the housing 4741, in some embodiments, a delivery member can be integrally formed with the delivery portion 4770, e.g., manufactured in a single manufacturing step. In some embodiments, the delivery member 4772a and/or the delivery member 4772b can be manufactured separately, and then disposed in cavity 4778a and cavity 4778b, respectively of the delivery portion 4770.

Figure 29:
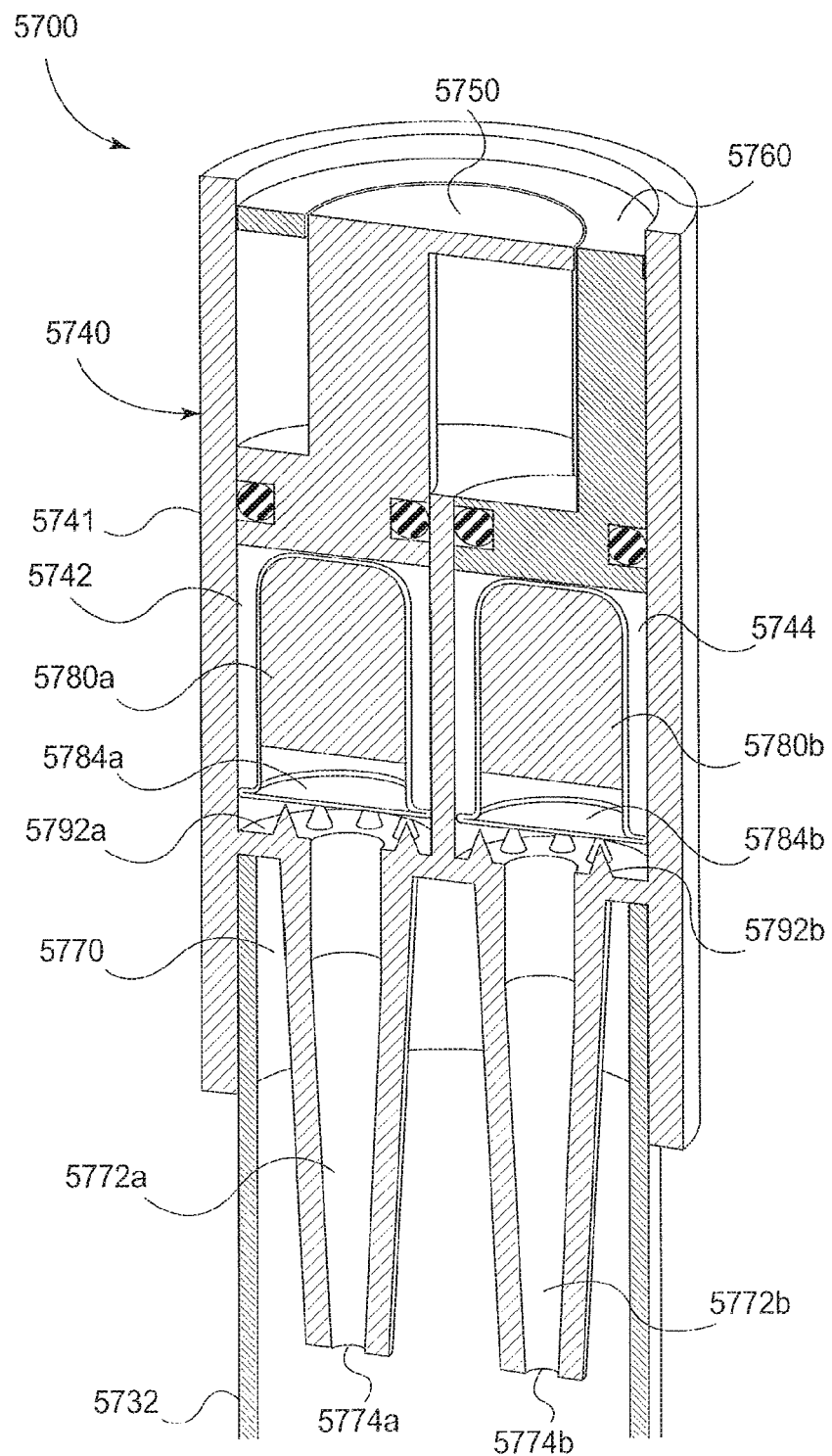
FIG. 29 is a side cross-sectional view of a container assembly, according to an embodiment.

In some embodiments, the reagent module of the container can include or define fluidic pathways configured to communicate the reagents directly into the sample solution, and having an exit point at any suitable distance within the container. For example, FIG. 29 shows a side cross-section view of a container assembly 5700 according to an embodiment. The container assembly 5700 includes a reaction chamber 5732 and a reagent module 5740. The reagent module includes a housing 5741 that defines a first reagent volume 5742 and a second reagent volume 5744. The housing 5741 contains a first actuator 5750 and a second actuator 5760. The housing 5741 also includes a delivery portion 5770. The container assembly 5700 can be used and/or manipulated by any instrument described herein, e.g., instrument 1100, 11000 and/or any components described herein. The container assembly 5700 can also be used to perform any methods described herein, e.g., methods 200 and/or 300.

The first reagent volume 5742 includes a first reagent container 5780a that can contain a first reagent (e.g., transduction particle of the types shown and described herein). The second reagent volume 5744 includes a second reagent container 5780b that can contain a second reagent (e.g., substrate of the types shown and described herein). The housing 5741 of the container assembly 5700 can be substantially similar to the housing 3741 of the container assembly 3700, and is therefore not described further in detail. The reagent containers 5780a, 5780b are substantially similar to the reagent containers 3780, 3780b of container assembly 3700 and are therefore not described in detail herein. The first actuator 5750 includes an engagement portion and a plunger portion. The second actuator 5760 includes an engagement portion and a plunger portion. The first actuator 5750 and the second actuator 5760 are substantially similar to the first actuator 3750 and second actuator 3760 of container assembly 3700, and are therefore not described in further herein.

The delivery portion 5770 of the housing 5741 defines a first fluidic pathway 5772a that provides a conduit for fluid communication of a first reagent, e.g., transduction particles, from the first reagent volume 5742 to the reaction chamber 5732 through a first outlet 5774a. The delivery portion 5770 of the housing 5741 also includes a second fluidic pathway 5772b that provides a conduit for fluid communication of a second reagent, e.g., substrate, from the second reagent volume 5744 to the reaction chamber 5732 through a second outlet 5774b.

As shown, the fluidic pathways 5772a, 5772b define a longitudinal axis that is parallel to the longitudinal axis defined by the reaction chamber 5732. This arrangement can allow the reagents to flow from the first reagent volume 5742 and the second reagent volume 5744 through the outlet 5774a and the outlet 577b, respectively, and straight into a sample solution disposed in the reaction chamber 5732. In some embodiments, a diameter of the fluidic pathway 5772a and/or the fluidic pathway 5772b at the respective outlet 5774a and 5774b can be smaller than a diameter at the interface of the fluidic pathway 5772a and/or the fluidic pathway 5772b and the first reagent volume 5742 and the second reagent volume 5744, respectively. In this manner, the fluidic pathways 5772a, 5772b perform substantially as nozzles to accelerate the flow of the transduction particles, reagents or the like. In some embodiments, the cross-sections can be configured such that the reagents are expelled from the outlet 5774a and/or the outlet 5774b at predefined flow rate, e.g., 1 ml/sec, 2 ml/sec, 3 ml/sec, 4 ml/sec, 5 ml/sec, or any other suitable flow rate, for example, to ensure rapid and complete mixing and/or minimize aeration. In some embodiments, the fluidic pathway 5772a and/or the fluidic pathway 5772b can be configured such that the outlet 5774a and/or the outlet 5774b are disposed beneath a surface of the sample within the reaction chamber 5732.

In some embodiments, the housing 5741 can include a series of puncturers 5792a, 5792b located at a base of the first reagent volume 5742 and the second reagent volume 5744, respectively. The series of punctures can be configured to rupture the frangible portion 5784a, 5784b of the reagent container 5780a, 5780b at multiple locations, for example, to ensure efficient expulsion of the reagents contained therein.

Figure 30:
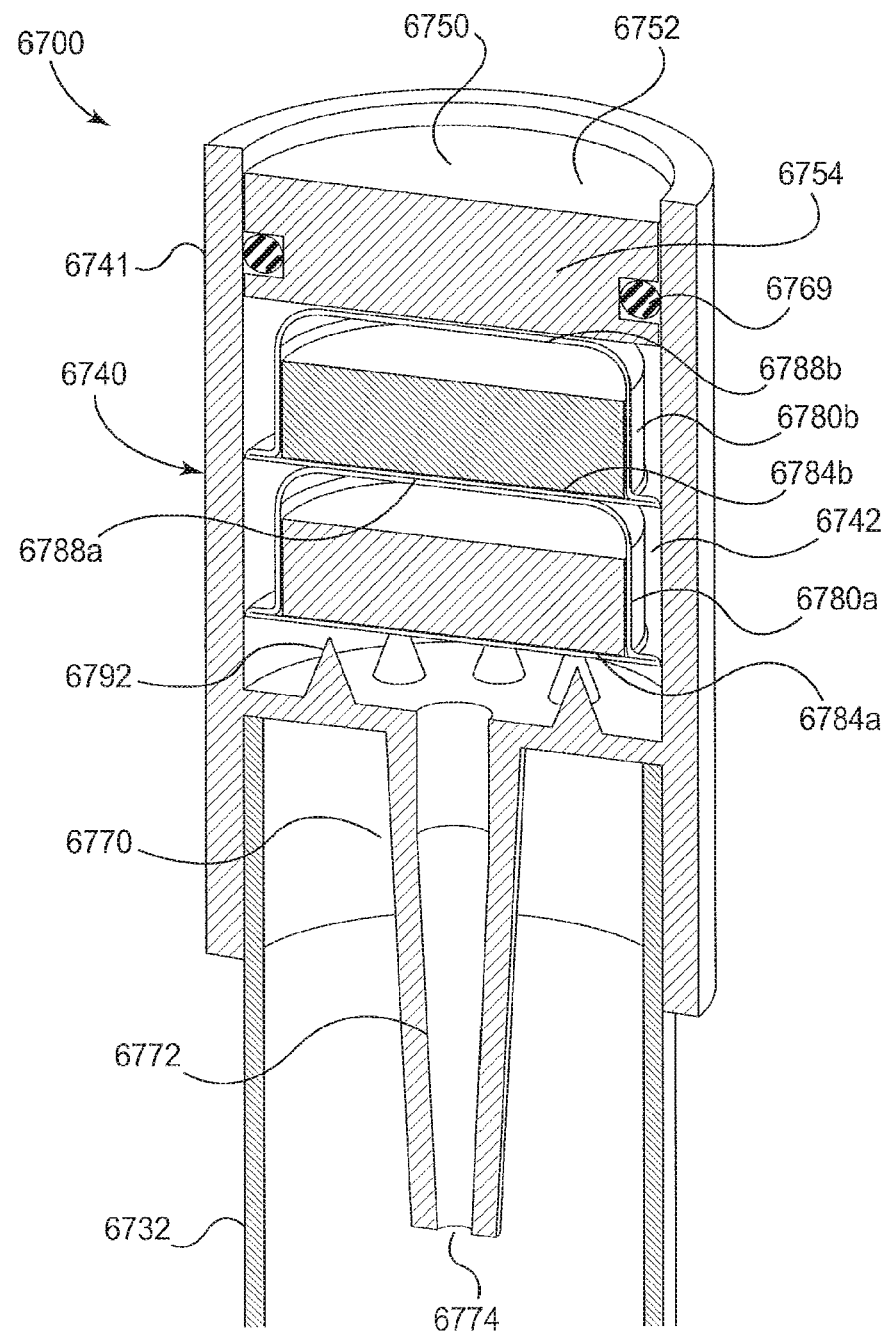
FIGS. 30-32 are side cross-sectional views of a container assembly according to an embodiment, in a first configuration, a second configuration and a third configuration, respectively.
Figure 31:
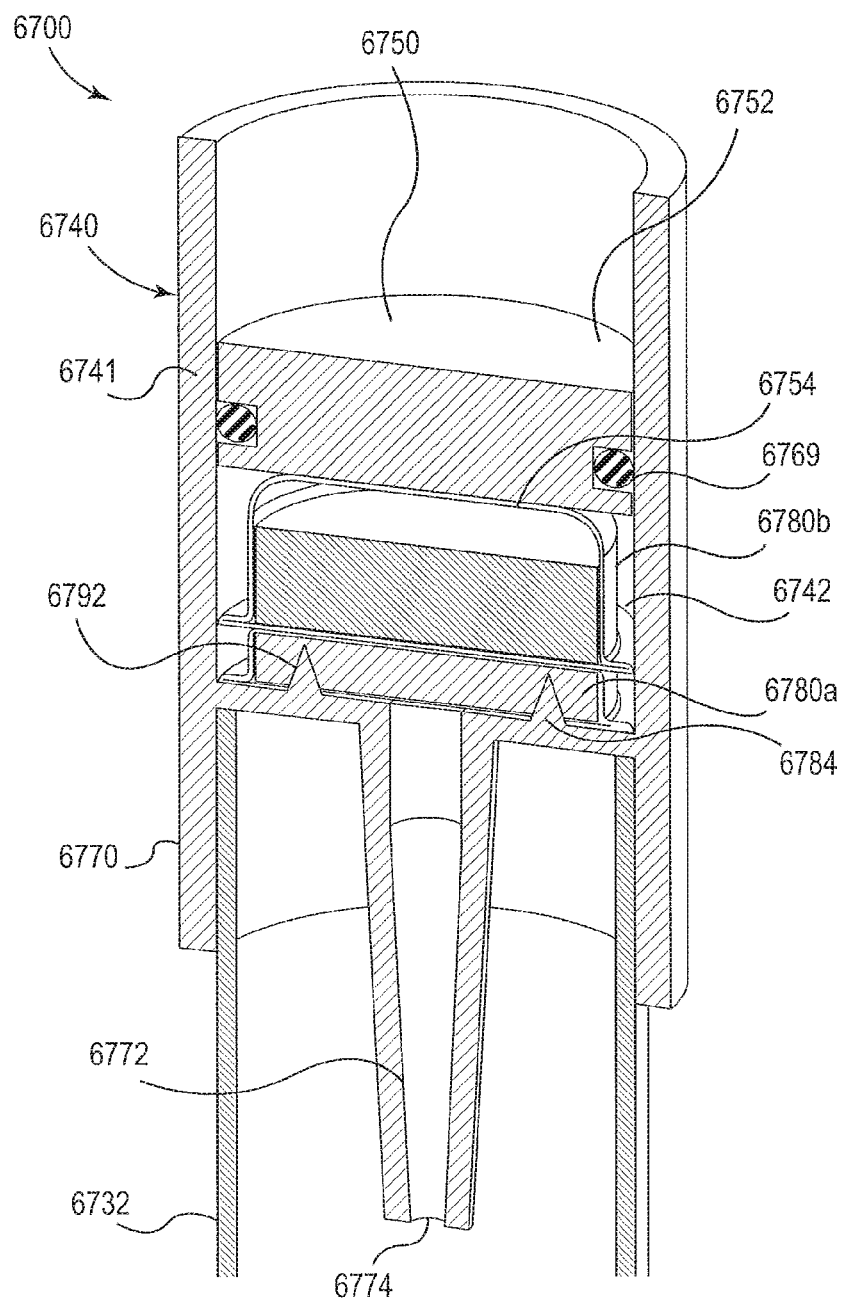
Figure 32:
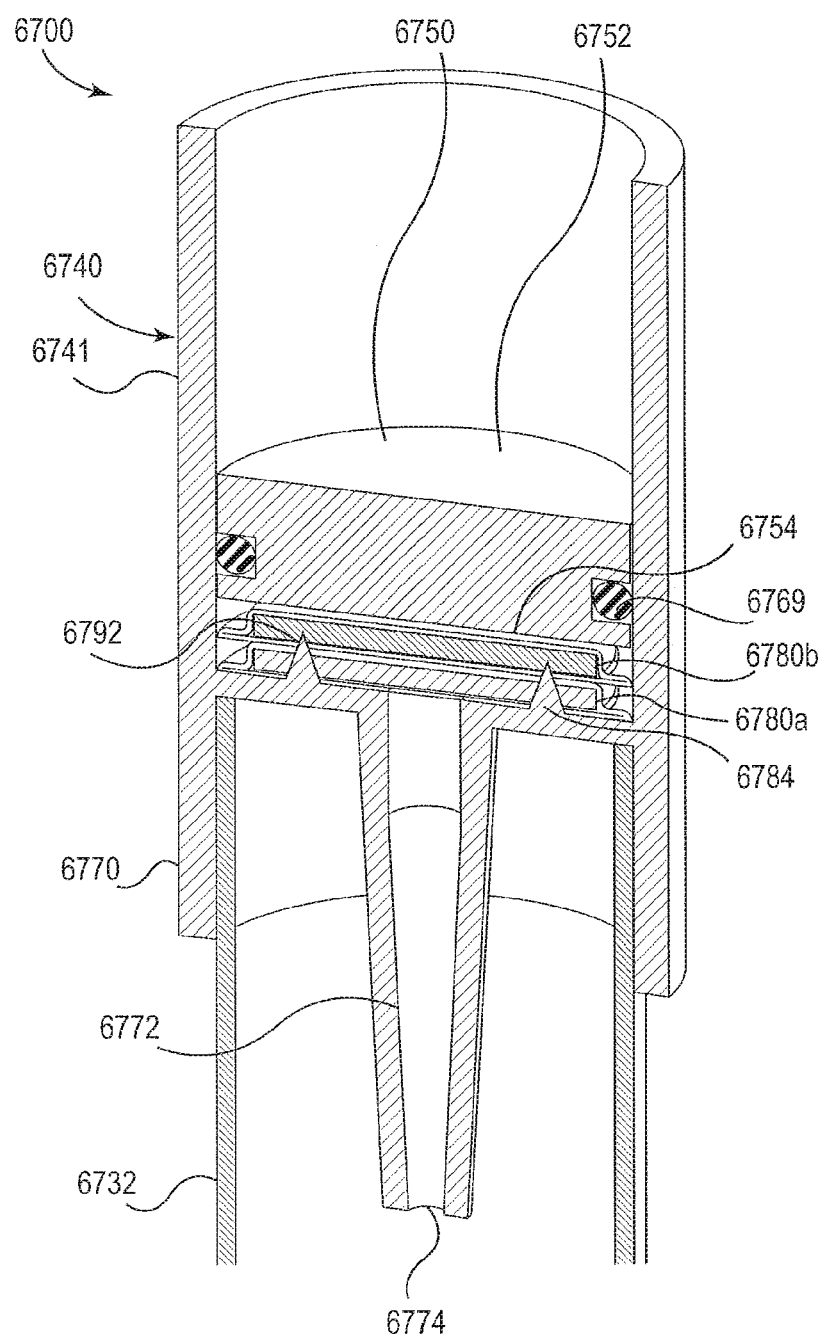

In some embodiments, a reagent module of a container can include a single actuator and a single reagent volume. FIG. 30-32 shows a side cross-section view of a container assembly 6700 according to an embodiment, in a first configuration, a second configuration and a third configuration, respectively. The container assembly 6700 includes a reaction chamber 6732 reversibly coupleable to a reagent module 6740. The reagent module 6740 includes a housing 6741, that defines a reagent volume 6742 that contains a first reagent container 6780a and a second reagent container 6780b. The housing also includes an actuator 6750 disposed in the reagent volume 6742, and a delivery portion 6770. The container assembly 6700 can be used and/or manipulated by any instrument described herein, e.g., instrument 1100, 11000 and/or any components described herein. The container assembly 6700 can also be used to perform any methods described herein, e.g., methods 200 and/or 300.

In some embodiments, the actuator 6750 can include an engagement portion 6752 and a plunger portion 6754. The engagement portion 6752 of the actuator 6750 can be configured to move the plunger portion 6754 within the reagent volume 6742. In some embodiments, the plunger portion 6754 of the actuator 6750 includes a fluid-tight seal 6769 to fluidically isolate the reagent volume 6742 from a volume outside of the housing 6741. In some embodiments, the seal 6769 can be, for example, a gasket, an o-ring, a rubber seal, or any suitable seal.

In some embodiments, the reagent containers 6780a, 6780b can be disposed in the reagent volume 6742, such that the first reagent container 6780a is proximal to the delivery portion 6770 of the housing 6741. In particular, the first reagent container 6780a is disposed between the delivery portion 6770 and the second reagent container 6780b. The first reagent container can contain a first reagent, e.g., the transduction particle. The second reagent container 6780b can be disposed on top of the first reagent container 6780a, such that the frangible portion 6784b of the second reagent container 6780b abuts the bottom portion 6788a of the first reagent container 6780a, and the bottom portion 6788b of the second reagent container 6780b abuts the plunger portion 6754 of the actuator 6750. The second reagent container 6780b can contain a second reagent, e.g., a substrate such as tridecanal. The reagent volume 6742 can also include a series of puncturers 6792 disposed in the reagent volume 6742, that are configured to puncture the frangible portion 6784a of the reagent container 6780a, and the frangible portion 6784b of the reagent container 6780b.

The delivery portion 6770 defines a fluidic pathway 6772 that can define a longitudinal axis that is parallel to a longitudinal axis defined by the reaction chamber 6732. In some embodiments, a diameter of the fluidic pathway 6772 at the outlet 6774 can be smaller than a diameter of the fluidic pathway 6772 at the interface of the reagent volume 6742, such that the fluidic pathway 6772 substantially resembles and/or performs as a nozzle. In some embodiments, the fluidic pathways can be configured such that the reagents are expelled from the outlet 6774 at predefined flow rate, e.g., 1 ml/sec, 2 ml/sec, 3 ml/sec, 4 ml/sec, 5 ml/sec, or any other suitable flow rate, for example, to ensure rapid and complete mixing and/or minimize aeration.

In operation, any suitable instrument can manipulate the engagement portion 6752 of the actuator 6750, such that the plunger portion 6754 is displaced from a first position as shown in the first configuration (FIG. 30) to a second position as shown in the second configuration (FIG. 31) within the reagent volume 6742. The plunger portion 6754 applies a force on the bottom portion 6788b of the second reagent container 6780b, displacing the second reagent container 6780b from a first position to a second position. The second reagent container 6780b communicates the pressure applied by the plunger portion 6754 to the bottom portion 6788a of the first reagent container 6780a, through the frangible portion 6784b. The force causes the frangible portion 6784a of the first reagent container 6780a to press against the series of puncturers 6792, such that the frangible portion 6784a ruptures and the reagent contained therein is communicated through the outlet 6774 of the fluidic pathways 6772 into the reaction chamber 6732.

In the third configuration (FIG. 31), the engagement portion 6752 of the actuator is manipulated further such that the plunger portion 6754 is displaced from the second position to a third position within the reagent volume 6742. Displacement of the plunger portion 6754 to the third position also displaces the second reagent container 6780b from the second position to a third position. In this configuration, the first reagent container 6780a is emptied of the contents contained therein and is in a collapsed state such that the puncturer 6792 penetrates through the bottom portion 6788a of the first reagent container 6780a and ruptures the frangible portion 6784b of the second reagent container 6780b. The second reagent container 6780b therefore is placed in fluid communication with the fluidic pathway 6772 and communicates the reagents container therein, e.g., substrate, through the outlet 6774 and into the reaction chamber 6732.

Figure 33:
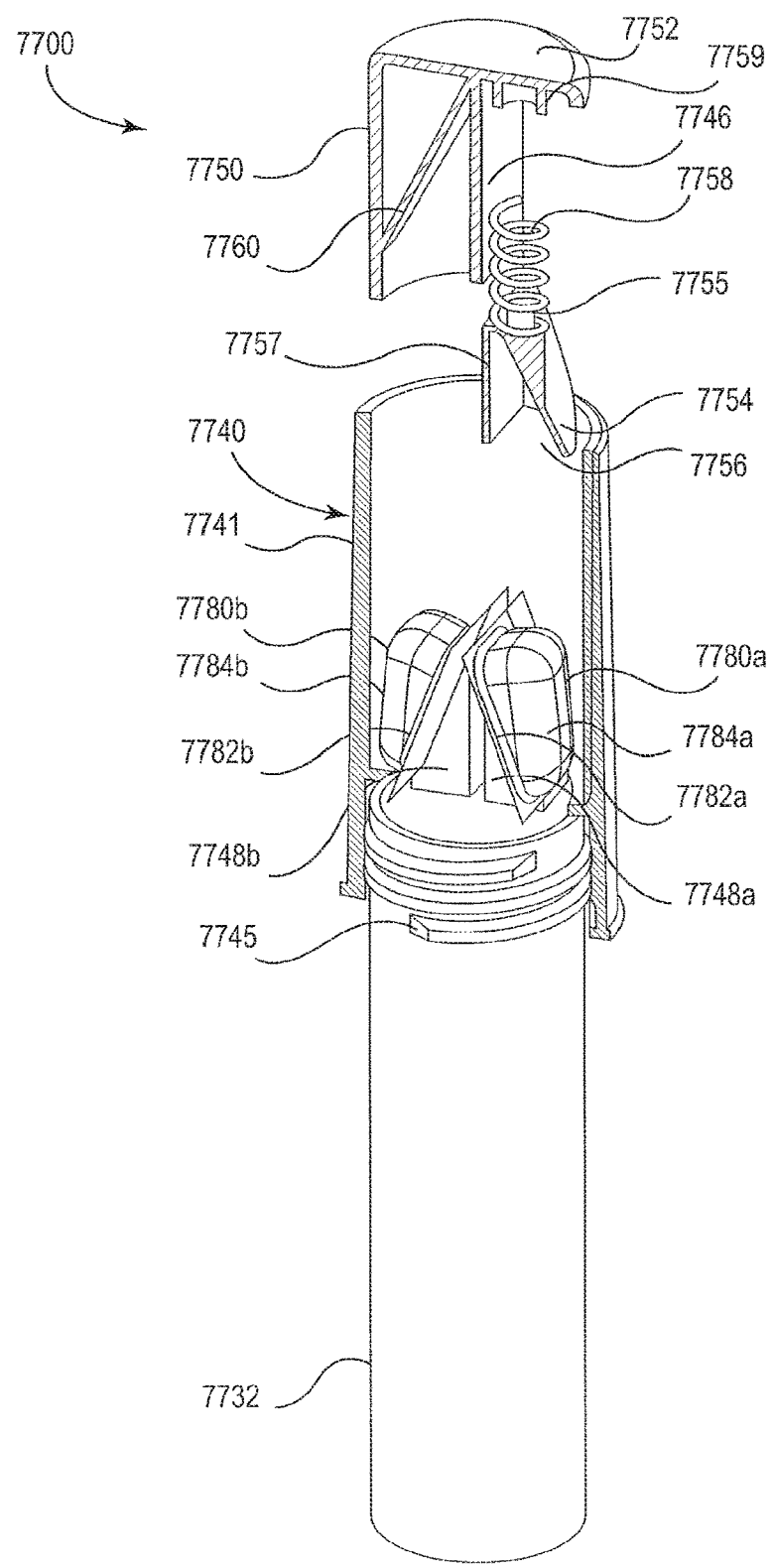
FIG. 33 shows an exploded side cross-section of a container assembly, according to an embodiment.
Figure 34:
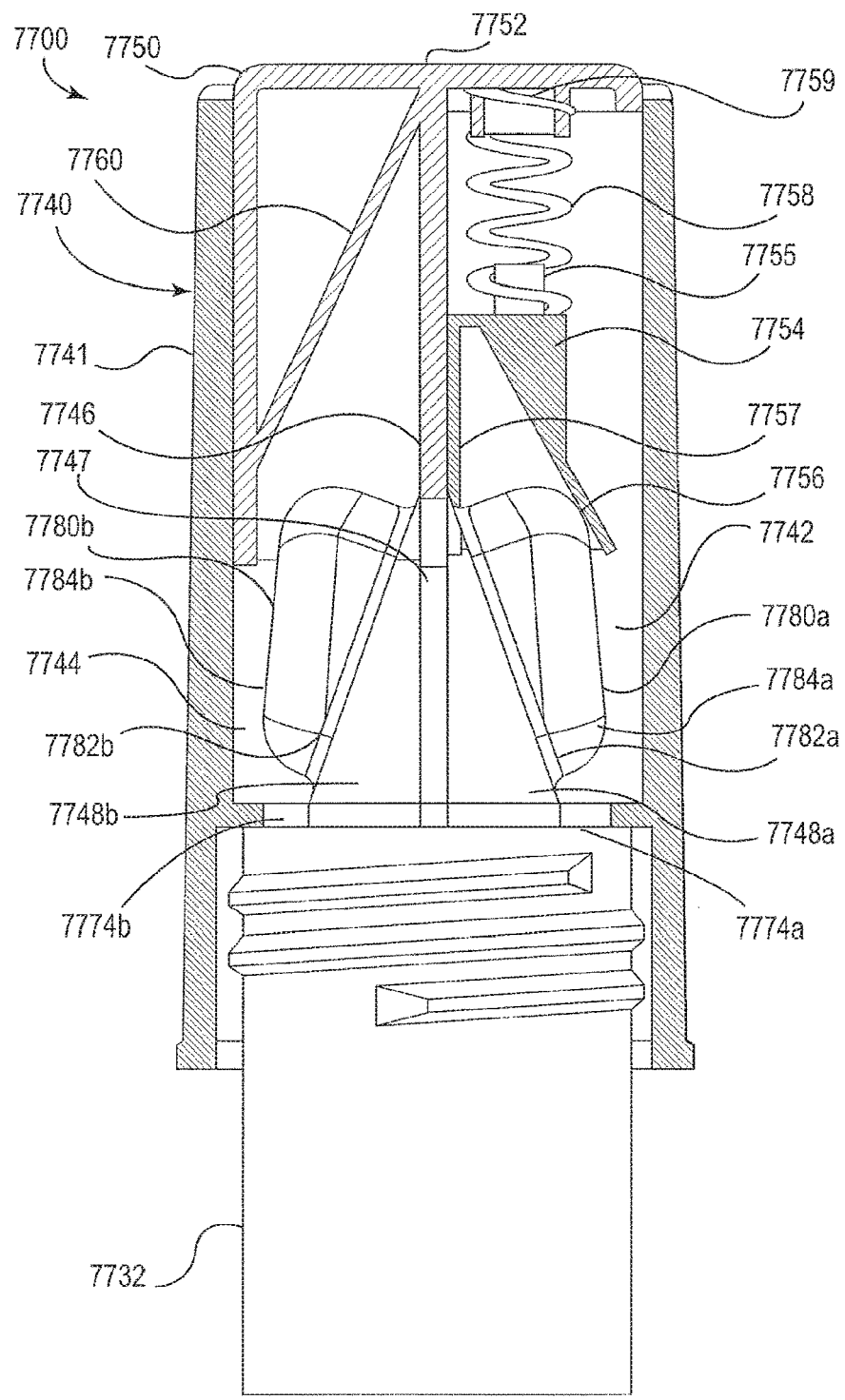
FIGS. 34-36 are side cross-sectional views of the container assembly of FIG. 33 in a first configuration, a second configuration and a third configuration, respectively.
Figure 35:
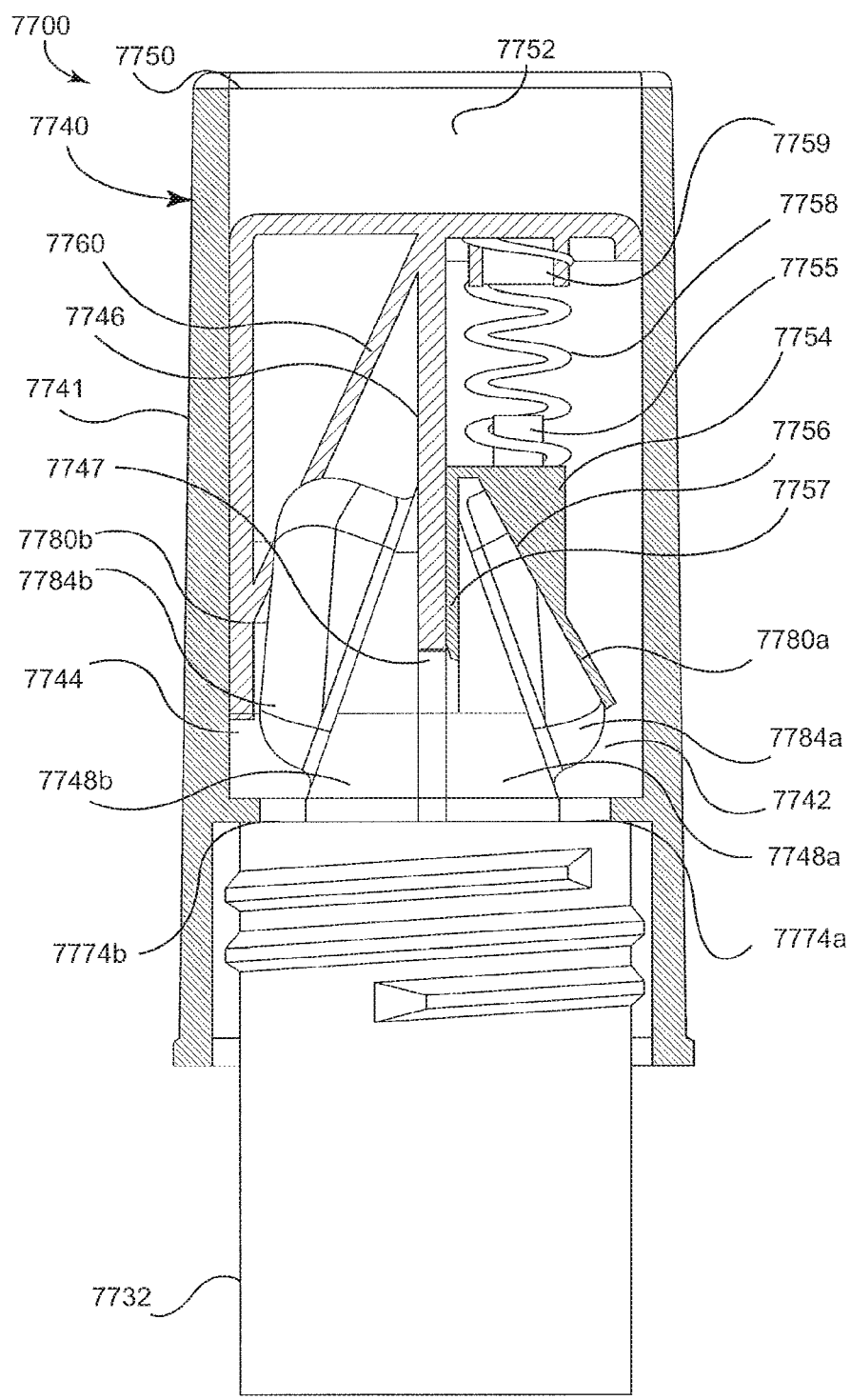
Figure 36:
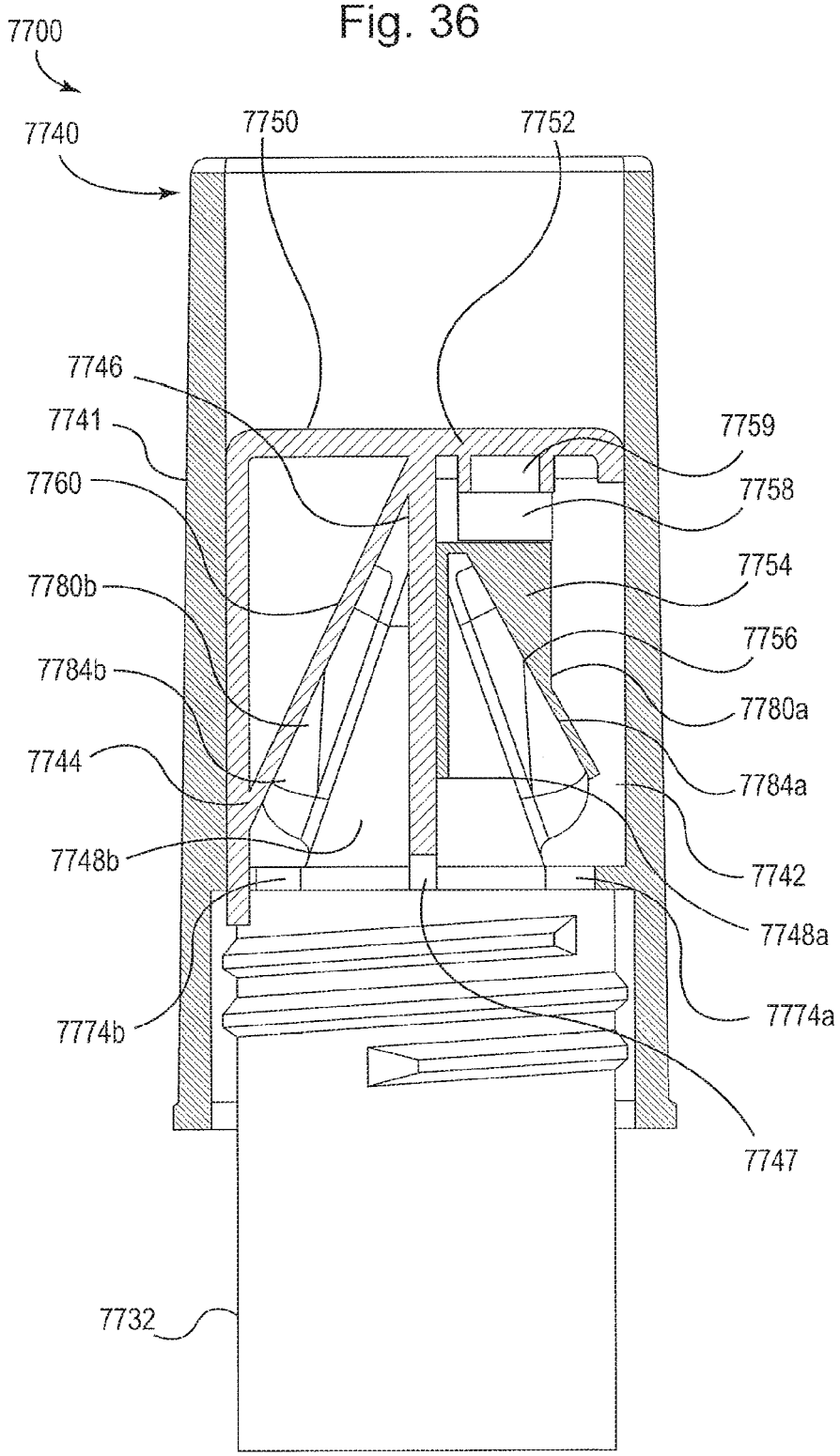

In some embodiments, a container can include a single actuator with staged actuation for delivery of a first reagent (e.g., biologic or abiologic vectors, transduction particles and/or engineered viral vector) and a second reagent (e.g., a substrate) at different stages of actuation. FIG. 33 shows an exploded view of a container assembly 7700 that includes a reaction chamber 7732 and a reagent module 7740. FIGS. 34-36 show the container assembly 7700 in a first configuration, a second configuration and a third configuration, respectively. The reaction chamber 7732 can be removably coupleable to the reagent module 7740. The container assembly 7700 can be used with and/or manipulated by any of the instruments described herein, e.g., instrument 1100, 11000 and/or any of the components described herein. The container assembly 7700 can also be used to perform any of the methods described herein, e.g., methods 200 and 300.

The reaction chamber 7732 can be formed from a light weight, rigid and inert material, e.g., plastics. At least a portion of the reaction chamber 7732 can be partially transparent, e.g., to allow detection and/or viewing of the internal volume of the reaction chamber 7732, for example, to detect a luminescence reaction occurring therein. In some embodiments, the reaction chamber 7732 can be shaped as a cylinder with a rounded bottom, or flat base. In some embodiments, the reaction chamber 7732 can have any other suitable shape, e.g., square, rectangular, oval, polygonal, etc. In some embodiments, the reaction chamber 7732 can have a diameter of 12 mm and a height of 75 mm. In some embodiments, the container assembly 7700 can include one or more solutions/reagents (e.g., bacterial nutrient solution, buffers, surfactants, transduction particle, and/or antibiotics), predisposed within the reaction chamber 7732. The reaction chamber 7732 can include threads 7745 for removably coupling with the reagent module 7740. In some embodiments, the reaction chamber 7732 can be removably coupled to the reagent module 7740 via a snap-fit, friction fit, or any other suitable mechanism.

As shown in FIG. 33, the reagent module 7740 can include a housing 7741. The housing 7741 can be formed from a lightweight and rigid material, e.g., injection molded plastic. The housing 7741 includes a first compression support 7748a and a second compression support 7748b. The compression supports 7748a, 7748b are configured to fixedly or removably mount a first reagent container 7780a and a second reagent container 7780b, respectively, and provide a rigid support during compression to the first reagent container 7780a and the second reagent container 7780b, as described further below. The compression supports 7748a, 7748b can include features for mounting the reagent containers 7780a, 7780b thereto. Such mounting features can include, for example, notches, grooves, detents, indent, slot, and/or an adhesive surface. A surface of the each of the compression supports 7748a, 7748b on which the respective reagent container 7780a, 7780b are mounted, are angled with respect to a longitudinal axis defined by the housing 7741 and/or the reaction chamber 7732. The angled surface can be beneficial, for example, to allow smooth (e.g., even and/or controlled) flow of the reagent and/or substrate and with low dead volume, from the reagent containers 7780a, 7780b into the reaction chamber 7732.

The reagent module 7740 includes an actuator 7750, that is configured to slide within an internal volume defined by the housing 7741. The actuator 7750 is configured such that a sidewall of the actuator 7750 and a sidewall of the housing 7741 form a fluid-tight seal. Thus, in use, the actuator 7750 can be displaced within the housing 7741 while maintaining a substantially fluid-tight seal. As shown in FIG. 34, the housing 7741 and the actuator 7750 can be configured to define a first reagent volume 7742 and a second reagent volume 7744 that are separated at least partially by a sidewall 7746 (FIG. 34-36), and at least partially by a sidewall of the compression supports 7748a, 7748b. The actuator includes an engagement portion 7752 configured to be manipulated by an instrument, e.g., instrument 1100 or any other instrument shown and described herein.

The actuator 7750 includes a first compression member 7754 that can be shaped to resemble, for example, an angled clip. The first compression member 7754 can be a separate component that can be formed from a rigid material, e.g., aluminum, steel, stainless steel, or plastics. The first compression member 7754 has an engagement portion 7755 and a compression portion 7756, that is inclined at an angle away from the longitudinal axis defined by the housing 7741. In particular, the angle is substantially similar to the angle defined by the angled surface of the first compression support 7748a. The first compression member 7754 also includes a sliding portion 7757 that abuts the sidewall 7746 of the actuator 7750 and is configured to slide in a space 7747 between the sidewall 7746 and the first compression support 7748a as described further below. The engagement portion 7755 of the first compression member 7754 can include an engagement spring 7758 coupled to the engagement portion 7755. The engagement spring 7758 can be a compression spring, for example, a helical spring, coil spring, Belleville spring, or tapered spring and can include washers (not shown) for mounting on the engagement portion 7755. An end of the engagement spring 7758 distal to the first compression member 7754 can be coupled to the actuator 7750, for example, mounted on a pin, mandrel, or the likes, further configured such that engaging the actuator 7750, engages the engagement spring 7758 and the first compression member 7754.

The actuator 7750 can also include a second compression member 7760 that can be an integral part of the actuator 7750, for example, formed in the same injection molded process. The second compression member 7760 can be shaped to resemble an inclined plane that is angled away from the longitudinal axis defined by the housing 7741. The angle can be substantially similar to the angle defined by the inclined surface of the second compression support 7748b. In some embodiments, the first compression member 7754 and/or the second compression member 7760 can include one or a series of puncturers, e.g., thorns, barbs, pins, or any other suitable puncturing member to puncture a frangible portion of the reagent containers 7780a, 7780b, as described herein.

The housing 7741 can also include a first fluidic outlet 7774a and a second fluid outlet 7774b for communicating reagents from the first reagent volume 7742, e.g., the biologic or abiologic vectors, transduction particle and/or engineered viral vector, and the second reagent volume 7744 e.g., substrate, into the reaction chamber 7732. The fluidic outlets 7774a, 7774b can be an opening and/or space between the compression supports 7748a, 7748b and a sidewall of the housing 7741. In some embodiments, the housing 7741 can include fluidic pathways, e.g., nozzles, angled nozzles, tubes, and/or any other suitable fluid conduit, e.g., to facilitate rapid mixing and/or minimize aeration, as described herein.

The first reagent container 7780a and the second reagent container 7780b can be disposed on the first compression support 7748a and the second compression support 7748b, respectively as described before. The reagent containers 7780a, 7780b can each include a sidewall 7782a, 7782b and a frangible member 7784a, 7784b that collectively define an internal volume. The internal volume of the reagent containers can be completely or partially filled with a reagent, e.g., the first reagent container 7780a can contain transduction particles (e.g., transduction particle 160 or any other transduction particles described herein), that can include an engineered nucleic acid (e.g., engineered nucleic acid 170) formulated to cause the target cell (e.g., bacteria) to produce a plurality or reporter molecules (e.g., luciferase). The second reagent container 7780b can contain a substrate, e.g., tridecanal, that can interact with the reporter molecule, e.g., luciferase, to trigger, catalyze, produce and/or enhance the production of a measurable signal, e.g., via a luminescence reaction.

The reagent containers 7780a/b can be constructed from materials that are substantially impermeable to and/or substantially chemically inert from the substance contained therein, e.g., transduction particle, substrate, antibiotics, buffers, surfactants, or any other reagent that can be required for the detection assay. In this manner, the reagents can be stored in the reagent containers 7780a/b for extended periods of time. For example, the reagent containers 7780a/b side wall 7782a/b can be formed from a flexible and inert material, e.g., blister plastic, aluminum foil, or any other suitable material. Moreover, in some embodiments, the frangible member 7784a/b can be constructed from a material having certain temperature characteristics such that the desired properties and integrity of the frangible member 7784a/b are maintained over a certain temperature. For example, in some embodiments, it can be desirable to store the reagent container 7780a/b containing reagent or substrate in a refrigerated condition or it can be desirable to manufacture the reagent container 7780a/b by thermally laminating the frangible member 7784a/b. In such embodiments, the frangible member 7784a/b can be selected such that the refrigeration condition and/or thermal lamination condition do not substantially degrade the desired properties and integrity of the frangible member 7784a/b for the intended application. In some embodiments, the frangible member 7784a/b can be constructed from a polymer film, such as any form of polypropylene. In some embodiments, the frangible member 7784a/b can be constructed from bi-axially oriented polypropylene (BOP). In some embodiments, the frangible member 7784a/b can be constructed from aluminum. The frangible portions 7784a/b of the reagent containers can be configured to rupture when compressed, e.g., by the compression members 7754/7760 of the actuator 7750 as described further below, and release the reagent contained therein.

As shown in FIG. 34 the container assembly 7700 can initially be maintained in a first configuration, in which the reagent module 7740 is coupled to the reaction chamber 7732, and the actuator 7750 is in a first position. The first compression member 7754 is in a first position, in which the engagement portion 7756 is in contact with the frangible portion 7784a of the first reagent container 7780a but not applying any compressive force, and the engagement spring 7758 is fully uncompressed. The second compression member 7760 is also in a first position wherein the second compression member is not contacting the frangible portion 7784b of the second reagent container 7780b.

In the second configuration (FIG. 35), the engagement portion 7752 of the first actuator 7750 is manipulated to displace the actuator 7750 within the housing 7741 from the first position, to a second position. The displacement of the actuator 7750 urges the engagement spring 7758 to compress and exert a force on the first compression member 7754. The force displaces the first compression member 7754, from the first position to a second position as shown in FIG. 35, wherein the sliding portion 7757 of the first compression member 7754 slides with the sidewall 7746 into the opening 7747 between the first and second compression supports 7748a, 7748b. The engagement portion 7756 of the first compression member 7754 exerts a compressive force on the frangible portion 7784a of the first reagent container 7780a, such that the frangible portion 7784a ruptures, releasing its contents (e.g., transduction particles) into the first reagent volume 7742. The reagent then flows through the first outlet 7774a and into a solution in the reaction chamber 7732, e.g., a patient sample containing target cell. The second compression member 7760 is also displaced from the first position to a second position, wherein it is near the frangible portion 7784b of the second reagent container 7780b and/or contacting the frangible portion 7784b without rupturing it.

In the third configuration (FIG. 36), the engagement portion 7752 of the actuator 7750 is manipulated to displace within the housing 7741 from the second position to a third position. The displacement of the actuator 7750 further urges the engagement spring 7758 to compress and exert a force on the first compression member 7754. In this position further displacement of the first compression member 7754 is prevented by the first compression support 7748a, and the engagement spring 7758 is substantially compressed. The second compression member 7760 is also displaced from the second position to a third position, wherein the second compression member 7760 exerts a compressive force on the frangible portion 7784b of the second reagent container 7780b. This causes the frangible portion 7784b to rupture and release its contents, e.g., substrate into the second reagent volume 7744. The reagent then flows through the second outlet 7774b and into a solution in the reaction chamber 7732, e.g., a sample containing target cell and reporter molecules produced by the target cells.

Figure 37:
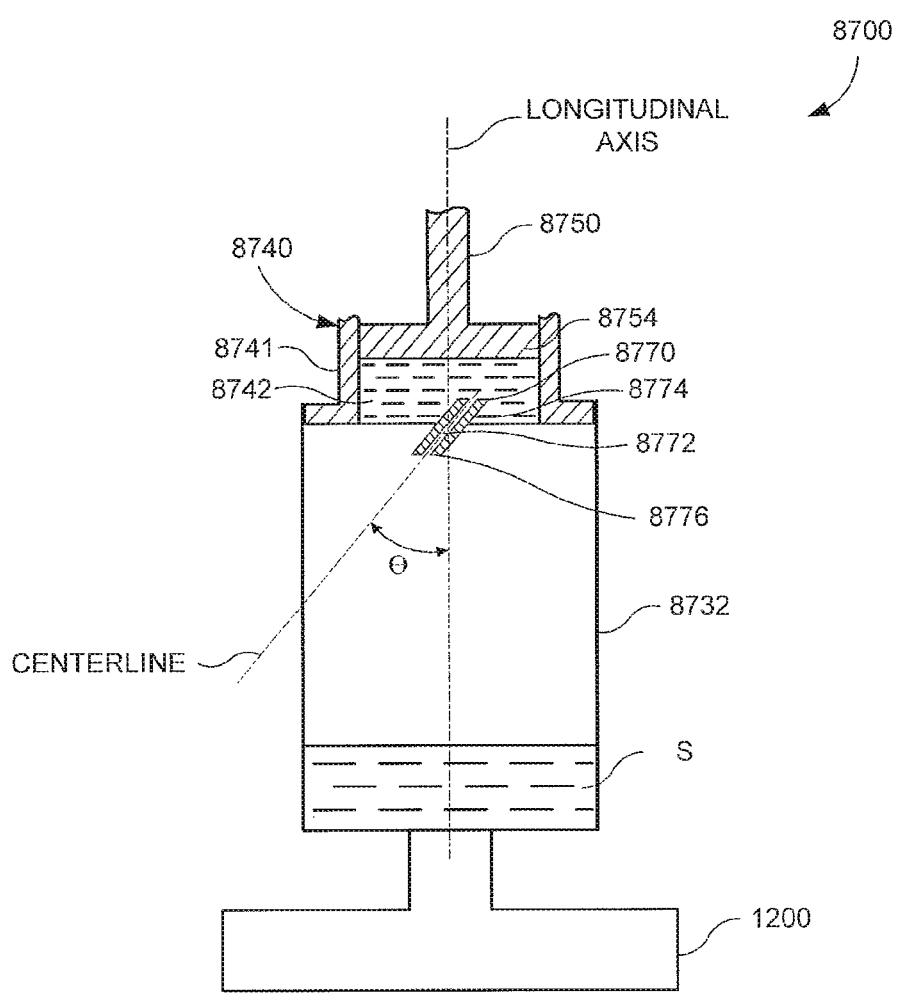
FIGS. 37 and 38 are side cross-sectional schematic illustrations of a container assembly according to an embodiment in a first configuration and a second configuration, respectively.
Figure 38:
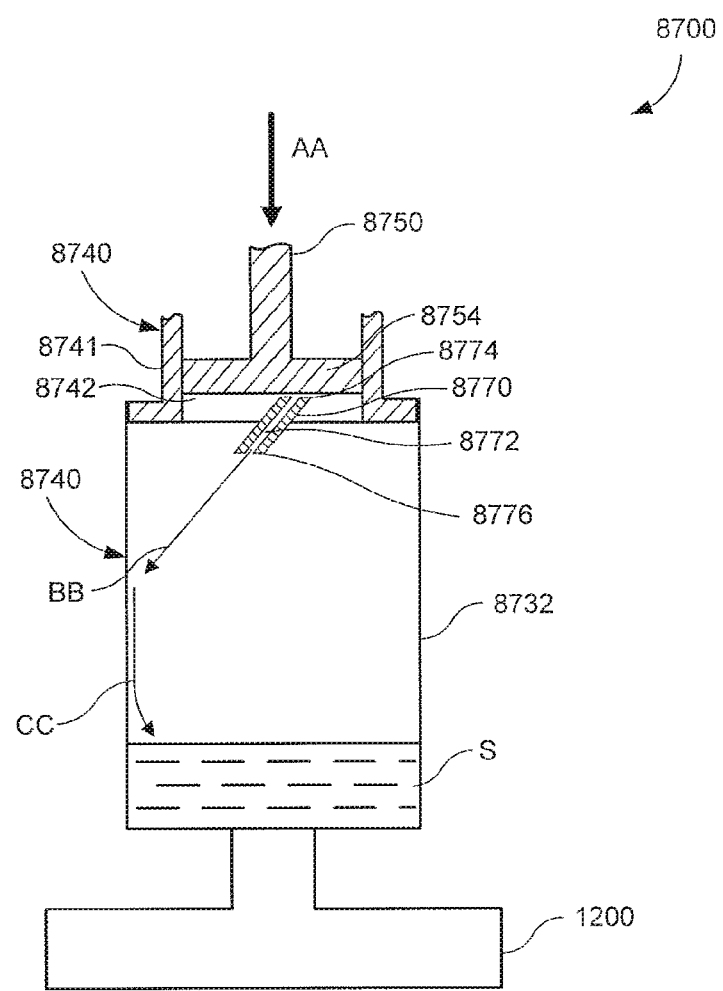

As described above, in some embodiments, a delivery portion can be configured to deliver one or more reagents into a reaction chamber in a manner that promotes mixing, that minimizes aeration, overspray and/or undesirable turbulence. For example, in some embodiments, a reagent module of a container can include a delivery portion that is inclined and/or angularly offset with respect to a longitudinal axis of the reagent module and/or the reaction chamber. Such an arrangement can direct a flow of reagent (e.g., transduction particles, substrate or the like) in a manner that improves mixing, detection or the like. In particular, FIGS. 37-38 show a side cross-sectional schematic view of a container assembly 8700 according to an embodiment, in a first configuration and a second configuration, respectively. The container assembly 8700 can be used with and/or manipulated by any of the instruments described herein, e.g., instrument 1100, 11000 and/or any of the components described herein. The container assembly 8700 can also be used to perform any of the methods described herein, e.g., methods 150, 200 and 300.

The container assembly 8700 includes a reaction chamber 8732 that is reversibly coupleable to a reagent module 8740. The reaction chamber 8732 can have a sample S disposed therein, e.g., a sample solution including a patient sample, target cell, transduction particles, and/or reporter molecules. In use, the container assembly 8700 can be operatively coupled to a detector 1200 such that reaction chamber 8732 is in communication (e.g., optical communication) with the detector 1200. Although the embodiments described herein have been shown as being optically coupled to the detector 1200, any other detector described herein can be used.

The reagent module 8740 includes a housing 8741, a delivery member 8770 and an actuator 8750. The housing 8741 defines a reagent volume 8742, which can contain a reagent disposed therein. The reagent can be any suitable reagent, such as any of the substrates described herein.

The actuator 8750 includes a plunger portion 8754 configured to be in fluid communication with the reagent disposed in the reagent volume 8742. The actuator 8750 can be configured to convey the reagent from the reagent volume 8742 to the reaction chamber 8732 through the delivery member 8770 (e.g., via a fluidic pathway 8772). The delivery member 8770 includes a first portion 8774 that is disposed substantially inside the reagent volume 8742 and proximal to the plunger. The delivery member 8770 also includes a second portion 8776 disposed substantially inside the reaction chamber 8732, when the reaction chamber 8732 is coupled to the reagent module 8740.

The delivery member 8770 is angularly offset with respect to a longitudinal axis of the reagent module 8740 and/or the reaction chamber 8732. More particularly, as shown in FIG. 37, the centerline of the fluidic pathway that defines the axis of the delivery member 8770 is oriented at an angle θ away from the longitudinal axis. In some embodiments, the angle θ can be about 30 degrees. In some embodiment, the angle θ can be between about 15-45 degrees.

In operation, the actuator 8750 can be manipulated by applying a force on the actuator 8750 as shown by the arrow AA in FIG. 38, e.g., using a manipulation mechanism of the instrument 1100. This urges the plunger portion 8754 to be displaced within the reagent volume 8742 from a first position, as shown in the first configuration (FIG. 37), to a second position as shown in the second configuration (FIG. 38). The plunger portion 8754 conveys and/or expels the reagent (e.g., substrate) contained in the reagent volume 8742 through the fluidic pathway 8772. Similarly stated, the plunger portion 8754 is moved within the reagent volume along the longitudinal axis to produce a flow of a reagent from the reagent volume via the fluidic pathway 8772.

As shown in the FIG. 38, the inclined orientation of the delivery portion 8770 causes the expelled reagent to follow an inclined path as shown by arrow BB (FIG. 38), such that the reagent stream impinges on a sidewall of the reaction chamber 8732. The reagent stream then flows down the sidewall of the reaction chamber 8732 as shown by arrow CC (FIG. 38) and mixes with the sample S at a lower fluid velocity, thereby minimizing and/or eliminating aeration and/or the production of bubbles within the sample. Minimizing aeration can, enable mixing of the reagent with the sample S and increase the quality of the signal that is detected by the detector 1200. For example, in some embodiments, the container assembly 8700 can be used in conjunction with a reporter system and reagent (e.g., substrate) that are collectively formulated to produce a flash reaction in response to the addition of the substrate to the sample within which reporter molecules have been expressed. In such embodiments, the arrangement of the delivery member 8770 can allow the substrate to sufficiently mix with the sample, while also minimizing aeration of the sample, the production of bubbles, excessive splashing, or the like, all of which can be detrimental to the optical detection to be completed a short time period (e.g., within seconds) after delivering the substrate.

Figure 39:
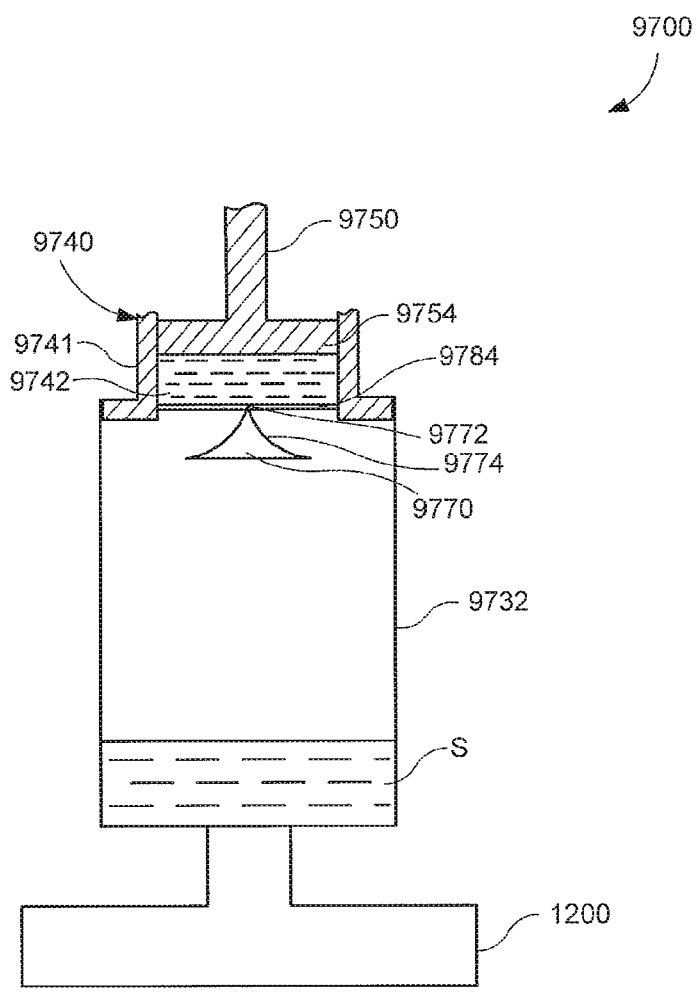
FIGS. 39 and 40 are side cross-sectional schematic illustrations of a container assembly according to an embodiment in a first configuration and a second configuration, respectively.
Figure 40:
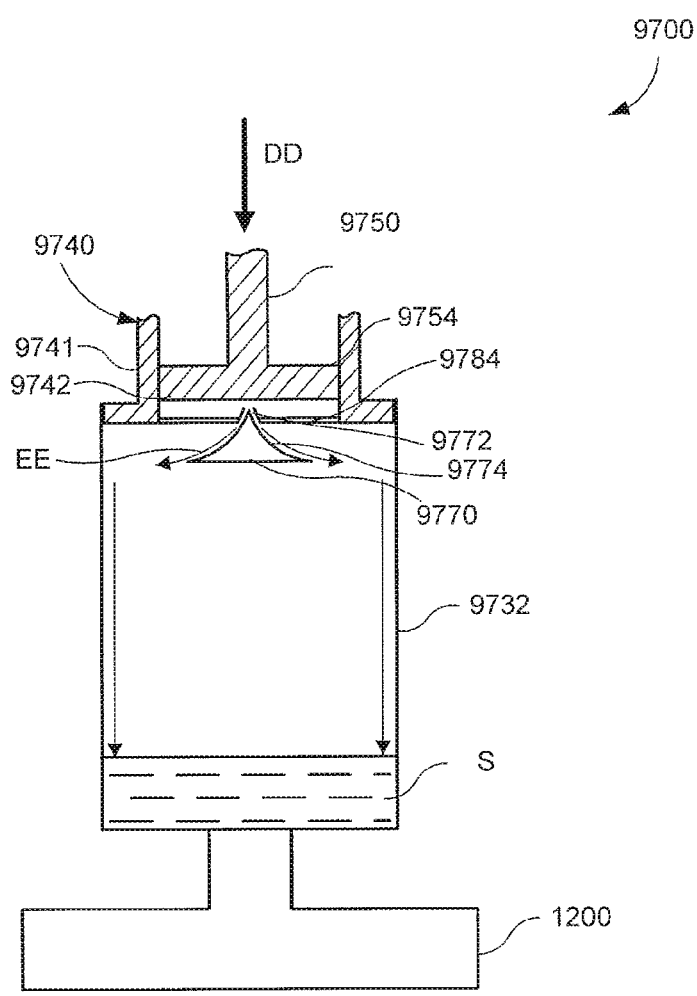

Although the reagent module 8740 is shown and described above as including a single delivery member that directs the flow of a reagent along a portion of a side wall of the reaction chamber 8732, in other embodiments, a reagent module 8740 can include multiple different delivery members and/or a delivery member with multiple exit points to facilitate rapid delivery of the reagent therein, while also minimizing aeration, the production of bubbles or the like. In some embodiments, a reagent module of a container can include a delivery member that is configured to produce an annular flow of a reagent disposed in the reagent module, such that the reagent flows substantially circumferentially about the sidewall of the reaction chamber. For example, FIGS. 39-40 show a side cross-sectional view of a container assembly 9700 according to an embodiment, in a first configuration and a second configuration. The container assembly 9700 includes a reaction chamber 9732 reversibly coupleable to a reagent module 9740. The container assembly 9700 is coupled to a detector 1200 such that reaction chamber 9732 is in optical communication with the detector 1200. The container assembly 9700 can be used and/or manipulated by any instrument described herein, e.g., instrument 1100, 11000 and/or any components described herein. The container assembly 9700 can also be used to perform any methods described herein, e.g., methods 150, 200 and/or 300. In some embodiments, the container assembly 9700 can be used to detect a signal produced by a flash luminescence reaction. While the embodiments described herein have been shown optically coupled to the detector 1200, any other detector described herein can be used.

The reaction chamber 9732 can have a sample S disposed therein, e.g., a sample solution including a patient sample, target cell, transduction particles, and/or reporter molecules. The reaction chamber 9732 can be similar to any of the reaction chambers described herein, and is therefore not described in detail.

The reagent module 9740 includes a housing 9741 defining a reagent volume 9742, which can have a reagent disposed therein, e.g., a substrate. The housing 9741 also includes an actuator 9750 disposed in the reagent volume 9742. The reagent module 9740 includes a frangible portion 9784 and a delivery member 9770.

The actuator 9750 includes a plunger portion 9754 in fluid communication with the reagent disposed in the reagent volume 9742. The plunger portion 9754 is configured to move within the housing 9741 to convey the reagent from the reagent volume 9742 to the reaction chamber 9732 through the frangible portion 9784.

The delivery member 9770 is configured to define a puncturing portion 9772 and a rounded and/or curved sidewall 9774. In some embodiments, the sidewalls 9774 can be tapered, contoured, and/or include gradations. Although the delivery portion 9770 is shown as being located substantially inside the reaction chamber 9732, in other embodiments, a substantial portion of the delivery member 9770 can be disposed within and/or coupled to the reagent module 9740. The delivery member 9770 can be an integral part of either the reaction chamber 9732 or the reagent module 9740.

As shown, when the reagent module 9740 is in the first configuration (FIG. 39), the puncturing portion 9772 is in contact with the frangible portion 9784 but is not applying any puncturing force on the frangible member 9784. Accordingly, the reagent within the reagent volume 9742 is maintained in fluidic isolation from the reaction chamber 9732. When the reagent module 9740 is moved to the second configuration (FIG. 40), a force is applied on the actuator 9750 in a direction as indicated by arrow DD. This causes the plunger portion 9754 to displace from the first position to a second position. The displacement of the plunger portion 9754 exerts a force on the frangible member 9784 (via the reagent). This causes the frangible member to press against the puncturing portion 9772 of the delivery portion and puncture (FIG. 40), thereby puncturing the frangible portion 9784. The contour and/or shape of the delivery member 9770 produces an annular flow of the reagent around the entire sidewall 9774 of the reaction chamber 9732, as shown by arrow EE. The reagent stream can then flow down along a sidewall of the reaction chamber 9732, thereby minimizing and/or eliminating aeration, the production of bubbles or the like.

Figure 41:
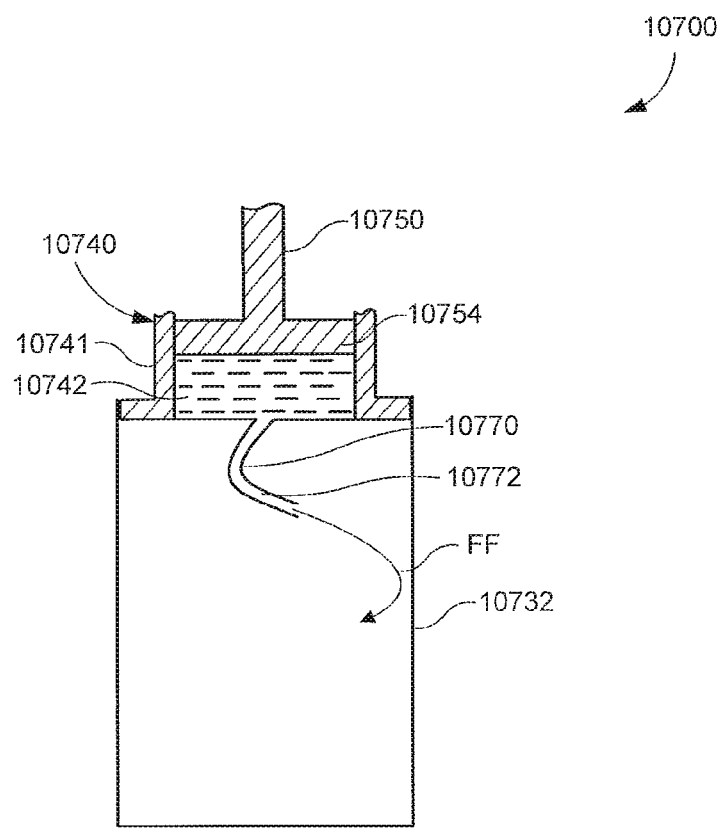
FIG. 41 is side cross-sectional schematic illustration of a container assembly, according to an embodiment.

In some embodiments, a reagent module of a container can include a delivery portion or delivery member that is curved. FIG. 41 shows a side cross-section of a container assembly 10700 according to an embodiment. The container assembly 10700 includes a reaction chamber 10732 reversibly coupleable to a reagent module 10740. The reagent module 10740 includes a housing 10741 defining a reagent volume 10742, which can have a reagent disposed therein, e.g., a substrate. The housing also includes an actuator 10750 disposed in the reagent volume 10742. The container assembly 10700 includes a delivery member 10770. The container assembly 10700 can be used and/or manipulated by any instrument described herein, e.g., instrument 1100, 11000 and/or any components described herein. The container assembly 10700 can also be used to perform any methods described herein, e.g., methods 150, 200 and/or 300. In some embodiments, the container assembly 10700 can be used to detect a signal produced by a flash luminescence reaction.

The actuator 10750 includes a plunger portion in fluid communication with the reagent, e.g., a substrate, disposed in the reagent volume 10742. The plunger portion 10754 is configured to displace within the reagent volume 10742 to convey the reagent from the reagent volume 10742 to the reaction chamber 10732 through the delivery portion 10770

The delivery member 10770 is shaped such that it defines a curved fluidic pathway 10772. The curved fluidic pathway 10772 is configured such that the reagent is dispensed from the fluidic pathway in a swirling motion. The swirling motion can, for example, create turbulence in the reagent flow that can, for example, enhance mixing of the reagent with a sample contained in the reaction chamber 10732. In some embodiments, the curved fluidic pathways 10772 can cause the reagent to impinge on a sidewall of the reaction chamber. The reagent can then flow along the sidewall of the container to reach the sample at a lower velocity, for example, to minimize aeration.

Figure 42:
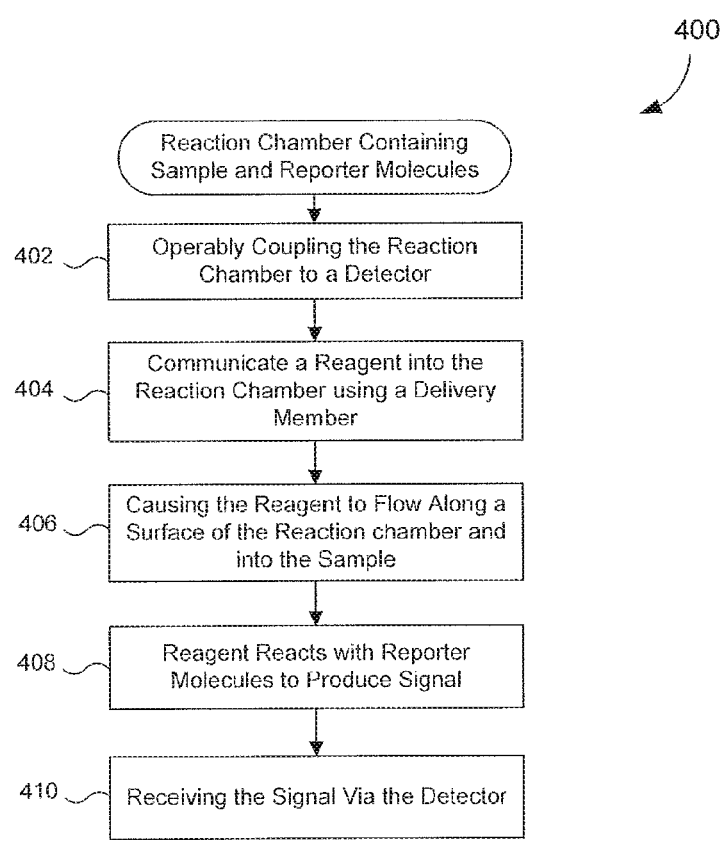
FIG. 42 illustrates a flow diagram of a method of signal detection, according to an embodiment.

The container assembly 4700 or any of the container assemblies described herein, can be operably coupled to a detector of any suitable type to detect a signal produced and/or enhanced by the interaction of a reporter molecule (e.g., luciferase) with a substrate (e.g., tridecanal). As described above, in some embodiments, methods of detection can include detection of a signal produced by a flash luminescence reaction. Such methods can include, for example, directing a flow of a reagent (e.g., substrate) in a manner to enhance the accuracy with which the signal is read. Similarly stated, such methods can include, for example, directing a flow of a reagent (e.g., substrate) in a manner to minimize undesirable turbulence, aeration, the production of bubbles or the like. For example, FIG. 42 shows a method 400 for detecting target cells using a container assembly and a detector. The method 400 can be used with any of the container assemblies described herein. The detector can be the detector 1200, the detector assembly 11200, or any other detector described herein. A reaction chamber of the container assembly can include a sample disposed therein. The sample can be, for example, a sample solution containing a patient sample target cell (e.g., a nasal swab potentially containing MRSA), biologic or abiologic vector such as a transduction particle (e.g., any of the transduction particles described herein), and a series of reporter molecules produced in accordance with any of the reporter systems disclosed herein.

The method includes operably coupling the reaction chamber of the container to a detector, 402. A reagent is then communicated into the reaction chamber using a delivery member, 404. In some embodiments, the reagent can be any suitable substrate. In some embodiments, the reagent can include a 6-carbon aldehyde (hexanal), a 13-carbon aldehyde (tridecanal) and/or a 14-carbon aldehyde (tetradecanal), inclusive of all the varying carbon chain length aldehydes therebetween. In some embodiments, the reagent can be formulated to include Tween 20 or any other surfactant, tridecanal or other aldehydes, and adjusted to a particular pH. The reagent can be disposed in a reagent module of the container, e.g., a reagent module 4740 of the container assembly 4700, or any other reagent module as described herein.

The delivery member can be, for example, the delivery portion 3770, the delivery member 4770, or any other structure and/or mechanism that defines a flow path through which the reagent can be conveyed. The reagent is conveyed in a manner to flow along a surface of the reaction chamber and into the sample, 406. In this manner, as described herein, the delivery of the reagent into the sample can be performed in a manner that enhances the accuracy with which the signal is read. In some embodiments, the conveying can include conveying the reagent in a direction non-perpendicular to a surface of the sample. In some embodiments, the reagent is conveyed at a flow rate of at least one milliliter per second. In some embodiments, the conveying includes moving a plunger in a direction within a reagent volume, a first end portion of the delivery member disposed within the reagent volume and a second end portion of the delivery member disposed within the reaction chamber. In some embodiments, the movement of the delivery member conveys the member in an exit direction non-parallel to the direction, e.g., the delivery portion 4770.

On reaching the sample, the reagent reacts with the series of reporter molecules and produces a signal, 408. The production of the reporter molecules can be in accordance with any of the systems, compositions and methods described herein. The signal is received via the detector, 410. The signal can be used, for example, to determine a viable cell and/or to report a gene present within a target cell in the sample. In some embodiments, the receiving of the signal is performed for less than 60 seconds after the conveying of the reagent.

Any of the container assemblies described herein can be manipulated, handled and/or actuated by any suitable instrument to perform an identification and/or detection process on a sample contained within the container assembly in accordance with any of the methods disclosed herein. For example, in some embodiments, any of the container assemblies described herein can be manipulated and/or actuated by an instrument to perform viable cell reporting and/or gene reporting of a target cell within a sample using biologic or abiologic vectors such as transduction particles methods and/or reporter systems of the types shown and described herein. In this manner, a system (e.g., the container or a series of container, the transduction particles, reagents and other compositions, and an instrument) can be used for many different assays, such as, for example, the rapid and/or automated detection of MRSA, *C. difficile*, Vancomycin resistant Enterococci, etc. In some embodiments, an instrument can also be configured to facilitate, produce, support and/or promote a reaction in a sample contained in a container and or series of containers of the types shown and described herein. Such reactions can include, for example, interaction and/or mixing of a transduction particles (e.g., any of the transduction particles described herein) with a sample, interaction and/or mixing of a reporter molecule (e.g., luciferase) with a substrate (e.g., tridecanal). Such reactions can, in accordance with the methods described herein, produce a signal, e.g., via a luminescence reaction, that can be detected by components included in the instruments described herein.

Figure 43:
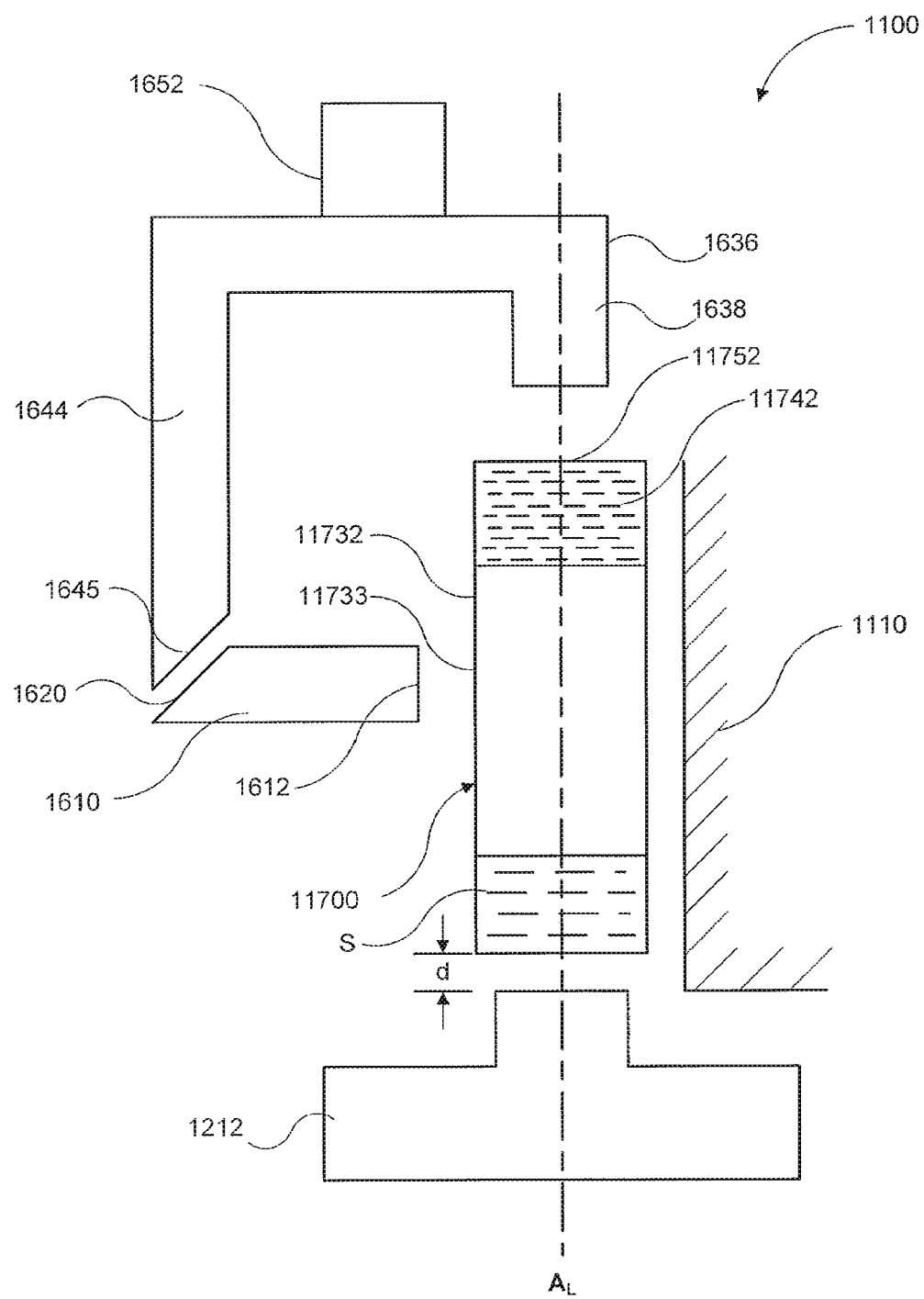
FIGS. 43-45 are schematic side views of a portion of an instrument according to an embodiment, in a first configuration, a second configuration and a third configuration, respectively.
Figure 44:
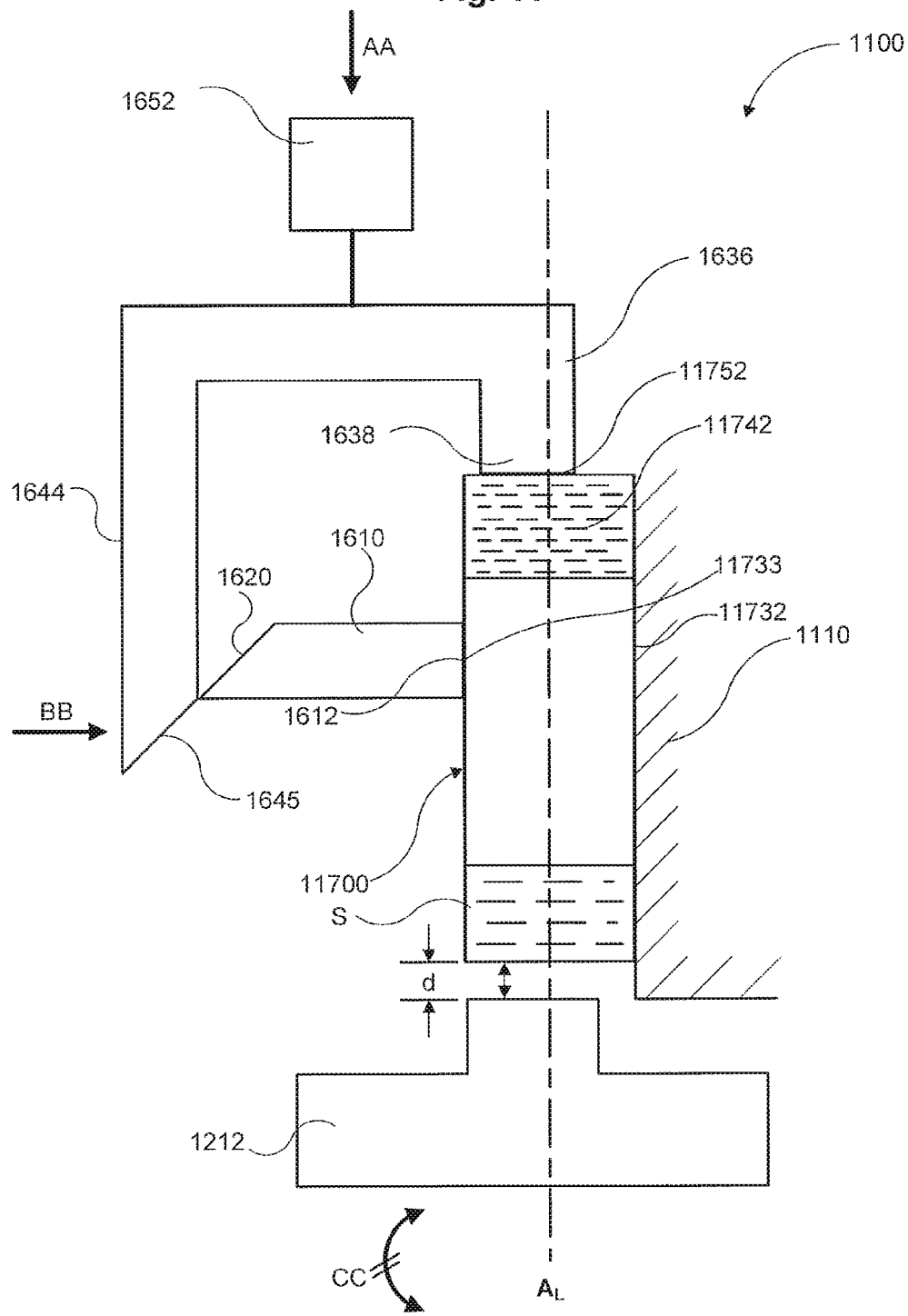
Figure 45:
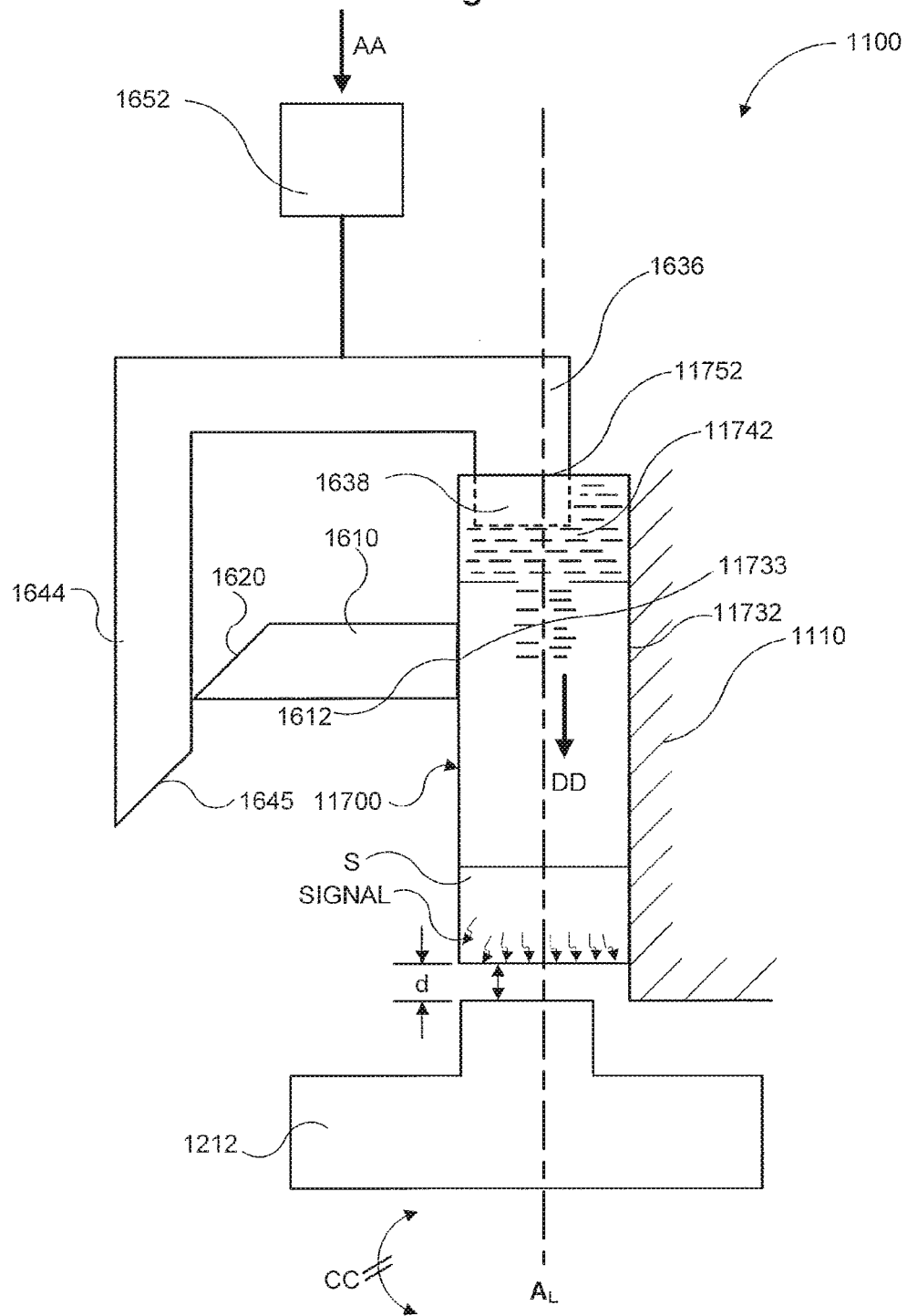

In some embodiment, a system can include an instrument including various subassemblies and configured to manipulate a container, actuate an actuation mechanism of a container, maintain a container and/or detect a signal produced in the container. For examples FIGS. 43-45 show a portion of an instrument 1100 in a first configuration, a second configuration and a third configuration, respectively. The instrument 1100 is configured to receive a container, e.g., container 11700, that can include a sample disposed therein, and can further be configured to manipulate the container 11700 and detect a signal produced therein, e.g., via a luminescence reaction. The container 11732 defines a reagent volume 11742 and a reaction volume 11732. The instrument 1100 includes a housing 1110 that defines an internal volume that contains and/or supports a detector 1212, a retention member 1610, an activation member 1636 and an actuator 1652. While shown as receiving container 11700, the instrument 1100 can be configured to receive any container assembly described herein, and can be used to perform any methods described herein, e.g., method 150, 200, 300 or 400.

As shown, the retention member 1610 is configured to contact a first portion 11733 of a sample container 11700 disposed in the instrument 1100 to limit movement of the container 11700. Similarly stated, the retention member 1610 is configured to contact the sample container 11700 to limit movement lateral movement and/or rotation of the sample container 11700 relative to portions of the instrument 1100 (e.g., the detector 1212). In some embodiments, the retention member 1610 can be configured to limit periodic movement (e.g., vibration) of the sample container 11700.

The activation member 1636 is coupled to the actuator 1652 and is also movably coupled to the retention member 1610. The activation member 1636 is configured to engage a second portion 11752 of the container 11700 to convey a reagent, e.g., substrate (e.g., tridecanal) from the reagent volume 11742 into the reaction volume 11732. The actuator 1652 is configured to move the activation member 1636 between a first position (FIG. 43), a second position (FIG. 44) and a third position (FIG. 45). Similarly stated, the actuator 1652 is configured to move the activation member 1636 relative to the instrument 1100 and/or the retention member 1610.

When the activation member 1636 is in the first position, the retention member 1610 is spaced apart from the first portion 11733 of the container 11700 and the activation member 1636 is spaced apart from the second portion 11752 of the container 11700. In this manner, the container 11700 can be moved relative to the detector 1212 (e.g., to position the container or the like. When the activation member 1636 is in the second position (FIG. 44) the retention member 1610 is configured to contact the first portion 11733 of the container 11700. In this manner, movement of the sample container 11700 relative to portions of the instrument 1100, such as the detector is limited. Furthermore, the activation member 1636 remains spaced apart from the second portion 11752 of the container 11700 in the second configuration. As shown in FIG. 45, when the assembly is moved to the second configuration, an engagement surface 1620 of the retention member 1610 is in contact with a corresponding surface 1644 included in the activation member 1636. The surface 1644 is shaped and/or configured to urge the engagement surface 1612 of the retention member 1610 to contact the first portion 11733 of the container 11700.

More particularly, as shown in FIG. 44, when the assembly is moved to the second configuration, the actuator 1652 moves the activation member 1636 in a first direction (shown by the arrow AA) defined by the longitudinal axis $A_L$ of the container 11700. The engagement of the engagement surface 1620 of the retention member 1610 and the corresponding surface 1644 of the activation member 1636 causes the retention member 1610 to move in a second direction, as shown by the arrow BB in FIG. 44. Similarly stated, the activation member 1636 engages the retention member 1610 to move the retention member 1610 in a direction perpendicular to the longitudinal axis $A_L$ and towards the container 11700.

As shown in FIG. 44, in the second configuration (when the activation member 1636 is in the second position), the container 11700 is disposed in the housing 1110 and/or in contact with a portion of the housing 1110 such that the container 11700 is separated from the detector 1212 by the distance d. The distance d defines the signal path length (e.g., optical path length) to be maintained during detection. Moreover, the retention member 1610 maintains the container 11700 in contact with a portion of the housing 1110 such that lateral movement, sideways wobble or vertical motion of the container 11700 is limited and/or eliminated (see, e.g., the arrow CC). Maintaining a consistent and repeatable signal path length can result in a repeatable and high quality measurement of the signal produced in the reaction volume of the container 11700. In some embodiments, the instrument 1100 can be used in conjunction with any of the methods described herein to detect a signal produced by a flash luminescence reaction.

When the activation member 1636 is in the third position (corresponding to a third configuration), the activation member 1636 is engaged with the second portion 11752 of the container 11700 to convey the reagent from the reagent volume 11742 to the reaction volume 11732, as shown by the arrow DD in FIG. 45. In some embodiments, the activation member 1636 can include a plunger portion configured to engage the container 11700 and move within the reagent volume 11742 of the container 11700, when the activation member 1636 moves from the first position to the second position. More particularly, when moved to the third configuration (FIG. 45), the actuator 1652 moves the activation member 1636 further along the direction shown by arrow AA, such that a plunger portion of the activation member 1636 contacts an engagement portion 11752 of the container 11700 and then moves into the reagent volume 11743. As the activation member 1636 moves from its second position to its third position (i.e., within the reagent volume 11742), it conveys the reagent contained therein, e.g., substrate such as tridecanal, into the reaction volume 11732. The reagent flows into the sample S and interacts with the sample S to produce a signal that can be detected by the detector 1212. For example, the reagent can be tridecanal that interacts with the reporter molecule luciferase present in the sample solution. The interaction produces luminescence which is detected by the detector 1212 which can be, e.g., a photodetector.

When the assembly is moved from the second configuration to the third configuration, the retention member 1610 remains in contact with the first portion 11733 of the container 11700 in the third configuration. In this manner, the reagent, which can be, for example, a substrate, can be added to the sample when the container is in a fixed position relative to the detector 1212. As discussed above, this arrangement facilitates repeatable measurement of the signal.

In some embodiments, the instrument 1100 can also include a second activation member (not shown) which can be configured to engage a third portion of the sample container 11700, e.g., to convey a second reagent e.g., transduction particle, from the second reagent volume into the reaction volume. The second activation member can be movably coupled to the first activation member 1636, and can be configured to contact the third portion of the container 11700 when the activation member 1636 is in the first position (i.e., the assembly is in the first configuration). Thus, in such embodiments, when the assembly is in the first configuration the second activation member can be moved (e.g., by a second actuator) to convey a second reagent.

In some embodiments, at least a portion of the second activation member can be movably disposed within the first activation member 1636. In some embodiments, the retention member 1610 can also be configured to rotate when the activation member 1636 is displaced from the first position to the second position.

In some embodiments, a portion of an instrument 2100 can include a retention assembly that can include a series of grippers to manipulate and/or actuate a container of the types shown and described herein. For example, referring now to FIGS. 46-48, an instrument 2100 includes a detector 2212, a retention assembly 2610, an instrument 2100, an activation member 2636 and an actuator 2652. The instrument 2100 includes the container assembly 11700, which is described herein with reference to FIGS. 43-45. The instrument 2100 can, however, be used to receive and/or manipulate any other container described herein, and can be used to perform any methods described herein, e.g., methods 150, 200, 300 or 400.

As shown in FIGS. 43-45, the retention assembly 2610 includes a first gripper 2612a and a second gripper 2612b each configured to contact a first portion 11733 of the container 11700 to limit movement of the container 11700. In this manner the retention assembly, among other functions, can facilitate repeatable detection as described before with reference to FIGS. 43-45. Each gripper is coupled to a biasing member 2622, e.g., a spring, configured to exert a force on the corresponding grippers 2612a, 2612b to urge the grippers towards a closed configuration.

Figure 46:
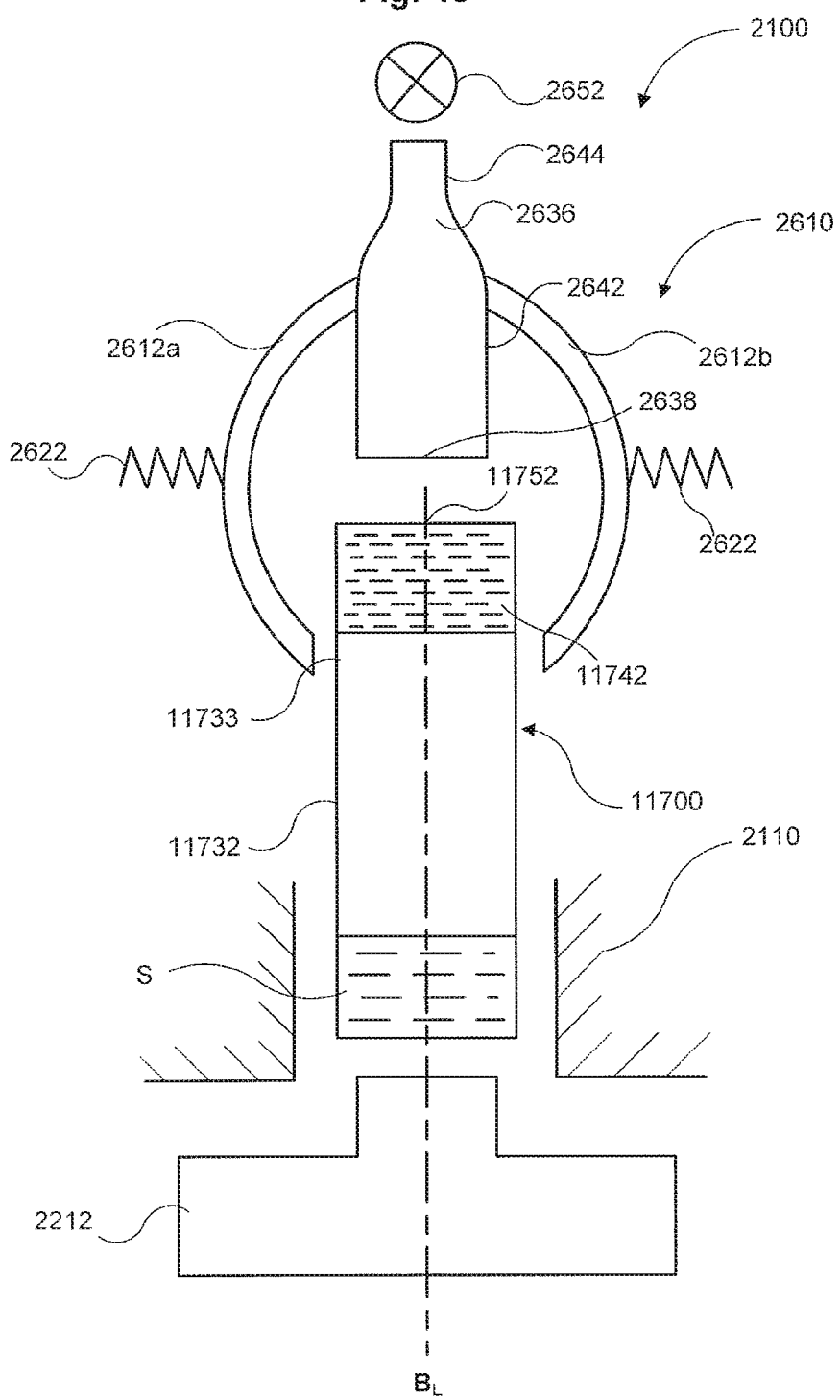
FIGS. 46-48 are schematic side views of a portion of an instrument according to an embodiment, in a first configuration, a second configuration and a third configuration, respectively.
Figure 47:
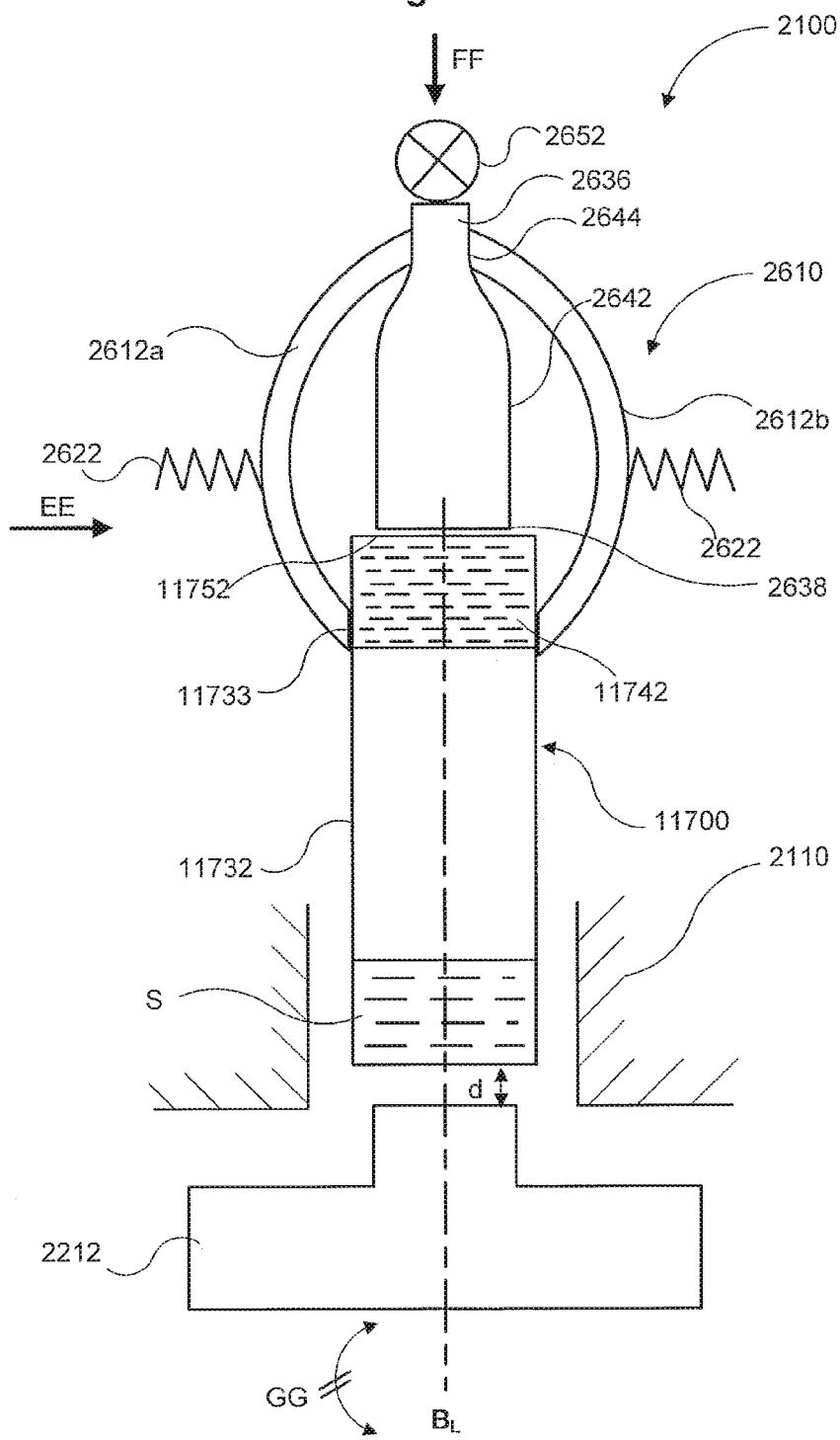

The activation member 2636 is movably coupled to the retention assembly 2610, and is operably coupled to the actuator 2652. The actuator 2652 is configured to move the activation member 2636 relative to the retention assembly 2610 and/or the container 11700 between a first position and a second position. The activation member includes a first surface 2642 configured to contact with a surface of the retention assembly 2610 to maintain the first gripper 2612a and the second gripper 2612b in an opened configuration when the activation member 2636 is in the first position. For example, FIG. 46 shows the instrument 2100 in the first configuration such that the activation member 2636 is in the first position and the surface 2642 of the activation member 2636 is in contact with the retention assembly 2610, thereby maintaining grippers 2612a, 2612b in the open configuration.

In the second position, a second surface 2644 of the activation member 2636 is configured to contact the surface of the retention assembly 2610 such that the biasing member 2622 urges the first gripper 2612a and the second gripper 2612b into a closed configuration. More particularly, when moving towards the second configuration (FIG. 47), the actuator 2652 moves the activation member 2636 from its first position to its second position along a longitudinal axis BL of the container 11700 in the direction shown by arrow FF. This motion of the activation member 2636 causes the retention assembly 2610 to be in contact with the second surface 2644 of the activation member 2636. In this position, the biasing members 2622 urge the gripper 2612a, 2612b to move in a second direction as shown by the arrow EE such that the grippers 2612a, 2612b contact the first portion 11733 of the container 11700. In some embodiments, the movement of the activation member 2636 from the first position to the second position can also cause the grippers to rotate towards the container 11700.

Figure 48:
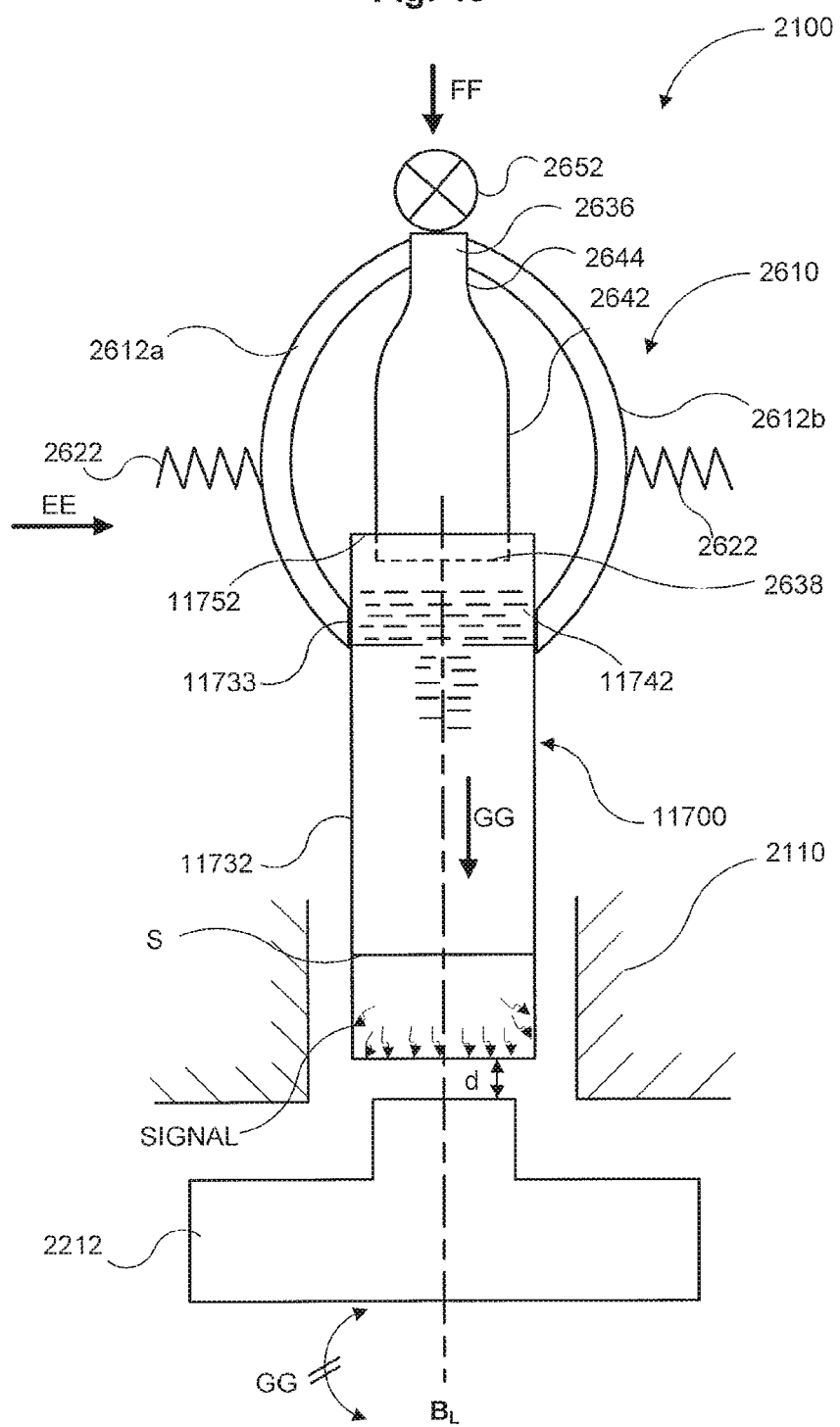

The activation member 2636 is configured to engage a second portion 11752 of the container 11700 and convey a reagent, e.g., substrate such as tridecanal, from the reagent volume 11742 into the reaction chamber 11732. More particularly, when moving towards the third configuration, as shown in FIG. 48, the actuator 2652 can continue to move the activation member 2636 in the direction shown by the arrow FF, until the plunger portion 2638 of the activation member 2636 contacts a second portion 11752 of the container 11700, and moves from a first position to a second position within the reagent volume 11742 of the container 11700. The plunger portion 2638 can therefore communicate the reagent disposed in the reagent volume e.g., substrate such as tridecanal, into the reaction volume 11732. The substrate can react with reporter molecules, e.g., luciferase, included in the sample S disposed in the reaction volume 11732 to produce a signal, e.g., luminescence that can be detected by the detector 2212.

As shown, the grippers 2612a, 2612b remain in contact with and otherwise engage, grasp, clamp or secure the container 11700 in the third configuration. This prevents lateral movement, sideway wobble or vertical motion of the container 11700 as shown by arrow GG, and maintains a consistent signal path length d from the detector 2212, as described above. As shown, the retention and the actuation (e.g., the plunging) of the container assembly 11700 is accomplished using a single actuator, and with the retention assembly 2610 and the activation member 2636 cooperatively configured such that the reagent cannot be conveyed into the sample container 11700 unless the sample container 11700 is in the desired position for the detection operation.

Figure 49:
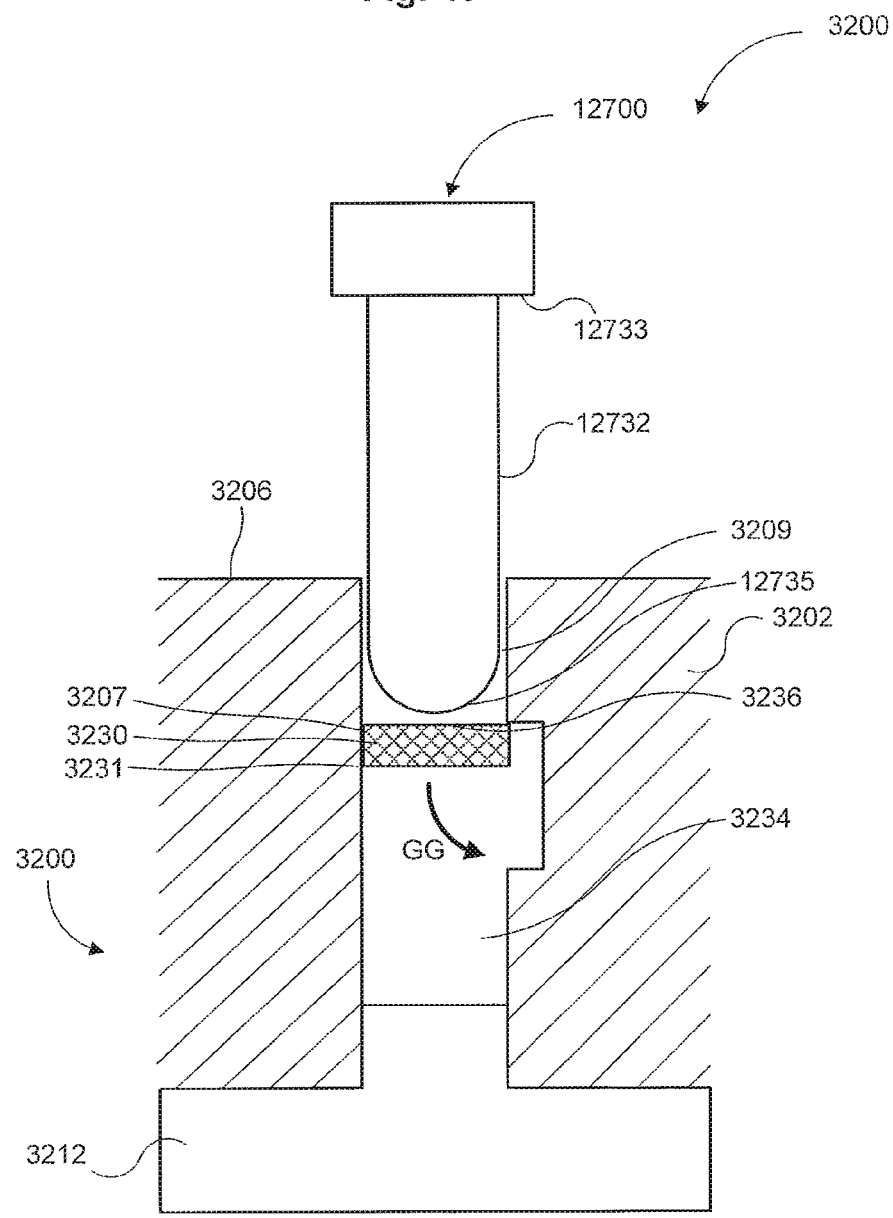
FIGS. 49 and 50 are schematic side views of a detection portion of an instrument according to an embodiment, in a first configuration and a second configuration, respectively.
Figure 50:
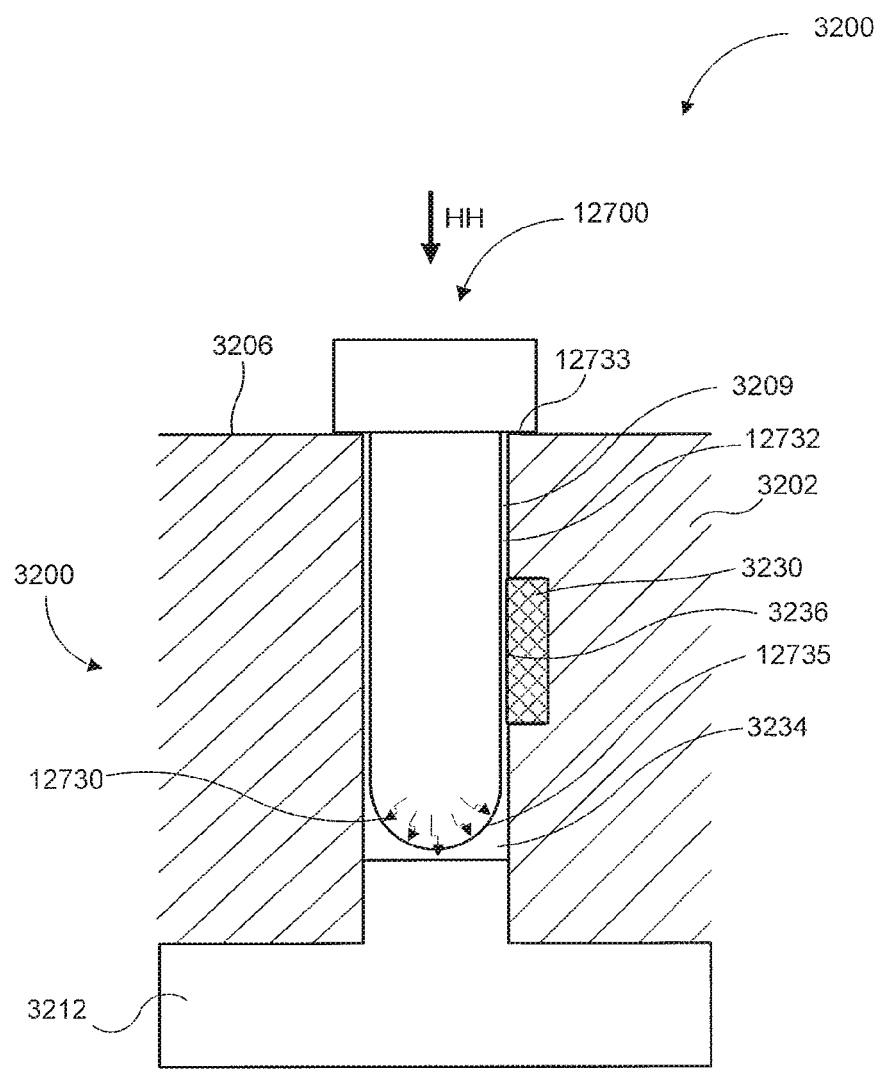
Figure 51:
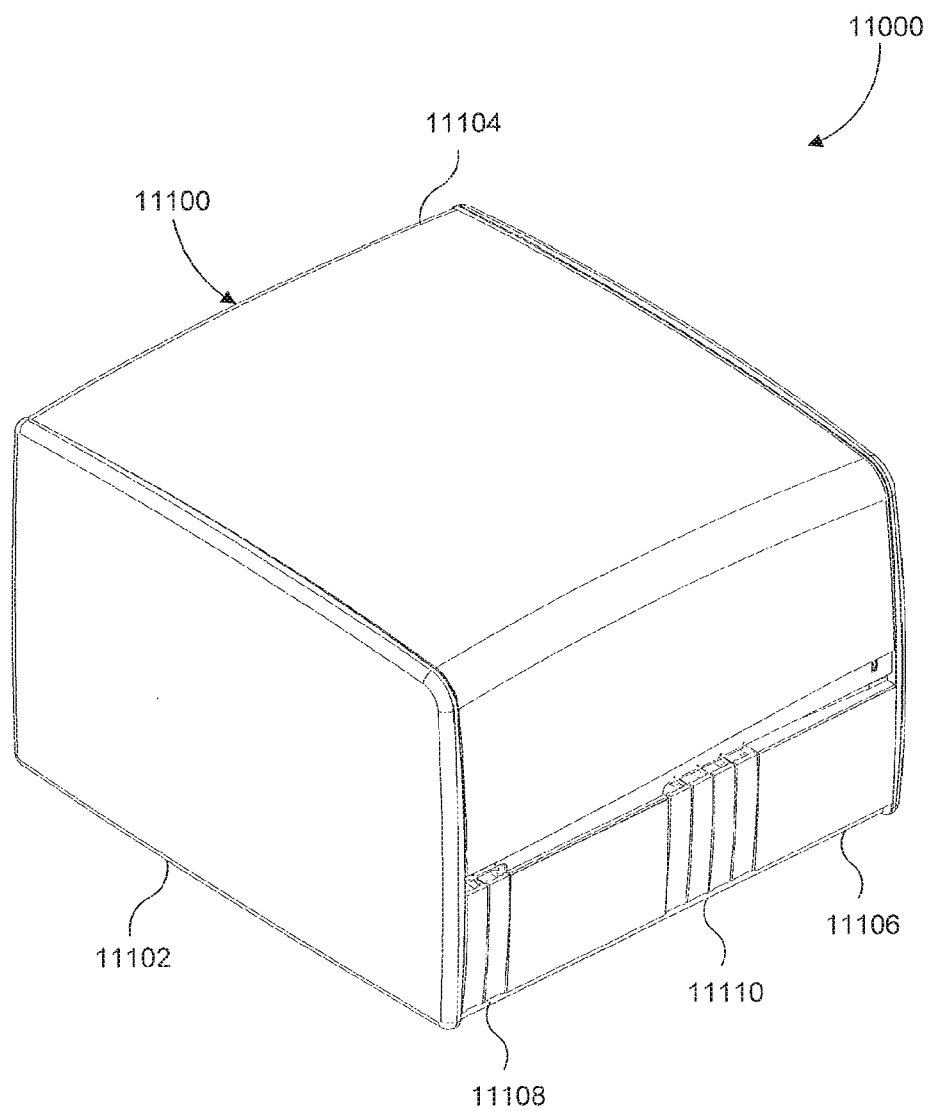
FIG. 51 shows a perspective view of an instrument, according to an embodiment.
Figure 52:
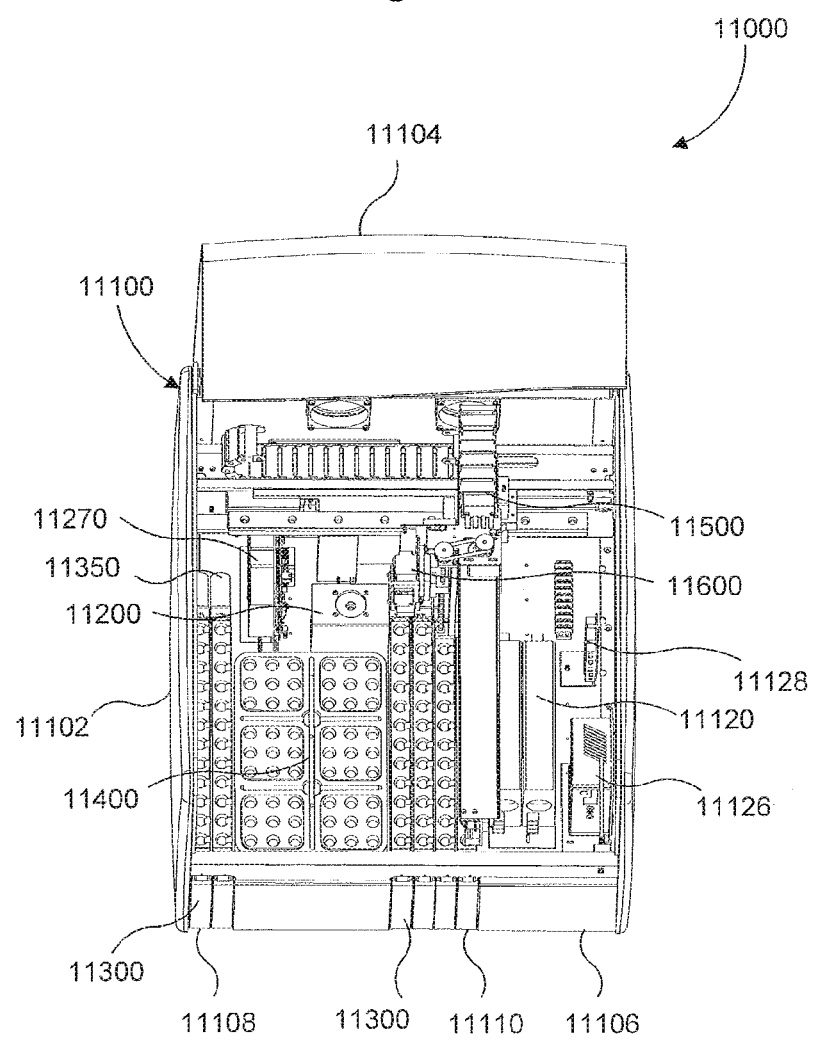
FIG. 52 shows an inclined front view of the instrument of FIG. 51 with a lid opened.
Figure 53:
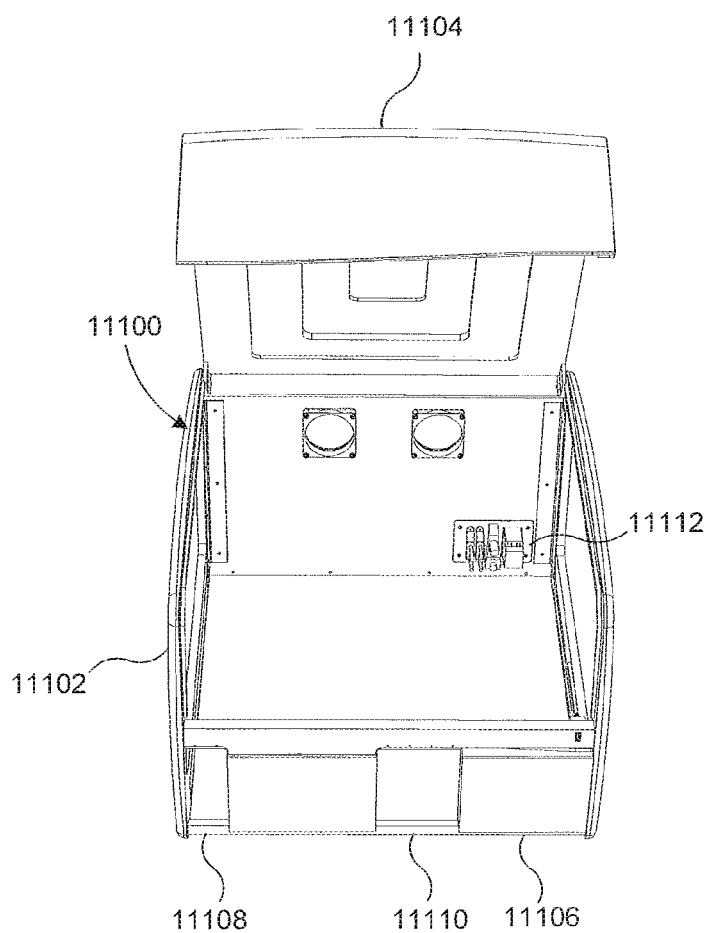
FIG. 53 shows an inclines front view of a housing included in the instrument of FIG. 51.
Figure 54:
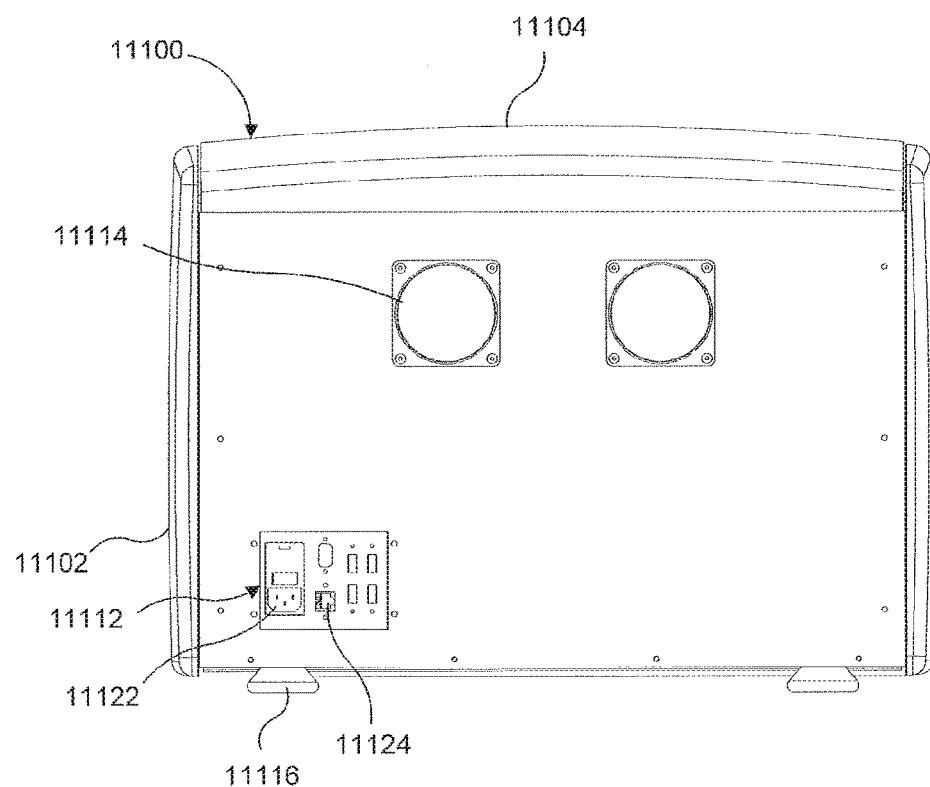
FIG. 54 shows a back view of the housing shown in FIG. 53.

In some embodiments, an instrument can include a detector assembly that can include a housing for receiving a sample container and a shutter configured to minimize background light, facilitate calibration of the signal detection or the like. For example, as shown in FIGS. 49-50, an instrument can include detector assembly 3200. The detector assembly 3200 includes a housing 3202, a detector 3212 and a shutter 3230. The detector assembly 3200 is configured to receive a container 12700 to analyze a signal produced therein. Such signals can be produced by any of the methods described herein, such as, for example, resulting from the interaction of a substrate and a reporter molecule. In some embodiments, the signal can be produced by a flash luminescence reaction. The detector assembly 3200 can be configured to receive any other container, e.g., container 1700 or any other container described herein, and can be used to perform any method described herein, e.g., method 150, 200, 300 or 400.

As shown, the housing 3202 defines a channel 3209 and a detection volume 3234. The channel 3209 is configured to receive the container 12700, or any other container. The detection volume 3234 is configured to place the channel 3209 in communication with the detector 3212. The housing 3202 further includes a first seal surface 3206 and a second seal surface 3207. In use, a first portion 12733 of the container 12700 and the first seal surface 12733 isolate the detection volume 3234 from a volume outside the housing 3202 when a second portion 12732 of the container 12700 is disposed within the detection volume 3234 (see e.g., FIG. 50). In this manner, the first portion 12733 of the container 12700 and the first seal surface 12733 can eliminate and/or limit the amount of background noise (e.g., ambient light) within the detection volume 3234 when the container 12700 is positioned within the channel 3209 for detection of the sample contained therein.

The shutter 3230 is disposed within the housing 3209. The shutter 3230 is movable between a first shutter position (FIG. 49) and a second shutter position (FIG. 50). When the shutter is in the first shutter position (i.e., a first configuration of the assembly), the shutter 3230 is in the first position such that the second seal surface 3207 of the housing 3202 and a seal surface 3231 of the shutter are in contact and isolate the detection volume 3234 from the channel 3209. In some embodiments, the first seal surface 3206 can be a gasket. In this manner, when in the first configuration, no background signal, e.g., light, can enter the detection volume 3232. Thus, when in the first configuration, the detector 3212 can be calibrated and/or background signals can be detected for later use in processing the signal data.

As shown in FIG. 50, the shutter 3230 can be moved to a second shutter position such that the channel 3209 of the housing 3202 is in communication with the detection volume 3234. When the shutter is in the second shutter position, the channel 3209 of the housing 3202 is in communication with the detection volume 3234. More particularly, in some embodiments, the shutter 3230 includes an activation surface configured to be engaged by the second portion 12735 of the container 12700 such that shutter 3230 can be moved from the first position to the second position (FIG. 50) when the container 12700 is moved within the channel 3209. In this manner, when the second portion 12735 of the container 12700 is placed into communication with the detection volume 3234, the shutter 3230 is moved. Said another way, in some embodiments, the shutter 3230 can be in the first shutter position when the second end portion 12735 of the container 12700 is within the channel 3209 outside of the detection volume 3234, and the shutter 3230 can be in the second shutter position, when the second end portion 12735 of the container 12700 is disposed within the detection volume 3234.

As shown in FIG. 49, the container 12700 can be moved from the first position downward (or distally) into the channel 3209 such that the second end portion 12735 of the container 12700 contacts the shutter 3230 to urge the shutter 3230 from the first shutter position to the second shutter position, as shown by the arrow GG. In some embodiments, the shutter 3230 can include a ramp configured to engage the second portion 12735 of the container 12700 when the second portion 12735 of the container 12700 moves within the channel 3209 towards detection volume 3234 to move the shutter 3230 towards the second shutter position.

In some embodiments, the shutter 3230 can be configured to translate within the housing 3202 in a direction offset a longitudinal axis of the channel 3209. In some embodiments, the detector assembly 2200 can also include a biasing member configured to urge the shutter 3230 towards the first shutter position.

In some embodiments, the shutter 3230 can define a calibration port (not shown). When the shutter 3230 is in the first position, the calibration port can be aligned and/or configured place a calibration light source in communication with the detection volume 3234 e.g., to calibrate the detector 3212. When the shutter 3230 is in the second position, the calibration port can be isolated from the detection volume 3234, thereby preventing any signal leakage from the detection volume and/or ambient light from entering the detection volume.

In some embodiments, a detector assembly, e.g., the detector assembly 3200 or any other detector assembly described herein, can include a housing defining a channel configured to receive a sample container. The housing can also define a seal surface and detection volume configured to place the channel in communication with a detector. The detector assembly can further include a shutter, e.g., shutter 3230 or any other shutter described herein, having a portion movably disposed within the housing between a first shutter position and a second shutter position. The shutter can include a seal surface and an actuation portion which is configured to engage a distal end portion of the sample container to move the shutter from the first shutter position to the second shutter position when the distal end portion of the container is moved towards the detection volume. The seal surface of the shutter and the seal surface of the housing can be configured to isolate the detection volume from the channel of the housing when the shutter is in the first shutter position, while the channel of the housing can be in communication with the detection volume when the shutter is in the second shutter position.

In some embodiments, a detector assembly, e.g., the detector assembly 3200 or any other detector assembly described herein, can include a housing defining a channel configured to receive a sample container. The housing also defines a detection volume configured to place the channel in communication with a detector, and further includes a seal surface. The detector assembly can also include a shutter, e.g., shutter 3230 or any other shutter described herein, shutter defining a calibration port configured to receive a calibration light source. The shutter can be movably disposed within the housing between a first shutter position and a second shutter position such that a seal surface of the shutter and a seal surface of the housing is configured to isolate the detection volume from the channel of the housing when shutter is in the first shutter position. Furthermore, in the first shutter position, the calibration port can be in communication with the detection volume. The shutter can be configured such that the channel of the housing can be in communication with the detection volume when the shutter is in the second shutter position and the calibration port can be isolated from the detection volume.

Referring now to FIGS. 51-95, an instrument 11000 can include a housing 11100, a heater assembly 11400, a drive assembly 11500, a manipulator assembly 11600, and a detector assembly 11200. The housing 11100, is configured to house, contain, and/or provide mounting for each of the components and/or assemblies of the instrument 11000, as described herein. The heater assembly 11400 is configured to receive a container, e.g., container assembly 3700, as described herein, and heat a sample contained therein. Similarly stated the heater assembly 11400 is configured to maintain a sample containing target cell, at a predetermined temperature and for a desired time period (e.g., at or above room temperature, 25 degrees Celsius, or 37 degrees Celsius, for approximately 2 hours or 4 hours, as described herein). The drive assembly 11500 is configured to drive, transfer and/or move the manipulator assembly 11600 (and the container assembly 3700 coupled thereto) in a 3-dimensional space within the housing 11100. Said another way, the drive assembly 11500 can move the manipulator assembly 11600 in an X, Y and/or Z direction within the housing 11100. The manipulator assembly 11600 is configured to manipulate, grip and/or actuate a container (e.g., the container assembly 3700) within the housing 11100. For example, the manipulator assembly 11600 is configured to releasably couple to, engage, hold, lock, and/or secure the container assembly 3700 to transfer the container from a first location within the housing 11100 to a second location. Similarly stated, the manipulator assembly 11600 and the manipulator assembly 11600 are collectively configured to transfer the container assembly 3700 between a first subassembly and another subassembly, and/or actuate an actuation mechanism of the container assembly 3700, to transfer reagents and/or solutions from one portion of the container assembly 3700 to another. The detector assembly 11200 is configured to detect a signal, e.g., luminescence, from within at least a portion of the container assembly 3700. The detected signal can be produced by a chemical reaction occurring within a reaction chamber of the container, for example, interaction of a reporter molecule (e.g., luciferase), with a substrate (e.g., tridecanal). Each of these assemblies is described further below in detail, followed by a description of various methods that can be performed by the instrument 11000. Although the instrument 11000 is shown and described as manipulating and/or actuating the container assembly 3700, the instrument 11000 can receive, manipulate and/or actuate any of the container assemblies described herein.

As shown in FIGS. 51-54, the housing 11100 is defines an internal volume to house, contain and/or mount the subassemblies of the instrument 11000. The housing 11100 can be formed from any suitable rigid, light weight and sturdy material. Example materials include polytetrafluoroethylene, high density polyethylene, polycarbonate, other plastics, acrylic, sheet metal such as aluminum, any other suitable material or a combination thereof. The housing can be relatively smooth and free of sharp edges. The housing includes sidewalls 11102, a lid 11104 and a front panel 11106. The lid 11104 is pivotally mounted on the sidewalls 11102, and can swivel about its pivot mounts from a first position wherein the housing 11100 is closed, to a second position wherein the housing 11100 is open, e.g., to allow access of the subassemblies disposed within the housing 11100. The front panel 11106 defines a first opening 11108 and a second opening 11110. The first opening 11108 and the second opening 11110 are configured to removably receive a series of cartridges 11300 (e.g., 1, 2, 3, 4, or even more; see FIG. 52) as described herein. Each cartridge 11300 can contain and/or hold a series of container assemblies, e.g., container assembly 3700. The first opening 11108 can be configured to be a loading zone, i.e. configured to removably receive the series of cartridges 11300 having a series of container assemblies 3700 disposed therein. The series of containers can include samples for analysis in accordance with any of the methods shown and described herein. In particular, the containers can include samples for which screening for the presence of a target cell (e.g., MRSA). The second opening 11110 is configured to be an unloading zone, i.e., configured to removably receive a series of cartridges 11300 having containers disposed therein, the containers housing samples that have been analyzed by the instrument, e.g., analyzed for the presence of bacteria using any of the subassemblies of the instrument 11000, and method described herein, e.g., method 400.

The housing 11100 includes an interface 11112 located on a backside of the housing 11100. The interface 11112 includes an electric plug 11122, e.g., for communicating electrical power to the instrument 11000. The interface 11112 also includes a communication interface 11124, for example, to enable communication with an external device, e.g., local computer, remote computer, and/or a laboratory information system 1900, via local area network (LAN), wide area network (WAN) and/or the Internet. The communication interface 11124 can be a hardwired interface, e.g., DSL and/or RJ45. The housing 11110 also includes vents 11114 on the backwall that are configured to allow air, e.g., air heated due to the heat generated by operation of the subassemblies of instrument 11000, to exhaust. In some embodiments, the vents 11114 can includes fans to produce a flow of the exhaust air from the instrument 11000 with increased velocity, for example, to enable rapid cooling of the instrument. The housing 11100 also includes a series of bumpers (e.g., four, five or six) on a bottom surface configured to provide cushioned seating of the instrument 11000 on a surface. The bumpers can be made from a vibration absorbent and high friction material e.g., rubber, and can be configured to absorb any vibrations of the instrument 11000, e.g., caused by a motion of the drive assembly 11500, and/or prevent the instrument 11000 from sliding on the surface upon which it is placed.

Figure 55:
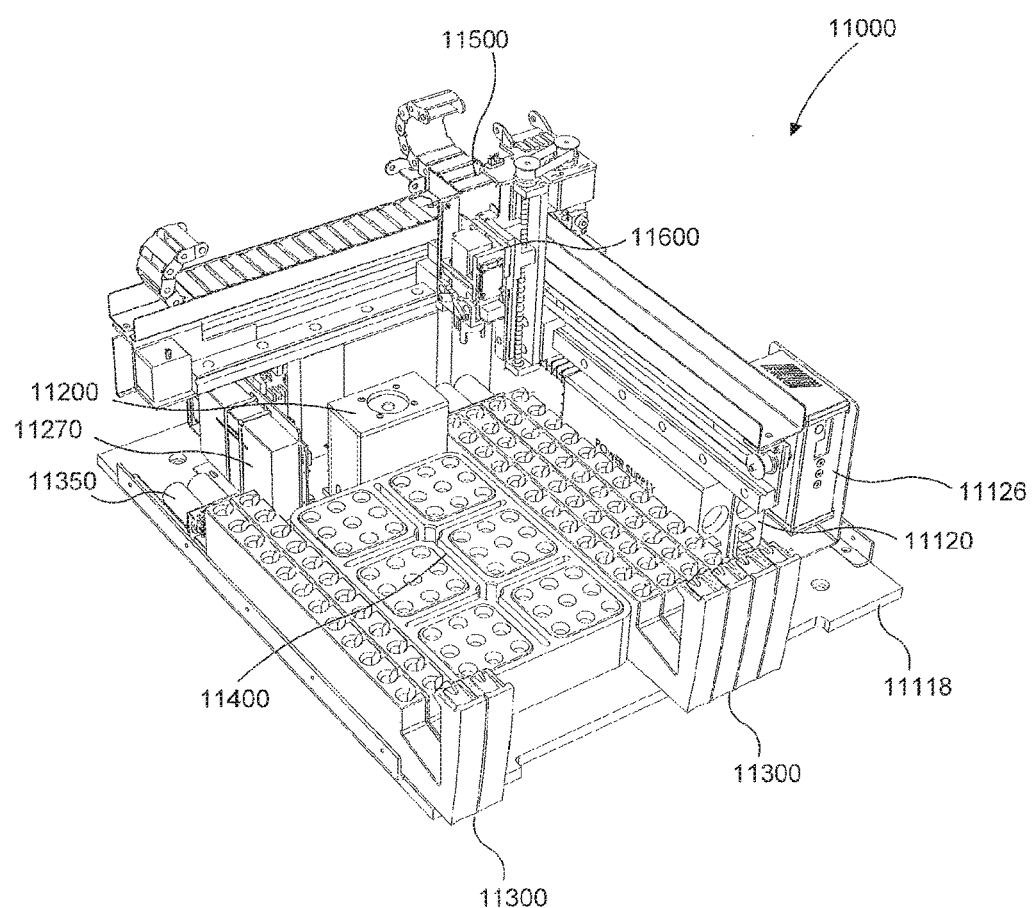
FIGS. 55-57 show perspective views of a portion of the internal components and subassemblies of the instrument of FIG. 51 with the housing removed for clarity.
Figure 56:
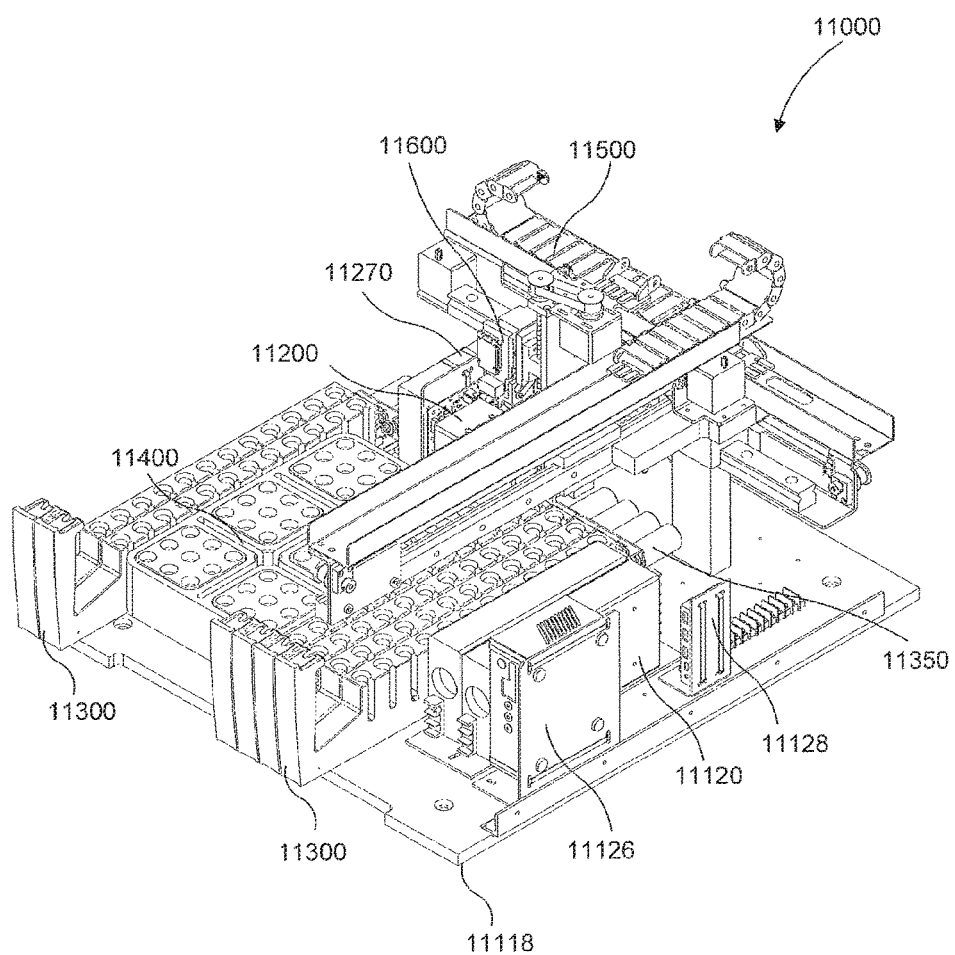
Figure 57:
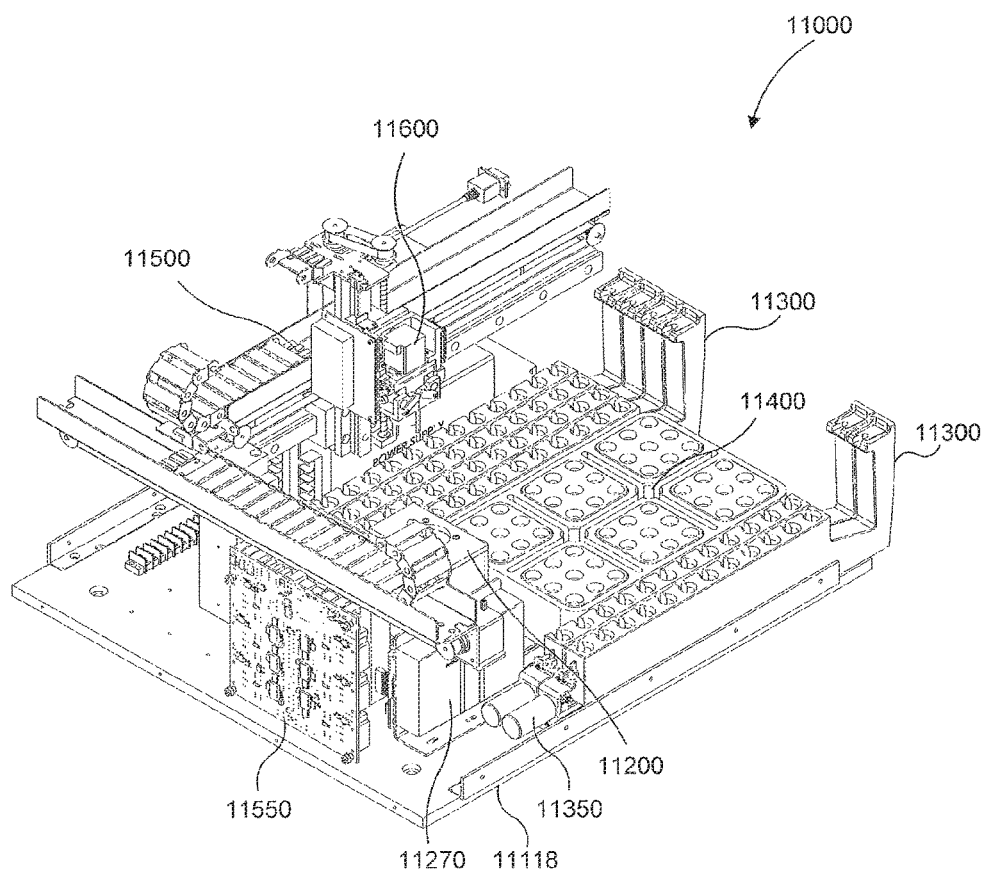
Figure 58:
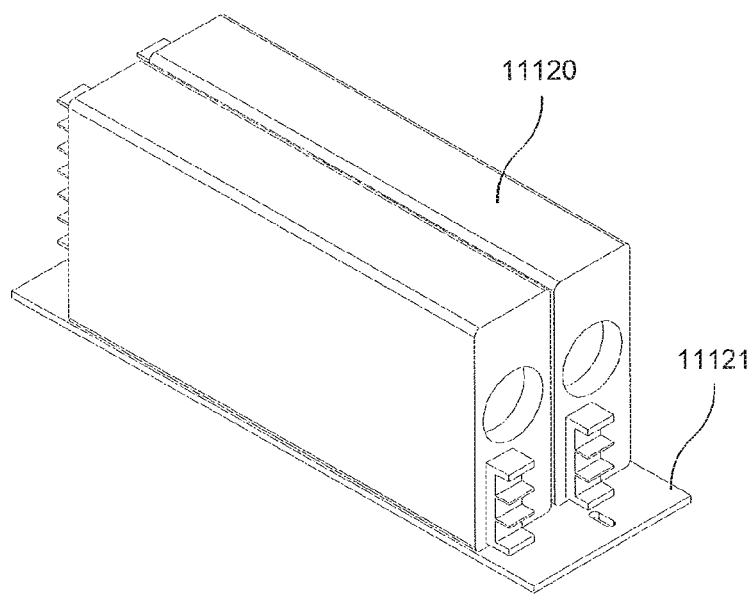
FIG. 58 shows a perspective view of a power supply included in the instrument of FIG. 51.

FIGS. 55-57 show perspective views of the instrument 11000 from various angles with the housing 11100 removed, to more clearly show the internal components and subassemblies. The instrument 11000 includes a baseplate 11118 configured to provide mounts for coupling the components and subassemblies of the instrument 11000. Referring also now to FIG. 58, the instrument includes a power supply 11120 mounted on the baseplate 11118. The power supply 11120 can be any commercially available power supply as is commonly known in the arts. The power supply 11120 is configured to receive electric power from the electrical plug 11122, e.g., 110V at 60 Hz or 220V at 50 Hz, and convert it into an electric power usable by the subassemblies of the instrument, e.g., step down the voltage, step up the voltage, control current, etc.

Figure 59:
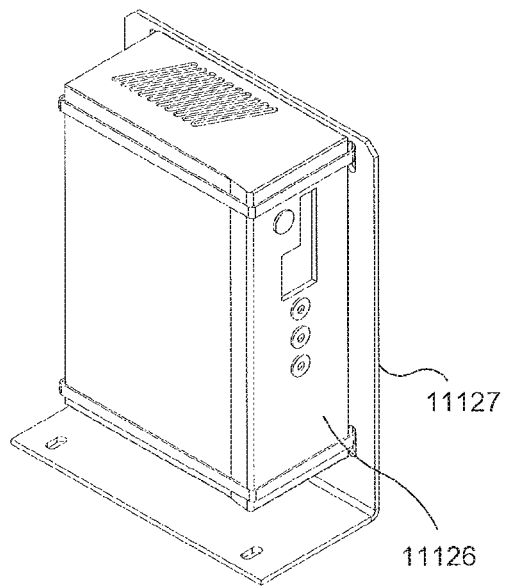
FIG. 59 shows a perspective view of a processor included in the instrument of FIG. 51.

Referring also now to FIG. 59, the instrument 11000 includes a processor 11126 coupled to a frame 11127 e.g., via zip ties, and disposed on the base plate 11118 via the frame 11127. The processor 11126 can be configured to control the operation of the various subassemblies included in the instrument 11000. For example, the processor 11126 can be a computer, a programmable logic chip (PLC), a microprocessor, an ASIC chip, an ARM chip, and/or a combination thereof. In some embodiments, the processor 11126 can included algorithms or software that can include instructions for operating the instrument 11000 subassemblies, e.g., heater assembly 11400, drive assembly 11500, manipulator assembly 11600, detector assembly 11200, and/or any other component included in the instrument 11000. In some embodiments, the processor 11126 can also be programmable, e.g., configured to accept instructions from a user, such as operating parameters of the instrument 11000. In some embodiments, the processor 11126 can also include a memory, e.g., to store the status and/or any other information (e.g., containers analyzed, positive samples, negative samples) or instructions.

Figure 60:
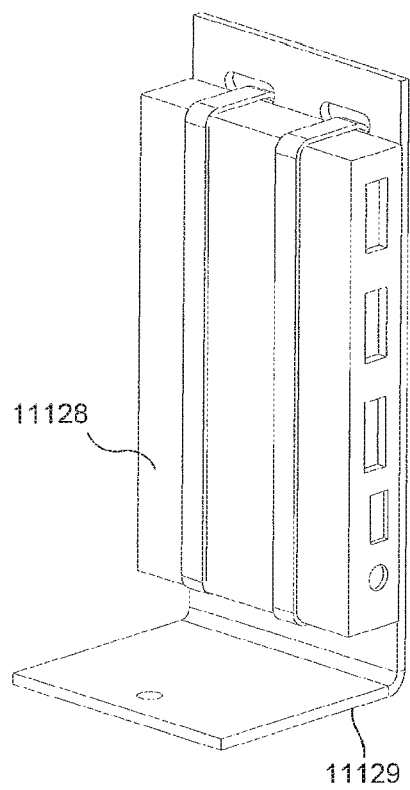
FIG. 60 shows a perspective view of a communications module included in the instrument of FIG. 51.

Referring also now to FIG. 60, the instrument 11000 also includes a communications module 11128 coupled to the mount 11129, e.g. via zip ties and disposed on the base plate 11118. The communications module 11128 is configured to communicate information to an external device, e.g., a laboratory information system (LIS), a remote computer, smartphone app and/or remote server from the processor 11126. In some embodiments, the communications module 11128 can also be configured to receive instructions to facilitate the performance of the methods described herein. The communications module 11128 can employ and/or be compatible with standard communication protocols, e.g., USB, firewire, ZigBee, Bluetooth®, low powered Bluetooth®, and/or any other communication equipment.

Figure 61:
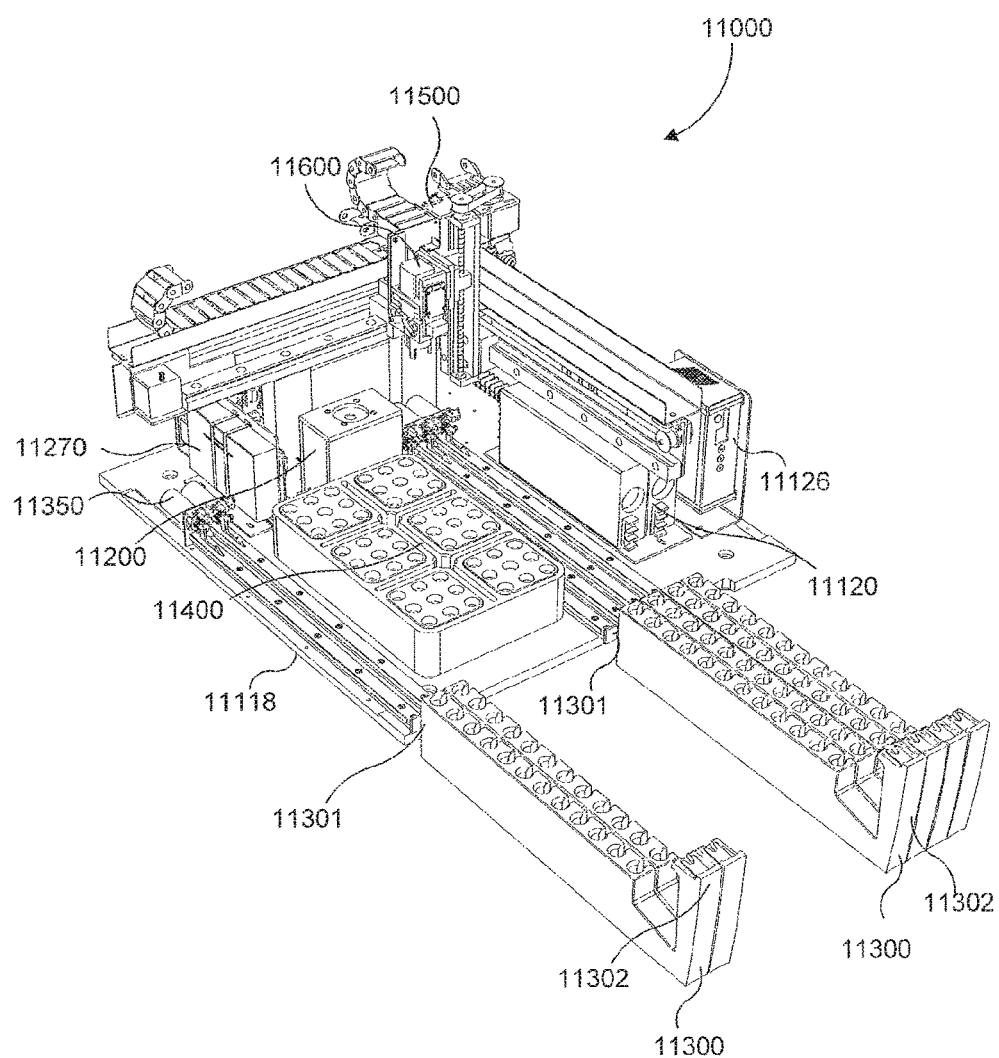
FIG. 61 shows a perspective view of the instrument of FIG. 51 in a first configuration.
Figure 62:
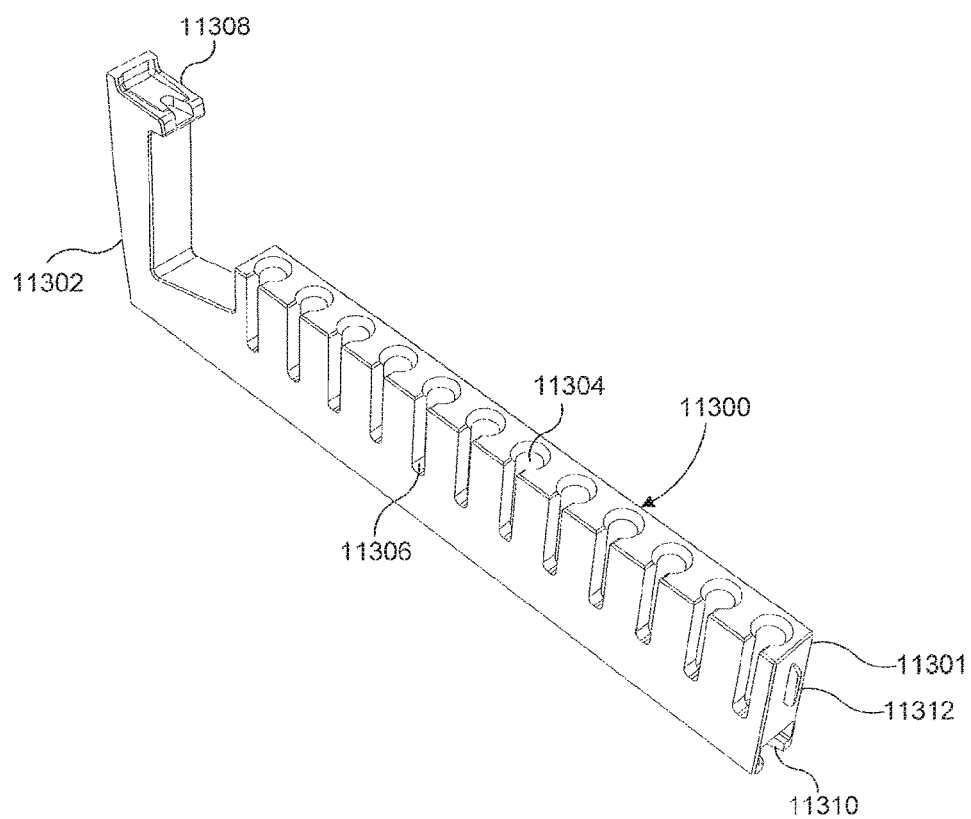
FIG. 62 shows a perspective view of a cartridge included in the instrument of FIG. 51.
Figure 63:
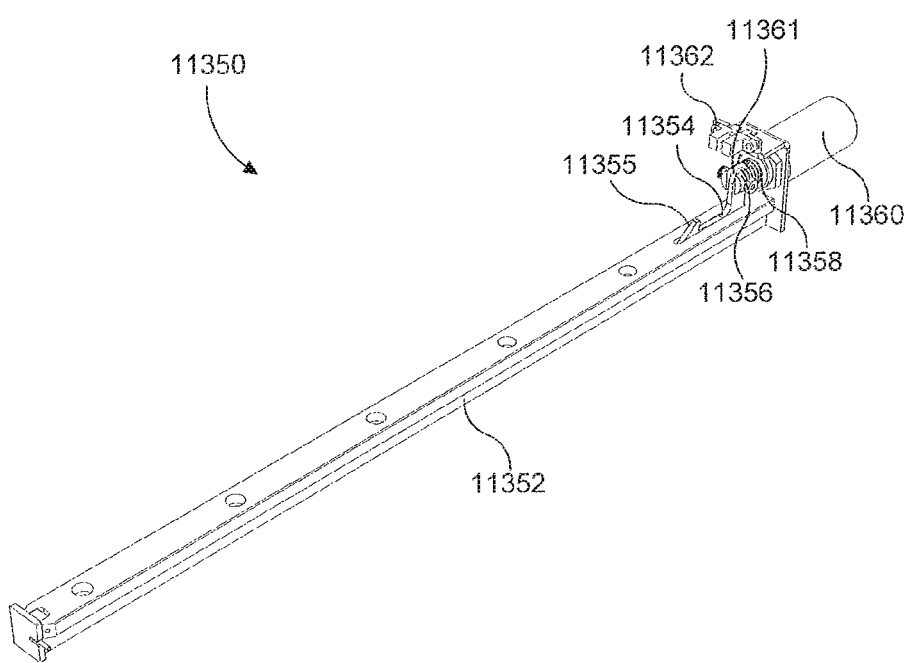
FIG. 63 shows a perspective view of a cartridge receiver included in the instrument of FIG. 51.

As shown in FIGS. 61-63 the instrument 11000 includes a series of cartridge receivers 11350 mounted on the baseplate 11118. Each of the cartridge receivers 11350 is configured to removably receive a cartridge 11300. FIGS. 55-57 show the series of cartridges 11300 in a first configuration, such that the series of cartridges 11300 are coupled to the series of cartridge receivers 11350, and are disposed substantially inside the housing 11100 of the instrument 11000. FIG. 61 shows the series of cartridges 11300 in a second configuration, wherein the series of cartridges 11300 are decoupled from the corresponding cartridge receiver 11350, and are disposed substantially outside the housing 11100 of the instrument 11000. Although the series of cartridges 11300 can include both "loading" and "unloading" cartridges 11300, as shown, the cartridges 11300 are substantially similar to each other and can be used interchangeably. In other embodiments, an instrument can include different cartridges for loading (e.g., input) of the container assemblies and unloading (e.g., output) of the container assemblies. Each cartridge 11300 includes a proximal end 11302 and a distal end 11301. The distal end 11301 is configured to engage with and reversibly couple to the cartridge receiver 11350. The proximal end 11302 is configured to allow a user to manipulate the cartridge 11300, for example, load or unload the cartridge 11300, as described herein.

FIG. 62 shows a perspective view of a cartridge 11300. The cartridge 11300 can be formed from a light weight and rigid material, e.g., plastics, and can have a surface that is smooth and relatively free of sharp edges. The cartridge 11300 defines a series of receptacles 11304 configured to removably receive at least a portion of a container, e.g., reaction chamber 3732 of the container assembly 3700, or any other container described herein. As shown herein, the cartridge 11300 includes twelve receptacles 11304. In other embodiments, however, the cartridge 11300 can include 1, 2, 4, 6, 8, 10, 14, 16 or an even higher number of receptacles 11304. Each of the series of receptacles 11304 can be shaped and sized to receive a reaction chamber of a container, e.g., reaction chamber 3732 of the container assembly 3700 or any other container described herein, with close tolerance. In this manner, the cartridge 11300 and the receptacles 11304 can restrict lateral movement of the container. Further, receptacle 11304 of the series of receptacles 11304 can have a depth such a reagent module, e.g., reagent module 3740 of the container assembly 3700 or any other container described herein, is disposed substantially outside the receptacle 11304. In this manner at least a portion of the container assembly can be exposed and/or accessible to be manipulated by the manipulator assembly 11600.

Each of the series of receptacles 11304 also includes a slot 11306 along at least a portion of the sidewall of the receptacle 11306. In some embodiment, the slot 11306 can be configured to allow a user to access a sidewall of a reaction chamber, e.g., reaction chamber 3732, of a container disposed within the receptacle 11304, e.g., to facilitate removal of the container from the receptacle 11304. In other embodiments, the slot 11306 can be configured to allow for optical monitoring and/or identification (e.g., via a label) of the container assembly within the receptacle 11304.

The proximal end 11302 of the cartridge 11300 includes an arm 11308 configured to be engaged by a user, e.g., to facilitate loading/unloading of the cartridge 11300 from the instrument 11000. The arm 11308 can have an ergonomic shape, e.g., to minimize physical stress on a user manipulating the cartridge 11300.

The cartridge 11300 includes a recess 11310 that runs from the proximal end 11302 to the distal end 11301 along the entire length of the cartridge. The recess can be shaped and sized to be slidably received by a guide rail 11352 of the cartridge receiver 11350, as described herein. The distal end 11301 of the cartridge 11300 also includes a tab 11312. The tab 11312 is configured to protrude from proximal end 11312 and interface with a sensor 11362 of the cartridge receiver 11350, as described herein.

FIG. 63 shows a perspective view of a cartridge receiver 11350 included in the instrument 11000. The cartridge receiver 11350 can be securely mounted on the base plate 11118, e.g., via screws, bolts, rivets, or the likes. The cartridge receiver can be formed from a lightweight, rigid and wear resistant material, e.g., metals such as aluminum. The cartridge receiver 11350 includes a guide rail 11352 configured to slide into the recess 11310 of the cartridge 11300, such that the cartridge 11300 can be slideably received by and/or coupled to the cartridge receiver 11350. The cartridge receiver 11350 includes a latch 11354 that can be at least partially disposed in an opening in the guard rail 11352. The latch 11354 includes a first portion 11355 configured to engage a notch 11314 (FIG. 64) included in the recess 11310 of the cartridge 11300 to lock, hold and/or secure the cartridge 11300 to the cartridge receiver 11350. The latch 11354 includes a second portion 11356 that is mounted on a shaft 11361 of an actuator 11360 included in the cartridge receiver 11350. A spring 11358 is also mounted on the shaft 11361. The spring 11358 is coupled to the latch 11354 and is operable to urge the latch 11354 to lock and/or engage the cartridge 11300 as described herein. The spring 11358 can be, e.g., a tension spring, such as e.g., a helical tension spring. The cartridge receiver 11350 includes the sensor 11362. The sensor 11362 can be any suitable sensor, such as a motion sensor, a position sensor, an optical sensor, a piezoelectric sensor, or any other suitable sensor. As described above, the sensor 11362 is configured to interface with the tab 11312 of the cartridge 11300 to determine and/or validate a position of the cartridge 11300, e.g., to ensure that the cartridge 11300 is completely in the second configuration, and is fully coupled to the cartridge receiver 11350.

Figure 64:
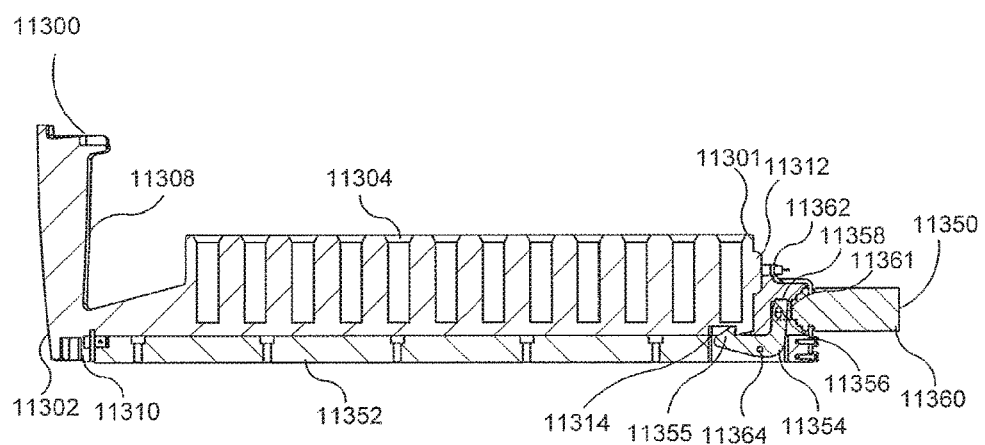
FIG. 64 is a side view of the cartridge of FIG. 62 and the cartridge receiver of FIG. 63 in a coupled configuration.

FIG. 64 shows a side cross-section of a cartridge 11300 in the second configuration, such that the cartridge 11300 is fully coupled with the cartridge receiver 11350. In the second configuration, the guide rail 11352 of the cartridge receiver 11350 is disposed substantially into the recess 11310, and the first portion 11355 of the latch 11354 is inserted into the notch 11314 included in the recess 11310 of the cartridge 11300. The latch 11354 is pivotally mounted on a pin 11364, such that the latch 11354 can pivot about the pin 11364 from a first position to a second position. In the first position, at least a portion of the first portion 11355 of the latch 11354 is inside the notch 11314. In the second position the first portion 11355 is outside the notch 11355. The spring 11358 is coupled to the second portion 11356 of the latch 11354, and is operable to urge the latch 11354 into first position.

In use, the cartridge 11300 can be loaded into the instrument 11000 by sliding the cartridge along the guide rail 11352 until the proximal end 11301 of the cartridge 11300 contacts the first portion 11355 of the latch 11354. The first portion 11355 of the latch 11354 has a tapered surface, such that an edge (e.g., a chamfered or tapered edge) of the proximal portion 11301 of the cartridge 11300 slides along the tapered surface of the first portion 11355 of the latch 11354, urging the latch 11354 to pivot from the first position to the second position. As the cartridge 11300 moves further along the guide rail 11352 towards the second configuration, the first portion 11355 of the latch 11354 encounters the notch 11314. The spring 11358 now urges the latch 11354 to pivot about the pin 11364 and move back into the first position such that the first portion 11355 of the latch 11354 is inside the notch 11314 and cartridge 11300 is locked in the second configuration.

In the second configuration, the tab 11312 engages the sensor 11362, as described above. In some embodiments, the sensor 11362 produce a signal indicating that the cartridge 11300 is fully coupled to the cartridge receiver 11350. The sensor 11362 can communicate the information validating the position of the cartridge 11300 to the processor 11126 and/or the user, e.g., using audio (e.g. beeps), visual (e.g., indicator lights) and/or tactile alerts. The actuator 11360 is configured to urge the latch 11354 from the first position to the second position to release the cartridge 11300 for removal from the instrument. For example, a user can actuate the actuator 11360 and/or the actuator 11360 can be configured to actuate after a given time period, such that the shaft 11361 extends towards the proximal end 11302 of the cartridge 11300. This causes the latch 11354 to pivot about the pins 11364 from the first position to the second position, so that the cartridge 11300 is no longer secured by the latch 11354 and can be slideably removed from the cartridge receiver 11350.

Figure 65:
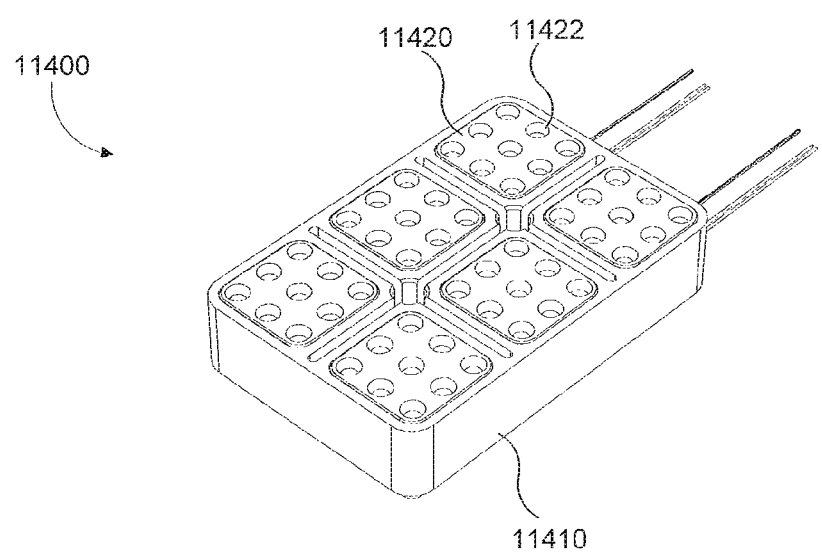
FIG. 65 shows a perspective view of a heater assembly included in the instrument of FIG. 51.
Figure 66:
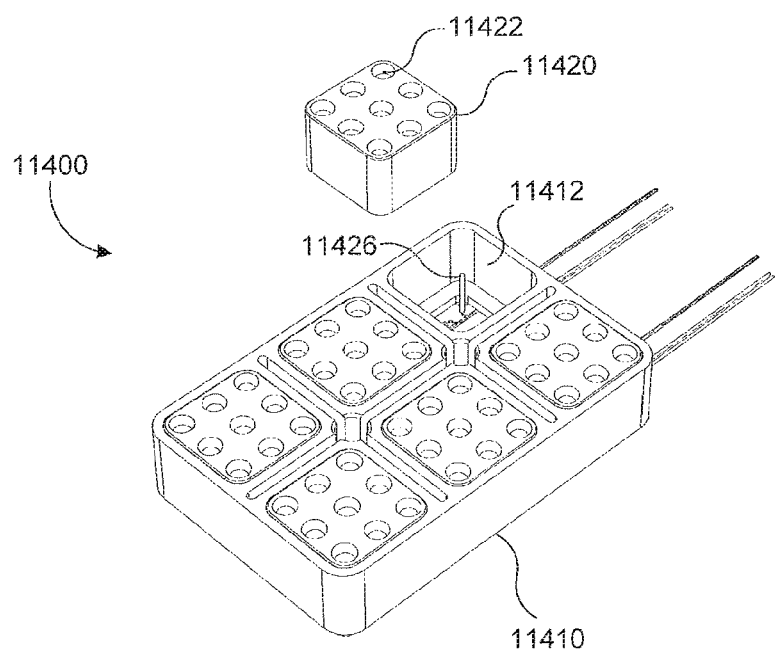
FIG. 66 is a partially exploded view of the heater assembly of FIG. 65.
Figure 67:
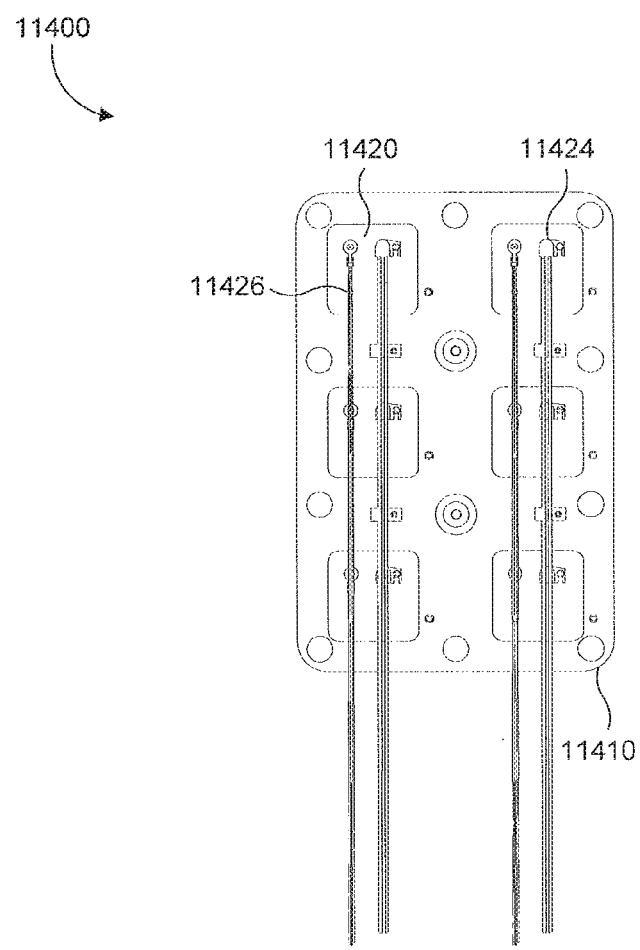
FIG. 67 shows a back view of the heater assembly of FIG. 65.
Figure 68:
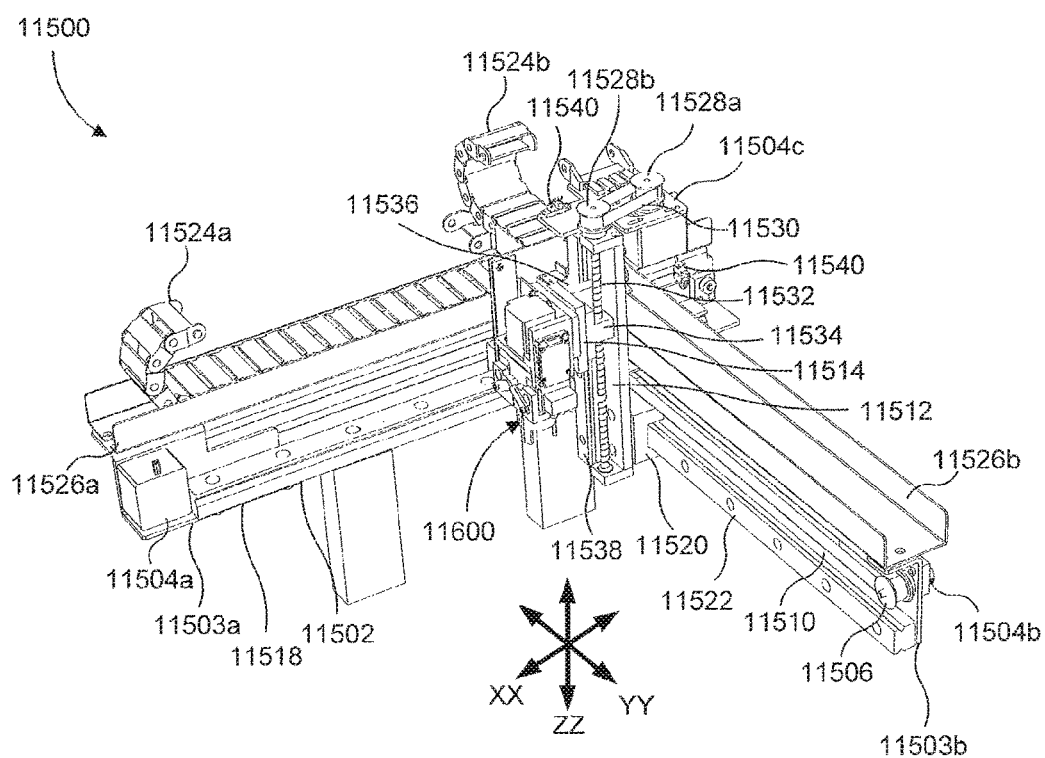
FIG. 68 is a perspective view of a drive assembly included in the instrument of FIG. 51, according to an embodiment.
Figure 69:
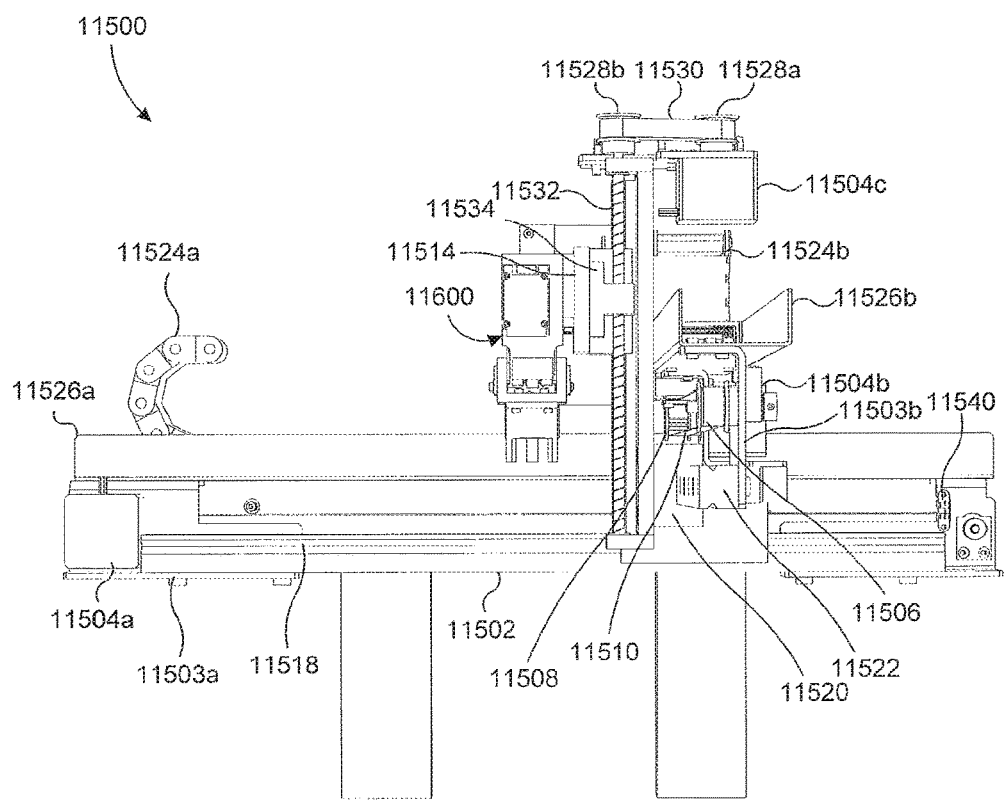
FIG. 69 shows a front view of the drive assembly of FIG. 68.
Figure 70:
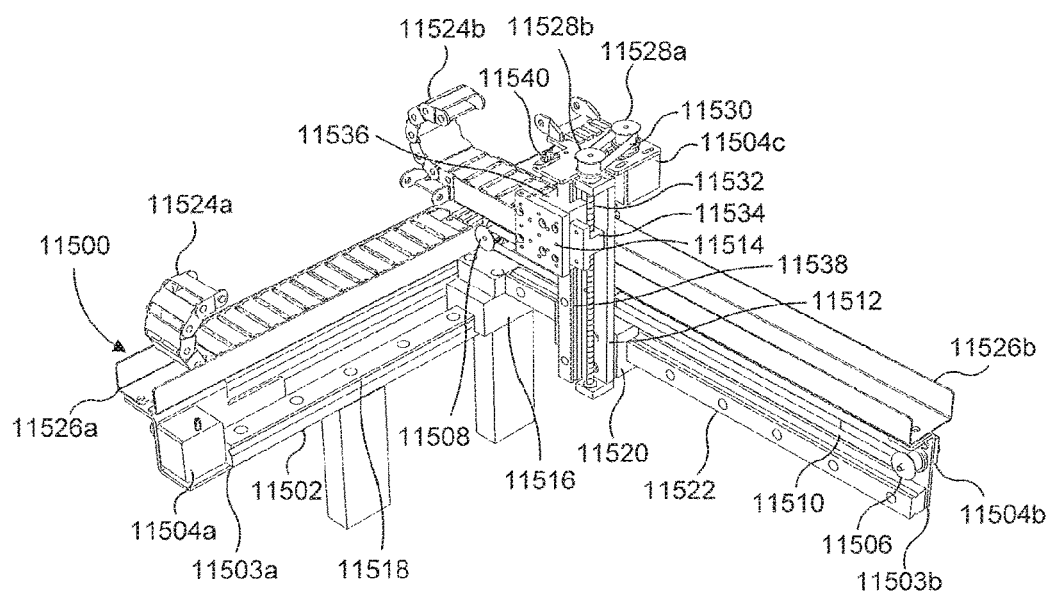
FIGS. 70 and 71 show the drive assembly of FIG. 68 in a first configuration and a second configuration, respectively.
Figure 71:
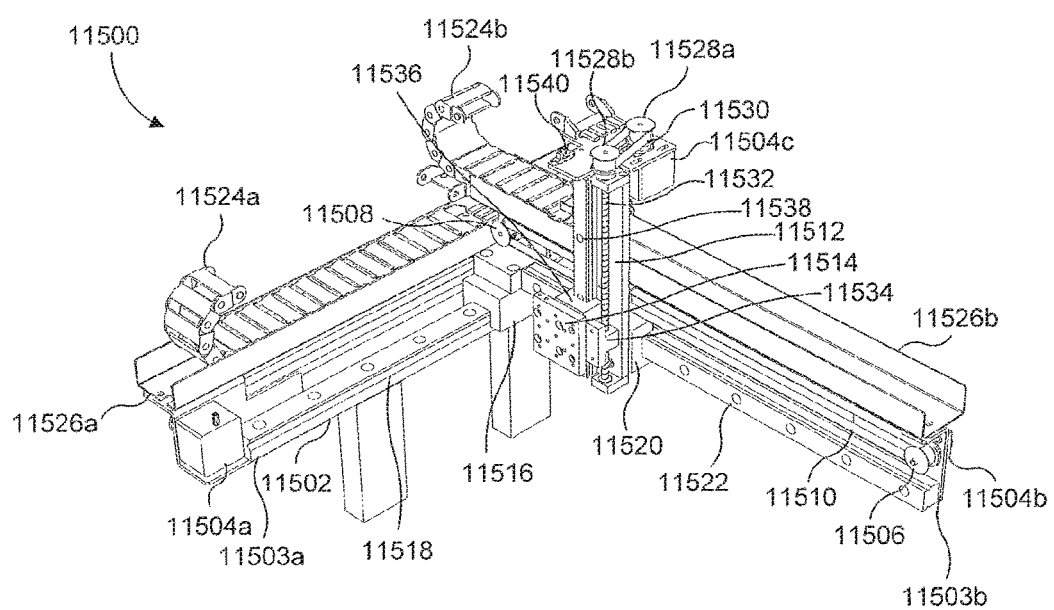

As shown in FIG. 55-57, the instrument 11000 includes a heater assembly 11400, configured to receive a series of containers, e.g., container assembly 3700 and/or any other container described herein. The heater assembly 11400 is configured to heat and/or maintain a temperature of the container assemblies therein according to any of the methods described herein. Referring now also to FIG. 65-67, the heater assembly 11400 includes a housing 11410 configured to house a series of heating blocks 11420. The housing 11410 is formed from a rigid, and heat insulating material such as thick stainless steel, other metals, polymers. The housing 11410 can include a lining of a heat resistant material, e.g., Mica, or any other heat insulation means. The housing 11410 defines a series of cavities 11412, each being sized and shaped to receive a heating block 11420 with close tolerance.

The heating block 11420 can be formed from a heat conducting, rigid and wear resistant material, e.g., anodized aluminum. The heating block 11420 defines a series of receptacles 11422, each of which is shaped and sized to receive at least a portion of a container, e.g., reaction chamber 3732 of the container assembly 3700, or any other container described herein. For example, a container can be disposed on any of the series of receptacles 11422 of any of the series of heating blocks 11420 by the manipulator assembly 11600, which is driven and/or positioned by the drive assembly 11500 as described herein.

Each heating block 11420 includes heating elements 11424 disposed on a bottom surface of the heating block 11420. In some embodiments, the heating element 11424 can be a micro heater, e.g., a ceramic plate heater. In some embodiments, the heating elements 11424 can be electrical wires that pass a current through the heating block 11420 to heat the heating block 11420 using electrical energy (i.e., resistive heating). Each heating block 11420 also includes a temperature sensor 11426, e.g., a thermocouple, disposed within a body of the heating block 11420. The temperature sensor 11426 is in electrical communication with the heating element 11420 directly, or through a processing unit (not shown) of the instrument 11000. In this manner, the heating elements 11424 can be deactivated and/or controlled to limit heating to the heating block 11420, e.g., when the temperature of the sensors exceeds a predefined temperature level. In this manner, the temperature of the heating block 11424, and the samples disposed therein can be controlled in accordance with the methods disclosed herein.

As shown in FIG. 55-57, the instrument 11000 includes a drive assembly 11500 configured to transport a container or assembly coupled thereto, e.g., by the manipulator assembly 11600, as described herein. For example, the manipulator assembly 11600 can be coupled to a container, and the drive assembly 11500 can be configured to enable transport of the container from a first location within the housing 11100 to a second location, e.g., from a loading cartridge 11300 to the heater assembly 11400, from the heater assembly 11400 to the detector 11200, from the detector 11200 to an unloading cartridge 11300, and/or any other location therewithin.

Referring also now to FIG. 68-71, the drive assembly 11500 includes a support 11502, e.g., a frame or a chassis, on which the components of the drive assembly 11500 are mounted. The support 11502 is securely mounted on the baseplate 11118, and can be configured to absorb any vibrations caused by the motion of the drive assembly 11500. The support includes a first section 11503*a* that is oriented along an X axis with respect to the X axis of the instrument 11000, as shown by the arrow XX, and a second section 11503*b* oriented along a Y-axis with respect to the instrument 11000, as shown by the arrow YY. The second section 11503*b* is movably disposed on and/or coupled to the first section 11503*a* via the second guide block 11520. The drive assembly 11500 includes a first actuator 11504*a* disposed on the first section 11503*a*, a second actuator 11504*b* disposed on the second section 11503*b*, and a third actuator 11504*c* mounted on the frame 11512. The first actuator 11504*a* and the second actuator 11504*b* are configured to drive the frame 11512 and any subassembly, e.g., the manipulator assembly 11600, disposed on the mount 11514, in an X and Y direction, respectively, as described herein. The third actuator 11504*c* is configured to drive the mount 11514 and any subassembly mounted thereon, e.g., the manipulator assembly 11600, in a Z direction with respect to the instrument 11000, as shown by the arrow ZZ. The actuators can be substantially similar to each other and can include, e.g., stepper motors, configured to drive the frame 11512 and/or mount 11514 a fixed distance with every step, e.g., each portion of a rotation of the actuators 11504*a*, 11504*b* and/or 11504*c*.

The first actuator 11504*a* and the second actuator 11504*b* include a first disc 11506 mounted on each of the actuators 11504*a*, 11504*b*. A second disc 11508 (FIG. 70) is disposed on each of the first section 11503*a* and the second section 11503*b* of the support 11502. A belt 11510 is looped around the first disc 11506 and the second disc 11508 in a taut manner, such that a rotation of the disc 11506 caused by the actuator 11504*a/b* urges the belt 11510 to be driven along its length (or rotated) over the second disc 11508. The belt 11510 can be, e.g., a rubber belt, a plastic belt or a polymer belt, and can include grooves on the surface contacting the discs 11506 and 11508, e.g., to provide friction and/or no slip translation of the belt. The belt 11510 coupled to the first actuator 11504*a* is operably coupled to a first guide block 11516 which is mounted on a first guide rail 11518. The belt 11510 is configured such that translation of the belt 11510 caused by the first actuator 11504*a* urges the first guide block 11516 and the second section 11503*b* of the support 11502 mounted thereon, to translate slidably along the guide rail 11518 in the X direction. Similarly, the second actuator 11504*b* also includes a belt 11510 disposed on the disc 11506 which is coupled to the second disc 11508 disposed on the frame 11512. The frame 11512 is coupled to the second guide block 11520. The second guide block 11520 is mounted on a second guide rail 11522. Driving the belt 11510 by the second actuator 11504*b*, drives the frame 11512 and the second guide block 11520 slidably along the second guide rail 11522. In this manner, a combination of translation of the second section 11503 of the support 11502 caused by the actuation of the first actuator 11504*a* along the X axis, and the translation of the frame 11512 along the Y axis caused by the actuator 11504*b*, can drive the frame to any location in an X-Y plane within the instrument 11000.

The frame 11512 is coupled to a first chain 11524*a* slidably disposed in a first chain guide 11526*a*, which is disposed on and coupled to the first section 11503*a*. A second chain 11524*b* is also coupled to the frame 11512, and is slidably disposed in a second chain guide 11526*b*, which is disposed on and coupled to the second section 11503*b*. The chains 11524*a/b* are configured to slide along the chain guides 11526*a/b* in close tolerance corresponding to an X-Y displacement of the frame 11512, such that the chains prevent any lateral motion of the frame 11512, e.g., to ensure accurate displacement of the frame 11512.

As described herein, the third actuator 11504*c* is disposed on the frame 11512 and includes a first disc 11528*a* coupled to the actuator 11504*c*. A belt 11530 is coupled to the first disc 11528, such that the belt 11530 loops over the first disc 11528*a* and a second disc 11528*b*. The second disc 11528*b* is coupled to a lead screw 11532 included in the frame 11512. The belt 11530 can be substantially similar to the belt 11510. The lead screw 11532 has a nut 11534 mounted on threads of the lead screw 11532. The nut is coupled to the mount 11514. The third actuator 11504*c* is configured to rotate the first disc 11528*a* which urges the belt 11530 to translate, thus rotating the second disc 11528*b*. Rotation of the second disc 11528*b* rotates the lead screw 11532 that urges the nut 11534 to displace along the length of the lead screw 11532 from a first position (FIG. 70), to a second position (FIG. 71) in the Z direction. Displacement of the nut 11534 also causes the mount 11514 coupled to the nut 11534, and any subassembly mounted thereon, e.g., the manipulator assembly 11600, to move from the first position to the second position in the Z direction. The mount 11514 is also coupled to a third guide block 11536 slidably mounted on a third guide rail 11538, such that displacement of the mount 11514 in the Z direction is guided by the third guide block 11536 and the third guide rail 11538, e.g., to prevent any radial motion of the mount 11514 about a longitudinal axis defined by the lead screw 11512.

Figure 72:
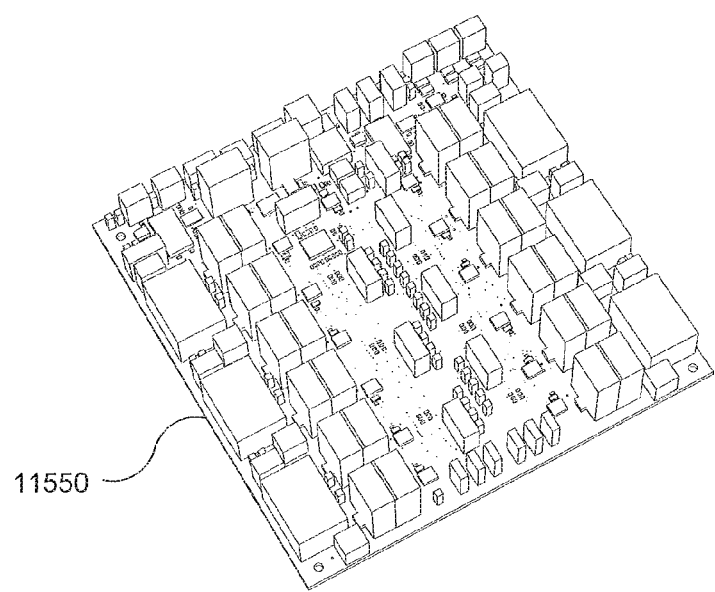
FIG. 72 shows a perspective view of an electronic circuit system for controlling the drive assembly included in the instrument of FIG. 51.
Figure 73:
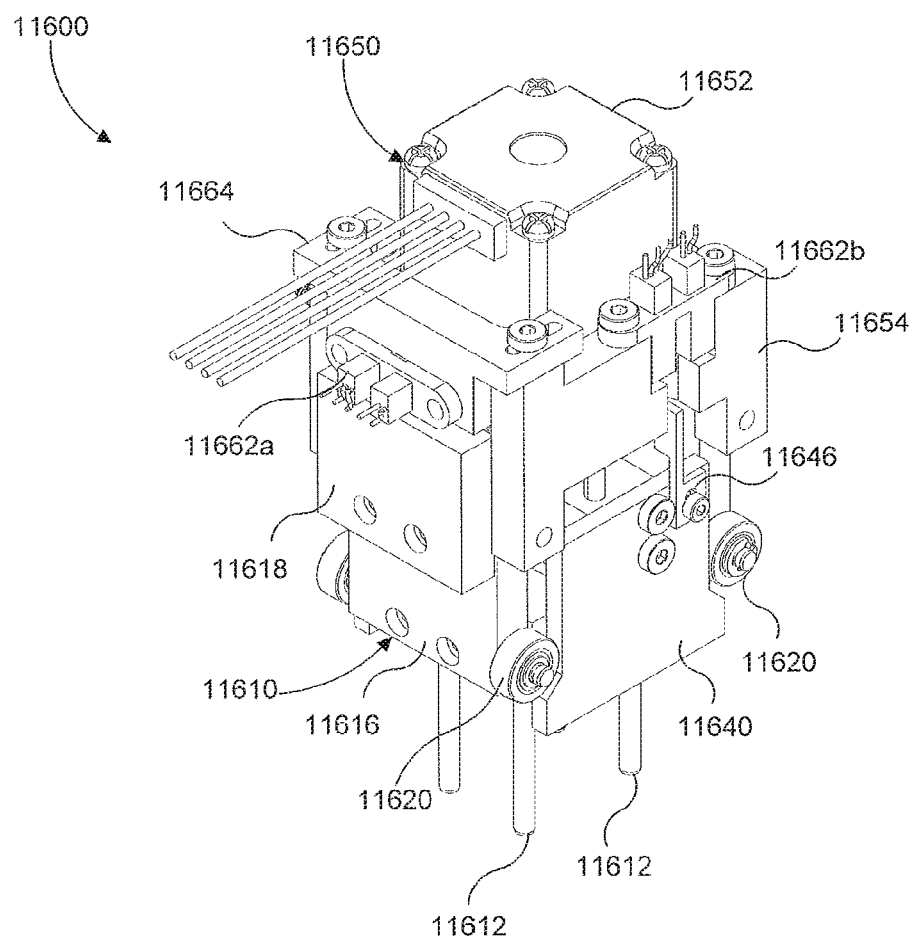
FIG. 73 shows a perspective view of a manipulator assembly according to an embodiment included in the instrument of FIG. 51.

The drive assembly 11500 includes sensors 11540 mounted each of the first section 11503*a*, the second section 11503*b*, and the frame 11512. The sensors 11540 can be position sensors such as, e.g., optical sensors, motion sensors, piezoelectric sensors, or any suitable sensor. The sensors 11540 can be configured to detect a location of the second section 11503*b* and the frame 11512, e.g., to prevent an overtravel that can damage the drive assembly and/or cause increased wear. As shown in FIG. 57 and FIG. 72, the instrument 11000, also includes circuitry 11500 for controlling the actuators 11504*a/b/c*. The circuitry 11500 can be any commercially available circuitry used for control of actuators 11504*a/b/c*, e.g., stepper motor controller circuitry.

As shown in FIG. 55-57, the instrument includes a manipulator assembly 11600 disposed on the mount 11514 included in the drive assembly 11500. The manipulator assembly 11600 is configured to grasp, hold, clamp, contact, engage and/or otherwise secure a container, e.g., container assembly 3700 as described herein. For example, the manipulator assembly 11600 can be configured to releasably engage and/or grip container and/or engage one or more actuators included in the container, such as for example the container assembly 3700.

Referring now to FIGS. 73-84, the manipulator assembly 11600 includes an articulation subassembly 11610, a plunger subassembly 11630 and an actuator subassembly 11650. The articulation assembly 11610 is configured to releasably contact, grasp or otherwise secure a container, e.g., container assembly 3700. For example, the articulation assembly 11610 can be configured to secure or grasp a container disposed in a first location, such as the loading cartridge 11300. The articulation subassembly 11601 can continuously secure the container during transport from the first location to a second location within the instrument 11000 by the drive assembly 11500. Such changes in position can include moving the container assembly from the loading cartridge 11300 to the heater assembly 11400, from the heater assembly 11400 to the detector assembly 11200 and/or from the detector assembly 11200 to the unloading cartridge 11300. The plunger subassembly 11630 is configured to contact, engage or otherwise manipulate one or more actuators in a container, e.g., actuator 3750 and/or 3760 included in the container assembly 3700, to urge the actuator and/or actuators to communicate a reagent (e.g., biologic or abiologic vectors such as transduction particles of the type shown and described herein) and/or a substrate (e.g., tridecanal) from a reagent volume to a reaction chamber of the container, as described herein. The actuator subassembly 11650 is configured to engage or manipulate the plunger subassembly 11630, e.g., to manipulate an inner plunger 11632 and/or an outer plunger 11636 of the plunger assembly 11630, as described herein. The actuator subassembly 11650 can also be configured to engage or manipulate the articulation subassembly 11610, e.g., to manipulate or otherwise urge the articulation subassembly 11610 to secure or release a container, e.g., container assembly 3700, as described herein. Similarly stated, the actuator subassembly 11650 can, with a single actuator, cause the manipulator assembly 11600 to both grip and/or secure a container, and actuate the container.

Figure 74:
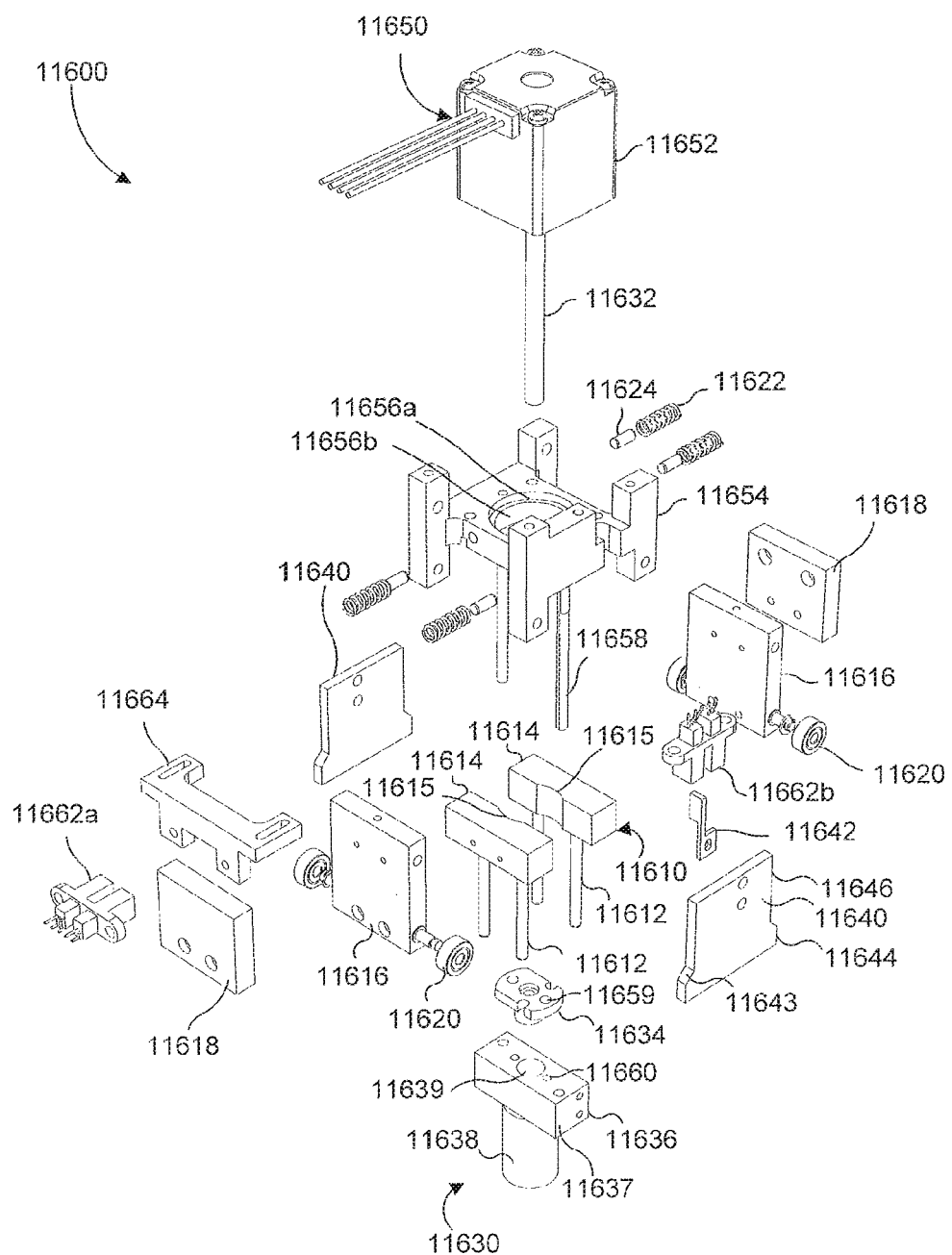
FIG. 74 shows an exploded view of the manipulator assembly of FIG. 73.
Figure 75:
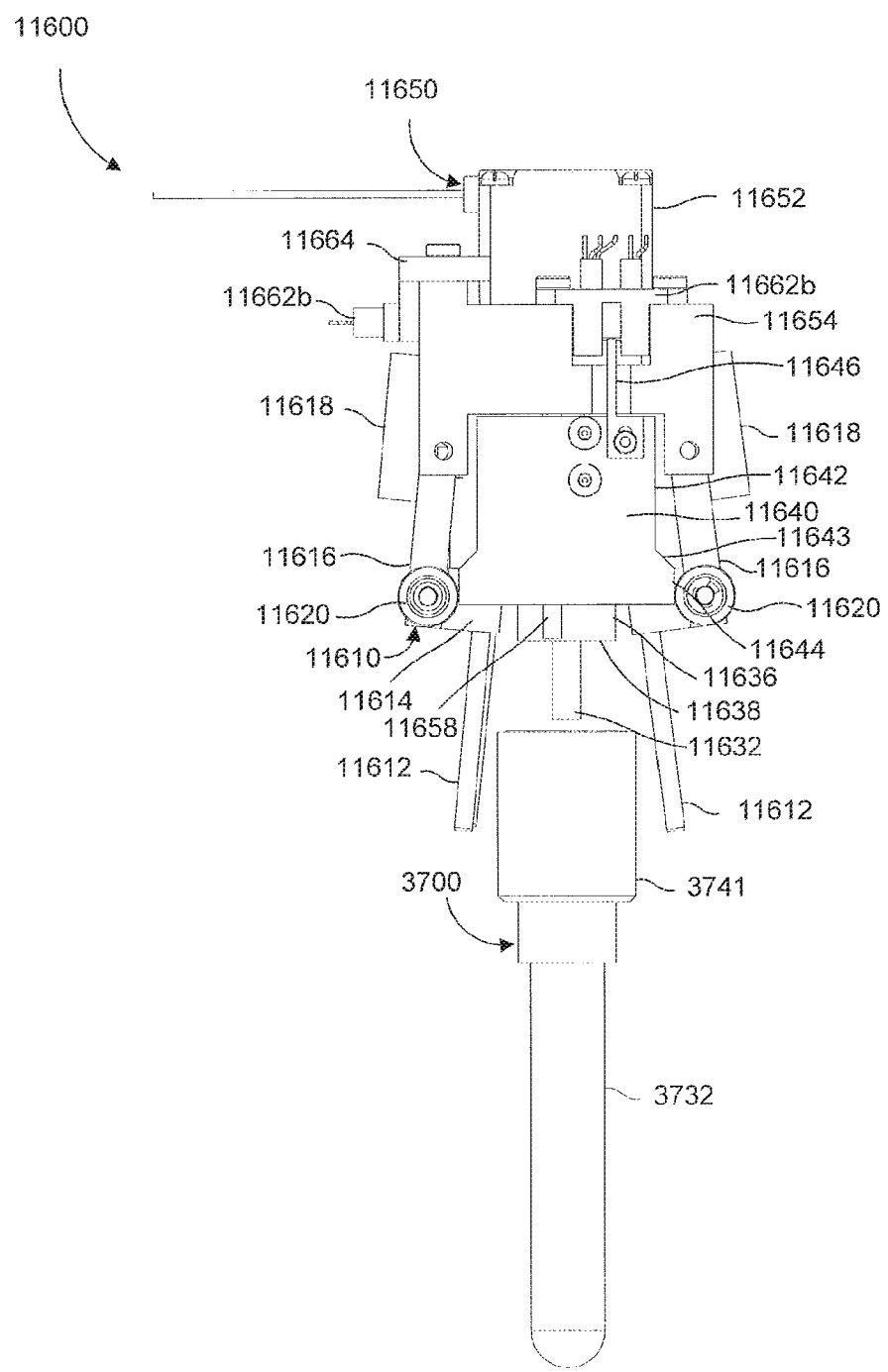
FIG. 75 shows a side view of the manipulator assembly of FIG. 73 in a first (or "open grip") configuration.

As shown in FIGS. 74-75, the articulation subassembly 11600 includes a set of grippers 11612, coupled or mounted on a set of gripper bases 11614. As shown two grippers 11612 are coupled to a single gripper base 11614. In some embodiments, each gripper base 11614 can include more than two grippers 11612, e.g., three or four. The grippers 11612 are configured to be elongated, pin-like members that can be formed from a strong and rigid material, e.g., metals such as stainless steel. In some embodiments, the grippers 11612 can include a surface that can have a high friction for contacting, grasping or otherwise securing a container, e.g., container assembly 3700. For example, the surface of the grippers 11612 can include grooves, abrasions, rubber coating, soft plastic and/or rubberized carbon. Each gripper base 11614 defines a groove (or channel) 11615 configured to allow a plunger portion 11637 of the outer plunger 11636 included in the plunger subassembly 11630, to move within a region between the grooves 11615, without contacting a sidewall defining the grooves 11615.

Each gripper base 11614 is coupled to a side plate 11616 by any suitable mechanism. The side plates 11616 are pivotally coupled to an actuator mount 11654 included in the actuator assembly 11650, as described herein. The side plates are configured to pivot or articulate about their mounts relative to the plunger assembly 11630, to urge the articulation assembly 11610 from a first configuration to a second configuration. In the first (or closed) configuration the set of grippers 11612 are in a closed position to selectively engage, grip, grasp or otherwise secure a container, e.g., container assembly 3700. In the second (or opened) configuration the set of grippers 11612 are distal to each other, e.g., to disengage or release the container. A set of guide wheels 11620 is disposed on a side wall of the each of the set of side plates 11616, e.g., mounted on pins, bolts, screws or the likes. Under certain conditions, the set of guide wheels 11620 is configured to be proximate to but not contacting, or in contact with a portion of a side wall of a set of guide members 11640 included in the plunger assembly 11630, as described herein. The guide members 11640 are configured to urge the side plates 11616 and thus the articulation assembly 11610 from the first configuration to the second configuration, as described herein.

The side plates 11616 are coupled to a set of compression plates 11618. The compression plates 11618 are in pressure contact with a set of springs 11622, which are mounted to the actuator mount 11654 via pins. The set of compression plates 11618 are configured to angularly displace with the pivotal motion of the set of side plates 11616, such that the set of compression plates 11618 engage the set of springs 11622, e.g., compress the springs 11622, when the articulation assembly 11610 is in the second configuration. Thus the compression plates 11618 are configured to urge the articulation assembly 11610 into the first configuration from the second configuration, e.g., to grasp or secure a container, e.g., container assembly 3700 or any other container described herein. The springs 11622 are configured to control the amount of force exerted by the grippers 11612 on the container, e.g., to prevent crushing of the container. At least one of the set of side plates 11616 can be configured to engage a position sensor 11662*a*, e.g., an optical sensor, motion sensor, piezoelectric sensor, or any other suitable sensor. The sensor 11662*a* is coupled to a sensor mount 11664, which is mounted a surface of the actuator mount 11654. The sensor 11662*a* can be configured to inform a control system and/or user about the position of the articulation assembly 11610, e.g., articulation assembly in first configuration (i.e., securing, engaging or grasping a container) or second configuration (i.e., disengaging or releasing a container). In some embodiments, the sensor 11662*a* can be a homing sensor, configured to identify a home position of the articulation assembly 11610.

The plunger subassembly 11630 includes an inner plunger 11632 and an outer plunger 11636. As shown, the inner plunger 11632 is also a lead screw of the actuator 11652. Accordingly, the inner plunger 11632 can rotate about a longitudinal axis of the plunger assembly 11630. The inner plunger 11632 can be configured to engage or manipulate a first actuator of a container, e.g., the actuator 3750 of the container assembly 3700 as described herein. The outer surface of the inner plunger 11632 is threaded and can be threadedly disposed within a collar 11634. The collar 11634 is configured to move along the threads of the inner plunger 11632 during the rotation of the inner plunger 11632. The collar 11634 is further coupled to an engagement portion 11637 of the outer plunger 11636, such that a rotation of the inner plunger 11632 results in a longitudinal displacement of the outer plunger 11636. This can, for example, allow control of the speed of the outer plunger 11636, which can be used to control delivery of a substrate into a reaction chamber of a container, as described herein. The outer plunger 11636 includes an engagement portion 11638 which can be configured to engage or manipulate a second actuator in a container, e.g., actuator 3760 of the container assembly 3700, as described herein. The outer plunger 11636 also includes a channel 11639 defined therethrough along a longitudinal axis of the outer plunger 11636. At least a portion of the inner plunger 11632 can be disposed in the channel 11639.

A set of guide members 11640 are disposed on a side wall of the outer plunger 11636. Each of the set of guide members 11640 includes a first section 11642 having a first width, a second section 11644 having a second width greater than the first width, and a third section 11643 which is angled with respect to a longitudinal axis of the guide member 11640 and connects the first section 11642 to the second section 11644. At least a portion of the plunger assembly 11630 e.g., the collar 11634, the outer plunger 11636 and the guide members 11640, are configured to move along a longitudinal axis defined by the inner plunger 11632. Furthermore, the plunger assembly 11630 is configured to engage and or manipulate a container, e.g., container assembly 3700, that is engaged, secured or otherwise grasped by the articulation assembly 11610, as described herein. The plunger assembly 11630 is also configured to manipulate the articulation assembly 11610, e.g., to urge the articulation assembly 11610 from the first configuration, in which the articulation assembly 11610 is engaging, grasping or otherwise securing a container, to the second configuration, in which the articulation assembly disengages or releases the container, as described below. A clip 11646 is also disposed on one of the guide members 11640 (FIG. 75). The clip 11646 is configured to selectively engage a sensor 11662*b* to validate and/or determine a position of the plunger assembly 11630. The sensor 11662*b* can be any suitable sensor, e.g., a position sensor, a motion sensor, an optical sensor, a piezoelectric sensor or any other suitable sensor, disposed on the actuator mount 11654. The sensor 11662*b* can be used to determine a position of the plunger assembly 11630, e.g., to prevent overtravel of the plunger assembly 11630.

The actuator subassembly 11650 includes an actuator 11652, e.g., a stepper motor, which is disposed on the actuator mount 11654. The actuator mount 11652 defines corresponding recesses 11656*a* and 11656*b*. The recess 11656*a* provides a mounting seat for at least a portion of the actuator 11652. The groove 11656*b* defines an opening through which at least a portion of the plunger assembly 11630, e.g., the inner plunger 11632, the collar 11634 and the outer plunger 11636 can move. The actuator mount 11654 further includes a set of alignment pins 11658 disposed on a bottom surface of the actuator mount 11654. The alignment pins 11658 are substantially parallel to the longitudinal axis defined by the plunger assembly 11630. At least a portion of each alignment pin 11658 is disposed in a corresponding channel 11659 included in the collar 11634 and the engagement portion 11637 of the outer plunger 11636. In this manner, the displacement of the plunger subassembly 11630 along the longitudinal axis defined by the plunger subassembly 11630, e.g., caused by a rotation of the inner plunger 11632, is guided by the alignment pins 11658, e.g., to prevent any rotation or sideways motion of the plunger assembly 11630.

As described herein, the manipulator assembly 11600 is configured to releasably contact, engage or otherwise secure a container. FIG. 75 shows a side view of the manipulator assembly 11600 in a first configuration, in which the housing 3741 of the container assembly 3700 is not contacted, grasped or otherwise secured by the manipulator assembly 11600. FIG. 75 shows a side view of the manipulator assembly 11600 in a second configuration, in which the manipulator assembly 11600 is securing or gripping the container assembly 3700. The manipulator assembly 11600 is configured such that the grippers 11612 secure the container assembly 3700 only from the top portion, i.e., the reagent module 3740. This can allow a bottom read of the container assembly 3700 by the detector 11200 or any other detector described herein.

As shown in FIG. 75, when in the first configuration, the actuator 11652 has rotated the inner plunger 11632 to move the collar 11634 coupled to the inner plunger 11632 along the length of the inner plunger 11632 in a direction towards the actuator 11652. In this manner, when in the first configuration the actuator 11652, at least a portion of the collar 11634 and/or the outer plunger 11636 coupled to the collar 11634, are within the opening defined by the recess 11656*b* of the actuator mount 11654. Moreover, the position of the plunger assembly 11630 relative to the actuator assembly 11650 (i.e., in an upward position) is such that the guide members 11640 engage the articulation assembly 11610. As shown in the first configuration illustrated in FIG. 75, the displacement of the guide member 11640 towards the actuator 11652 places the guide wheels 11620 in contact with the second section 11644. In this configuration, the set of side plates 11616 pivot or articulate about their pivot mounts relative to the longitudinal axis of the plunger assembly 11630, such that the gripper bases 11614 and the set of grippers 11612 are angled with respect to the longitudinal axis of the plunger assembly 11630. An end of corresponding grippers 11612 is a first distance apart, such that the first distance is greater than a diameter of the housing 3741 of the container assembly 3700.

In the first (or "open grip") configuration, the manipulator assembly 11600 is configured to disengage or release the container assembly 3700 and/or is ready to receive the container assembly 3700. For example, in some embodiments, the container assembly 3700 can be disposed in a cartridge 11300. The manipulator assembly 11600 can be driven by the drive assembly 11500 to the location where the container assembly 3700 is disposed, and then urged into the first configuration. The manipulator assembly 11600 can then be displaced along a longitudinal axis defined by the manipulator assembly 11600 towards the container assembly 3700, until the grippers 11612 are adjacent to the housing 3741, and a bottom portion of the inner plunger 11632 is in close proximity to but not contacting an engagement portion 6752 of an inner plunger 6750 (not shown in FIG. 75-76) disposed in the housing 3741 of the container assembly 3700.

Figure 76:
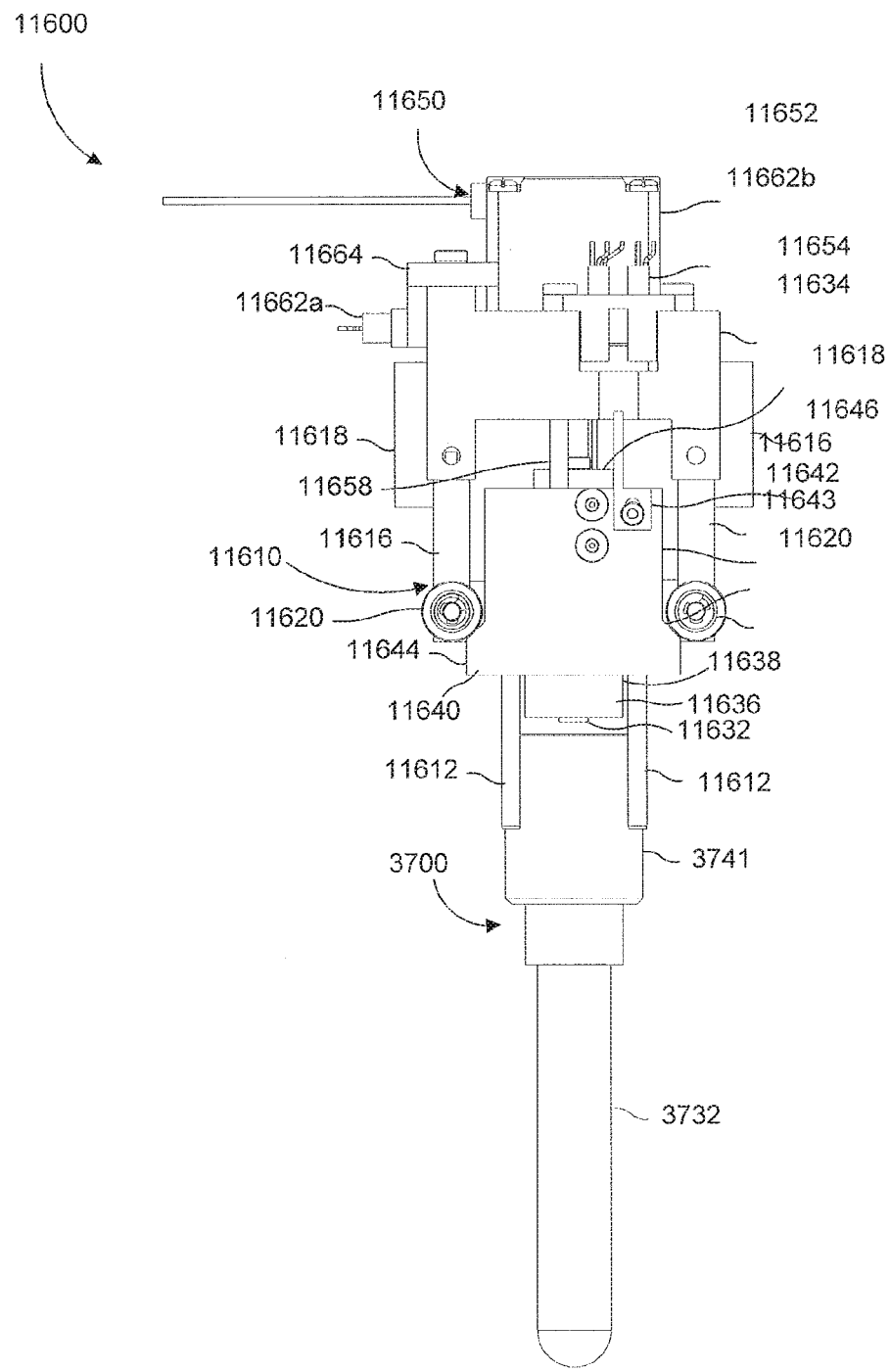
FIG. 76 shows a side view of the manipulator assembly of FIG. 73 in a second (or "closed grip") configuration.
Figure 77:
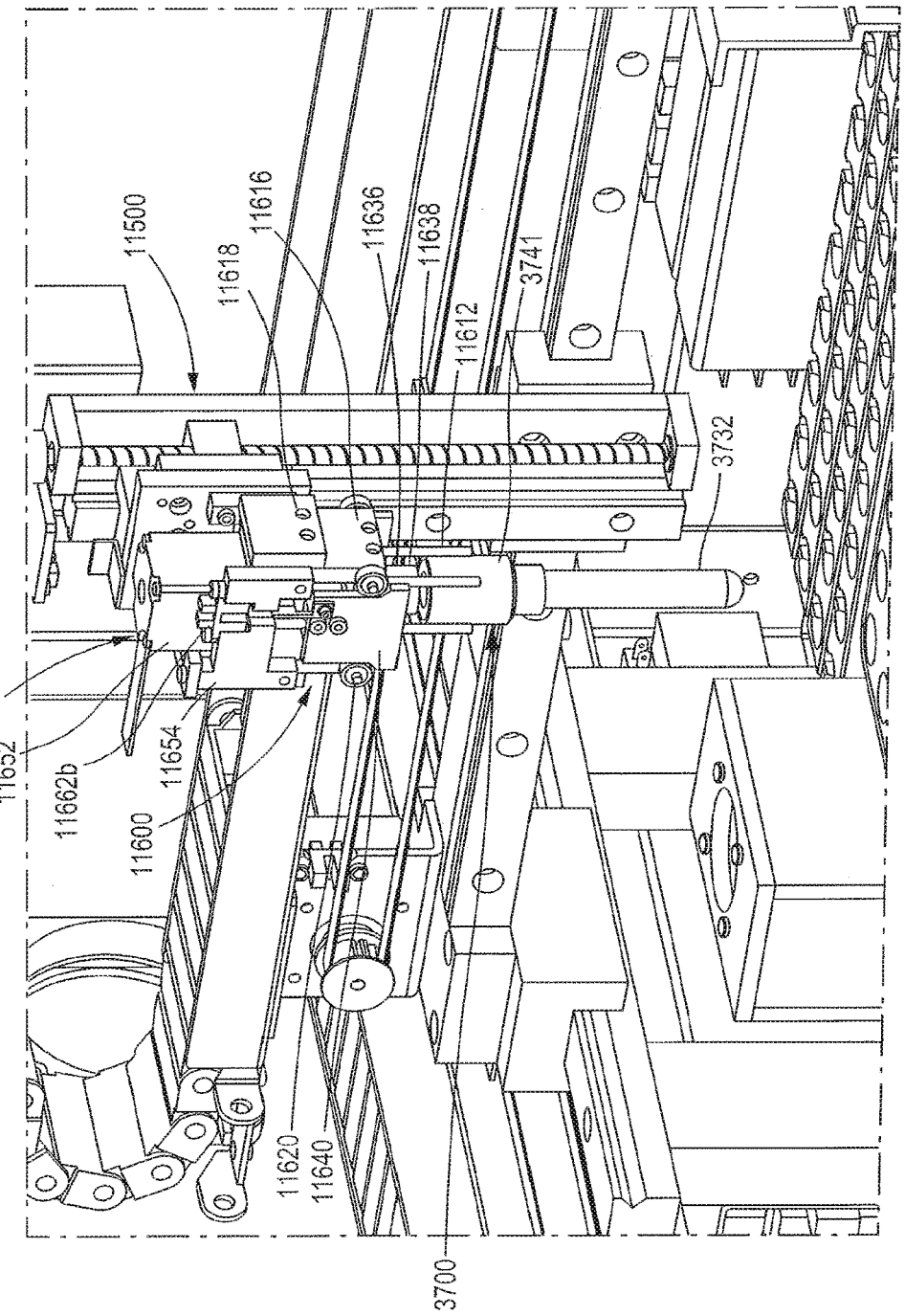
FIG. 77 shows a perspective view of the manipulator assembly of FIG. 73 in second ("closed grip") configuration and transporting a container.

As shown in FIG. 76, the articulation assembly 11610 can be moved into the second configuration to engage, grip, grasp or otherwise secure the container assembly 3700. For example, to move the articulation assembly to the second configuration, the inner plunger 11632 is rotated by the actuator 11652. This urges the collar 11634 to move along the length of the inner plunger 11632 in a direction away from the actuator 11652 (e.g., downward as shown in FIG. 76). Displacement of the collar 11634 also urges the outer plunger 11636 and the set of guide members 11640 coupled thereto, to move along a longitudinal axis defined by the plunger assembly 11630 away from the actuator 11650. This causes the guide wheels 11620 to ride along a side wall of the second section 11644 of the guide member 11640 onto the narrower inclined section 11643. In this configuration, the set of springs 11622 that are in pressure contact with the set of compression plates 11618, urge the set of compression plates and hence the set of side plates 11616 to pivot relative to the longitudinal axis defined by the plunger assembly 11630. This also causes the gripper bases 11614 and the set of grippers 11612 coupled thereto to displace towards the housing 3741 of the container assembly 3700, such that in the second configuration, the set of grippers 11612 are contacting, engaging or otherwise securing the container assembly 3700. The manipulator assembly 11600 can be maintained in the second configuration to transport the container assembly 3700 from a first location within the housing 11100 of the instrument 11000 to a second location as shown in FIG. 77, via the drive assembly 11500.

Figure 78:
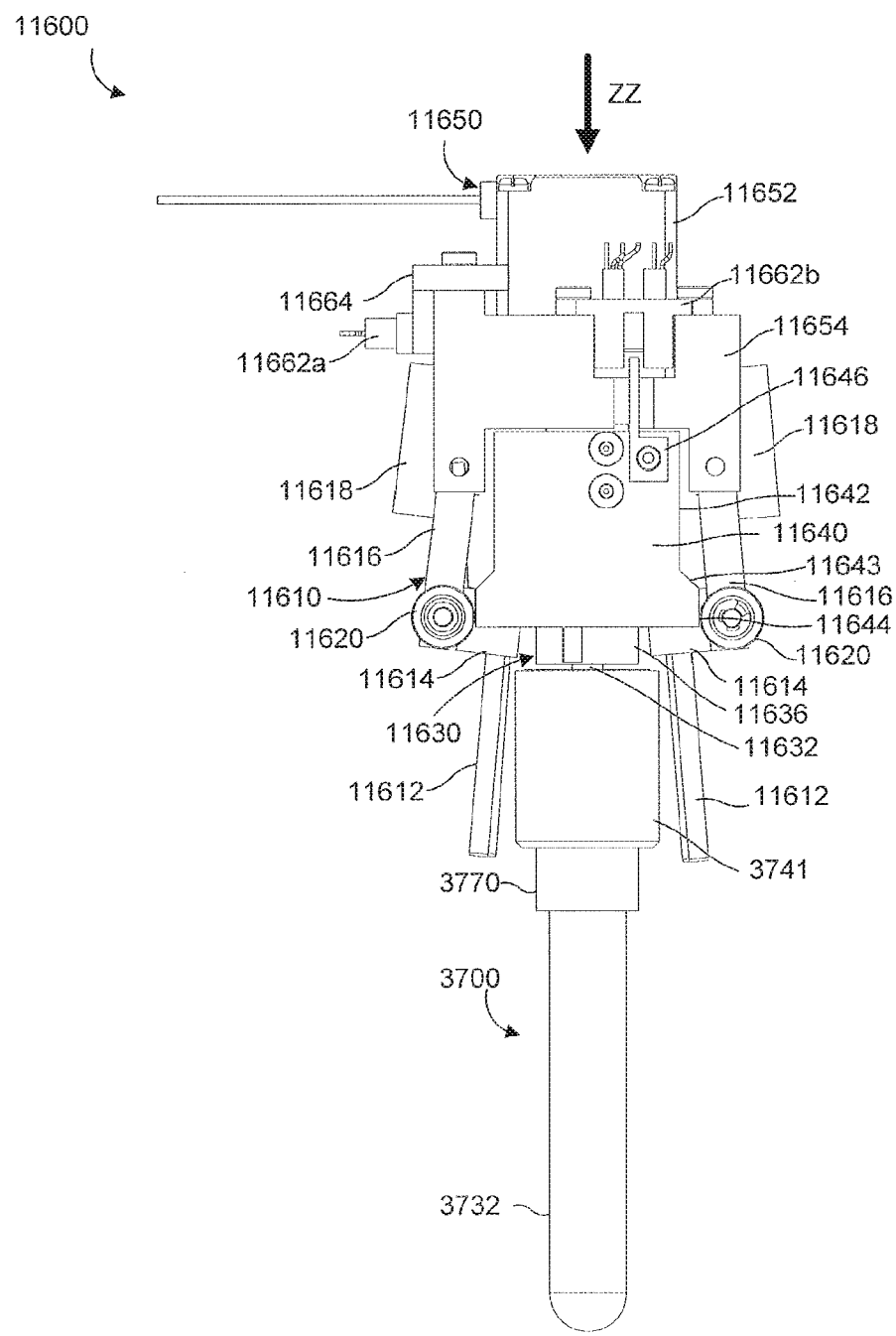
FIGS. 78 and 79 show side views of the manipulator assembly of FIG. 73 in the first ("open grip") configuration and engaging a container.
Figure 79:
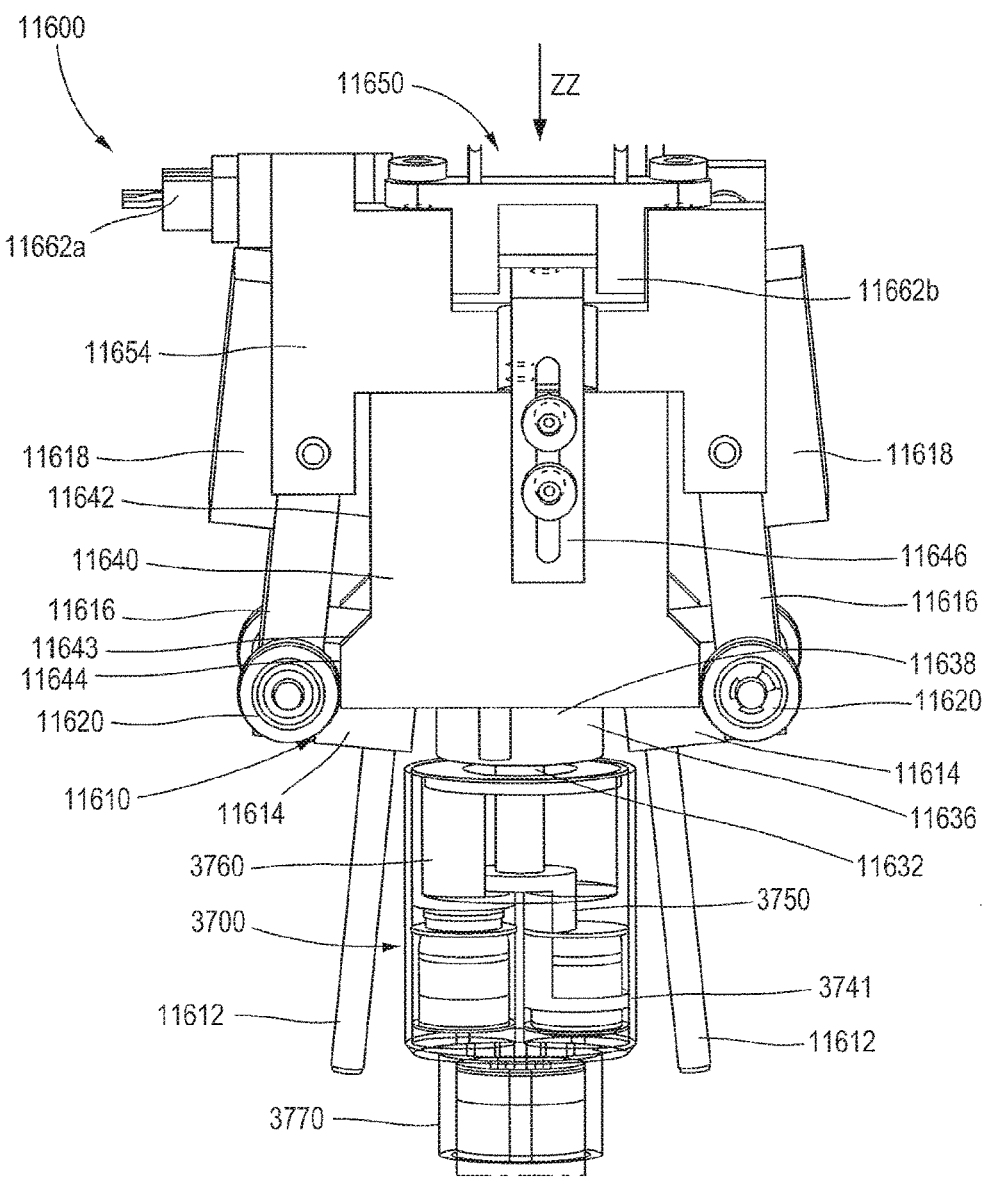
Figure 80:
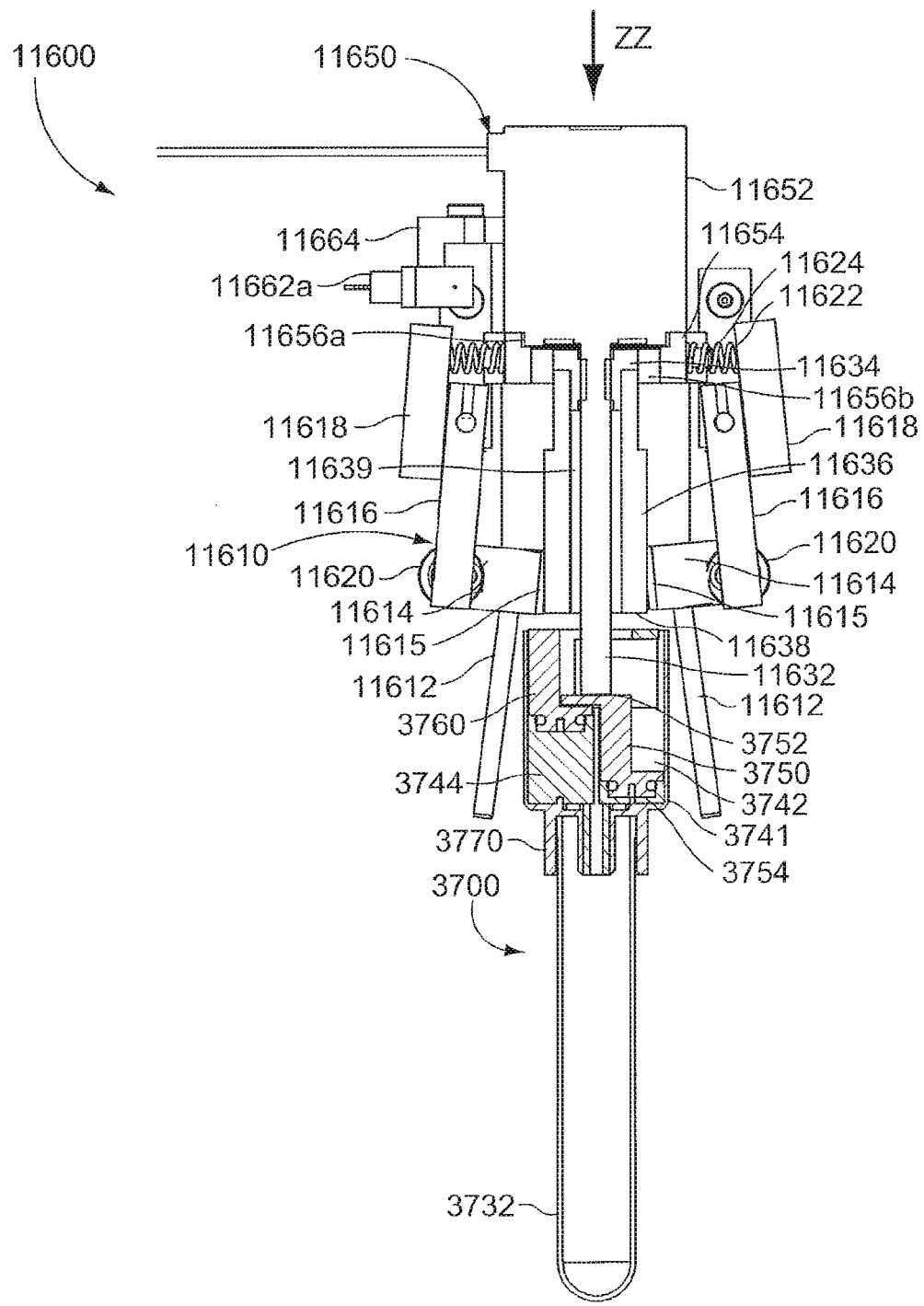
FIG. 80 shows a side cross-section of the manipulator assembly of FIG. 78 in the open configuration and engaging the container in a "first plunge" operation.

As described herein, the manipulator assembly can also be used to engage and or manipulate the container assembly 3700, e.g., the actuators 3750 and 3760 disposed in a housing 3741 of the container assembly 3700. FIGS. 78 and 79 show side views of the manipulator assembly 11600 in the first configuration (also referred to as "open grip") and FIG. 80 shows a side cross section of the manipulator assembly 11600 shown in FIG. 78. In this configuration, the plunger assembly 11630, the articulation assembly 11610 and the actuator assembly 11650 are in the same relative positions as discussed above with regard to FIG. 75. The positioning of the manipulator assembly 11600 relative to the container assembly 3700, however, is different. In particular, the inner plunger 11612 engages the engagement portion 3752 of the actuator 3750 as described below herein.

In this configuration (the "inner plunge" configuration), the container assembly 3700 can be disposed e.g., in a recess 11412 of a heating block 11420 included in the heater assembly 11400 as described herein, such that the container assembly 3700 cannot be displaced laterally with respect to a longitudinal axis of the manipulator assembly 11600. When the articulation assembly 11610 is in the first configuration ("open grip" and the "inner plunge"), at least a portion the collar 11634 and the outer plunger 11636 is located within the opening defined by the recess 11656b such that a bottom portion of the inner plunger 11632 is protruding from the bottom of the channel 11639 of the outer plunger 11636. Moreover, as described above, the set of guide wheels 11620 are contacting the surface 11644 of the set of guide members 11640 and the set of compression plates 11618 are compressing the set of springs 11622 to maintain the grippers in position.

To execute the "inner plunge" operation as shown in FIG. 78-80, the drive assembly 11500 is actuated to displace the manipulator subassembly 11600 in a downwards direction defined by a longitudinal axis of the plunger assembly 11630, as shown by the arrow ZZ. The downwards motion of the manipulator assembly 11600 causes the inner plunger 11632 to move downwards, such that a bottom portion of the inner plunger 11632 contacts the engagement portion 3752 of the actuator 3750, urging the plunger portion 3754 of the actuator 3750 within the internal volume 3742 defined by the housing 3741. The plunger portion 3754 can move from a first position to a second position, such that the plunger portion 3754 communicates a reagent disposed in the internal volume 3742 into the container assembly 3700, as described above. The reagent can be any reagent or substance described herein, such as a biologic or abiologic vector or transduction particle of the types described herein. After actuation of the first actuator 3750 by the manipulator assembly 11600, the container assembly 3700 can remain disposed in the heater assembly 11400 for a predefined time period and at a predetermined temperature. As described above, in some embodiments, maintaining the container assembly will allow a target cell within the sample to express a sufficient quantity of reporter molecules such as, for example, luciferase or any other reporter molecule described herein.

Figure 81:
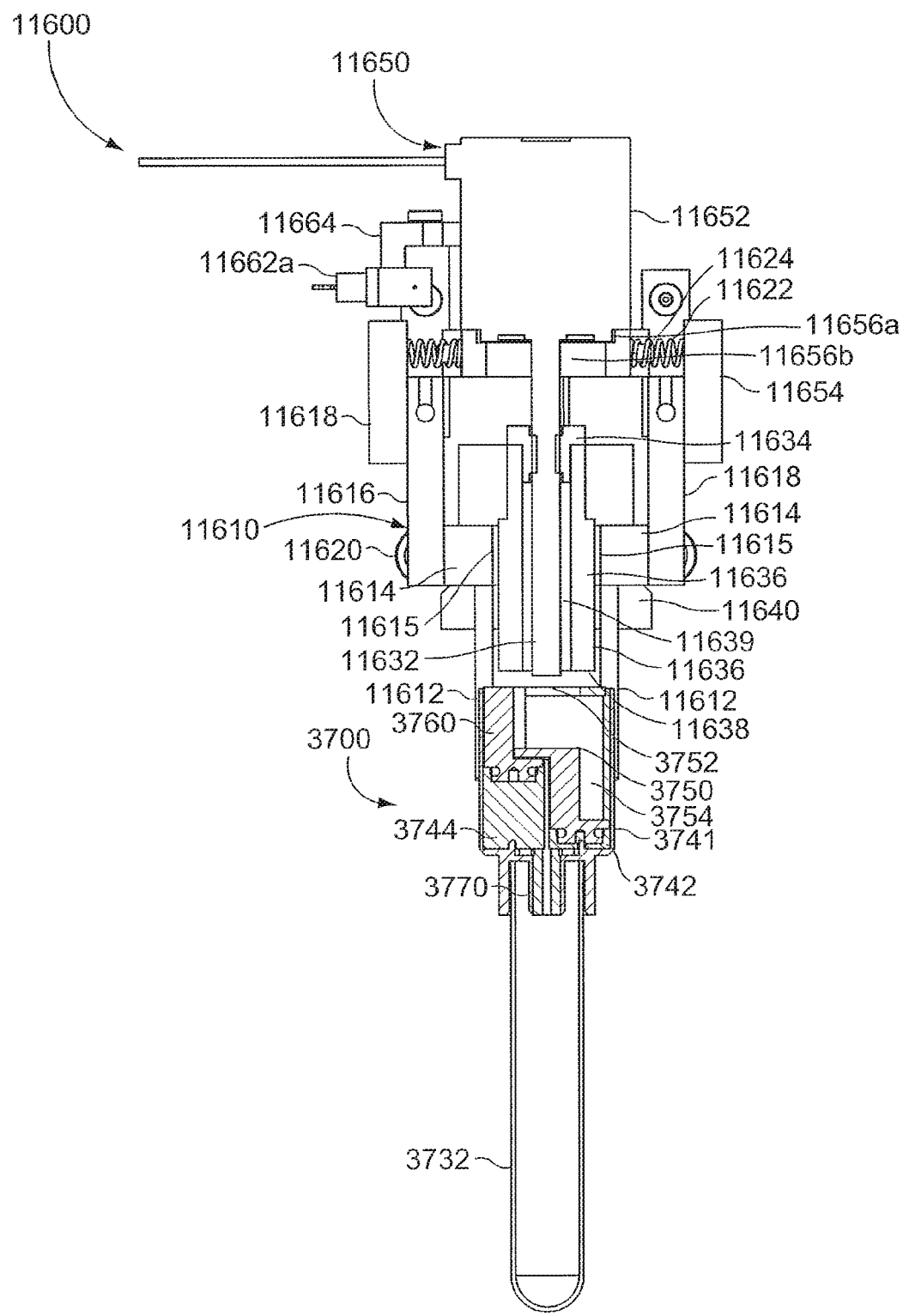
FIG. 81 shows a side cross-section of the manipulator assembly of FIG. 73 in the second ("closed grip") configuration.

FIG. 81 shows a side cross-section of the manipulator assembly 11600 in the second configuration (also referred to as "gripper closed"). In the second configuration, the manipulator assembly 11600 is in contact with, engaged, grasped or otherwise secured to the container assembly 3700, as described herein with reference to FIGS. 76 and 77. In the gripper closed configuration, the inner plunger 11632 is disposed substantially within the outer plunger 11636, such that the bottom portion of the inner plunger 11632 is proximal to but not contacting the engagement portion 3752 of the first actuator 3750 disposed in the housing 3741 of the container assembly 3700, as described herein. Furthermore, the set of guide wheels 11620 are contacting the third section 11643 of the set of guide members 11640. The gripper closed configuration can be used to transport the container assembly 3700, e.g., from the heater assembly 11400 to the detector assembly 11200. The articulation assembly 116500 is also configured to prevent overtravel. For example, if the in the closed grip configuration, the set of guide wheels contact the second surface 11644 of the set of guide members 11640, this indicates the outer plunger 11636 has overtravelled. In this situation, a pin (not shown) mounted on one of the set of side plates 11616 triggers the position sensor 11662a, that can send an overtravel signal, e.g., an alarm, to the processor 11126 or a user.

Figure 82:
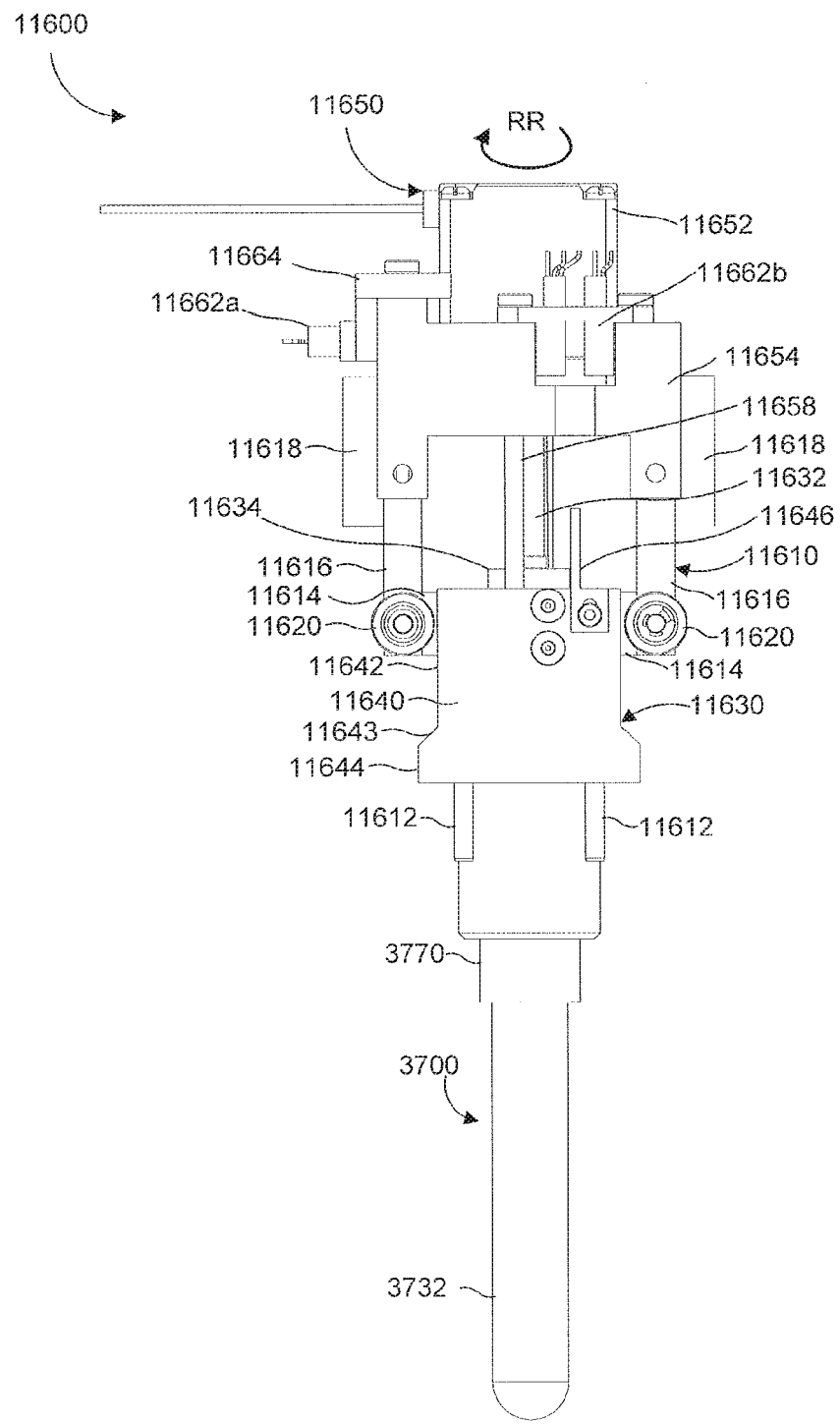
FIGS. 82 and 83 are a side view and a perspective view, respectively, of the manipulator assembly of FIG. 73 in a third configuration ("closed grip") configuration engaging the container in a "second plunge" operation.
Figure 83:
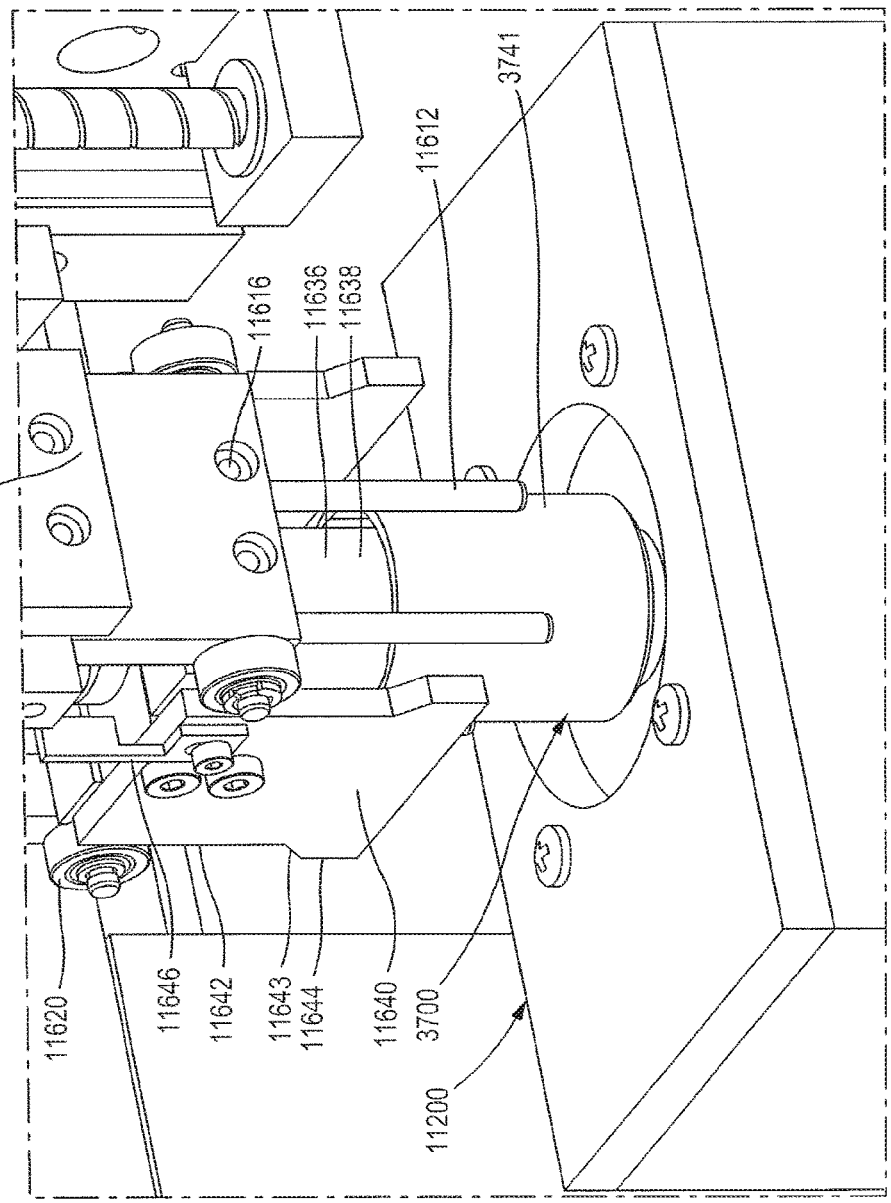
Figure 84:
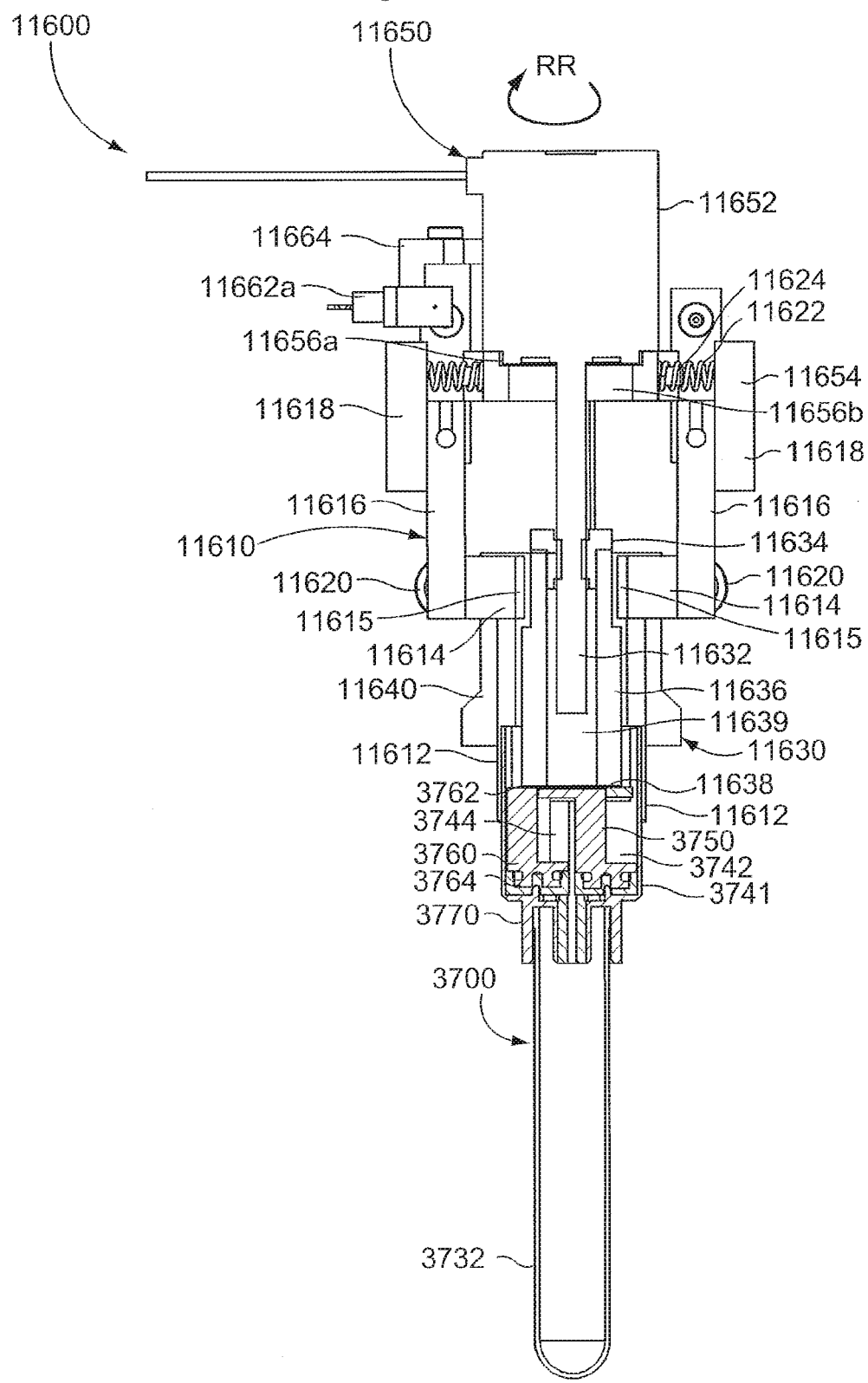
FIG. 84 shows a side cross section of the manipulator assembly of FIG. 82.
Figure 85:
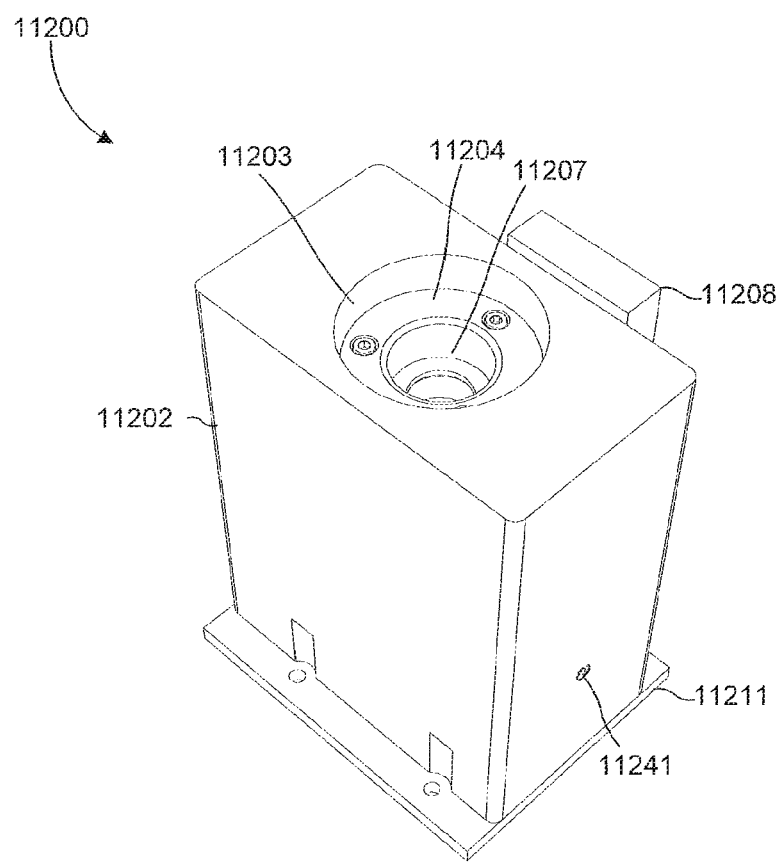
FIG. 85 shows a perspective view of a detector assembly, according to an embodiment, included in the instrument of FIG. 51.

Referring now to FIGS. 82-84, FIGS. 82 and 83 show a side view of the manipulator assembly 11600 and FIG. 84 shows a side cross-section of view shown in FIG. 82, in a third configuration (also referred to as "substrate plunge"). In the substrate plunge configuration, the outer plunger engages the engagement portion 3762 of the actuator 3760 as described below. In this configuration, the container assembly 3700 can be disposed, e.g., in the detector assembly 11200 as described herein, such that the container assembly 3700 cannot be displaced laterally with respect to a longitudinal axis of the manipulator assembly 11600. For example, in this configuration, the reaction chamber 3732 of the container assembly 3700 can be disposed in a slot 11234 of a shutter 11230 included in the detector assembly 11200, as described further below herein. Furthermore, when moved to the third configuration, the articulation assembly 11610 can be maintained in an engage, clamp, grip or otherwise secure configuration. In this manner, the container assembly 3700 can remain secured by the articulation assembly 11610 during the substrate plunge. This can, for example, ensure that all force of the outer plunge is transferred only to the second actuator 3760 of the container assembly 3700 and/or to maintain the container assembly 3700 flush with a gasket 11206 included in the detector assembly 11200 to prevent any ambient noise (e.g., light) from entering the detector assembly 11200, as described herein.

To move from the second configuration to the third ("substrate plunge") configuration, the inner plunger 11632 rotates in a direction opposite to the open grip configuration, e.g., as shown by the arrow RR in FIG. 82, such that the collar 11634 displaces along the longitudinal axis defined by the inner plunger 11632 in a direction away from the actuator 11652. Displacement of the plunger also displaces the outer plunger 11636 and the set of guide members 11640 attached thereto, in the same direction. Displacement of the outer plunger 11636 effected by the rotation of the inner plunger 11632 is continued such that a bottom portion of the outer plunger 11636 engages the engagement portion 3762 of the second actuator 3760 urging the plunger portion 3764 of the actuator 3760 to displace within the internal volume 3744 defined by the housing 3741 of the container assembly 3700. The plunger portion 3764 can move from a first position to a second position, such that the plunger portion 3764 communicates a reagent disposed in the internal volume 3742 through the delivery portion 3770 into the reaction chamber 3732 included in the container assembly 3700. For example, the reagent can be a substrate, e.g., tridecanal or any other substrate described herein, that can be formulated to react with reporter molecules present in the reaction chamber 3732, e.g., luciferase or any other reporter molecule, as described above. The reaction of the substrate with reporter molecules can produce a signal, e.g., luminescence or any other signal described herein, which can be detected by the detector assembly 11200, as described further below herein. Longitudinal displacement of the outer plunger 11636 effected by a rotary motion of the inner plunger 11632 can allow, for example, better control over the displacement of the outer plunger 11636, and therefore better control over communication of a substrate from the internal volume 3744 to the reaction chamber 3732 of the container assembly 3700.

It is to be noted that a single actuator 11652 is employed by the manipulator assembly 11600 to perform a series a functions, including: i) manipulating outer plunger 11636 by actuating the inner plunger 11632 to cause the substrate plunge and; ii) manipulating the guide members 11640 coupled to the outer plunger 11636 to urge the articulation assembly 11610 from the open grip to the gripper closed configuration. A second actuator, e.g., actuator 11504c included in the drive subassembly 11500 as described herein, can be used to displace the manipulator assembly 11600 in the Z-direction. In some embodiment, the reagent plunge functionality can be included in the actuator 11652, e.g., the actuator 11652 can also be capable of linearly displacing the inner plunger 11632.

As shown in FIG. 55-57, the instrument includes a detector assembly 11200. The detector assembly 11200 is configured to detect a signal, e.g., luminescence, produced by a chemical reaction, e.g., interaction of a reporter molecule (e.g., luciferase) with a substrate (e.g., tridecanal) in accordance with any of the methods described herein. The detector assembly 11200 is configured to receive a container assembly 3700, and detect a signal produced therein. The detector assembly 11200 can include any suitable detector that can detect the signal produced by a reporter molecule, e.g., luciferase. For example, as shown, the detector is an optical detector. In some embodiments a detector can be a fluorescence detector (e.g. to detect a fluorescent reporter molecule such as GFP, etc.), a luminescence detector (e.g. to detect bioluminescence produced by a reporter molecule such as luciferase), color detector (e.g. to detect a colored precipitant produced by reporter enzyme such as HRP), a spectrometer, and/or an image capture device. In some embodiments, the detector can further include a light source. Although described as being primarily based on optical detection, in some embodiments, the detector can be an electrochemical detector. For example, the detector can include an amperometric detector, potentiometric detector, conductometric, and/or impedometric detector, configured to detect a current, voltage, or conductance, resistance/impedance change produced by the reporter, e.g., luciferase. In some embodiments employing electrochemical detection, the detector can be configured to come in physical contact with the sample solution that can contain a sample. In some embodiments, the detector 11200 can use other detection methods, e.g. surface acoustic wave, surface plasmon resonance, Raman spectroscopy, magnetic sensors, and/or any other suitable detection method known in the art.

In some embodiments, the detector assembly 11200 can only provide a qualitative answer, for example, a YES/NO answer on the presence of target cell. In some embodiments, the detector 11200 can quantify the target cell, for example, determine the cfu/ml of target bacteria in the sample according to any of the methods described herein, e.g., method 400. In some embodiments, the detector assembly 11200 can include an end read system, e.g., to allow flexible placement of a label on the container, e.g., container assembly 3700. In some embodiments, the end read system includes direct contact and/or proximal disposal of a transparent end of a container, e.g., container assembly 3700 with the detector 11200, e.g., to minimize optical instruments and/or background signal interference. In some embodiments, the detector assembly 11200 is devoid of an incident light source. Said another way, no external light is needed for signal detection from the reporter molecules, e.g., luciferase, produced by a target cell, e.g., bacteria, disposed in the container, e.g., container assembly 3700.

Referring now also to FIGS. 85-94, the detector assembly 11200 includes a detector 11212 and a shutter 11230 disposed in a housing 11202. The detector assembly 11200 is configured to removably receive a container, e.g., container assembly 3700, and detect a signal produced therein, e.g., a luminescence signal resulting from a chemical interaction of a reporter molecule (e.g., luciferase) with a substrate (e.g., tridecanal).

Figure 86:
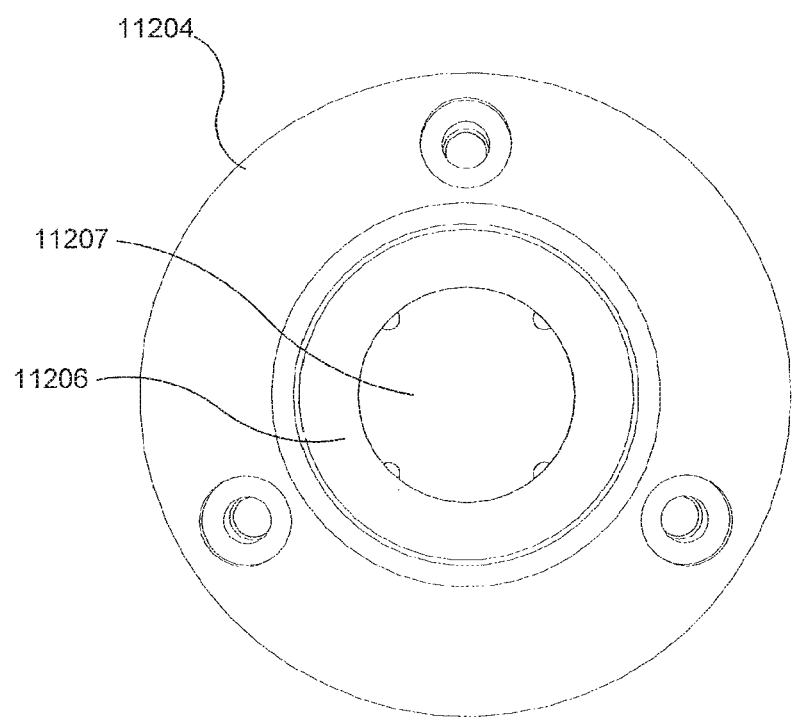
FIG. 86 shows a top view of a portion of the detector assembly of FIG. 85.

The housing 11202 can be formed from a strong, rigid and substantially opaque material, e.g., metals. In some embodiments, the housing can be painted a dark color, e.g., black, to minimize internal reflections and/or refractions because of a luminescence reaction produced in a container disposed in the detector assembly, e.g., container assembly 3700. The housing 11202 is also configured to prevent external light from entering the detector assembly 11200, e.g., to reduce background noise and/or signal quality. The housing 11202 includes a groove 11203. A receptacle 11204 is disposed in the groove 11203 which defines an opening 11207 sized and shaped to removably receive a container, e.g., container assembly 3700. The receptacle 11204 can be fixedly or removably coupled to the housing 11202, e.g. via screws, bolts, rivets, glues, hot welded, or snap fitted in to the groove 11203 of the housing 11212. As shown in FIG. 86, the receptacle 11204 includes a gasket 11206 fixedly disposed in the receptacle 11204. The gasket 11206 can be formed from a rigid and crush and/or wear resistant material, e.g., high density neoprene. The gasket 11206 is configured such that when the container assembly 3700 is disposed in the receptacle 11204, the gasket 11206 and a portion of the reagent module 3740 form a light-tight seal to prevent any external light from entering inside the housing 11202. In some embodiments, the height of the receptacle 11204 can be varied, e.g., to accommodate containers of various lengths. This can ensure that any variations in length of the container, e.g., because of variations in the manufacturing process and/or user preference, does not change the distance of a bottom end of the container, e.g., container base, from the detector 11212 e.g., to enhance signal quality and/or repeatability. The housing 11202 further defines a channel 11209 configured to receive at least a portion of the container, e.g., a reaction chamber 3732 of the container assembly 3700. The housing 11202 also includes an internal volume 11210 configured to house the shutter 11230, such that the shutter 11230 is free to be manipulated and/or displaced from a first position to a second position within the internal volume 11210. The housing 11202 further includes circuitry 11208 disposed on a sidewall of the housing 11202. The circuitry is configured to control the operation of a light source 11246, as described below herein.

Figure 87:
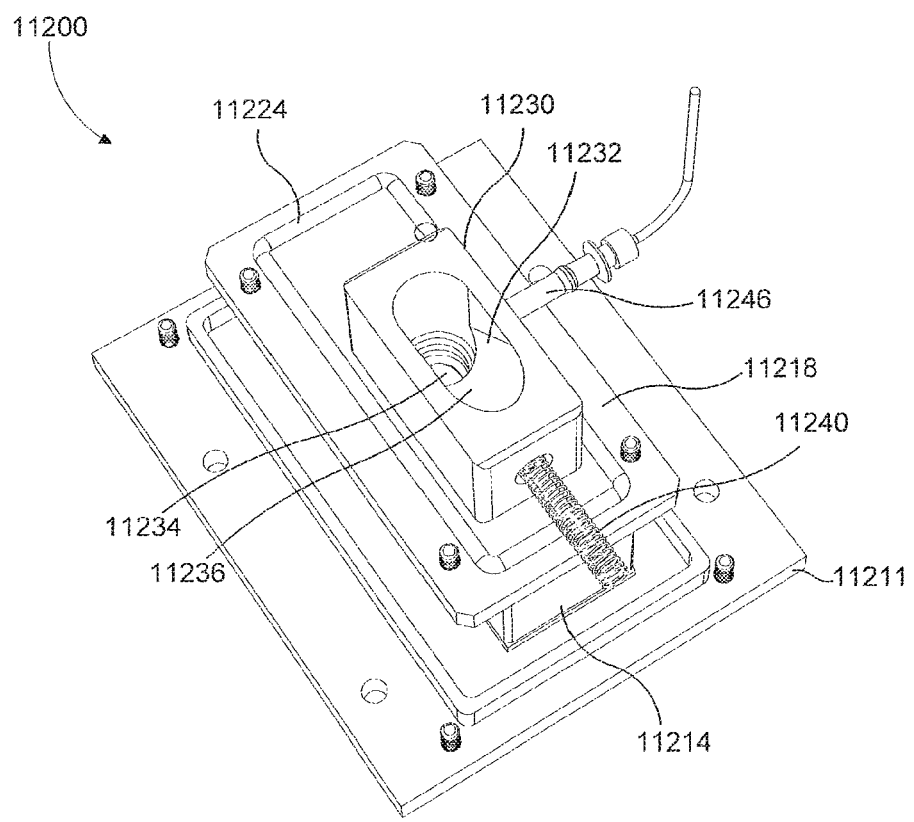
FIG. 87 shows a perspective view of the detector assembly of FIG. 85 with a housing removed.
Figure 88:
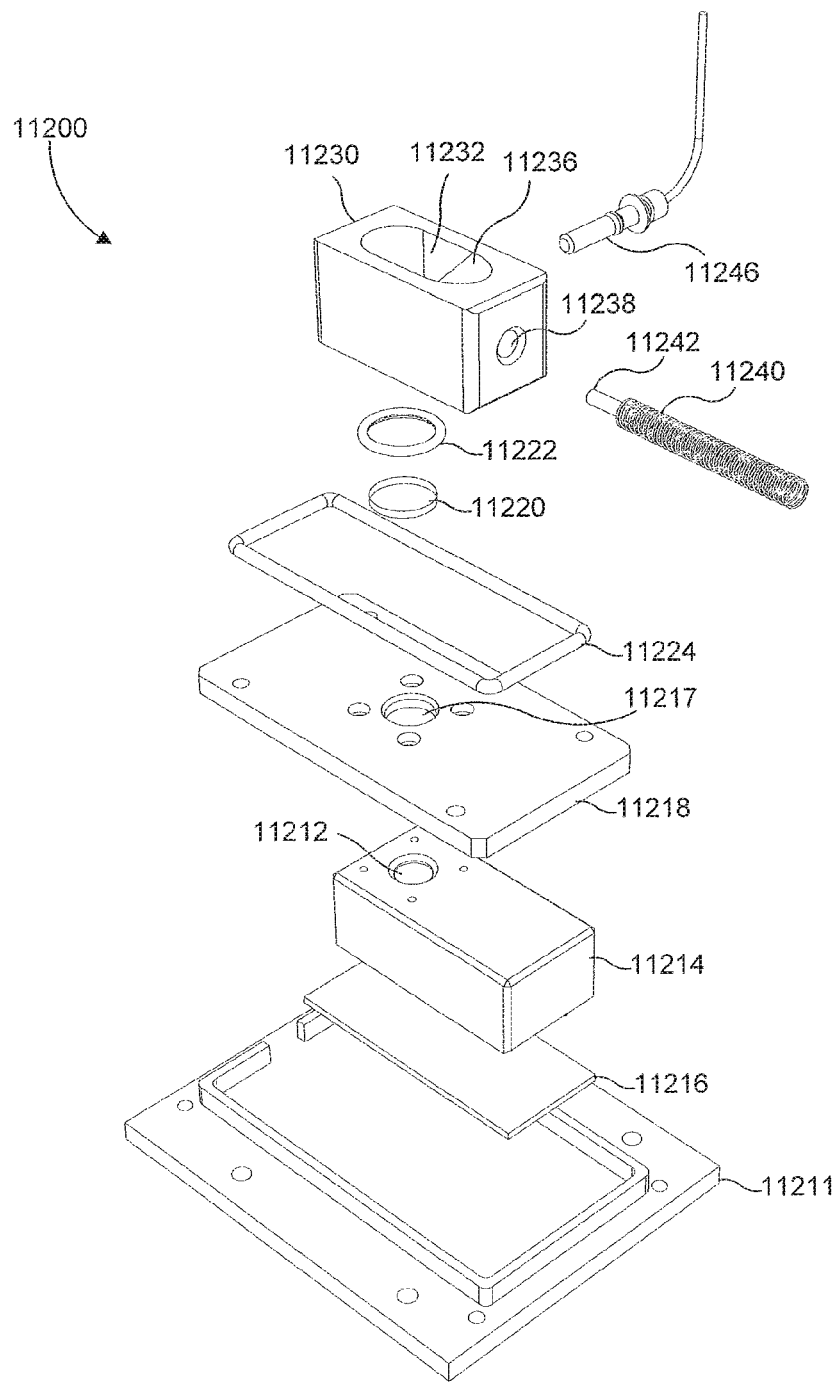
FIG. 88 shows an exploded view of the detector assembly of FIG. 85 with the housing removed.

FIG. 87 shows the internal components of the detector assembly 11200 with the housing 11202 removed and FIG. 88 shows an exploded view of the components of the detector assembly 11200. As shown herein, the detector assembly 11200 includes a baseplate 11211 configured to mount the detector assembly 11200 on the baseplate 11118 of the instrument 11000. The base plate 11211 is also configured to provide a base for mounting the components of the detector assembly 11200 and the housing 11202.

The detector assembly 11200 includes a detector 11212 disposed in a detector enclosure 11214. The detector 11212 can be an optical detector, e.g., a photomultiplier tube (PMT), a luminometer, a spectrophotometer, fluorescence detector, and or any other suitable optical detector. The detector 11212 is configured to detect an optical signal, e.g., luminescence, produced due to a chemical reaction in a container, e.g., container assembly 3700 as described herein. In some embodiments, the detector 11212 can include an amperometric detector, potentiometric detector, conductometric, and/or impedometric detector, configured to detect a current, voltage, or conductance, resistance and/or impedance change produced by the reporter, e.g., luciferase. A bottom surface of the detector enclosure 11214 is coupled to a mount 11216 that is disposed on the base plate 11211. The mount 11216 can be made from a rigid but soft material, e.g., rubber or foam pad, to provide a cushioned support to the detector enclosure 11214. A top surface of the detector enclosure 11214 is coupled to a separator 11218, e.g., screwed, bolted, and/or riveted to the separator 11218. The separator 11218 can be made from strong, rigid and low friction material, e.g., a polished metal plate (e.g., aluminum, stainless steel, etc.). The separator 11218 is configured to provide a separation layer between the detector enclosure 11214 and the shutter 11230, e.g., to prevent wear of the detector enclosure 11214 due to a displacement of the shutter 11230, as described herein. The separator 11218 includes an aperture 11219 which is configured such that when the separator 11218 is coupled to the detector 11212, the aperture 11219 is located directly above the detector 11212 and provides unhindered optical access to the detector 11212. The aperture 11219 also includes a window 11220, e.g., a circular glass or transparent plastic piece, disposed therein. The window 11220 is configured to protect the detector 11212, e.g., from dust particles and/or physcial damage due to accidental contact by an end of a container, e.g., container assembly 3700. A seat 11222 is also disposed in the aperture 11219, configured to securely seat the window 11220 in the aperture 11219. The seat 11222 can also be configured to contact a top surface of the detector enclosure 11214 and encircling the detector 11212, for example, to light seal the detector 11212 from ambient light. In some embodiments, the seal 11214 can be formed from rubber, plastic and/or polymers and can be an o-ring. A seal 11224, e.g., a rubber seal, is also disposed on the separator 11224. The seal 11224 can be configured to light seal the internal volume 11210 of the housing 11202, e.g., the internal volume 11210 housing the shutter 11230 from ambient light, e.g., to reduce background noise, increase signal quality and/or repeatability.

Figure 89:
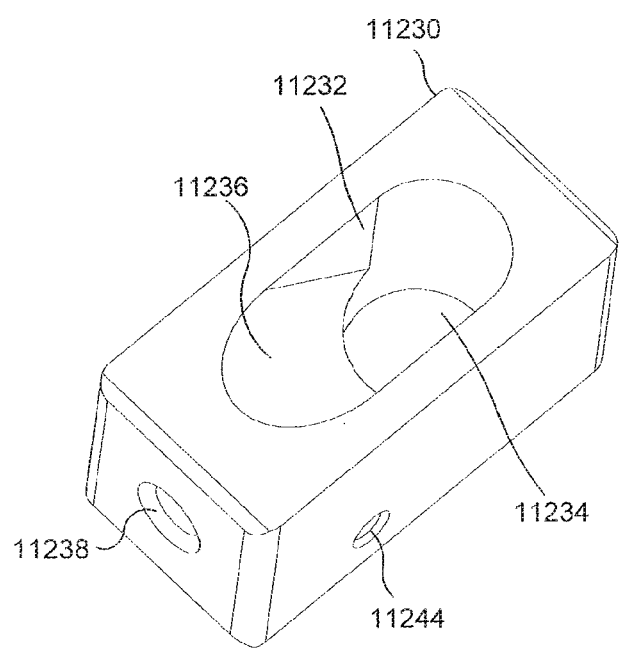
FIG. 89 shows a shutter included in the detector assembly of FIG. 85, according to an embodiment.
Figure 90:
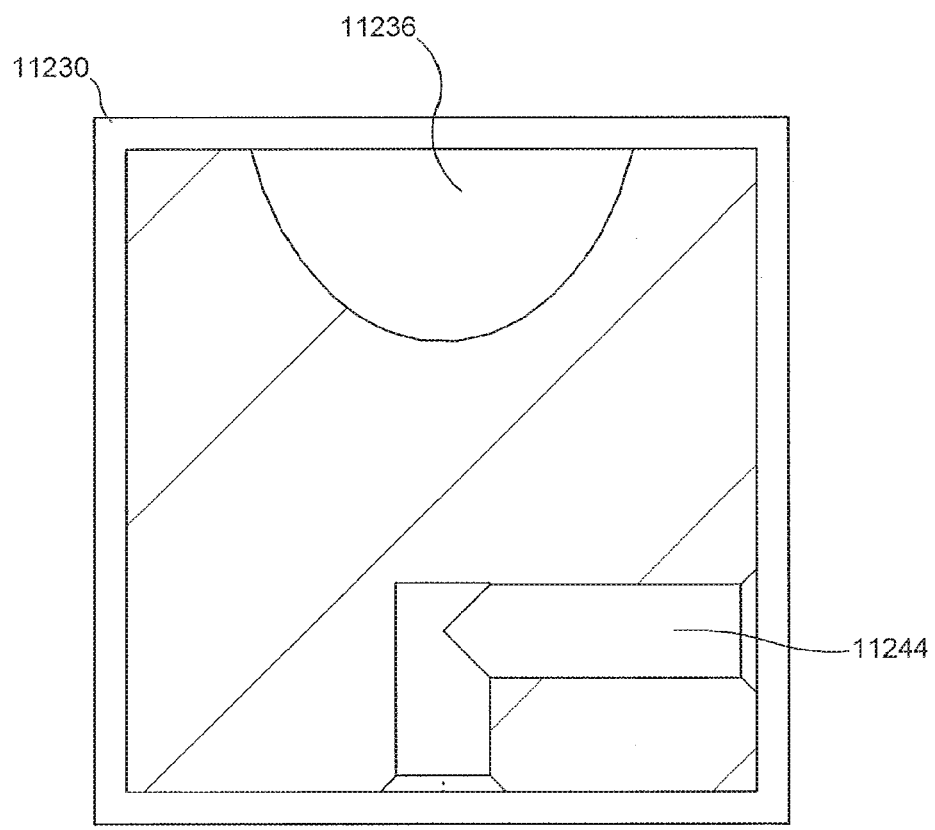
FIG. 90 shows a side cross-section of the shutter of FIG. 89.
Figure 91:
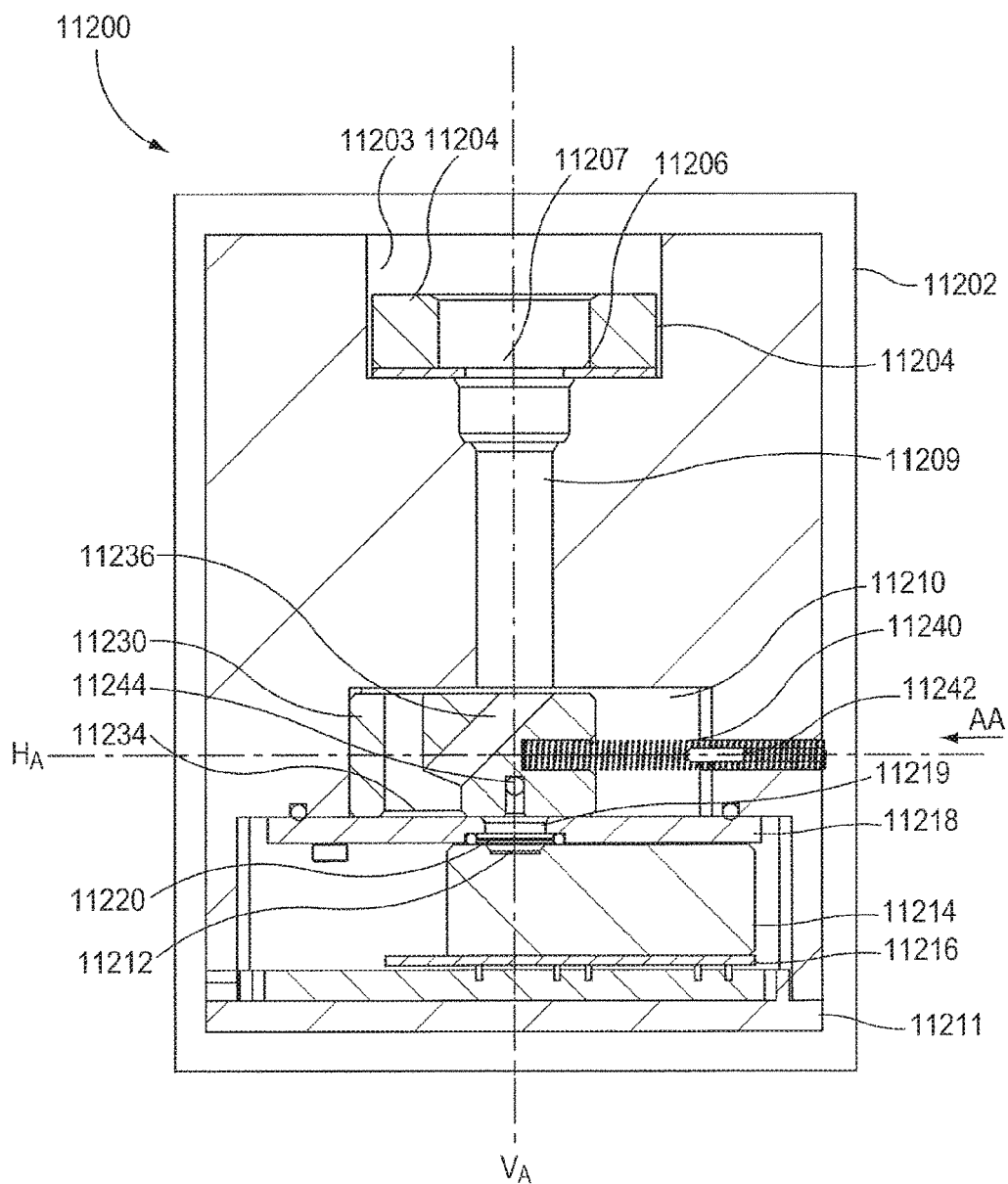
FIGS. 91-94 are side cross-sectional views of the detector assembly of FIG. 85 in a first configuration, a second configuration, a third configuration and a fourth configuration, respectively.

The detector assembly 11200 also includes a shutter 11230 slidably disposed on the separator 11218 and configured to move from a first shutter position wherein the shutter 11230 is closed and the detector 11212 is optically uncoupled with a container, e.g., container assembly 3700 disposed in the detector assembly 11200, to a second shutter position wherein the shutter 11230 is open and the detector 11212 is optically coupled to the container. As shown in FIG. 89-90, the shutter 11230 includes a recess 11232, which includes a slot 11234 and a surface 11236. The slot 11234 is shaped and sized to receive an end portion of a container, e.g., container assembly 3700. The surface 11236 is contoured, e.g., curved to conform to a contour of a bottom end of the container. The surface 11236 is inclined at angle leading from a top surface 11236 of the shutter 11230 to a top edge of the slot 11234. In some embodiments, the surface 11236 can be inclined at an angle of 30 degrees, 40 degrees, 45 degrees, 50 degrees, or 60 degrees from a top horizontal surface of the shutter 11230. The surface 11230 is configured to be engaged by a bottom end of the container, e.g., container assembly 3700, to manipulate the shutter 11230 from the first position to the second position, as described herein. The shutter 11230 includes a sleeve 11238 having a spring 11240 disposed therein. A second end of the spring 11240 is disposed in a notch 11241 in the housing 11202 (FIG. 85) mounted on a pin 11242. The spring 11240 is configured to urge the shutter 11230 from the second shutter position to the first shutter position, and/or secure, hold and/or prevent lateral movement of a container, e.g., container assembly 3700 disposed in the slot 11234, as described herein.

The shutter 11230 further includes a channel 11244 configured to define an optical pathway for an electromagnetic radiation, for example, luminescence emitted by a light source 11246. The channel 11244 is configured such that the channel 11244 optically couples the light source 11246 to the detector 11212 only when the shutter is in the first position. In some embodiments, the light source 11246 can include a light emitting diode (LED) or a laser, and can further include a light guide, e.g., a fiber optic cable. The light source 11246 can be configured to emit a reference luminescent signal, e.g., a calibrating signal for calibrating the detector 11212.

As described herein, the shutter 11230 is configured to displace from a first position within the internal volume 11210, wherein the shutter 11230 is closed, to a second position wherein the shutter 11230 is open. FIG. 91-94 show a side cross-section of the detector assembly 11200 in a first configuration, a second configuration, a third configuration and a fourth configuration. In the first configuration (FIG.

72), no container is disposed in the detector assembly 11200. The spring 11240 applies a force on the shutter 11230 along a horizontal axis $H_A$ of the shutter in a direction shown by the arrow AA to manipulate and maintain the shutter 11230 into the first shutter position, such that the slot 11234 of the shutter 11230 is not aligned with the aperture 11219 and the detector 11212, such that no ambient light is incident on the detector 11212. The channel 11244 is aligned with the detector 11212, such that the light source 11246 is optically coupled to the detector 11212. Therefore, in the first configuration, the light source 11246 can be used to send a reference signal to the detector 11212, e.g., to calibrate the detector 11212.

Figure 92:
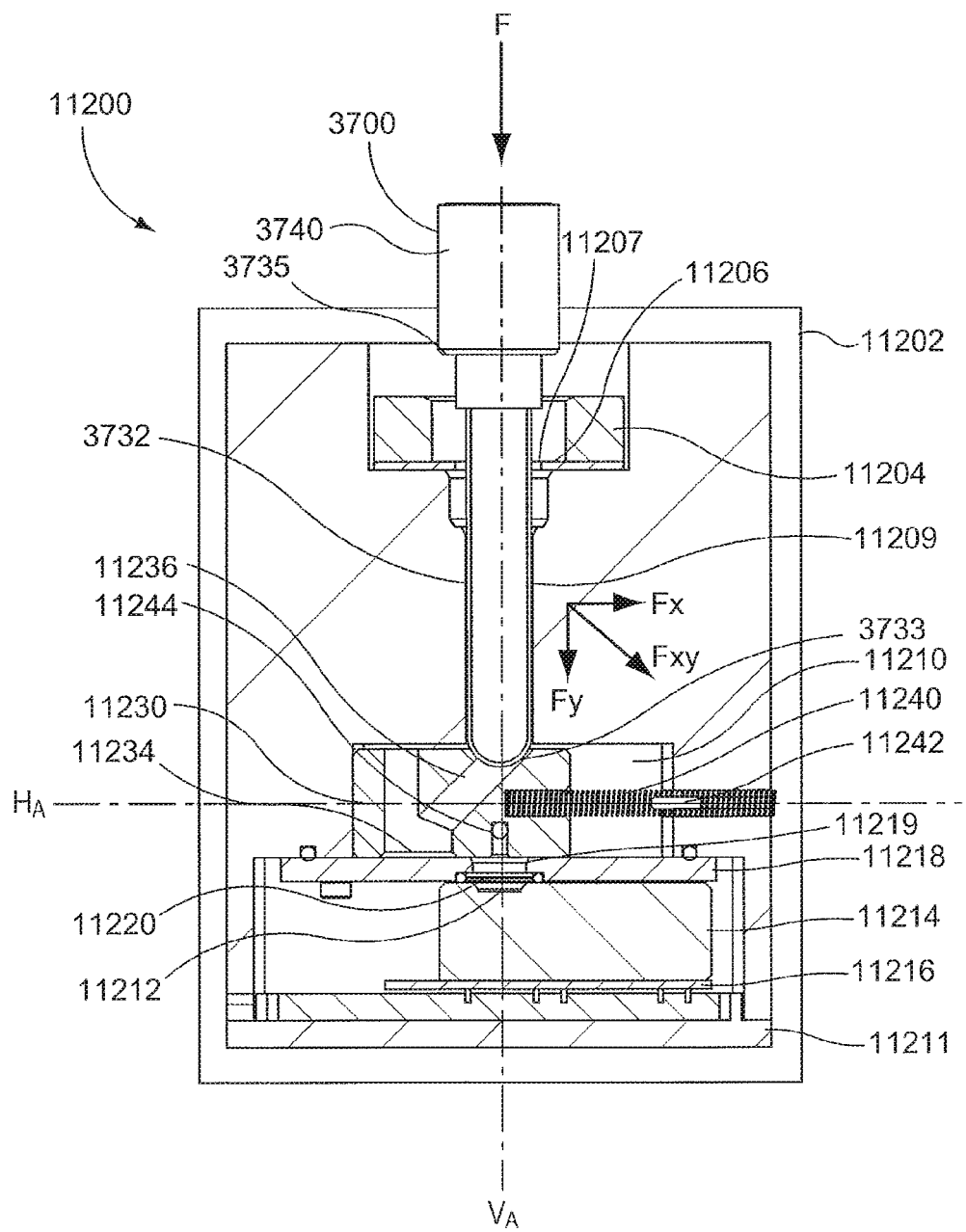
Figure 93:
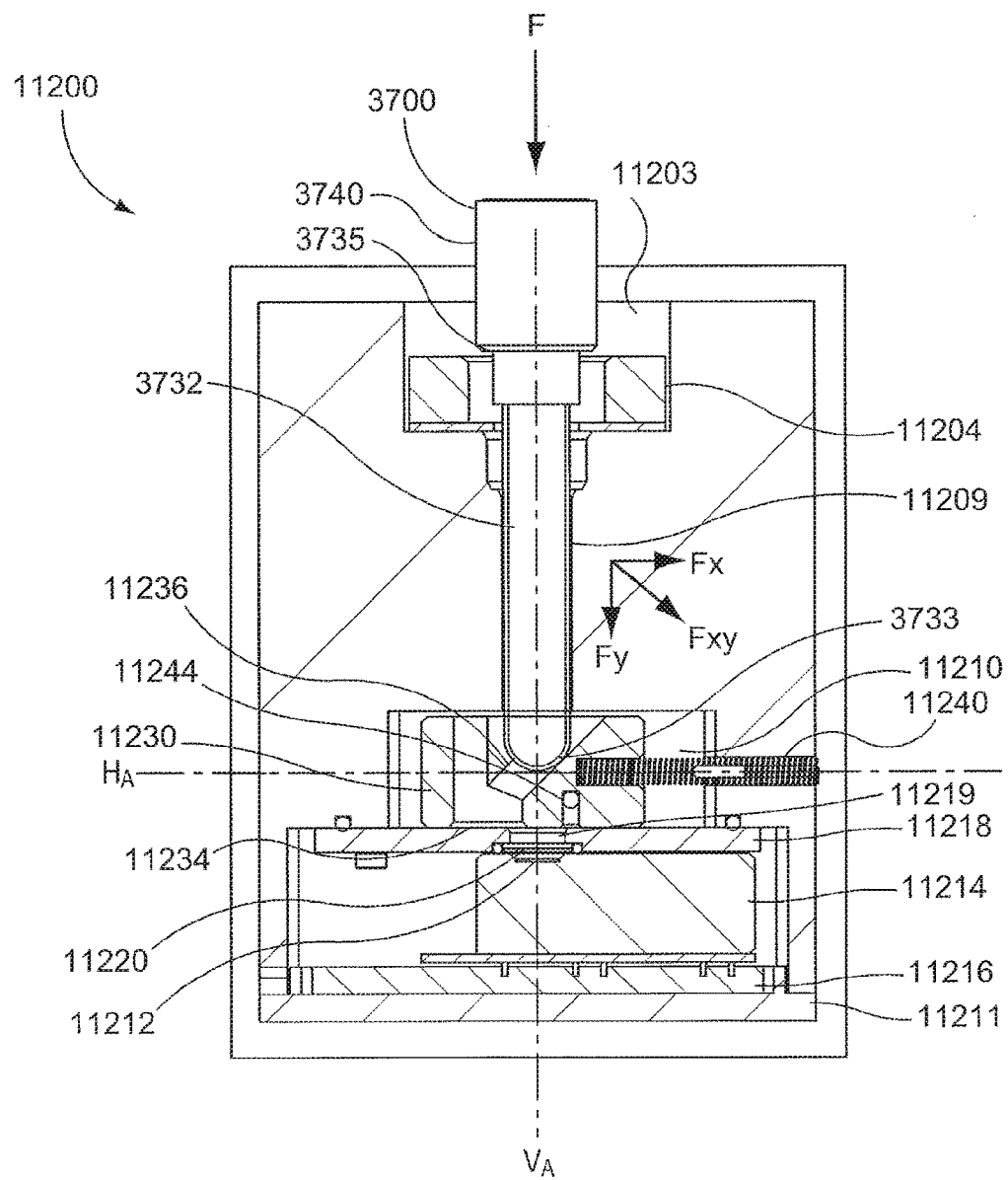

In the second configuration (FIG. 92), a container assembly 3700 as described before herein, is disposed in the detector assembly 11200 in a first position. The container assembly 3700 includes a reaction chamber 3732 and a reagent module 3740 as described before herein. The container assembly 3700 can be disposed in the detector assembly 11200, e.g., by the manipulator assembly 11600. The reaction chamber 3732 of the container assembly 3700 is substantially disposed in the channel 11209 while at least a portion of the reagent module 3740 is disposed in the receptacle 11204. An end portion 3733 of the reaction chamber 3732 is in contact with the surface 11236. A downwards force is applied on the container assembly 3700, e.g., by the manipulator assembly 11600 as described herein, along a vertical axis $V_A$ of the detector assembly 11200 as shown by the arrow F which is communicated to the surface 11236 of the shutter 11230 by the end portion 3733 of the reaction chamber 3732 included in container assembly 3700. Because the surface 11236 is inclined, e.g., at 45 degrees with respect to a horizontal axis of the shutter 11230, the end portion 3733 of the container assembly 3700 exerts an angular force Fxy on the surface 11236 as shown. The force Fxy has a horizontal component Fx and a vertical component Fy as shown in FIG. 92. The horizontal component Fx urges the shutter 11230 assembly to displace horizontally along the horizontal axis $H_A$ in the direction indicated by the arrow Fx such that the slot 11234 of the shutter 11230 displaces towards the detector 11212 as shown in the third configuration (FIG. 93). The spring 11240 can be configured to exert a reactive force on reaction chamber 3732, but not large enough to prevent the reaction chamber 3732 from manipulating the shutter 11230. The channel 11209 of the housing 11202 can be in close tolerance or only slightly larger than the diameter of the reaction chamber 3732, e.g., to prevent any lateral movement of the container assembly 3700 by the reactive force exerted by the spring 11240.

Figure 94:
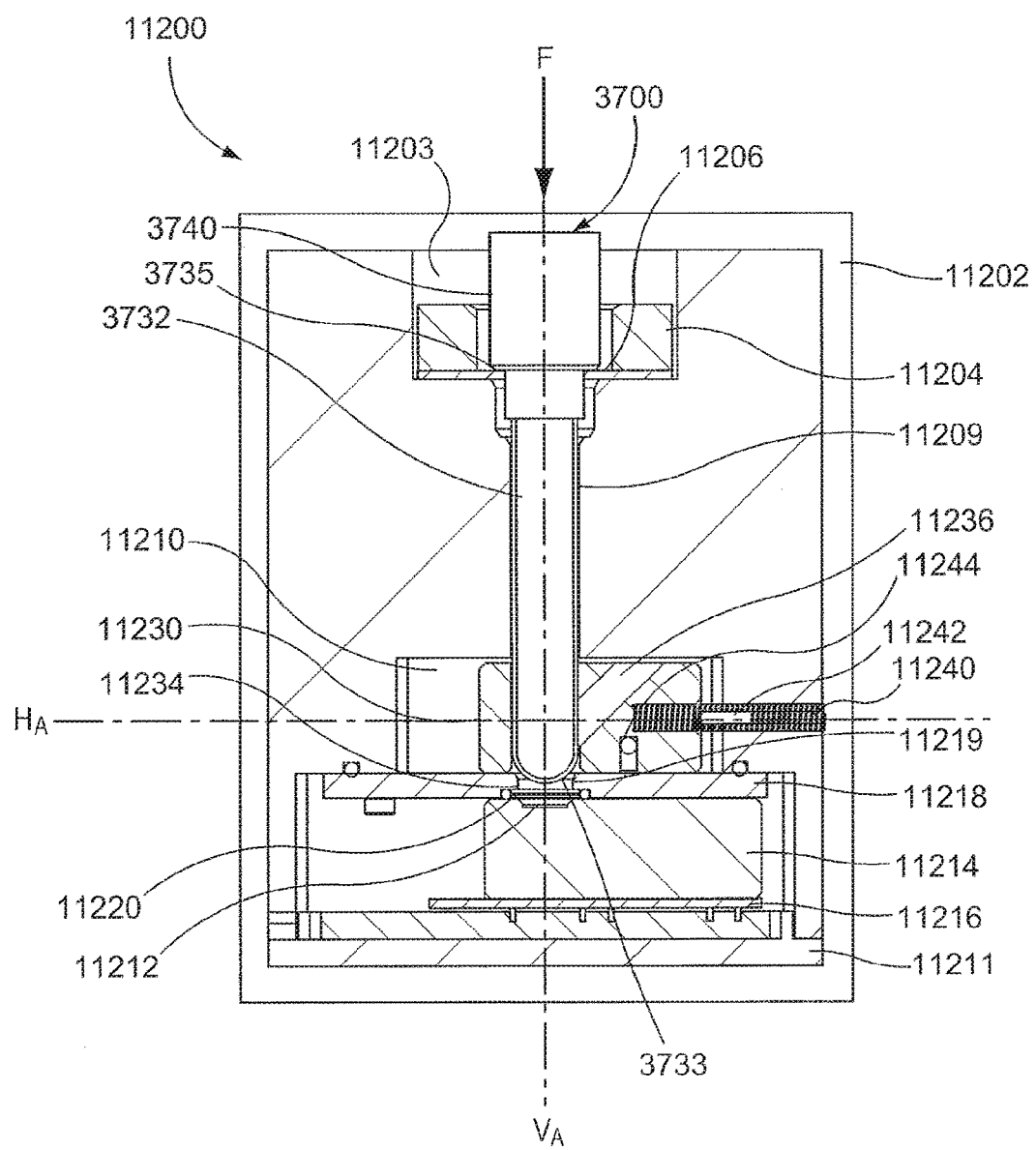

The downward force F on the container assembly 3700 can be maintained until in the fourth configuration, the shutter 11230 is displaced to a second position such that the slot 11234 is aligned with the detector 11232 and the end portion 3733 of the reaction chamber 3732 is disposed in the slot 11234, as shown in FIG. 94. The end portion 3733 of the reaction chamber 3732 can be proximal to but not contacting the window 11220, e.g., to prevent scratching and/or wear of the window. In this configuration, the spring 11240 applies a force on the shutter 11230 urging the shutter 11230 towards the first shutter position. This force is communicated to a side wall of the end portion 3733 of the reaction chamber 3732 through a side wall of the slot 11234 included in the shutter 11230, which prevents the shutter 11230 from sliding into the first shutter position. In some embodiments, the slot 11234 can define a detection volume configured to restrict any signal produced in the reaction chamber 3732, e.g., luminescence produced by the interaction of a reporter molecule, e.g., luciferase, with a substrate, e.g., tridecanal, for example, to increase signal quality, sensitivity, repeatability and/or reduce background noise. Furthermore, a bottom surface 3735 of the reagent module 3740 included in the container assembly 3700 rests on and is flush with the gasket 11206 such that no ambient light can enter the housing 11202 of the detector assembly 11200. In some embodiments, the manipulator assembly 11600 can maintain the downward force F on the container assembly 3700 in the fourth configuration, e.g., to maintain strong contact between the bottom surface 3735 of the reagent module 3740 included in the container assembly 3700, and the gasket 11206

Figure 95:
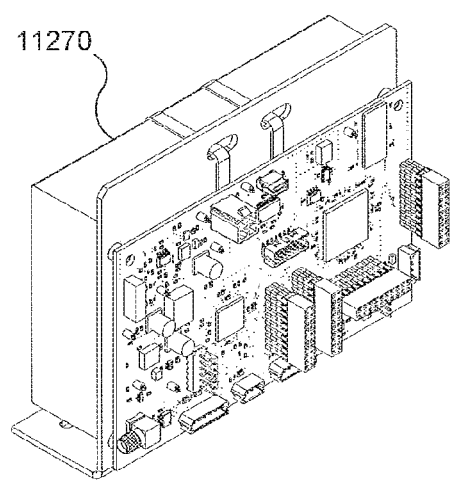
FIG. 95 shows a perspective view of a circuitry included in the instrument of FIG. 51 for controlling the detector assembly of FIG. 85, according to an embodiment.

FIG. 95 shows the detector circuitry 11270 that can be used to control detector assembly 11200, according to an embodiment. The circuitry 11270 is disposed in the housing 11202 of the instrument 11200, mounted on the base plate 11118. In some embodiments, the circuitry 11270 can include a photon detector and/or any other circuitry for processing opto-electronic signals, as are commonly known in the arts.

In some embodiments, a reagent, e.g., a substrate can be communicated into the reaction chamber 3732 in the fourth configuration such that a chemical reaction produces a signal in the reaction chamber 3732 which can be detected by the detector 11212. For example, the second plunger 11636 included in the manipulator assembly 11600 can engage the actuator 3760 included in the reagent module 3740 of the container assembly 3700 to communicate a substrate, e.g., tridecanal or any other substrate described herein, into the reaction chamber 3732. The substrate can interact with a reporter molecule present in a sample solution disposed in the container, e.g., the reporter molecule luciferase or any other reporter molecule described herein produced by the interaction of a biologic or abiologic vector such as a transduction particle (e.g., transduction particle 160 or any other transduction particle described herein) with a target cell, e.g., bacteria such as MRSA. The interaction of the substrate and reporter molecule can produce a signal, e.g., luminescence that is detected by the detector 11212. In some embodiments, the reaction between the substrate and the reporter molecule can be an instantaneous, e.g., flash reaction, such that a signal is produced instantly after communication of the substrate into the sample solution including the reporter molecules. Detection of the signal indicates that the sample disposed in the reaction chamber 3732 contains the target cell.

Figure 96:
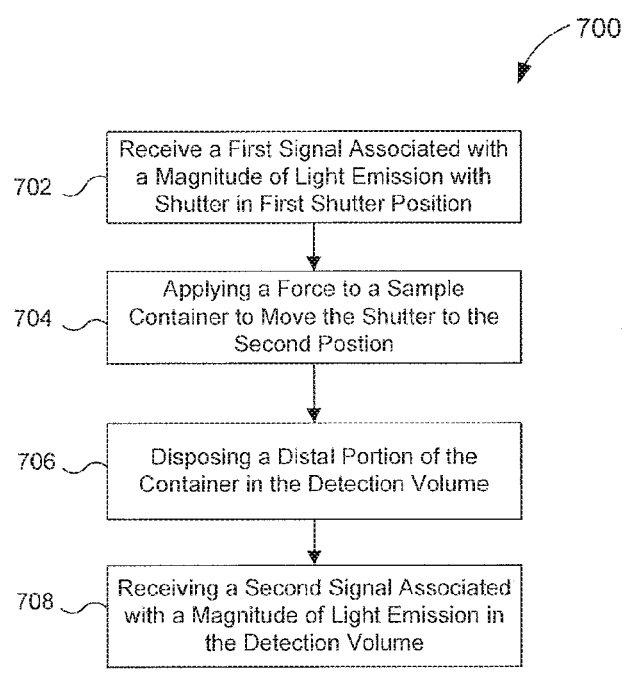
FIG. 96 illustrates a flow diagram of a method for receiving a signal, according to an embodiment.

As described herein, the detector 11212 or any other detector described herein can be calibrated before making a signal measurement. FIG. 96 illustrates a flow diagram of a method for calibrating and making a measurement with a detector, e.g., detector 11212 included in an instrument, e.g., instrument 11000. The method includes receiving a first signal associated with a magnitude of light emission in a detection volume, 702, at a first time such that the detection volume is optically isolated from a channel by a movable shutter, e.g., shutter 11230, which is disposed in a first shutter position. In some embodiments, a light emission e.g., a calibration signal, can be transmitted into the detection volume via a light channel defined by the shutter when the shutter is in the first position. A force is applied to sample container to move the shutter into the second position, 704. The container can initially be in the at least partially disposed within the channel such that the application of a force on the container, allows a distal end portion of the container to move the shutter from the first shutter position to the second shutter position. This allows the distal end portion of the container to move into the detection volume, 706, such that the channel is now in optical communication with the detection volume. In this position a second signal associated with a light emission in the detection volume can be received, 708. In some embodiments, before receiving the second signal, a reagent, e.g., a substrate can be conveyed into the distal end portion of the container. The substrate, e.g., tridecanal can be configured to react with, for example, reporter molecules present in the sample to produce a light emission. In some embodiments, the detector 11212, or any other detector described herein, can include internal calibration controls, e.g., software algorithms, such that an external calibration light source is not required.

As described herein, the instrument 11000 or any other instrument described herein can be used to manipulate a container (e.g., container assembly 3700 or any other container described herein), for example, to transport a container, communicate reagents into a reaction volume of the container and/or detect a signal, e.g., luminescence produced within the container. FIG. 97 illustrates a flow chart of a method for manipulating a container within an instrument. A container that can have a sample disposed therein containing target cells, e.g., bacteria, can be loaded into a loading zone of the instrument 802, e.g., the loading cartridge 11300. The container is transported to a heater included in the instrument 804, e.g., by the manipulator assembly 11600 via the drive assembly 11500 to the heater assembly 11400. A biologic or abiologic vector such as a transduction particle is communicated into a reaction volume of the container 806, e.g., by a manipulation of the inner plunger 11632 of the manipulator assembly 11600. The container is maintained at a predetermined temperature for a predetermined time 808, e.g., at 37 degrees Celsius for 4 hours by the heater assembly 11400. The transduction particles interact with the target cells included in the sample, such that the target cells produce a series of reporter molecule 810. In some embodiments, the heater assembly 11400 can be configured maintain the container (e.g., container assembly 3700 or any other container described herein) at a series of temperatures, for predetermined times. For example, the container and the sample disposed therein can be maintained at 37 degrees Celsius for a first time, e.g., 4 hours. The temperature of the container can then be lowered to a second temperature lower than the first temperature (e.g., 30 degrees Celsius), for example, by transferring to a heating block 11422 at the second temperature. The container can, for example, be maintained at the second temperature until detection. The container is then transported to a detector included in the instrument 812, e.g., the detector assembly 11200. For example, the manipulator assembly 11600 can be used to transport the container via the drive assembly 11500. A substrate is then communicated into the container 814, e.g., via a manipulation of the outer plunger 11636 of the manipulator assembly 11600. The substrate interacts with reporter molecules to produce a signal 816 that is detected using the detector 818. The analyzed container is then transported to an unloading zone of the instrument 820, e.g., an unloading cartridge 11300, and can be removed from the container 822.

In some embodiments, an instrument, e.g., instrument 11000 or any other instrument described herein, can be in communication with a laboratory information system (LIS), e.g., the LIS 1900 as shown in FIGS. 2-3.

While various embodiments have been described above, it should be understood that they have been presented by way of example only, and not limitation. Where methods and/or schematics described above indicate certain events and/or flow patterns occurring in certain order, the ordering of certain events and/or flow patterns may be modified. Additionally, certain events may be performed concurrently in parallel processes when possible, as well as performed sequentially. While the embodiments have been particularly shown and described, it will be understood that various changes in form and details may be made.

In some embodiments, the fluidic pathways defined by any of the reagent modules (e.g., 1740) can include valves or any other flow control mechanism. Such mechanisms include a flap valve, membrane valve, duckbill valve, umbrella valve, septum, or any other suitable valving mechanism to allow reagents to flow in one direction. In some embodiments, the valves can be pressure sensitive such that they allow fluid communication only above a predefined pressure threshold, e.g., to prevent accidental communication of reagents.

In some embodiments, any of the systems and methods described herein include a reporter system that reports on the presence of inducer molecules within target cells can be developed by incorporating into a non-replicative transduction particle, of the types shown and described herein, a reporter gene that is operably linked to an inducible promoter that controls the expression of a target gene within a target cell. When the reporter vector is introduced into the target cell that expresses the inducer of the target gene promoter, expression of the reporter gene is possible via induction of the target gene promoter in the reporter vector.

In one embodiment, a VanR reporter system can be developed for the purpose of detecting Vancomycin Resistant Enterococci (VRE). The Tn1546 transposon that can be present in *E. faecium* may contain the vanR inducer gene and the vanA target gene. A VRE reporter system can be developed by developing an *E. faecium*-targeting non-replicative transduction particle that incorporates a reporter gene operatively linked to the promoter $P_H$ that controls the expression of the vanHAX operon that includes the vanA gene. When the transduction particle delivers the $P_H$-controlled reporter gene into the *E. faecium* cell, the reporter gene will be expressed via induction of the $P_H$ promoter by the product of vanR.

In another embodiment, a reporter system for detecting TcdD, the inducer of the promoters of the toxins A and B genes (tcdA and tcdB, respectively) of *C. difficile* can be developed by developing a non-replicative transduction particle targeting *C. difficile* and that incorporates reporter gene that is operatively linked to the tcdA gene promoter. The PaLoc transposon in *C. difficile* may contain the tcdD gene and the tcdA target gene. In the native cell, when the tcdD gene is expressed and produces the TcdD protein, TcdD is able to induce PtcdA in the PaLoc transposon thus causing the expression of the tcdA gene and thus producing the toxin A protein. By introducing a reporter gene that operatively linked to the tcdA gene promoter (PtcdA) into a target cell, TcdD is then also able to induce PtcdA that controls the reporter gene, thus causing the expression of a reporter molecule.

A reporter system can be developed for reporting on the presence of a target intracellular enzyme by developing a non-replicative transduction particle-based viable cell reporter that employs a reporter that requires a substrate for signal generation and by caging the substrate such that it is not capable of triggering a signal via the reporter unless the substrate is un-caged via interacting with the target enzyme. A target cell is exposed to the transduction particle such that the reporter is expressed within the target cell and the caged substrate is applied. If the target cell contains a target enzyme, an interaction between the target enzyme and the caged substrate un-cages the substrate thus allowing the un-caged substrate to trigger a signal from the expressed reporter molecules.

In one embodiment, the reporter molecule to be expressed can be *Renilla* luciferase and the caged substrate can be *Renilla* luciferin that is caged such that a β-lactamase enzyme that is endogenous to the target cell is able to cleave the caging compound from the caged luciferin and release un-caged luciferin. By incorporating these components into a non-replicative transduction particle that targets a cell that may contain a β-lactamase enzyme, a target-cell-specific β-lactamase enzyme reporter system can be developed.

An intracellular molecule reporter system can be developed by incorporating into a non-replicative transduction particle a switchable reporter molecule that does not emit a signal unless it interacts with an intracellular target molecule.

In one embodiment, a non-replicative transduction particle can be designed to incorporate a gene expressing switchable aptamer designed to undergo a conformational change upon its binding to an intracellular target molecule. The conformational change allows the aptamer to then bind a fluorophore that exhibits enhanced fluorescence when bound by the aptamer.

An antisense RNA-based reporter system for detecting target transcripts within viable cells by causing the expression of a reporter molecule if a target transcript is present within a cell can be developed. In the general embodiment a non-replicative transduction particle incorporates a DNA sequence encoding an antisense message that is complementary to a region of a target transcript (target), and a sequence encoding a mutated version of the target transcript (target*) fused to a reporter gene (reporter) is used. The mutation of the target transcript is such that the antisense transcript binds to the mutated target transcript with a lower affinity than that of it's binding to the native target transcript. The antisense sequence is controlled by a promoter sequence (P), and the mutated target sequence linked to the reporter gene is controlled by an identical promoter sequence (P). When the reporter system is introduced into a cell that does not contain an endogenous target transcript, the expressed antisense transcript inhibits the translation of the reporter gene and the antisense transcript and reporter transcript are consumed in the process. However, when the vector is inserted into a cell that does contain an endogenous target transcript, the expressed antisense transcript preferably binds to the native target transcript and the antisense transcript and target transcript are consumed in the process, leaving the reporter gene to be translated thus producing a reporter protein that may be detected. In this manner, this vector causes the expression of a detectable signal when it is introduced into a target cell containing the target transcript.

In some embodiments, non-replicative transduction particles targeting S. aureus cells are designed to report on the presence of mecA transcripts thus resulting in a MRSA detection system. The transduction particles deliver DNA sequences that encode an antisense message that is complementary to a region of mecA transcript (mecA), and a sequence encoding a mutated version of mecA transcript (mecA*) fused to the bacterial luciferase genes luxA and luxB0 (luxAB). The mutation of the mecA* transcript is such that the antisense transcript binds to its transcript with a lower affinity than that of it's binding to the native mecA transcript. The mecA*-luxAB fusion and the antisense mecA gene fragment are each operatively linked to the constitutively expressed promoters. When the reporter construct is introduced into MRSA cells by the transduction particle, if the cell does not produce an endogenous mecA transcript, then the antisense sequence fragment of the mecA gene can only bind to the mecA sequence of the transcript of the modified fragment of the mecA gene fused to the luxAB genes. This binding event then prevents the translation of the luxAB genes thus preventing the production of luciferase within this cell. If, on the other hand, cell does contain an endogenous mecA transcript, then the transcript of the antisense sequence fragment of the mecA gene will preferentially bind to the endogenous mecA transcript over the transcript of the modified fragment of the mecA gene fused to the luxAB genes thus leaving this transcript available for translation of the luxAB genes thereby producing luciferase. In this manner, the mecA transcript reporter vector can report on the presence of endogenous mecA transcripts within a cell.

Although various embodiments have been described as having particular features and/or combinations of components, other embodiments are possible having a combination of any features and/or components from any of embodiments as discussed above.

What is claimed is:

1. A method of detecting the presence a target cell within a biological sample using an instrument, comprising:
    conveying a plurality of transduction particles associated with the target cell from a reagent module into a sample container containing the biological sample, the reagent module coupled to the sample container during the conveying such that the sample container is fluidically isolated from an exterior volume, the plurality of transduction particles engineered to be non-replicative and to include a nucleic acid molecule formulated to cause the target cell to produce a plurality of reporter molecules, the plurality of transduction particles formulated to bind to and deliver the nucleic acid molecule into the target cell;
    maintaining, after the conveying, the biological sample and the plurality of transduction particles within the sample container for a time period to allow the plurality of reporter molecules to be produced within the sample container when the target cell is present in the biological sample;
    exerting a force on the reagent module to place a seal surface of the reagent module in contact with a corresponding surface of the instrument to optically isolate the sample container from the exterior volume, the seal surface in a fixed location relative to the sample container;
    conveying, after the exerting, a reagent from the reagent module into the sample container, the reagent formulated to react with the plurality of reporter molecules to catalyze production of a signal, the seal surface being maintained in contact with the corresponding surface during the conveying the reagent; and
    receiving via a detector of the instrument, the signal associated with a quantity of the plurality of reporter molecules.

2. The method of claim 1, wherein the plurality of transduction particles is derived from a bacteriophage and is engineered to be incapable of lysogenic replication and lytic replication.

3. The method of claim 1, wherein the plurality of transduction particles includes a viral vector devoid of a wild-type DNA capable of exhibiting wild-type viral functions associated with a virus from which the viral vector is derived.

4. The method of claim 1, wherein the target cell is a bacteria selected from the group consisting of *Escherichia, Mycobacterium, Staphylococcus, Li steria, Clostridium, Enterococcus, Streptococcus, Helicobacter, Rickettsia, Haemophilus, Xenorhabdus, Acinetobacter, Bordetella, Pseudomonas, Aeromonas, Actinobacillus, Pasteurella, Vibrio, Legionella, Bacillus, Calothrix, Methanococcus, Stenotrophomonas, Chlamydia, Neisseria, Salmonella, Shigella, Campylobacter* and *Yersinia.*

5. The method of claim 1, wherein a reporter molecule from the plurality of reporter molecules is any one of a bacterial luciferase, a eukaryotic luciferase, a fluorescent protein, an enzyme suitable for colorimetric detection, a protein suitable for immunodetection, a peptide suitable for immunodetection, or a nucleic acid that function as an apatamer or that exhibits enzymatic activity.

6. The method of claim 1, wherein:
the plurality of transduction particles is stored within the reagent module such that the plurality of transduction particles is fluidically isolated from the biological sample after the reagent module is coupled to the sample container and before the conveying the plurality of transduction particles; and
the conveying the plurality of transduction particles includes manipulating an actuator of the reagent module to convey the plurality of transduction particles into the biological sample.

7. The method of claim 6, wherein the maintaining includes maintaining the biological sample at a temperature of less than or equal to approximately 45degrees Celsius, the time period being less than approximately eight hours.

8. The method of claim 7, wherein:
the actuator of the reagent module is a first actuator; and
the conveying the reagent includes manipulating, a second actuator of the reagent module to convey the reagent into the biological sample.

9. The method of claim 8, wherein the reagent includes a fatty aldehyde, the signal being a light emission signal associated with a flash luminescence reaction.

10. A method of detecting the presence of a target cell within a biological sample, comprising:
coupling a reagent module to a sample container such that a reaction chamber defined by the sample container is fluidically isolated from an exterior volume, the reaction chamber containing the biological sample, the reagent module containing a plurality of transduction particles associated with the target cell and a reagent;
disposing, after the coupling, at least a distal end portion of the sample container into an instrument; and
actuating the instrument to cause the instrument to:
manipulate the reagent module to convey the plurality of transduction particles into the reaction chamber of the sample container, the plurality of transduction particles associated with a target cell, the plurality of transduction particles engineered to be non-replicative and to include a nucleic acid molecule formulated to cause the target cell to produce a plurality of reporter molecules;
maintain the biological sample and the plurality of transduction particles within the reaction chamber within a predetermined temperature range to allow the plurality of reporter molecules to be produced within the reaction chamber when the target cell is present in the biological sample;
move the reagent module within the instrument to place a seal surface of the reagent module contact with a corresponding surface of the instrument to optically isolate the reaction chamber from the exterior volume, the seal surface in a fixed location relative to the sample container;
manipulate the reagent module to convey the reagent into the reaction chamber of the sample container, the reagent formulated to react with the plurality of reporter molecules to catalyze production of a signal, the seal surface being maintained in contact with the corresponding surface when the reagent module is manipulated; and
receive the signal associated with a quantity of the plurality of reporter molecules.

11. The method of claim 10, wherein the biological sample is a raw sample that has not undergone a separation operation or a washing operation, the raw sample being maintained within the sample container fluidically isolated from the exterior volume after the distal end portion of the sample container is disposed into the instrument.

12. The method of claim 10, wherein:
the biological sample is a raw sample that has not undergone a separation operation or a washing operation; and
the target cell within the biological sample is non-isolated.

13. The method of claim 10, wherein the instrument is configured to maintain the biological sample and the plurality of transduction particles in fluidic isolation from the exterior volume such that no reporter molecules are added from the exterior volume.

14. The method of claim 10, wherein:
the signal is a light emission associated with a flash luminescence reaction; and
the reagent comprises a fatty aldehyde formulated to catalyze the luminescence reaction.

15. A method of detecting the presence of a target cell within a biological sample, comprising:
coupling a reagent module to a sample container such that a reaction chamber defined by the sample container is fluidically isolated from an exterior volume, the reaction chamber containing the biological sample, the reaction chamber devoid of a reporter molecule before the coupling, the reagent module defining a first volume and a second volume, the first volume containing a plurality of transduction particles associated with the target cell, the second volume containing a reagent;
disposing, after the coupling, at least a distal end portion of the sample container into an instrument; and
actuating the instrument to cause the instrument to:
manipulate the reagent module to convey the plurality of transduction particles from the first volume into the reaction chamber of the sample container, the plurality of transduction particles associated with the target cell, the plurality of transduction particles engineered to be non-replicative and to include a nucleic acid molecule formulated to cause the target cell to produce a plurality of reporter molecules;
maintain the biological sample and the plurality of transduction particles within the reaction chamber in fluidic isolation from the exterior volume for a time period to allow the plurality of reporter molecules to be produced within the reaction chamber when the target cell is present in the biological sample;
exert a force on the reagent module to place a seal surface of the reagent module in contact with a corresponding surface of the instrument to optically isolate the reaction chamber from the exterior volume, the seal surface in a fixed location relative to the sample container;

manipulate the reagent module to convey the reagent from the second volume into the reaction chamber of the sample container, the reagent formulated to react with the plurality of reporter molecules to catalyze production of a signal, the seal surface being maintained in contact with the corresponding surface when the reagent module is manipulated; and receive the signal associated with a quantity of the plurality of reporter molecules.

16. The method of claim 15, wherein the instrument is configured to maintain the biological sample and the plurality of transduction particles at a substantially constant temperature to allow the plurality of reporter molecules to be produced.

17. The method of claim 15, wherein:

the biological sample is a raw sample that has not undergone a separation operation or a washing operation; and the target cell within the biological sample is non-isolated.

18. The method of claim 15, wherein:

the signal is a light emission associated with a flash luminescence reaction; and the reagent comprises a fatty aldehyde formulated to catalyze the luminescence reaction.

19. The method of claim 15, wherein the target cell is a bacteria selected from the group consisting of *Escherichia, Mycobacterium, Staphylococcus, Listeria, Clostridium, Enterococcus, Streptococcus, Helicobacter, Rickettsia, Haemophilus, Xenorhabdus, Acinetobacter, Bordetella, Pseudomonas, Aeromonas, Aetinobacillus, Pasteurella, Vibrio, Legionella, Bacillus, Calothrix, Methanococcus, Stenotrophomonas, Chlamydia, Neisseria, Salmonella, Shigella, Campylobacter* and *Yersinia*.

* * * * *